(12) United States Patent
Merola

US008841281B2

(10) Patent No.: US 8,841,281 B2
(45) Date of Patent: Sep. 23, 2014

(54) TRANSITION METAL COMPLEXES OF AMINO ACIDS AND RELATED LIGANDS AND THEIR USE AS CATALYSTS, ANTI-MICROBIALS, AND ANTI-CANCER AGENTS

(71) Applicant: Virginia Tech Intellectual Properties, Inc., Blacksburg, VA (US)

(72) Inventor: Joseph S. Merola, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 13/653,883

(22) Filed: Oct. 17, 2012

(65) Prior Publication Data

US 2013/0096090 A1    Apr. 18, 2013

Related U.S. Application Data

(60) Provisional application No. 61/547,844, filed on Oct. 17, 2011.

(51) Int. Cl.
*A61K 31/66* (2006.01)
*C07D 207/00* (2006.01)

(52) U.S. Cl.
USPC ........... 514/102; 514/492; 514/502; 548/402; 548/215; 548/300.1

(58) Field of Classification Search
USPC ........ 514/102, 492, 502; 548/402, 215, 300.1
See application file for complete search history.

(56) References Cited

U.S. PATENT DOCUMENTS

2010/0291236 A1* 11/2010 Sadler et al. .................. 424/649

OTHER PUBLICATIONS

Yuki et al. CAS: 153: 619065, 2010.*
Blakemore et al. CAS: 153: 652529, 2010.*
Heck et al. CAS: 101: 152018, 1984.*
Miller et al. CAS: 101: 113707, 1985.*
Ciancaleoni et al. CAS: 147: 235293, 2007.*
Scharwitz et al. CAS: 149: 238690, 2008.*
Glockner et al. CAS: 152: 97590, 2009.*
Das et al. CAS: 152: 278885, 2009.*
Peacock et al. CAS: 146: 434174, 2007.*
Ciancaleoni et al. CAS: 146: 296035, 2007.*
Zuccaccia et al. CAS: 142:411468, 2005.*
Ahlford, K.; Adolfsson, H., Amino acid derived amides and hydroxamic acids as ligands for asymmetric transfer hydrogenation in aqueous media, Catalysis Communications 2011, 12 (12), 1118-1121.
Beck, W., "Metal Complexes of Biologically Important Ligands, CLXXVI.[1] Formation of Peptides within the Coordination Sphere of Metal Ions and of Classical and Organometallic Complexes and Some Aspects of Prebiotic Chemistry", Z. Anorg. Allg. Chem. 2011, 637, 1647-1672.
Bruijnincx, P. C. A.; Sadler, P. J., New trends for metal complexes with anticancer activity. Curr. Opin. Chem. Biol. 2008, 12, 197-206.
Carmona, D.; Viguri, F.; Pilar Lamata, M.; Ferrer, J.; Bardaji, E.; Lahoz, F. J.; Garcia-Orduna, P.; Oro, L. A., Ruthenium amino carboxylate complexes as asymmetric hydrogen transfer catalysts, Dalton Transactions 2012, 41 (34), 10298-10308.
Habtemariam, A. et al., Structure-Activity Relationships for Cytotoxic Ruthenium(II) Arene Complexes Containing N,N-, N,O-, and O,O-Chelating Ligands, J. Med. Chem. 2006, 49, 6858-6868.
Infectious Diseases Society of America, "The 10×'20 Initiative: Pursuing a Global Commitment to Develop 10 New Antibacterial Drugs by 2020", Clin Infect Dis. (2010) 50 (8):1081-1083, e-published Mar. 9, 2010, doi: 10.1086/652237.
Manville, C. V.; Docherty, G.; Padda, R.; Wills, M., Application of Proline-Functionalised 1,2-Diphenylethane-1,2-diamine (DPEN) in Asymmetric Transfer Hydrogenation of Ketones, European Journal of Organic Chemistry 2011, (34), 6893-6901.
Rosenberg, B., Platinum compounds: a new class of potent antitumour agents, Nature (London) 1969, 222 (5191), 385-6.
Roy, Christopher P. et al, Iridium(III) hydrido amino acid compounds: Chiral complexes and a helical extended lattice, Journal of Organometallic Chemistry 691 (2006) 2270-2276.
Schreiner, B.; Robl, C.; Wagner-Schuh, B.; Beck, W., Metal complexes of biologically important ligands, CLXXIV, Palladium(II) and Platinum(II) Complexes with Schiff bases from 2-(diphenylphosphino)benzaldehyde and alpha-amino acid esters, Zeitschrift fuer Naturforschung, B: A Journal of Chemical Sciences 2010, 65b, 503-510.
Schreiner, B.; Wagner-Schuh, B.; Beck, W., Metal complexes of biologically important ligands, CLXXIV, Pentamethylcyclopentadienyl half-sandwich complexes of rhodium(III) and iridium(III) with Schiff bases from 2-(diphenylphosphino)benzaldehyde and alpha-amino acid esters, Zeitschrift fuer Naturforschung, B: A Journal of Chemical Sciences 2010, 65 (6), 679-686.

(Continued)

*Primary Examiner* — Rei-tsang Shiao
(74) *Attorney, Agent, or Firm* — New River Valley IP Law, PC; Michele L. Mayberry

(57) ABSTRACT

The present invention relates to the fields of chemistry and pharmaceuticals. Embodiments of the present invention provide transition metal complexes of amino acids. Transition metal complexes of embodiments of the invention according to Categories I, II, III, and/or IV may be used as antimicrobial, anti-malarial, and anti-cancer agents, as well as catalysts in chemical reactions. Such compounds of the invention are particularly useful for combating multi-drug resistance against a broad range of microbials (such as MRSA and mycobacteria), including gram positive and gram negative bacteria, as well as can be used as anti-cancer agents against bladder cancer, breast cancer, colon cancer, rectal cancer, endometrial cancer, kidney cancer, leukemia, lung cancer, melanoma, non-Hodgkin's lymphoma, pancreatic cancer, prostate cancer, and thyroid cancer, to name a few.

12 Claims, 81 Drawing Sheets

(56) References Cited

OTHER PUBLICATIONS

Schwartz M., Aug. 9, 2006, Drug-resistant strains of tuberculosis are more virulent than experts assumed, Stanford Report.

Slyudkin, O. P.; Tulupov, A. A., Chiral complexes of Pt with amino acids: Synthesis, structure, properties, Russ. J. Coord. Chem. 2005, 31, 77-85.

Spera, M. B. M.; Quintao, F. A.; Ferraresi, D. K. D.; Lustri, W. R.; Magalhaes, A.; Formiga, A. L. B.; Corbi, P. P., Palladium(II) complex with S-allyl-L-cysteine: new solid-state NMR spectroscopic measurements, molecular modeling and antibacterial assays. Spectrochim Acta A Mol Biomol Spectrosc 2011, 78 (Copyright (C) 2011 U.S. National Library of Medicine.), 313-8.

Vasić, G. P.; Glodjović, V. V.; Radojević, I. D.; Stefanović, O. D.; Čomić, L. R.; Djinović, V. M.; Trifunović, S. R., Stereospecific ligand and their complexes: V. Synthesis, characterization and antimicrobial activity of palladium(II) complexes with some alkyl esters of (S,S)-ethylenediamine N,N-di-2 propanoic acid, Inorg. Chim. Acta, 63 (2010) 3606-3610; ISSN: 0020-1693; DOI: 10.1016/j.ica.2010.05.046.

Vicol, O., Some complex combinations of Pd(II) with methionine, Journal of inorganic & nuclear chemistry 1979, 41 (3), 309-315.

Ziegler, C. J.; Sandman, K. E.; Liang, C. H.; Lippard, S. J., Toxicity of platinum(II) amino acid (N,O) complexes parallels their binding to DNA as measured in a new solid phase assay involving a fluorescent HMG1 protein construct readout, JBIC, J. Biol. Inorg. Chem. 1999, 4; 402-411.

\* cited by examiner

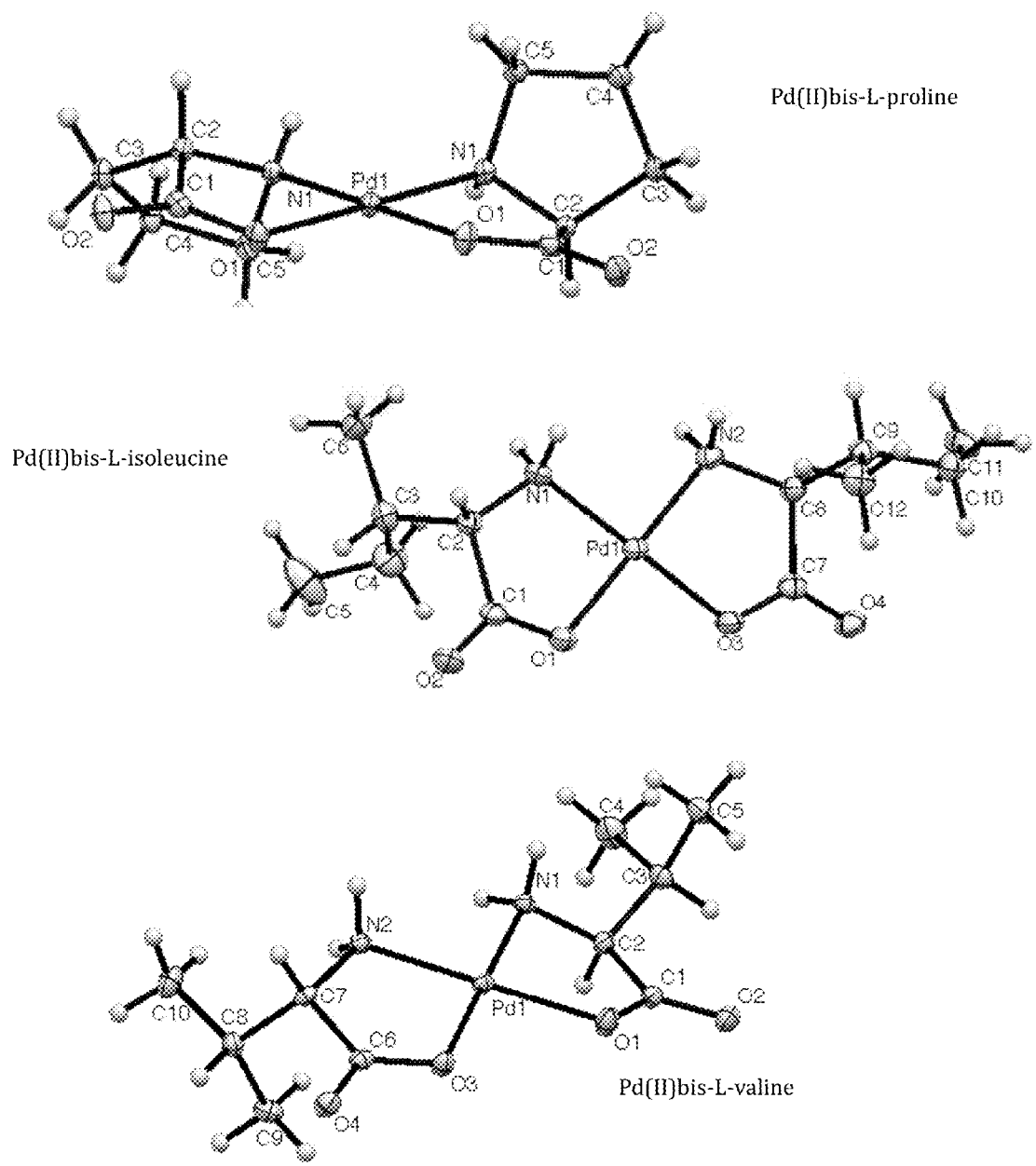
Figure 1A. Structures of Crystallographically Characterized Amino Acid Complexes of Palladium

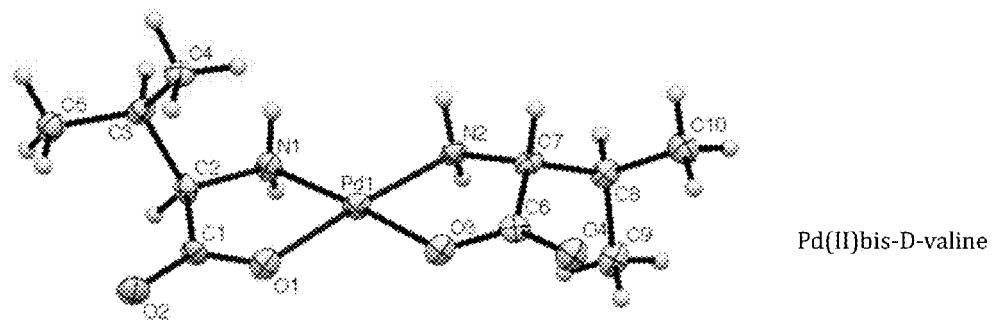
Pd(II)bis-D-valine
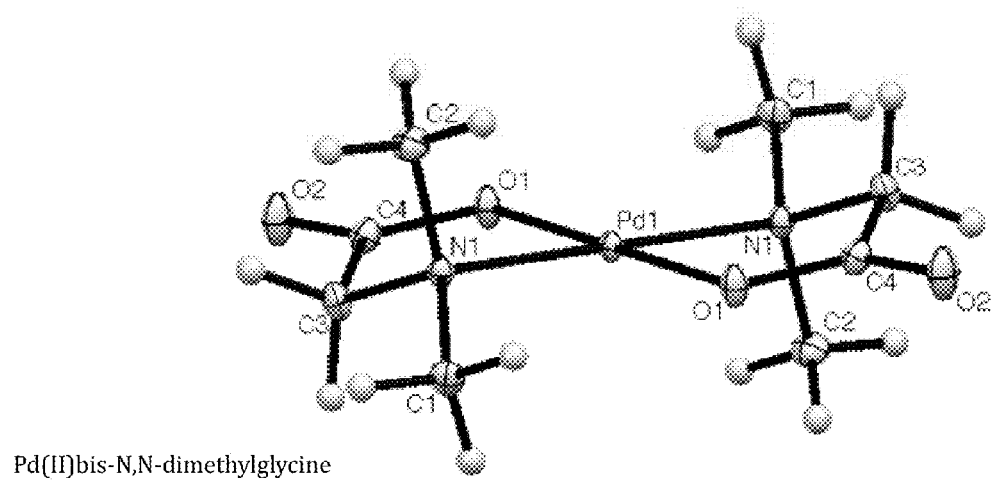
Pd(II)bis-N,N-dimethylglycine
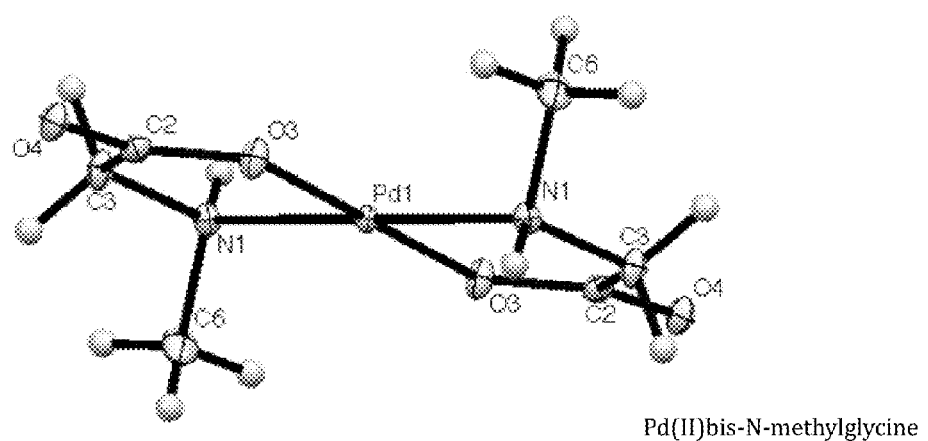
Pd(II)bis-N-methylglycine
Figure 1B. Structures of Crystallographically Characterized Amino Acid Complexes of Palladium

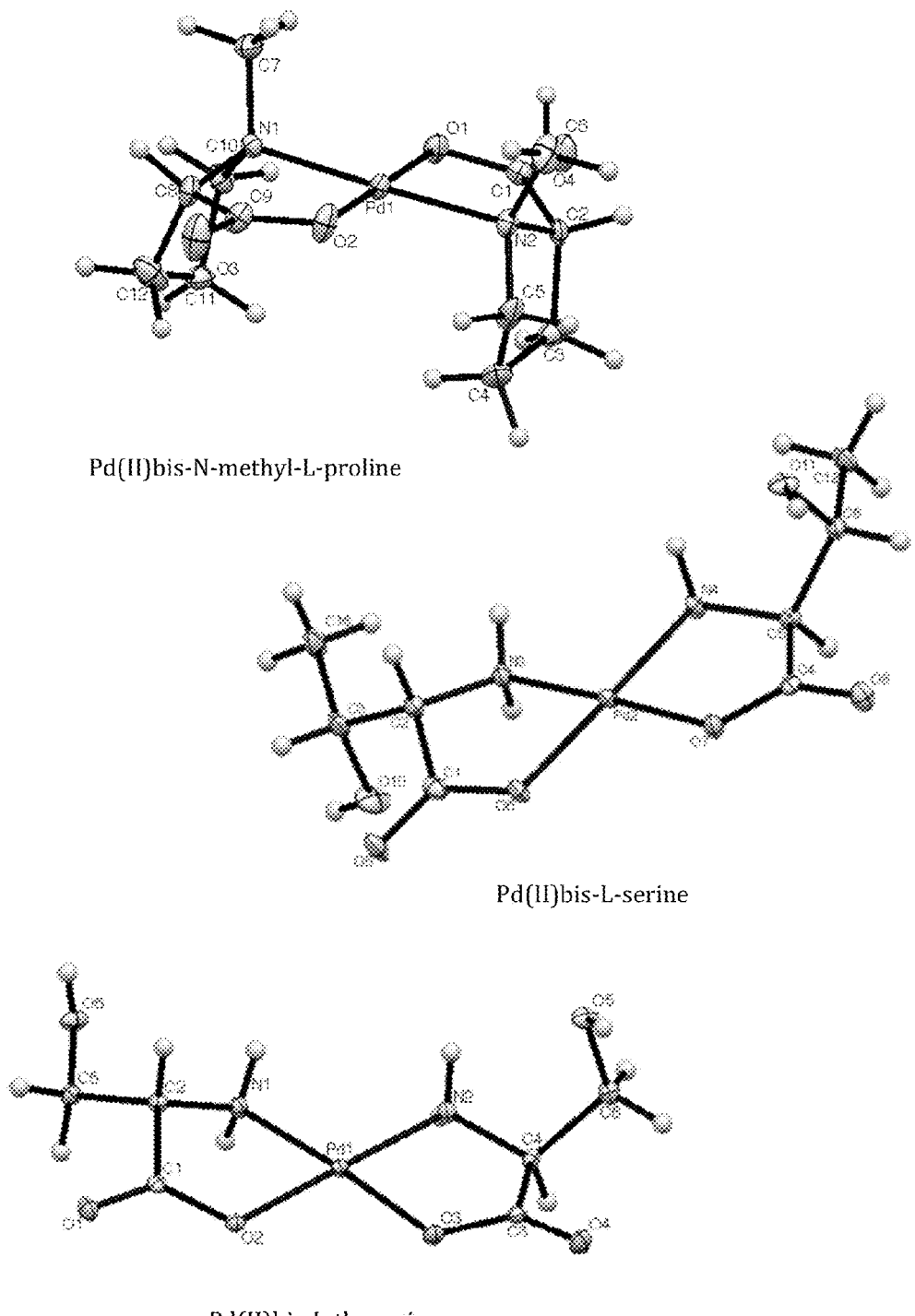
Figure 1C. Structures of Crystallographically Characterized Amino Acid Complexes of Palladium Representative Formula 1 Type Complexes Representative Fused Ring Formula 1 Type Complexes

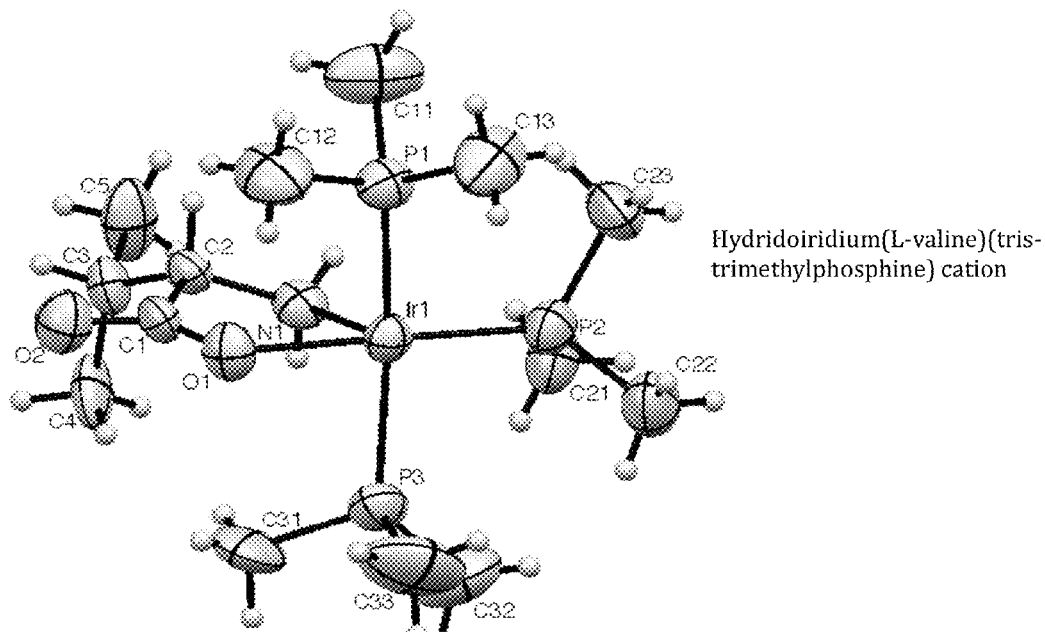
Hydridoiridium(L-valine)(tris-trimethylphosphine) cation
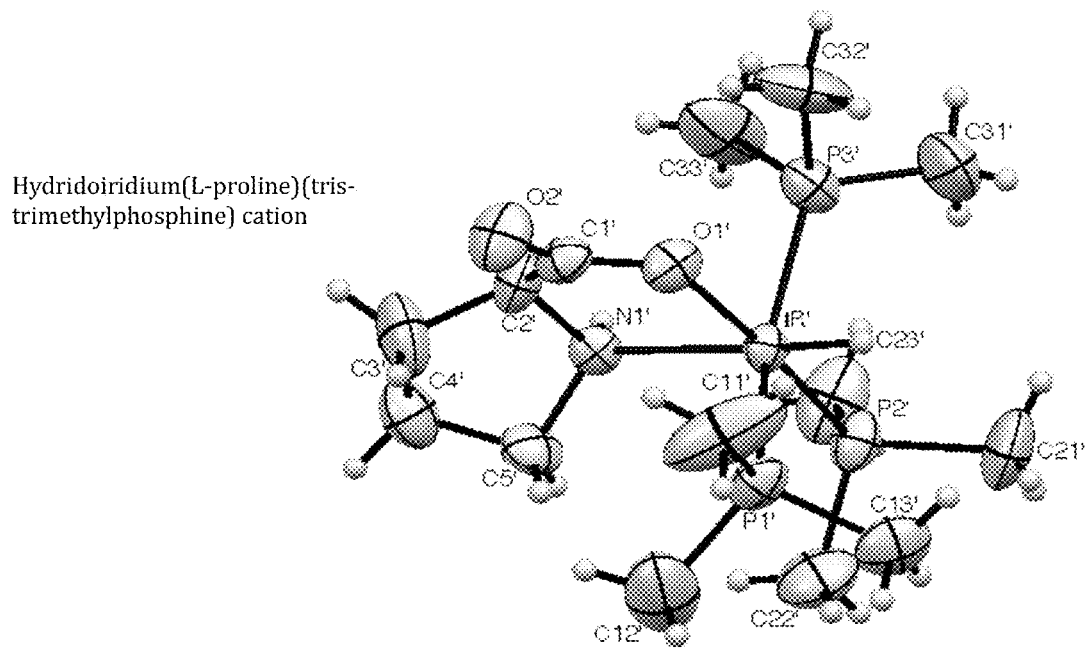
Hydridoiridium(L-proline)(tris-trimethylphosphine) cation
Figure 2A. Structures of Crystallographically Characterized Amino Acid Complexes of Iridium(III)

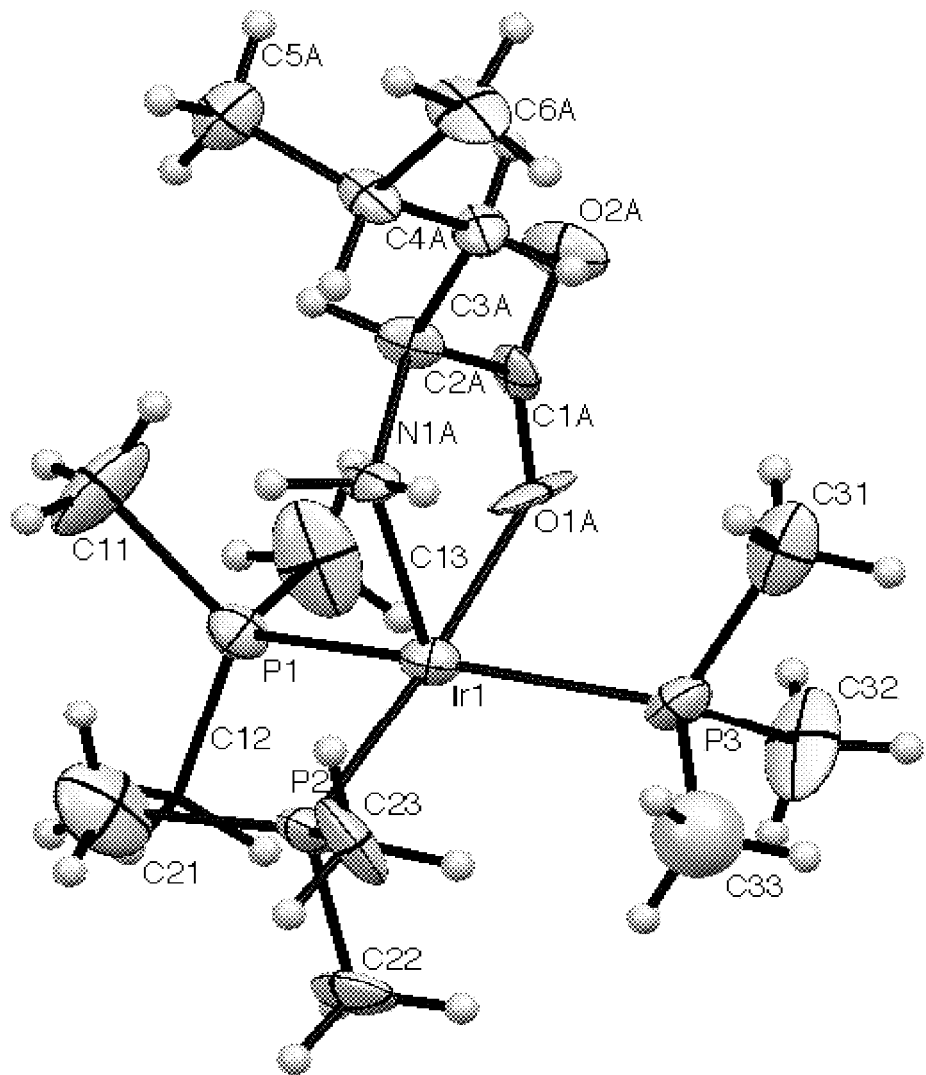
Hydridoiridium(L-leucine)(tris-trimethylphosphine) cation
Figure 2B. Representative Structure of Crystallographically Characterized Amino Acid Complexes of Iridium(III)

Figure 3C:
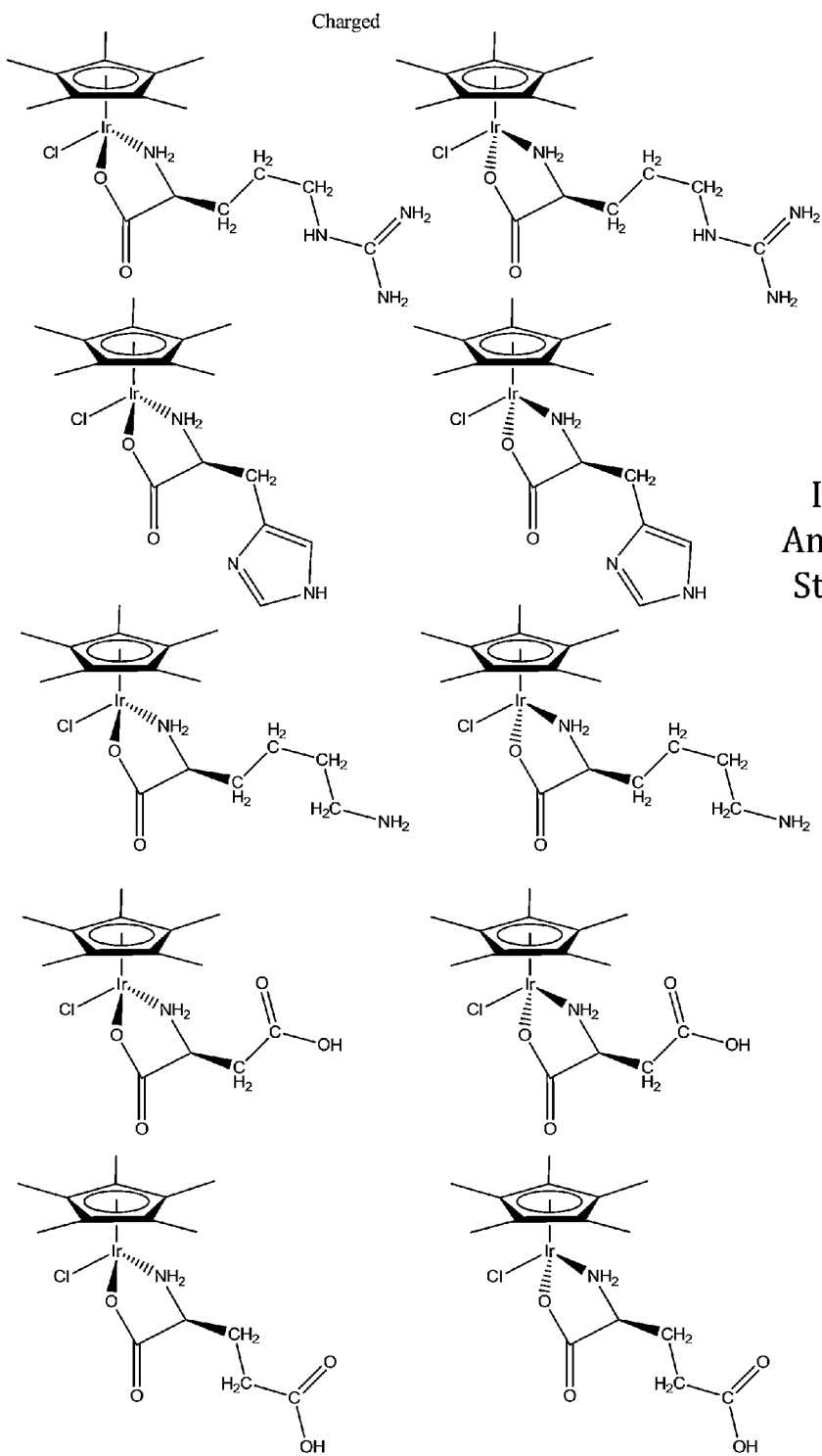
Figure 3D:
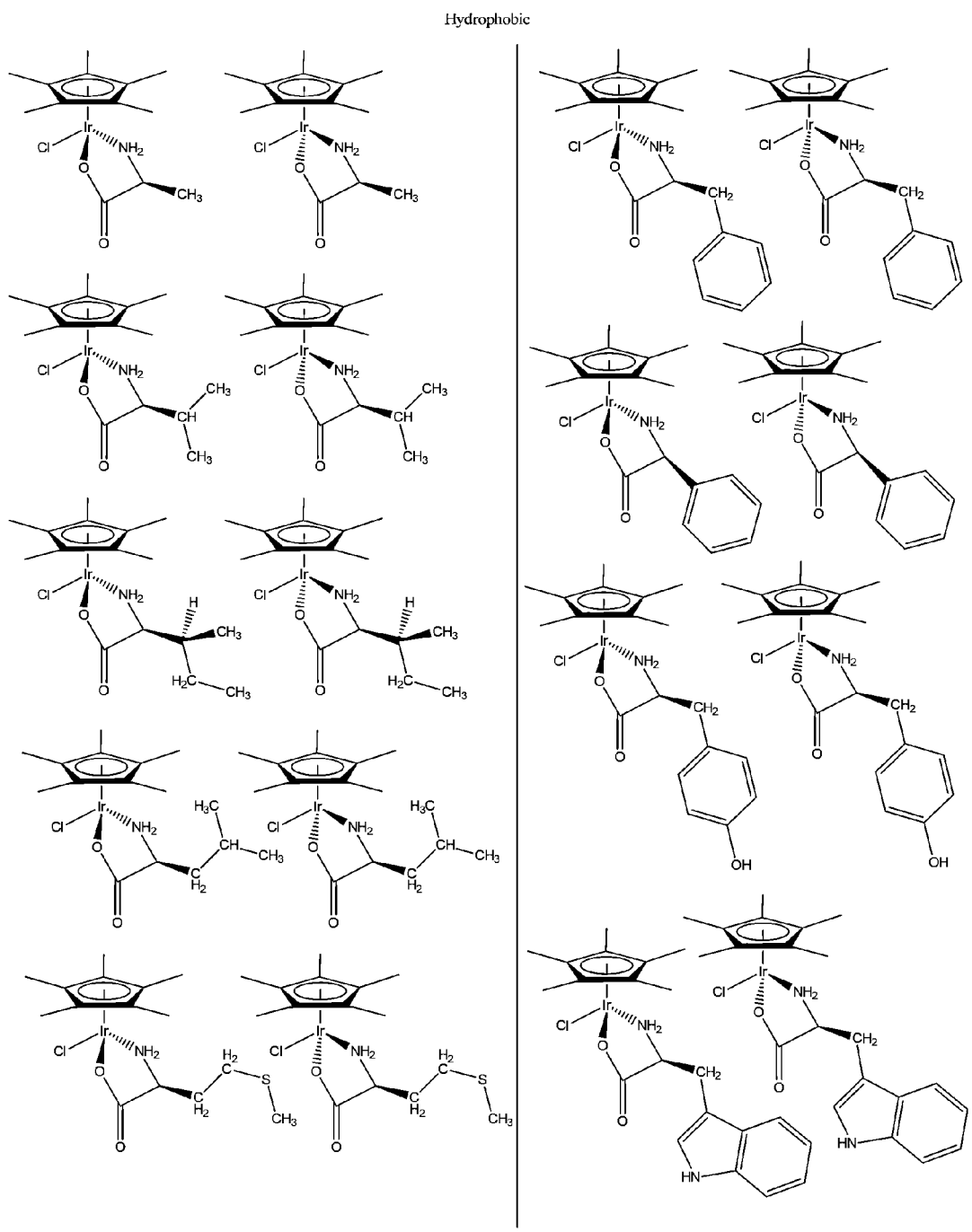
Figure 3E:
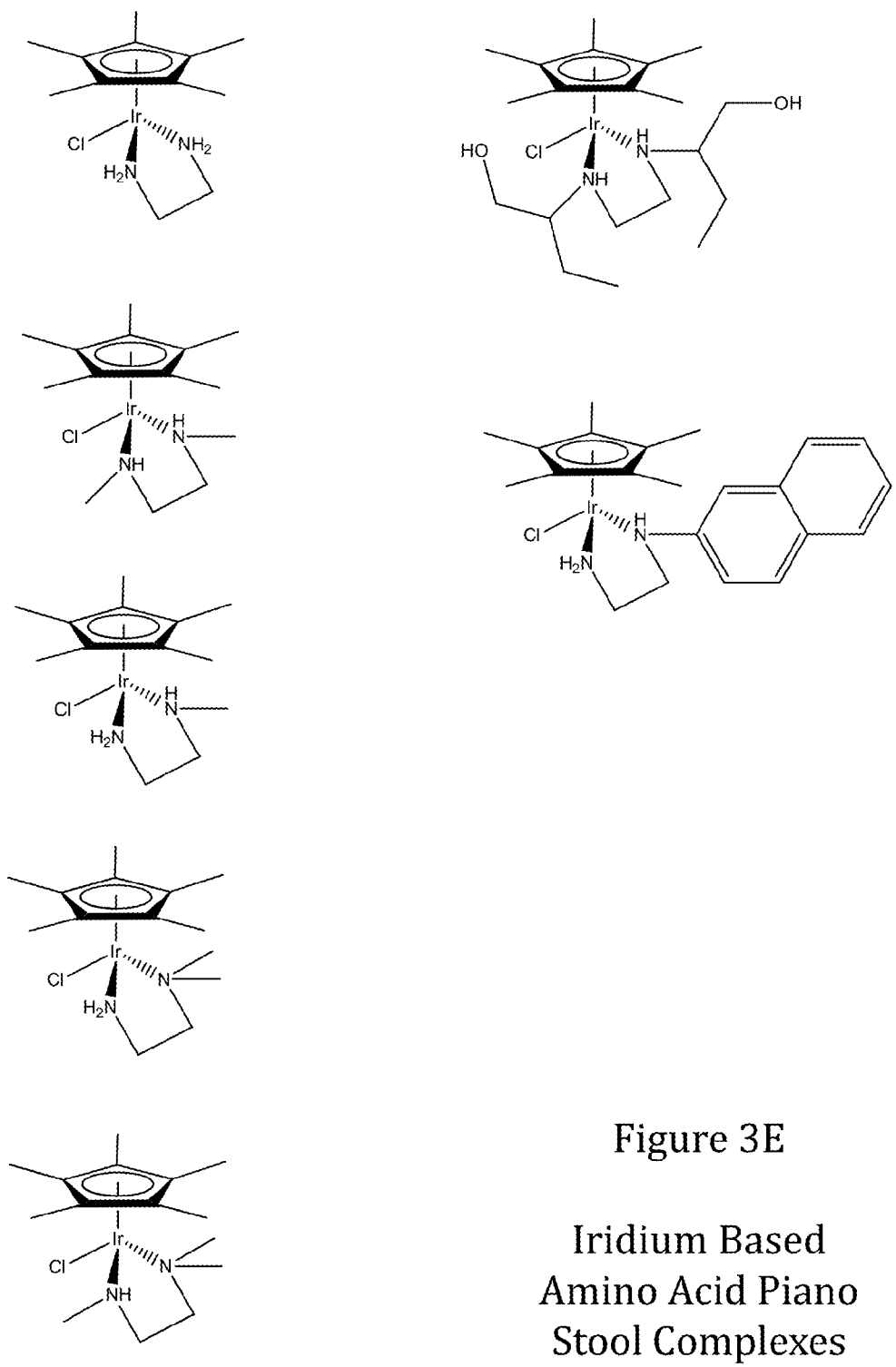
Figure 3F:
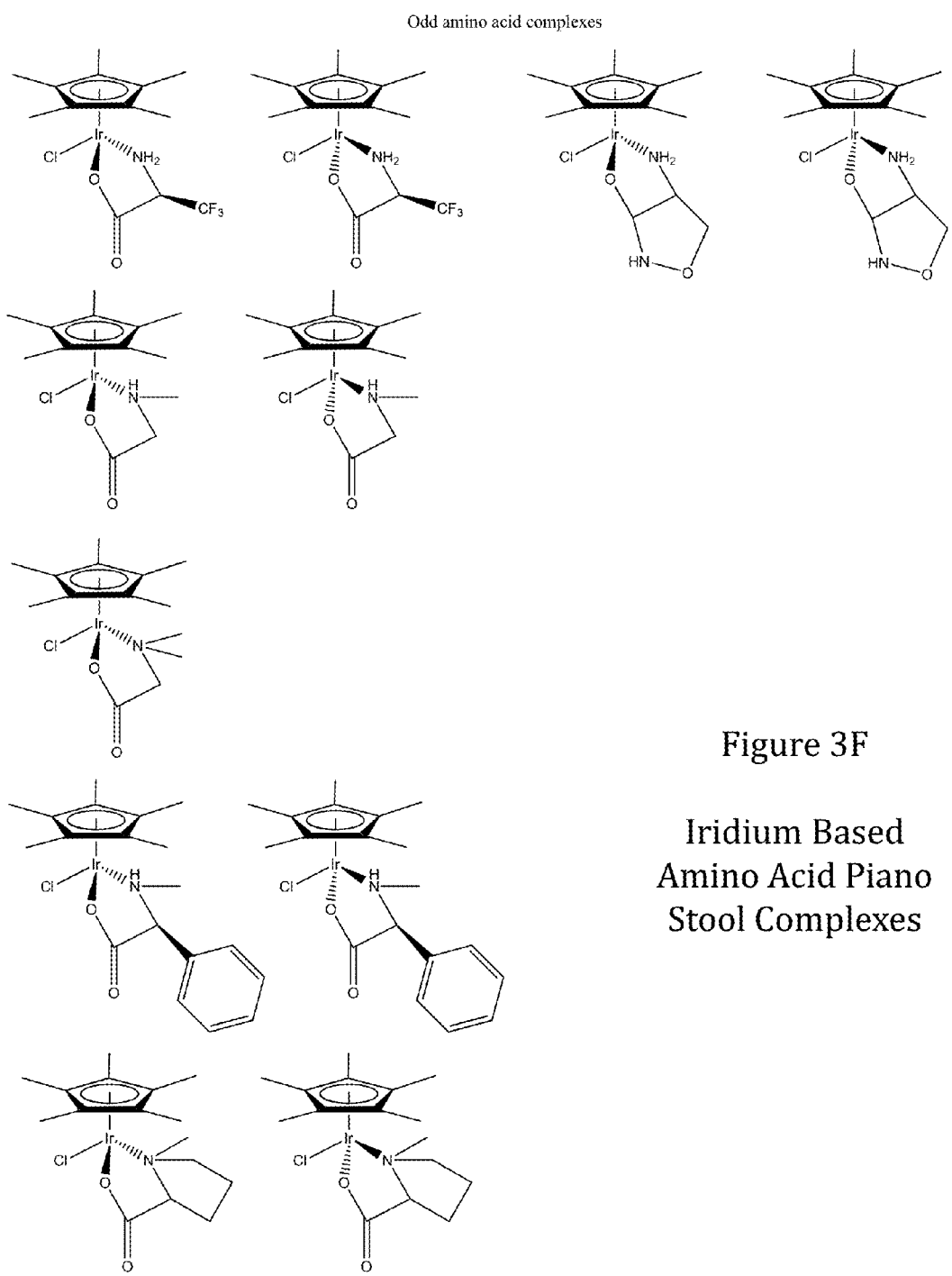
Figure 3G:
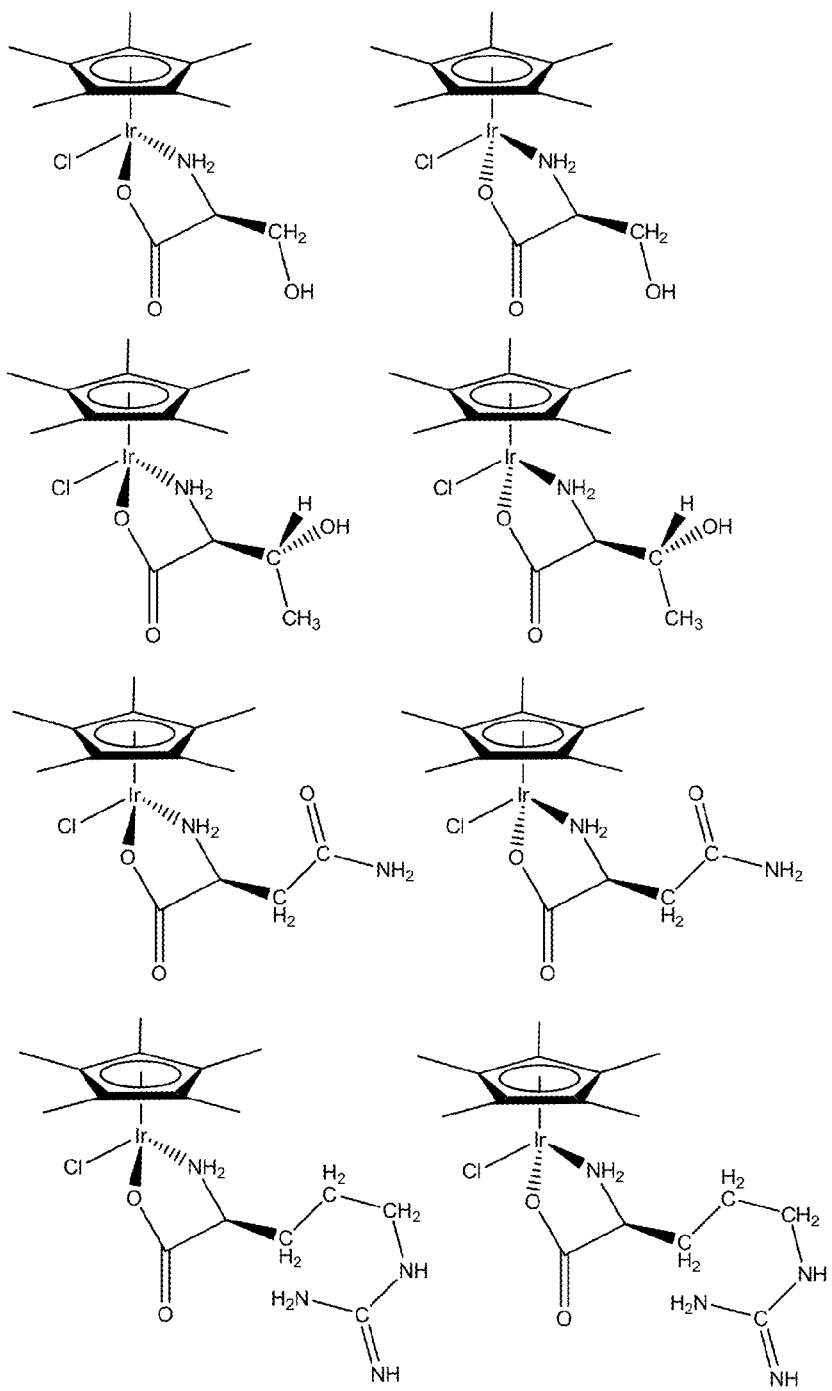
Figure 3H:
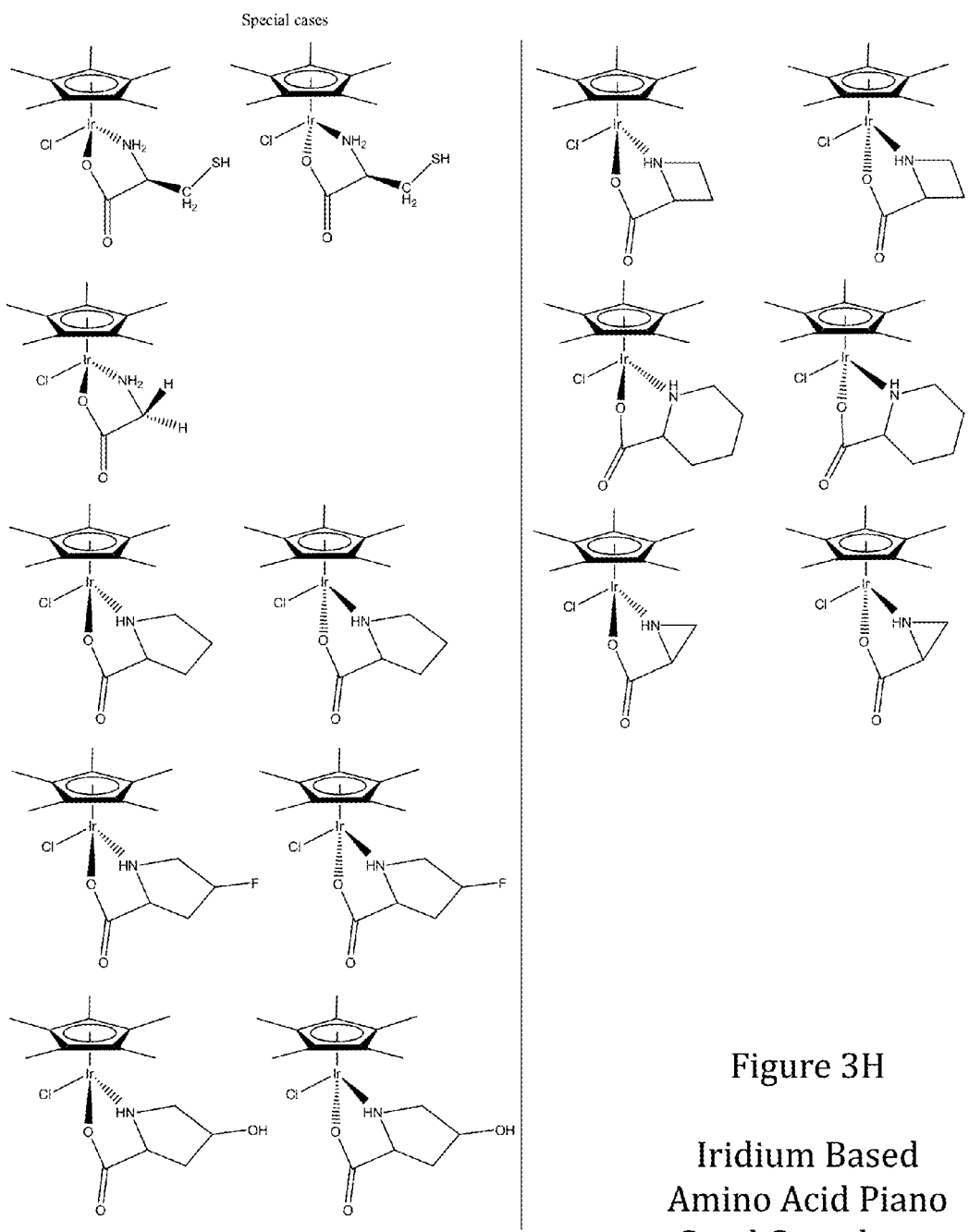
Figure 3I:
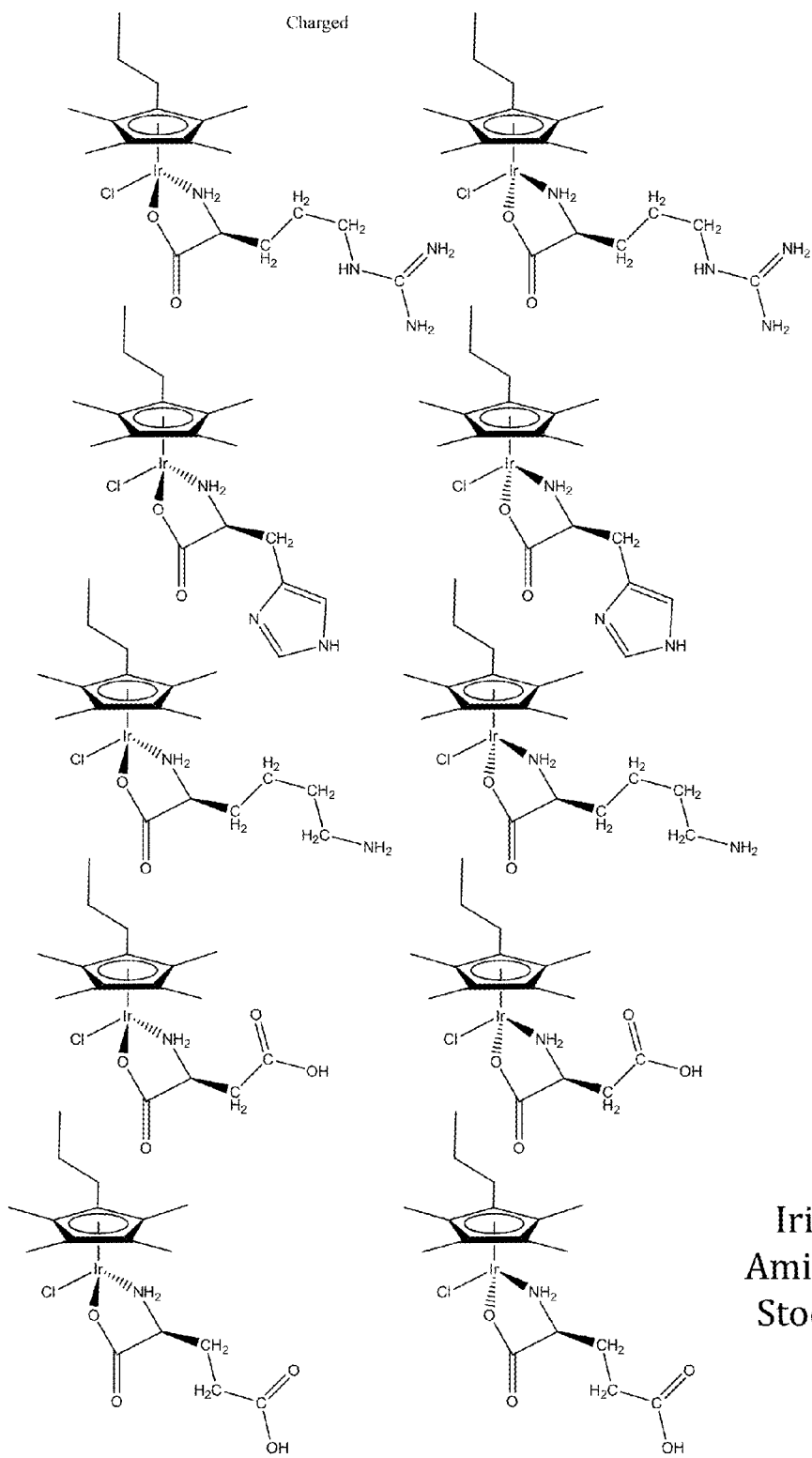
Figure 3J:
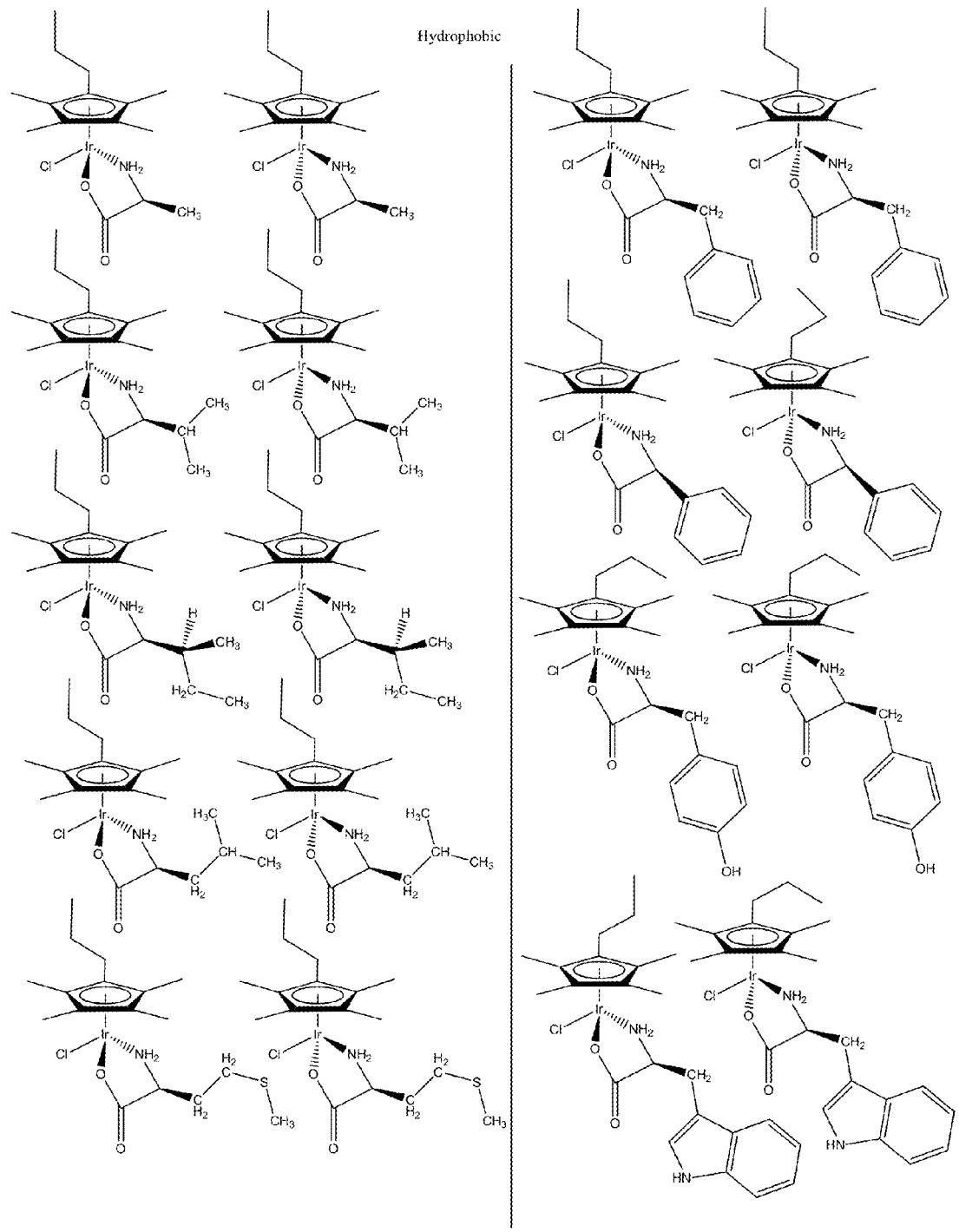
Figure 3K:
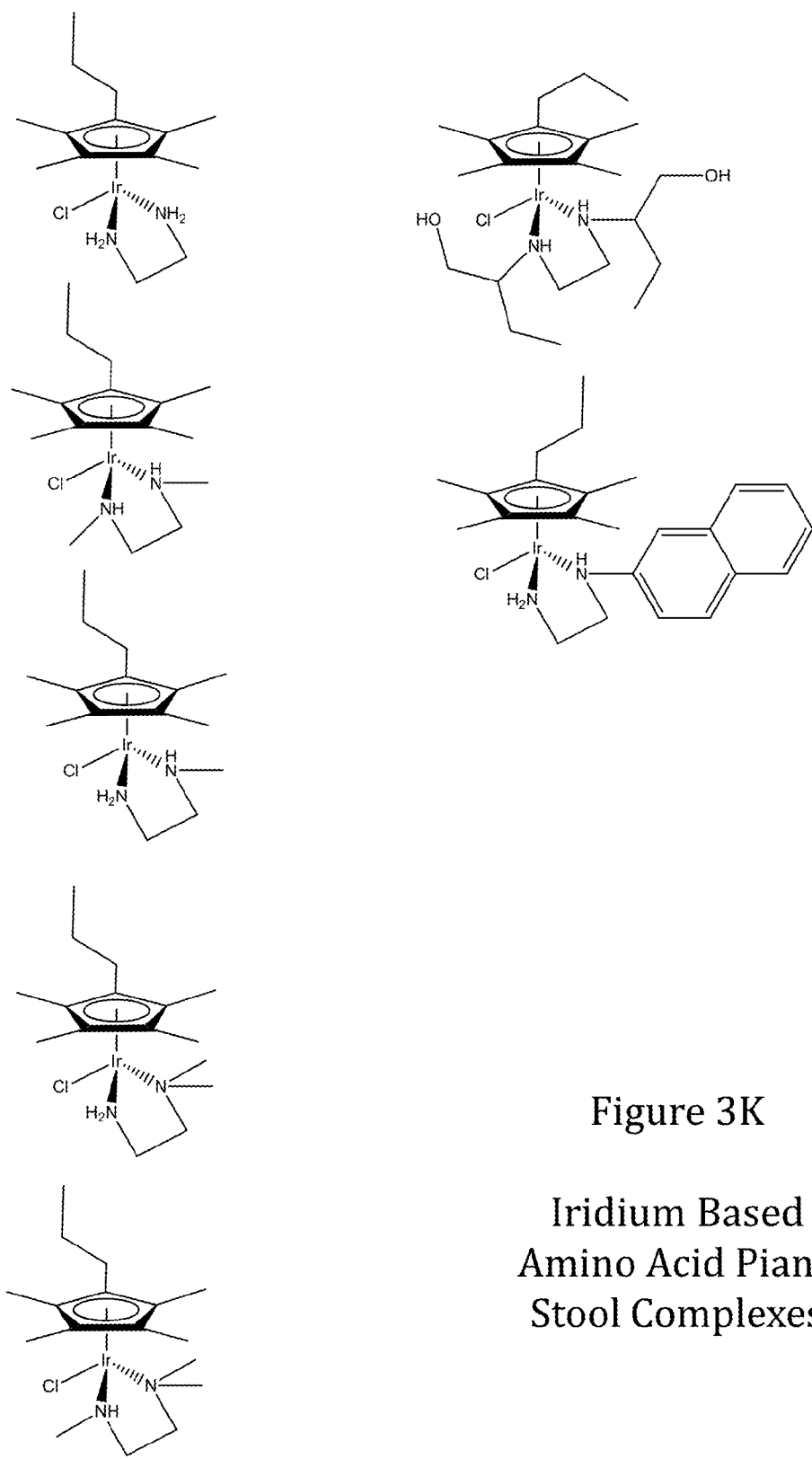
Figure 3L:
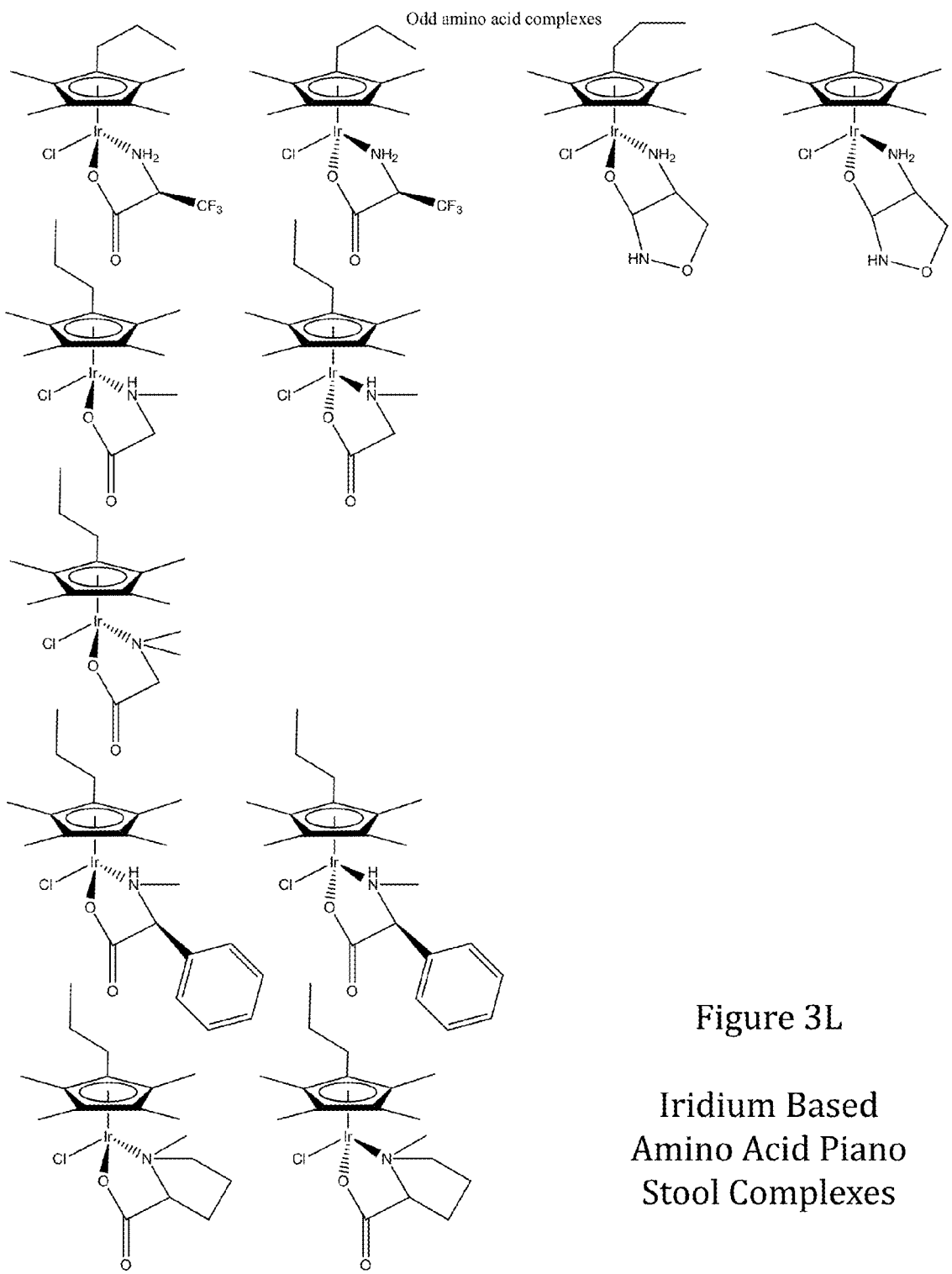
Figure 3M:
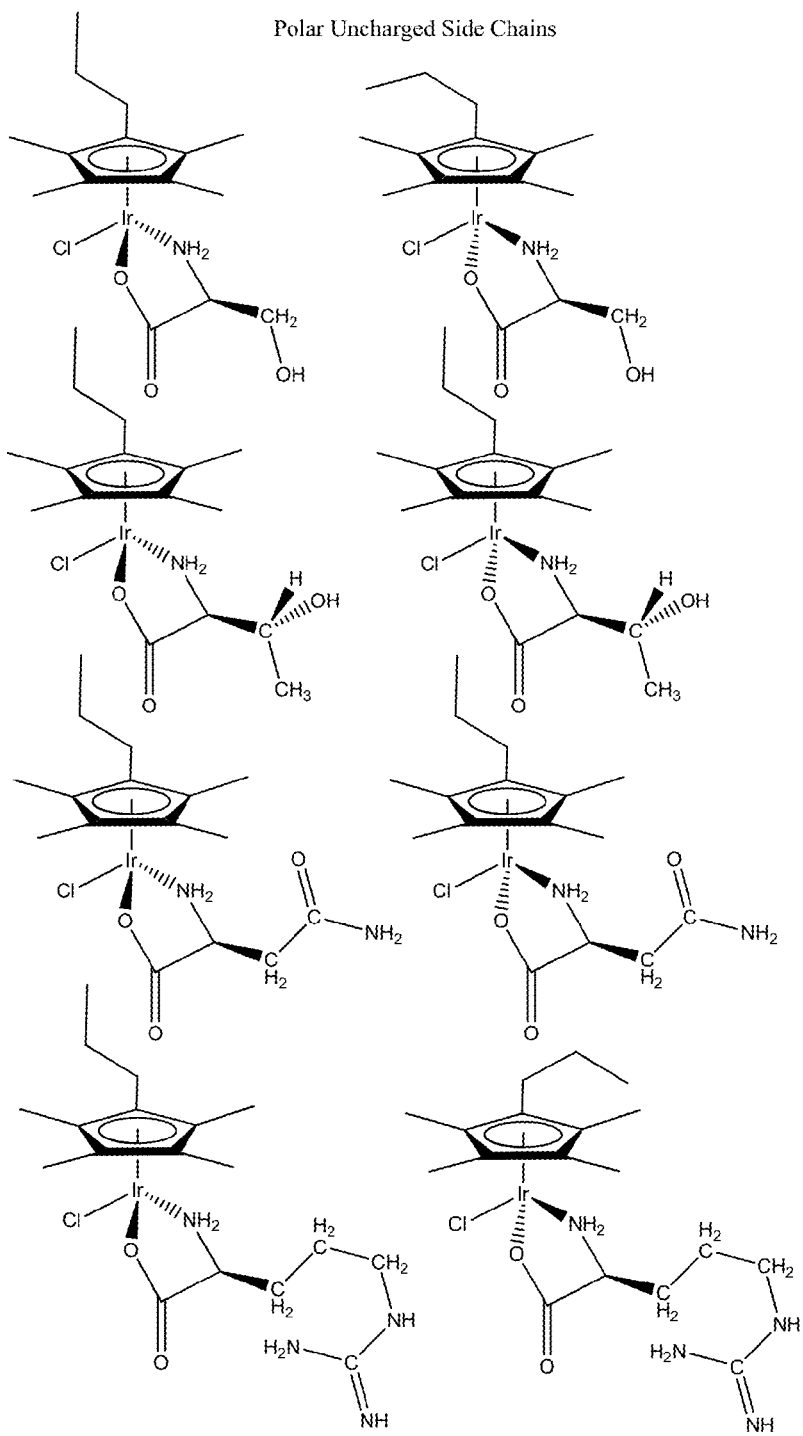
Figure 3N:
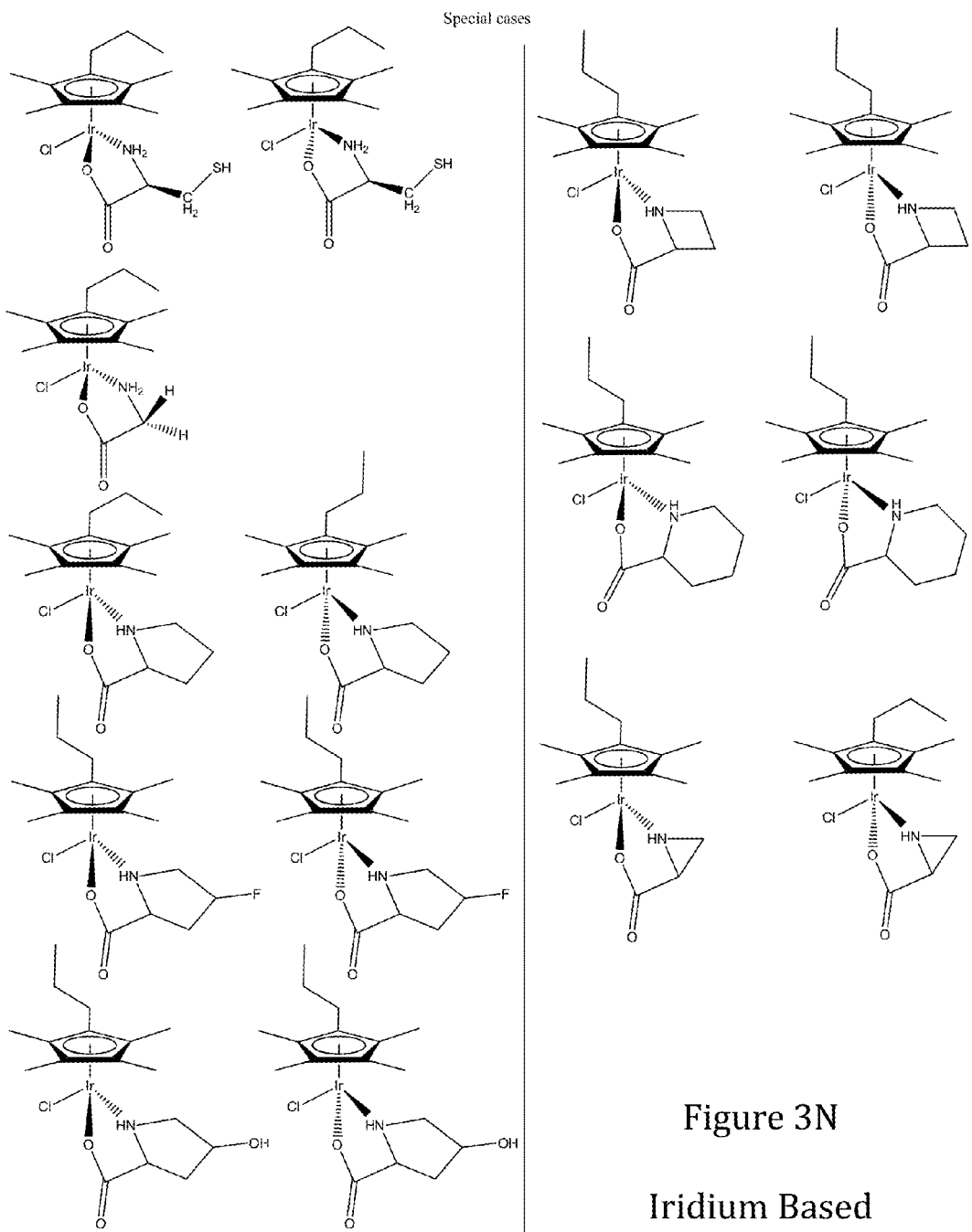
Figure 30:
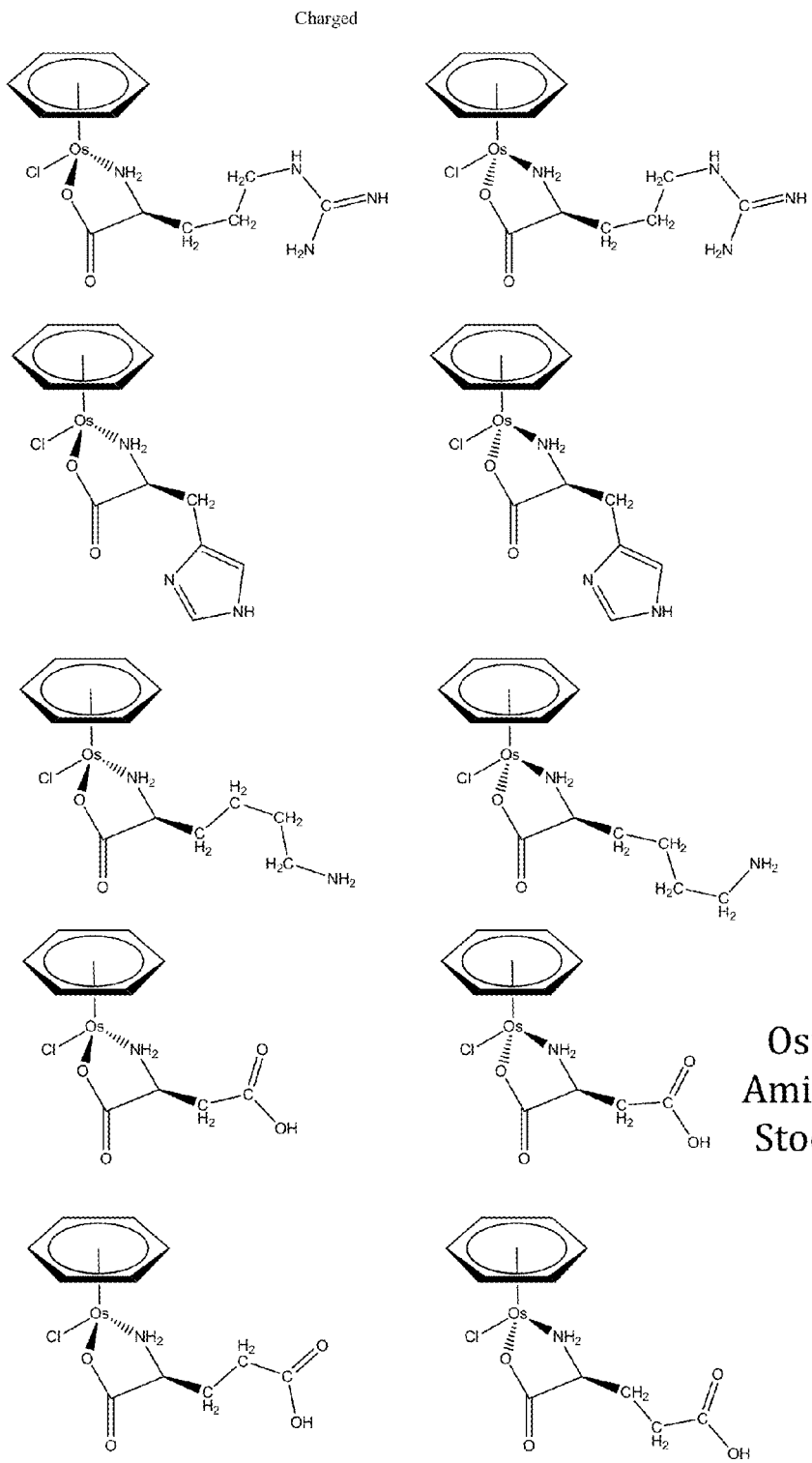
Figure 3Q:
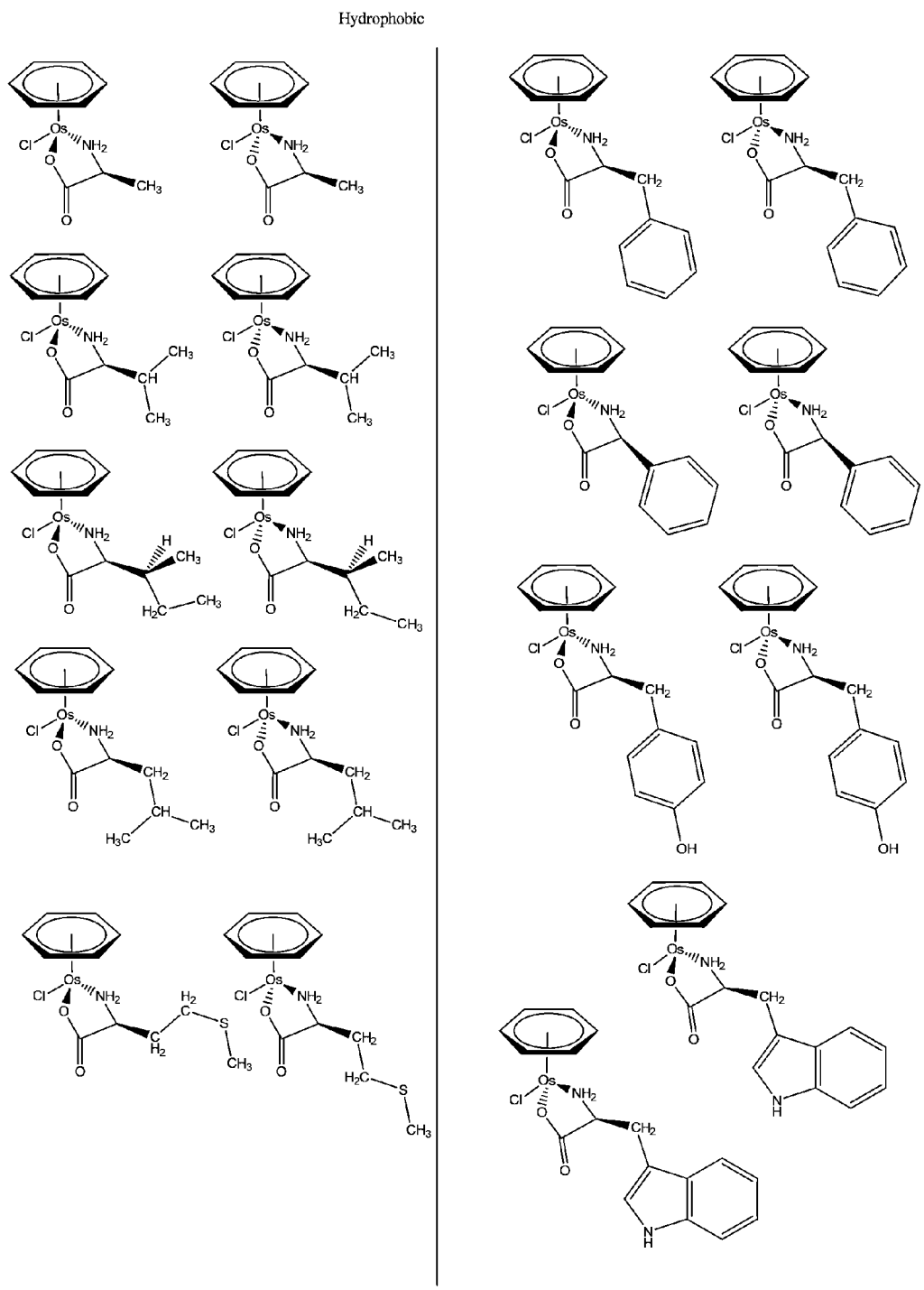
Figure 3R:
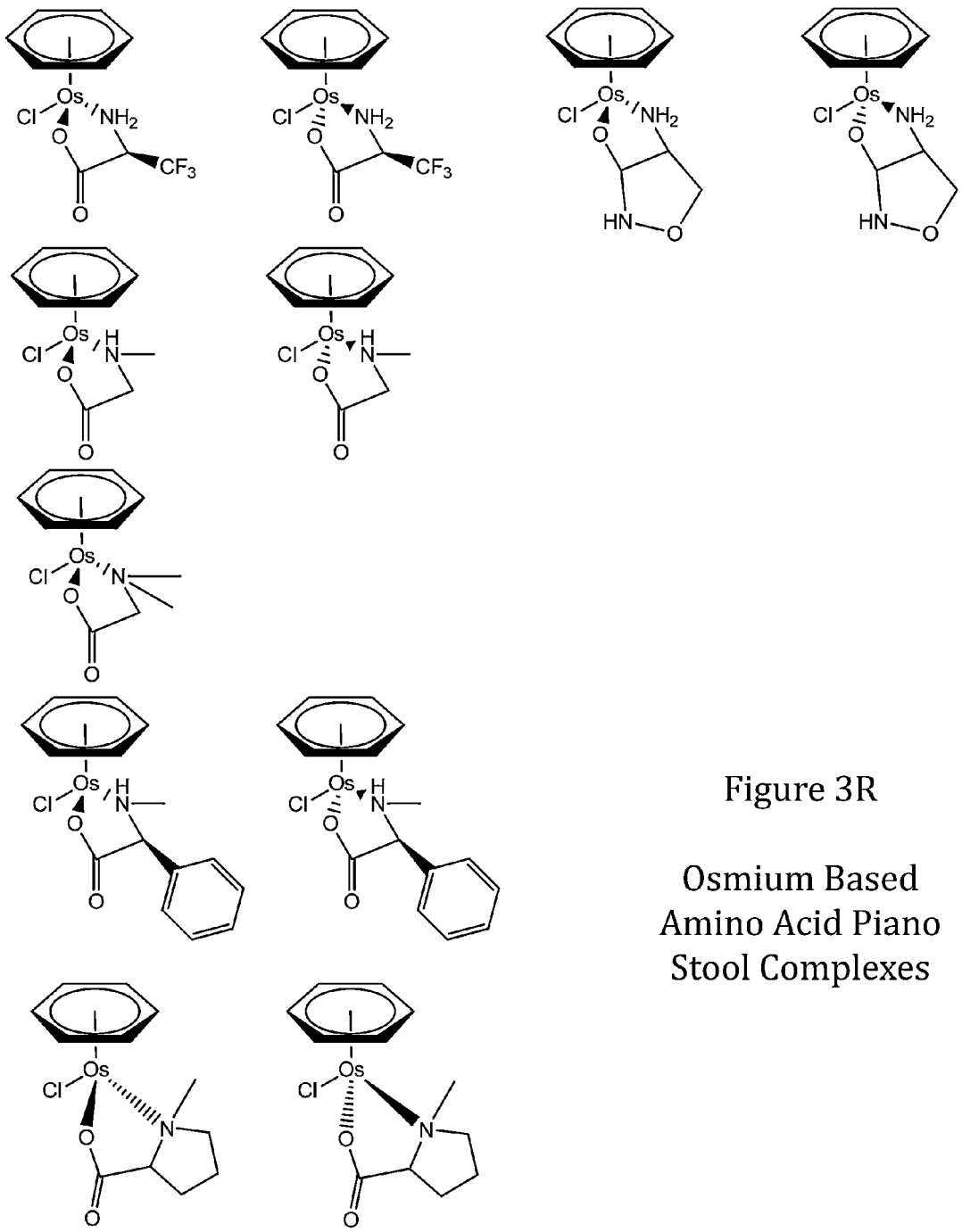
Figure 3S:
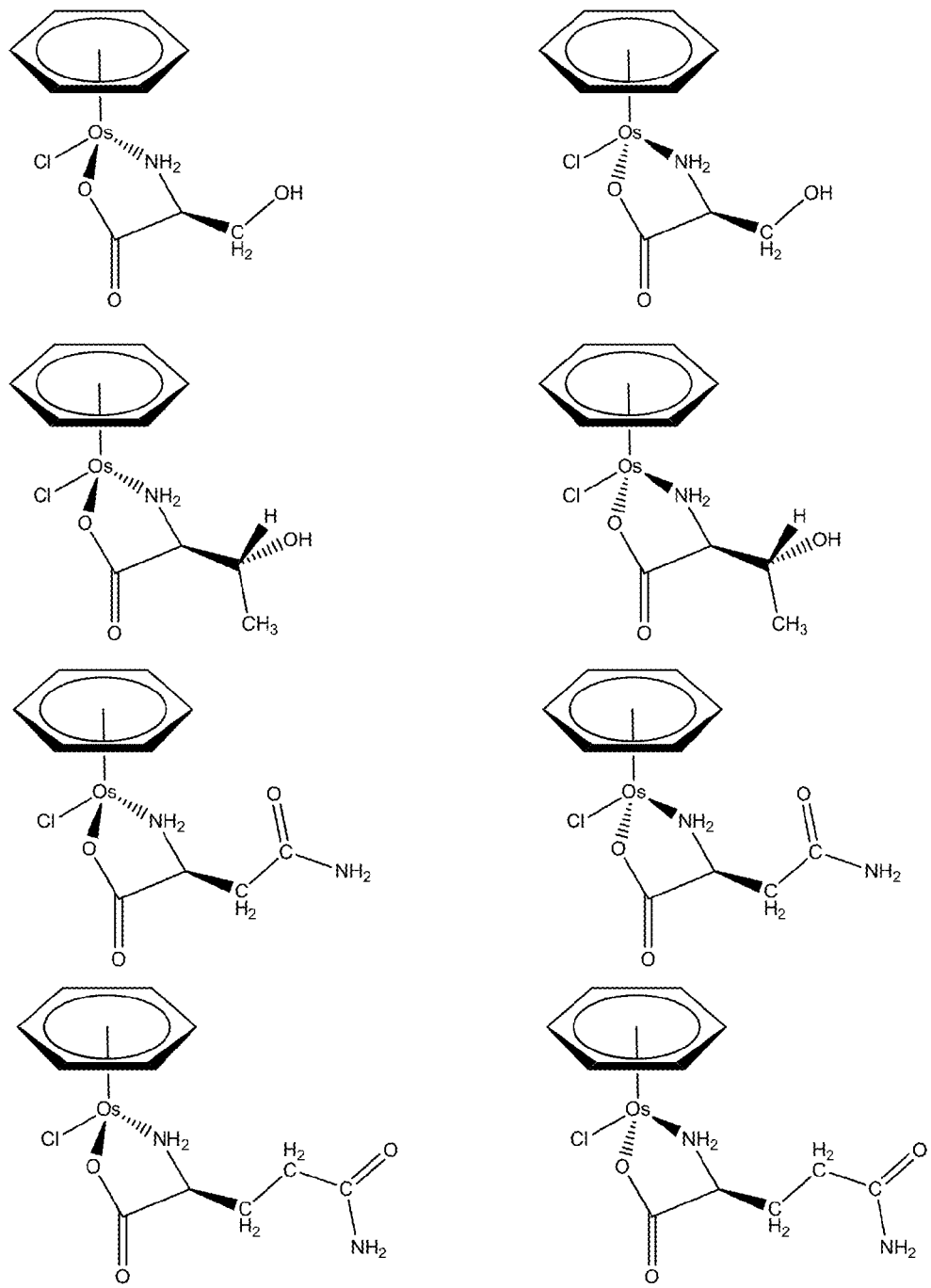
Figure 3T:
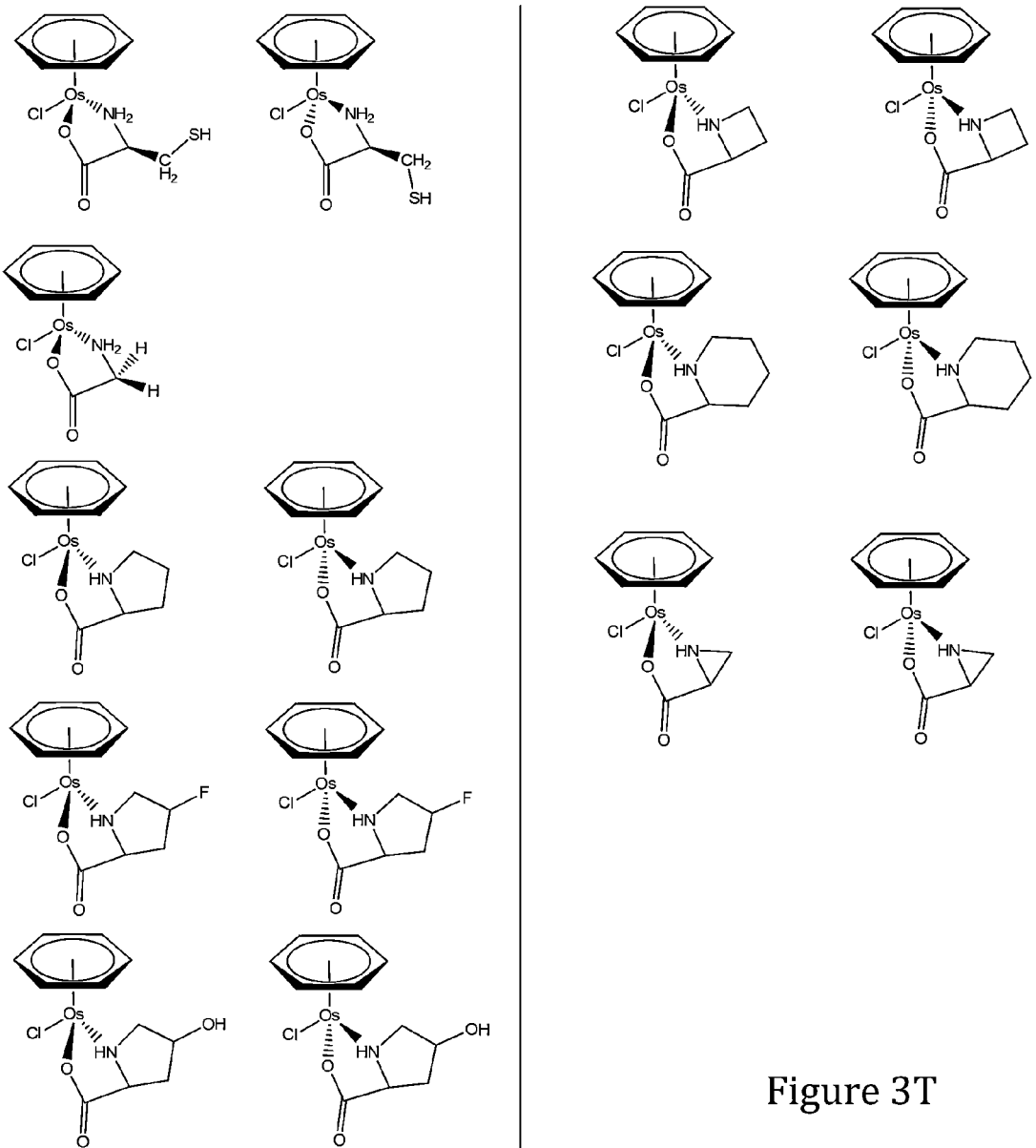
Figure 3U:
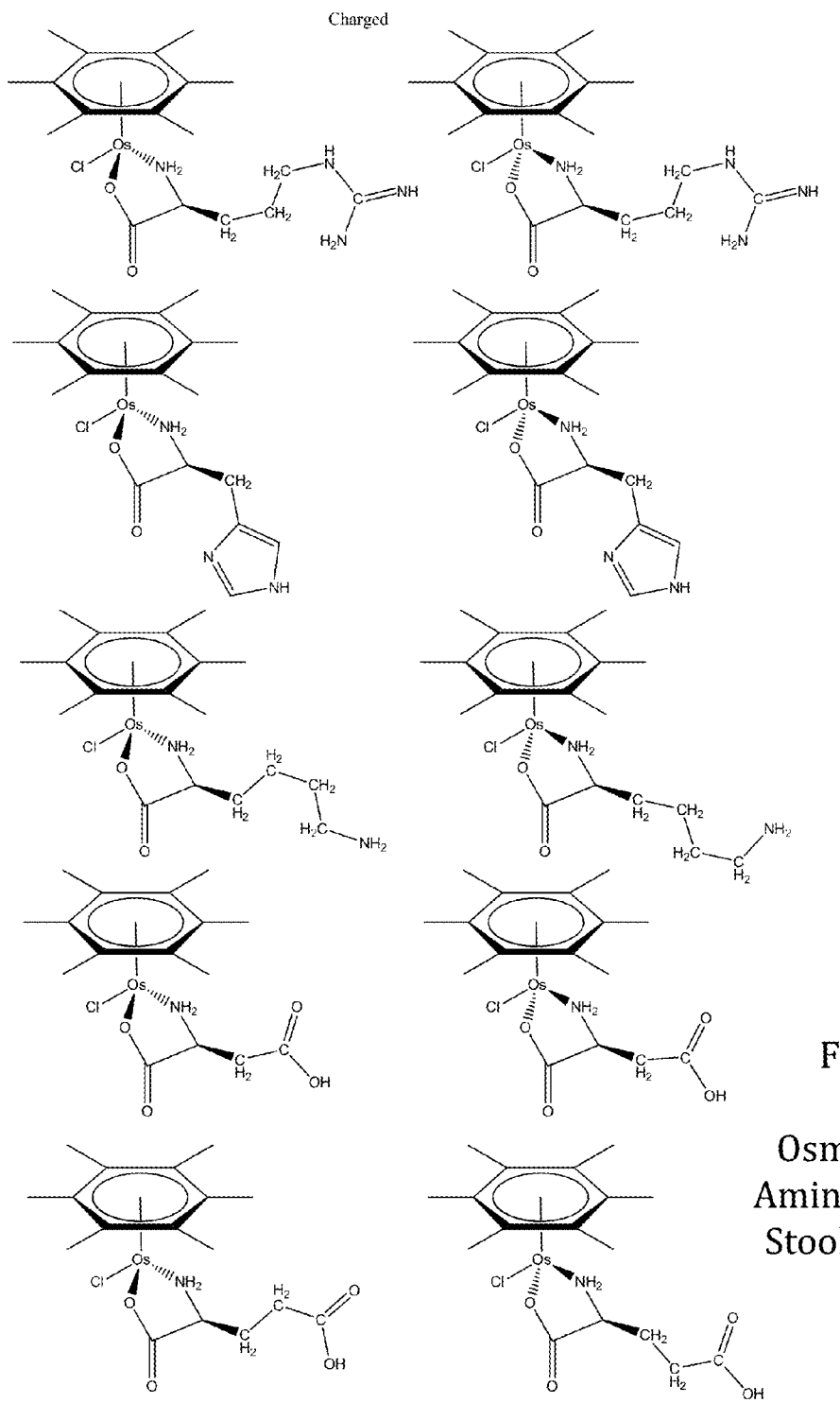
Figure 3V:
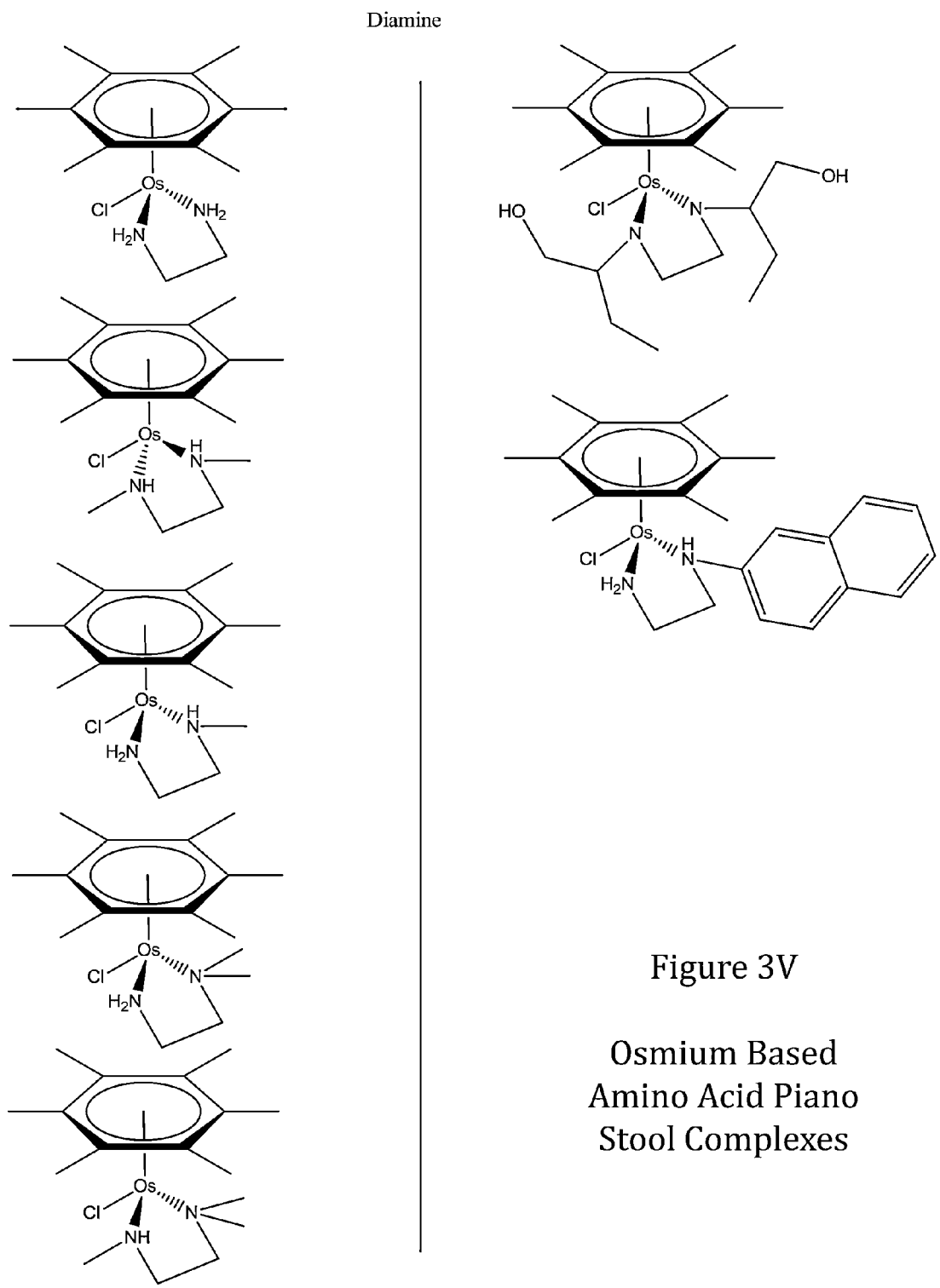
Figure 3W:
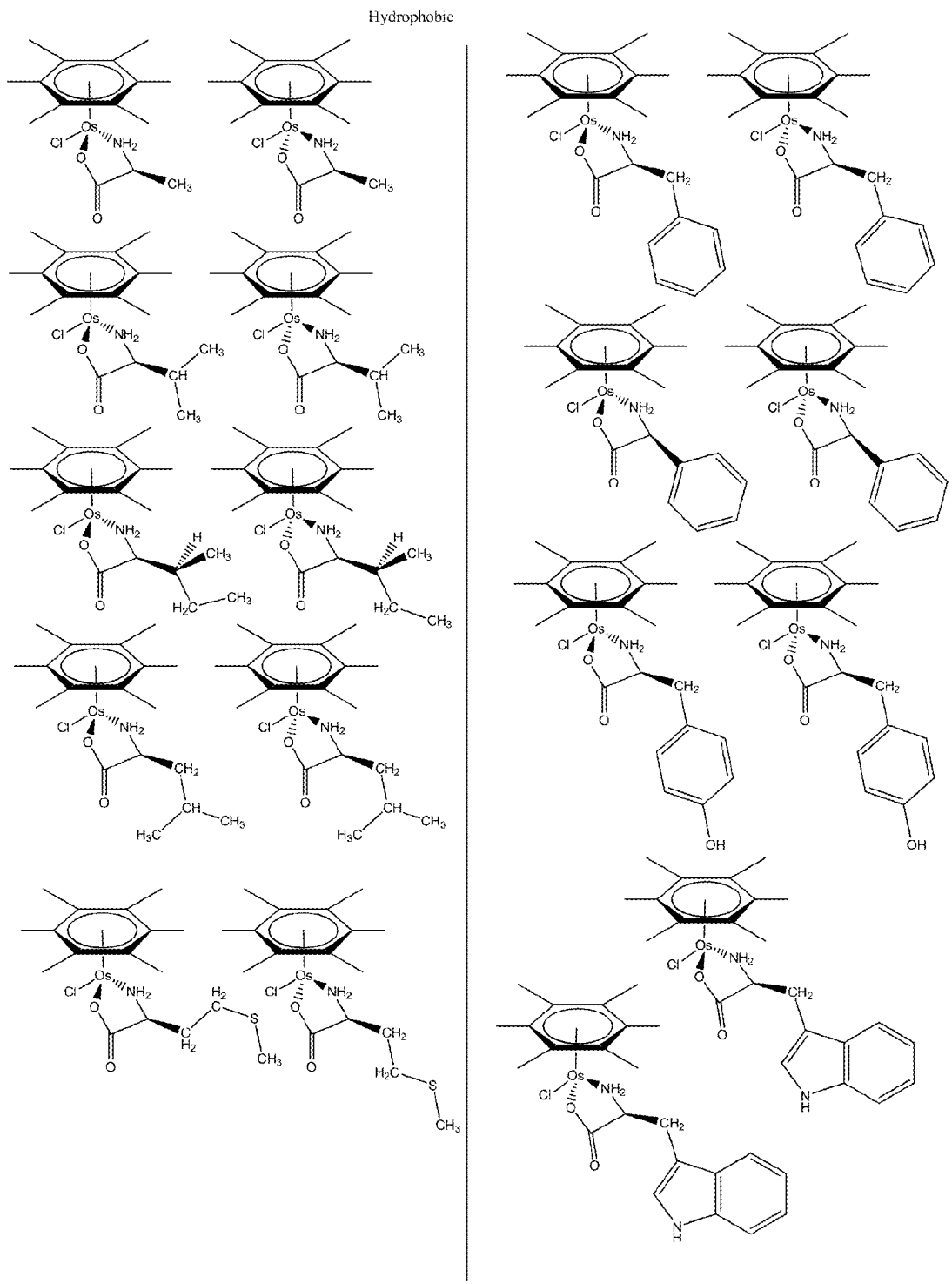
Figure 3X:
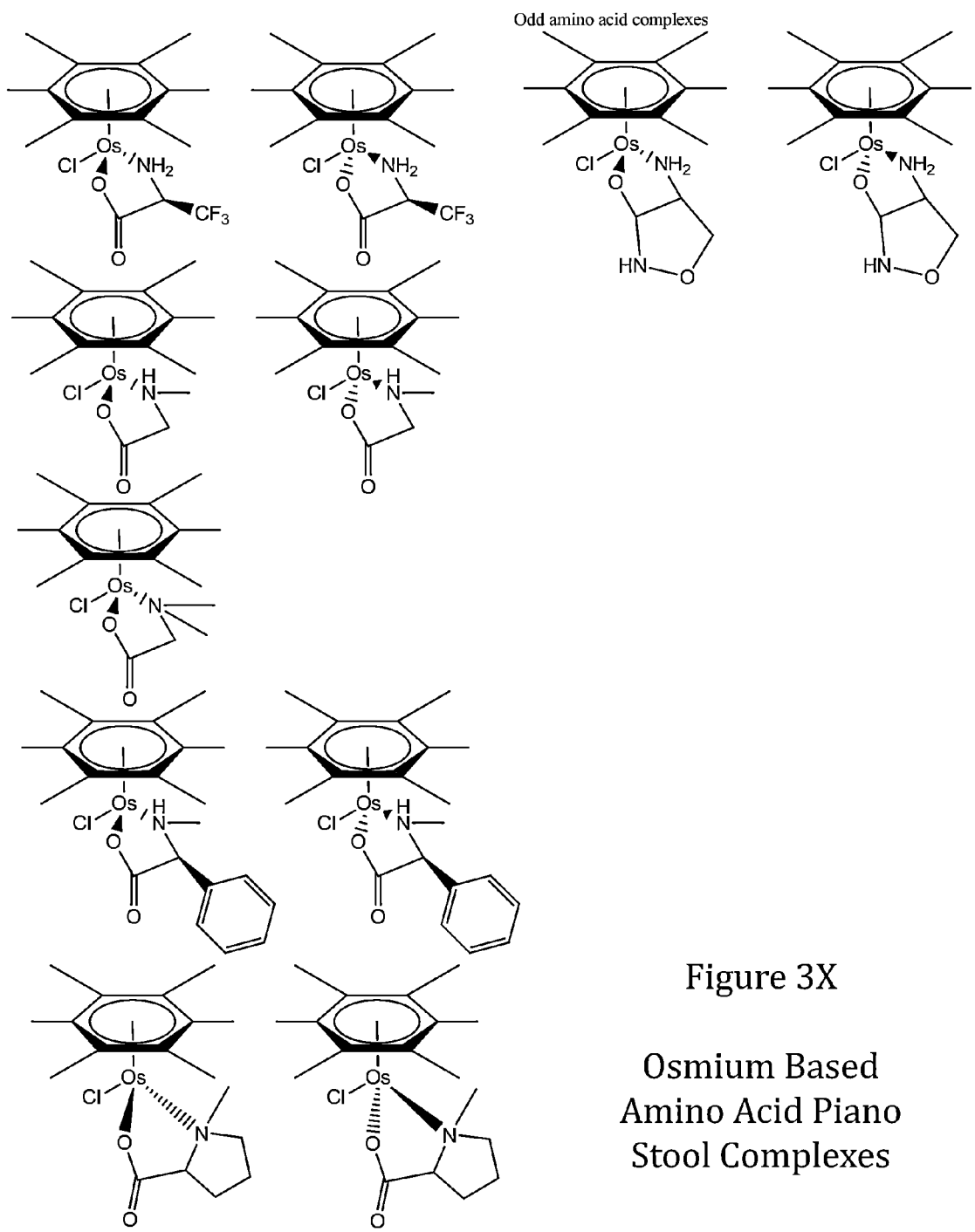
Figure 3Y:
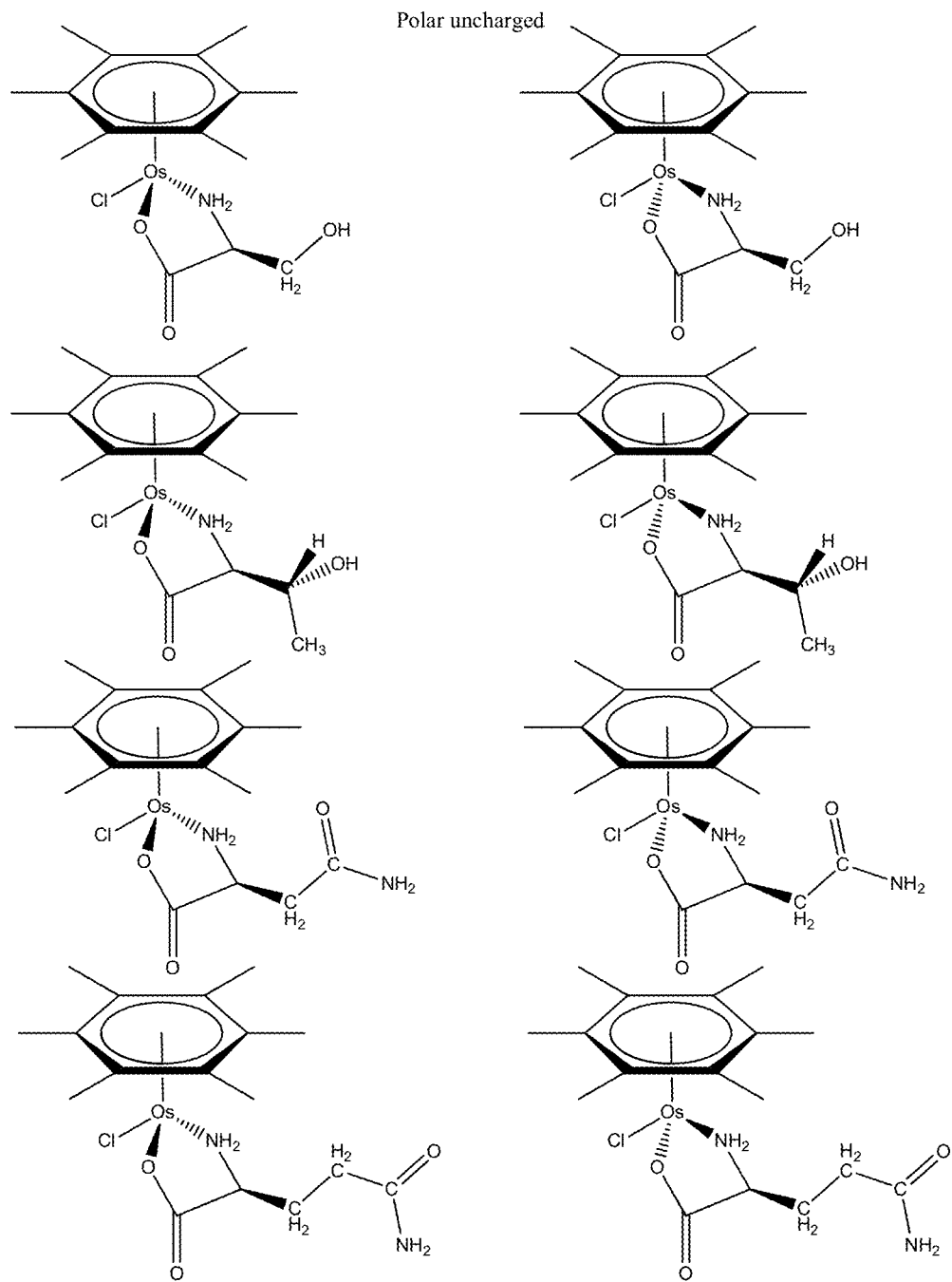
Figure 3Z:
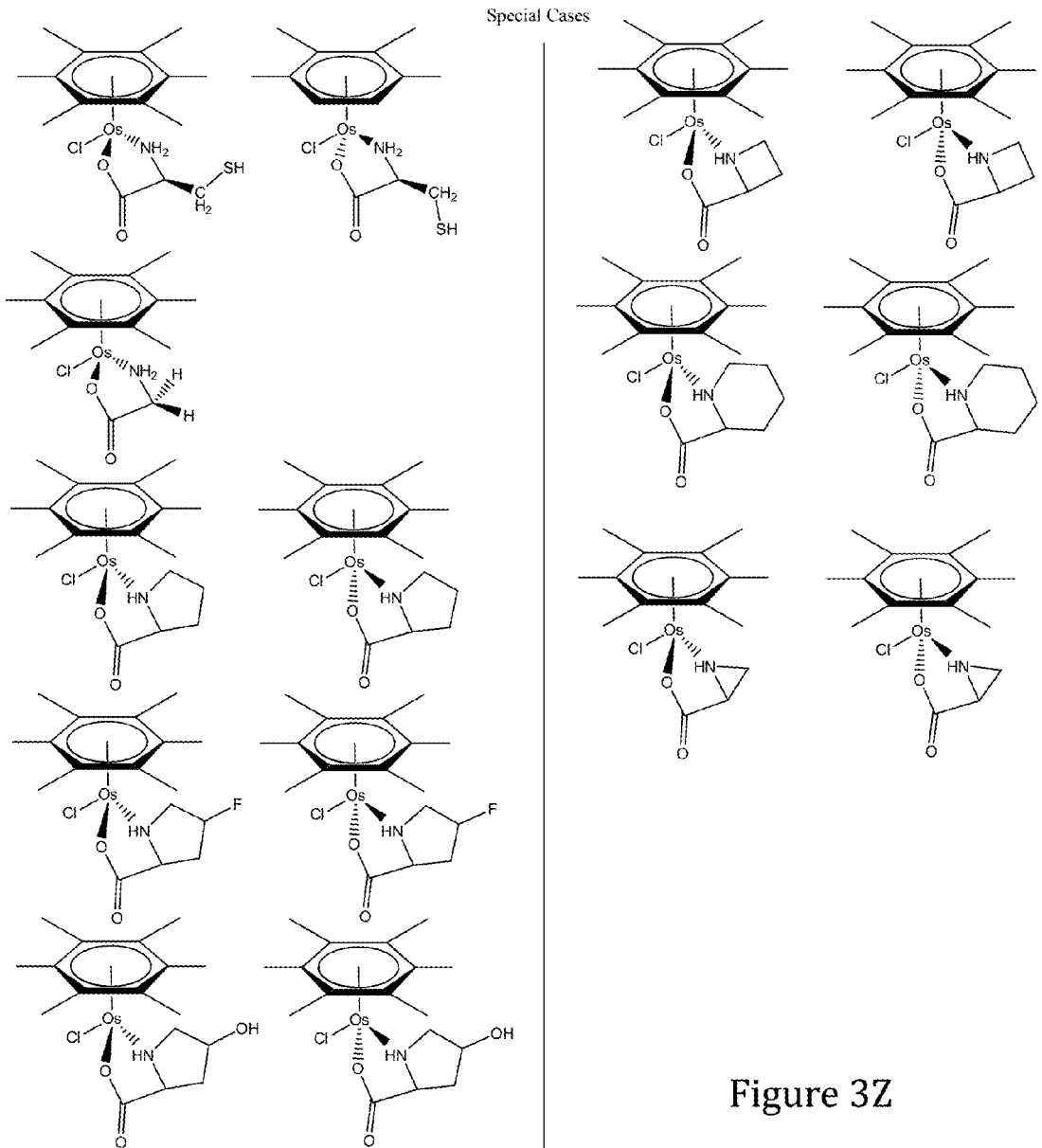
Figure 3A:
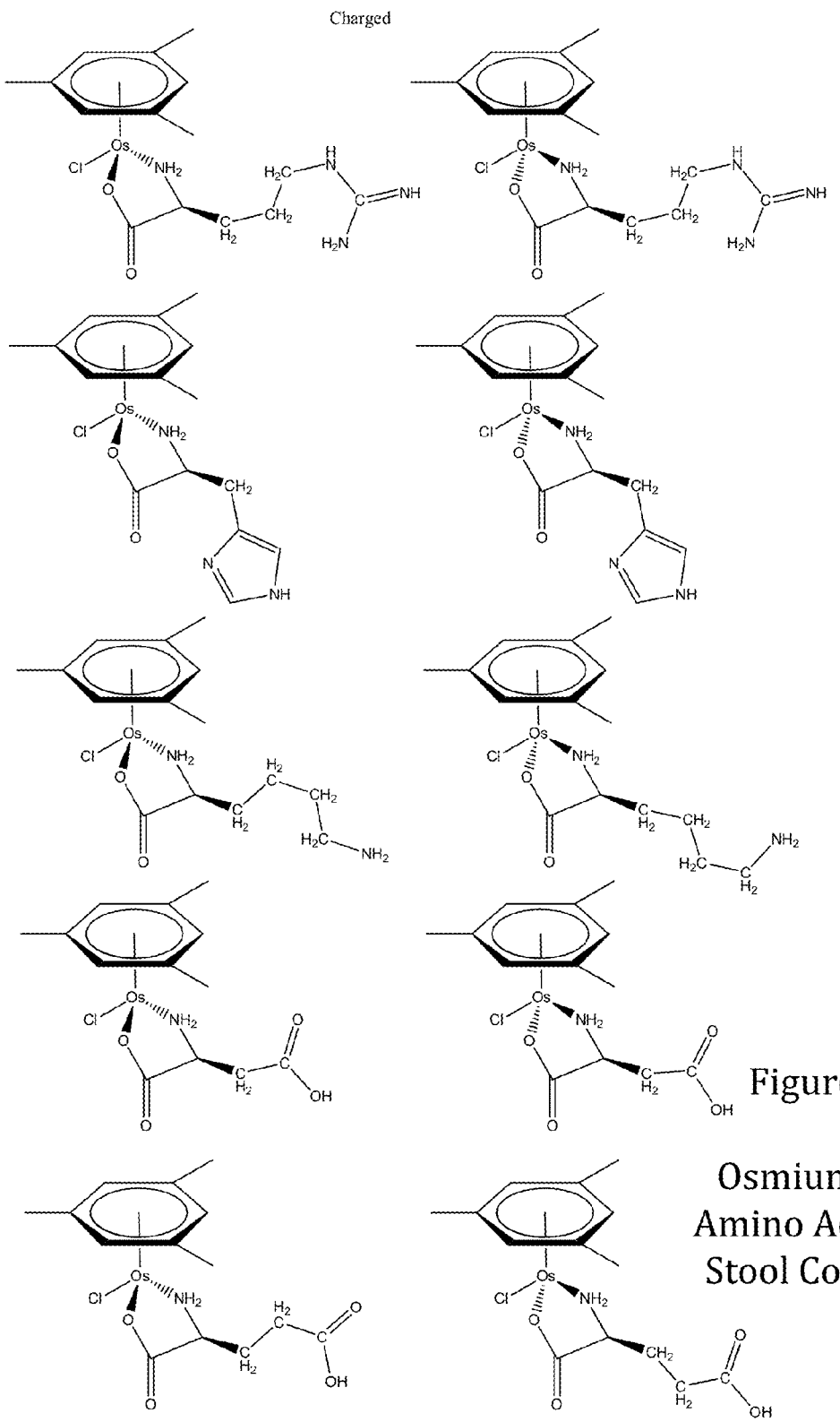

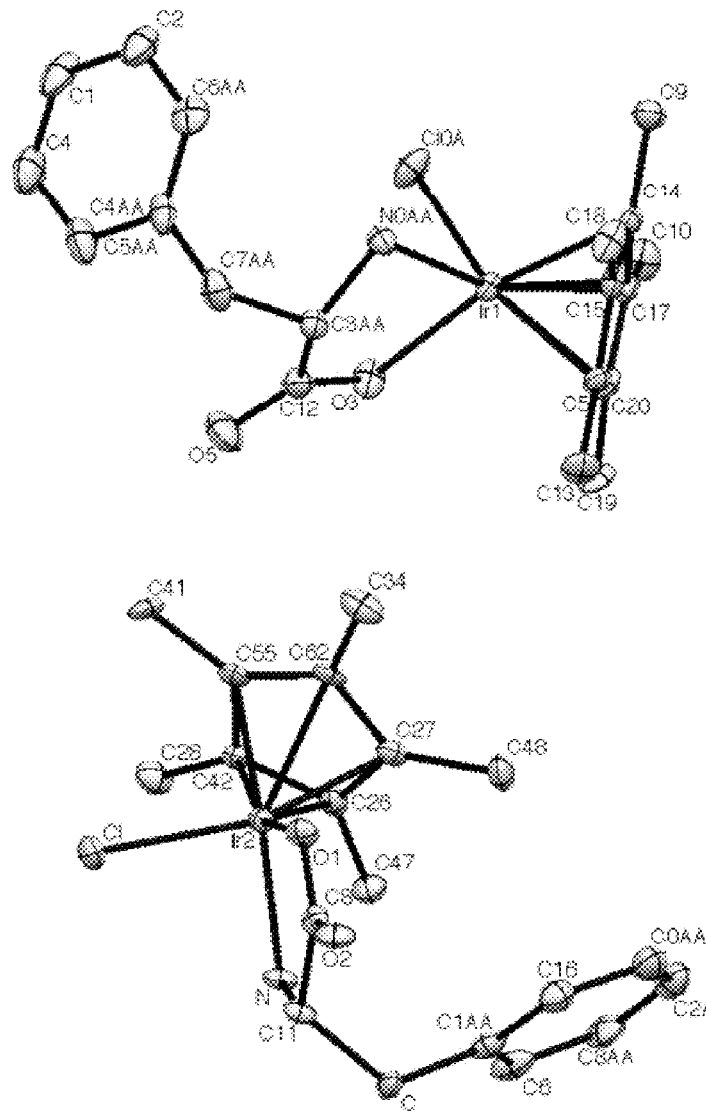
Figure 3A. Structures of Crystallographically Characterized Amino Acid Piano Stool Complexes of Ir and Rh

Figure 3B:
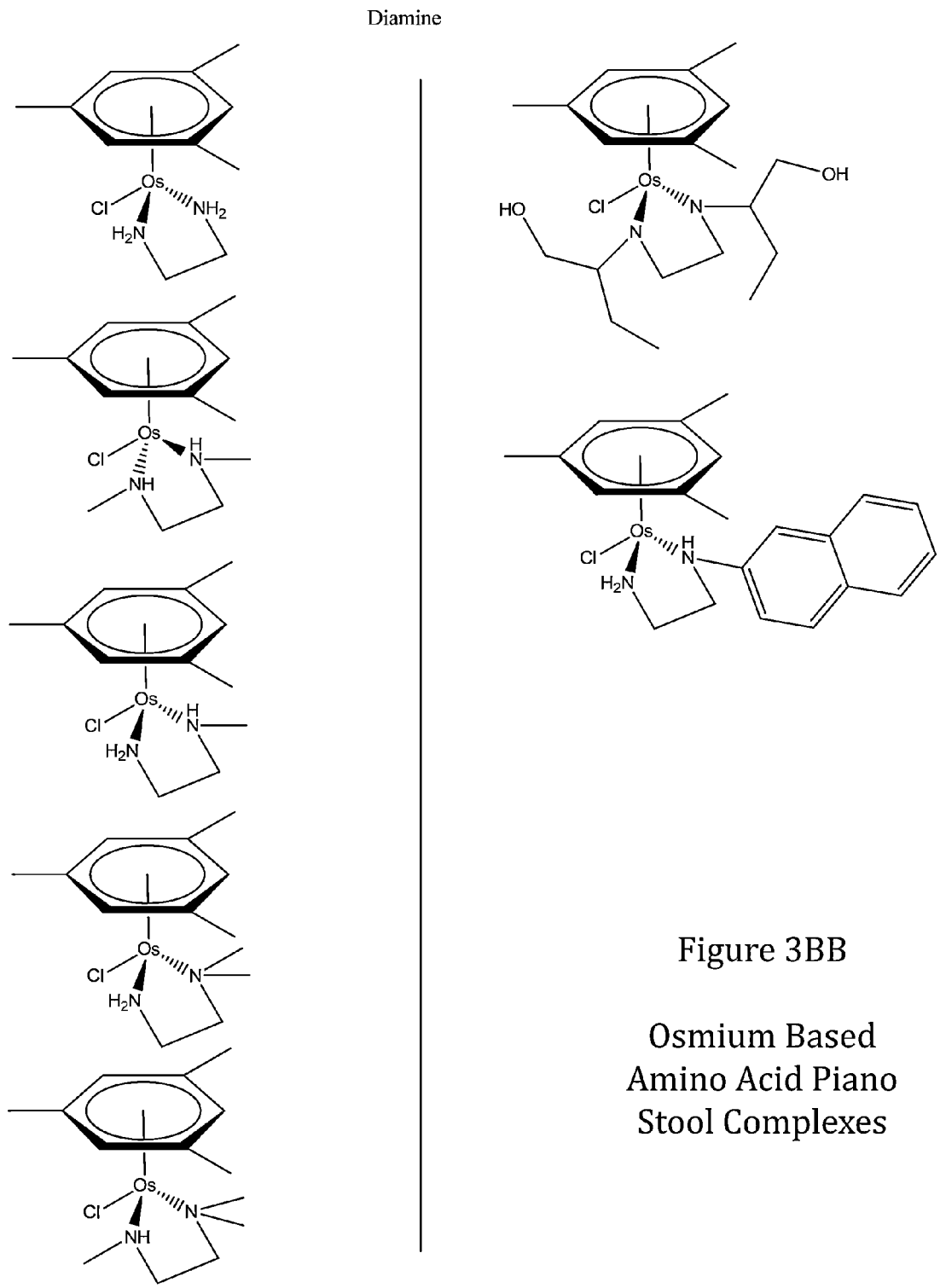
Figure 3C:
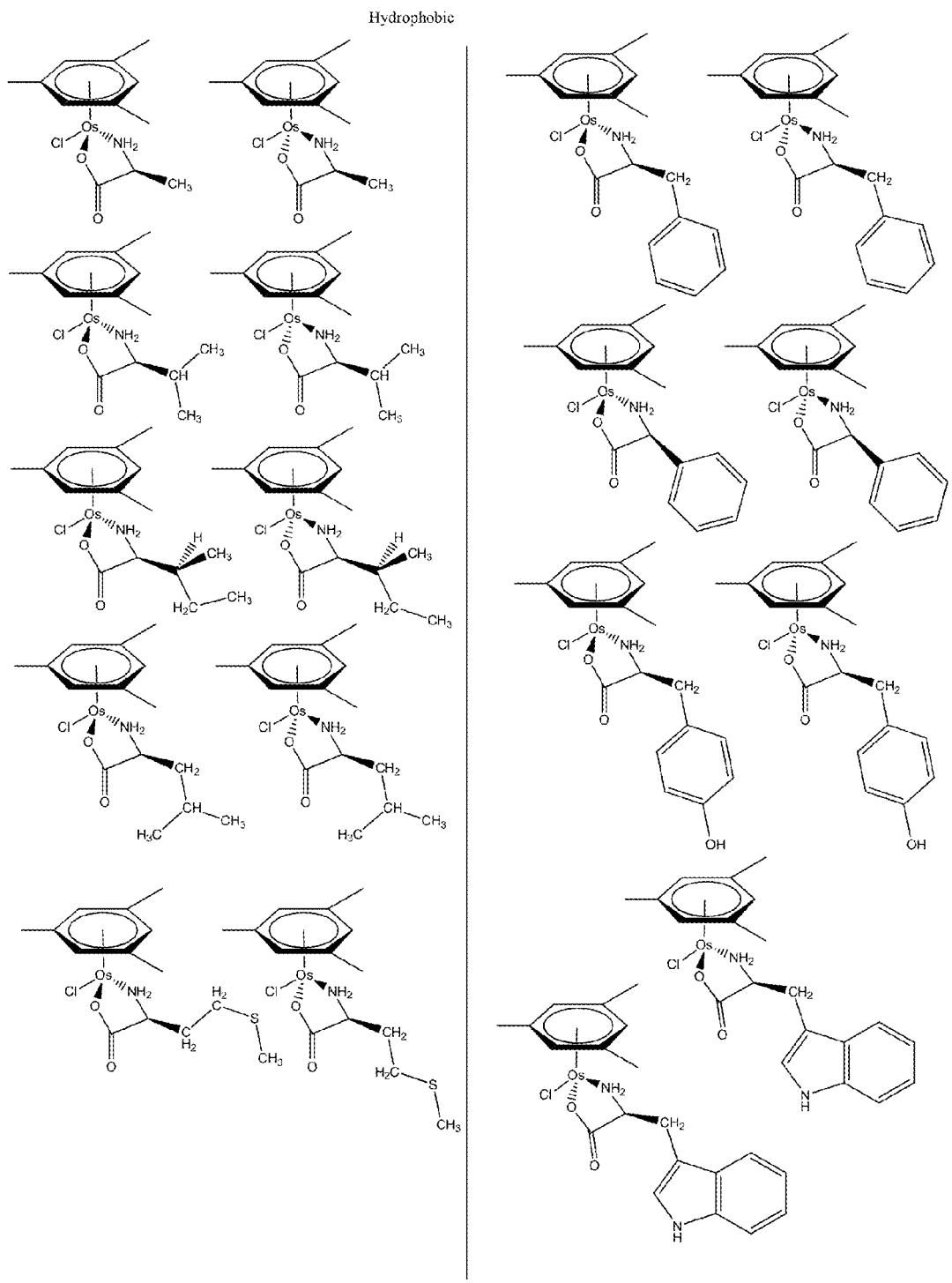
Figure 3D:
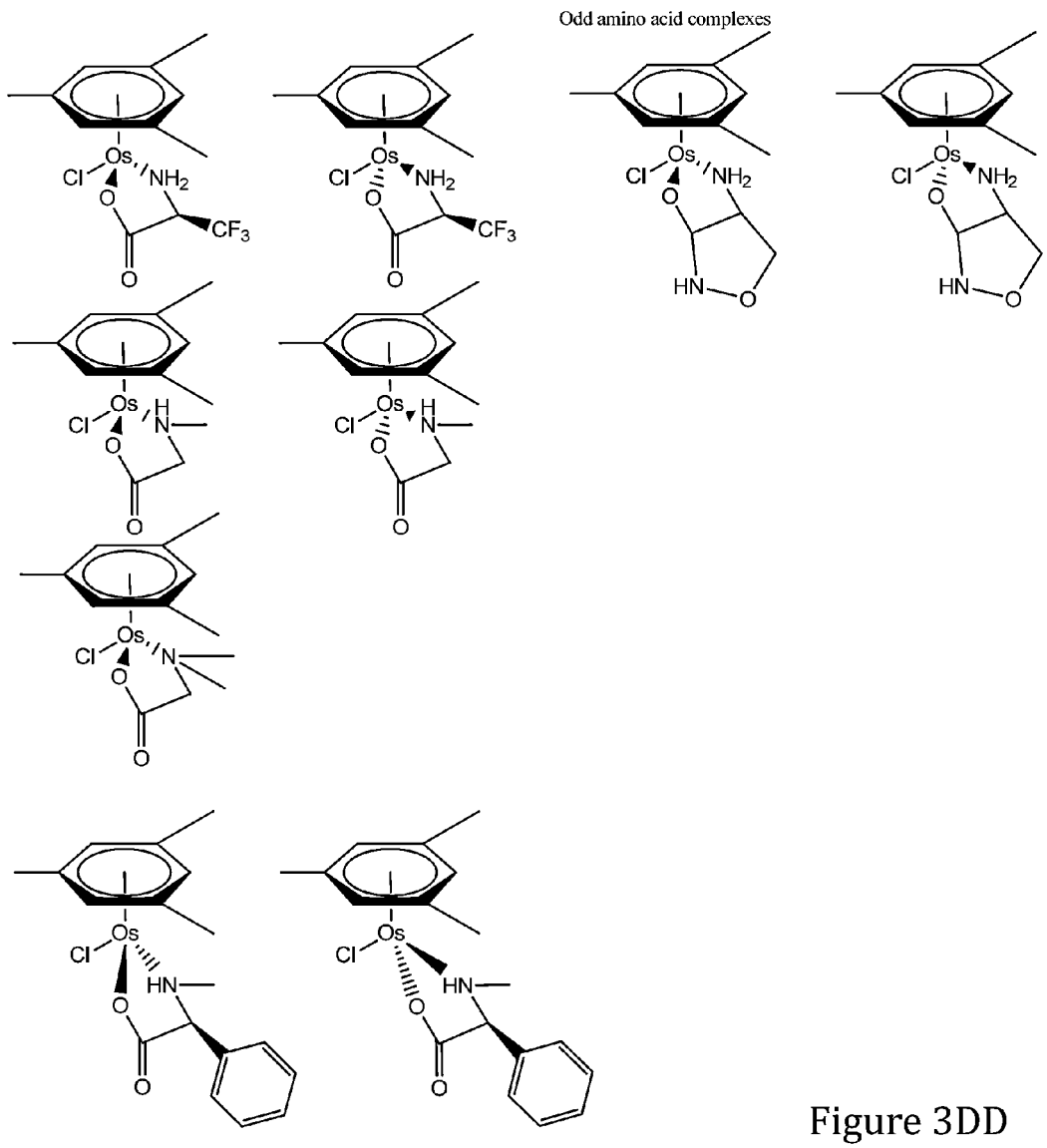
Figure 3E:
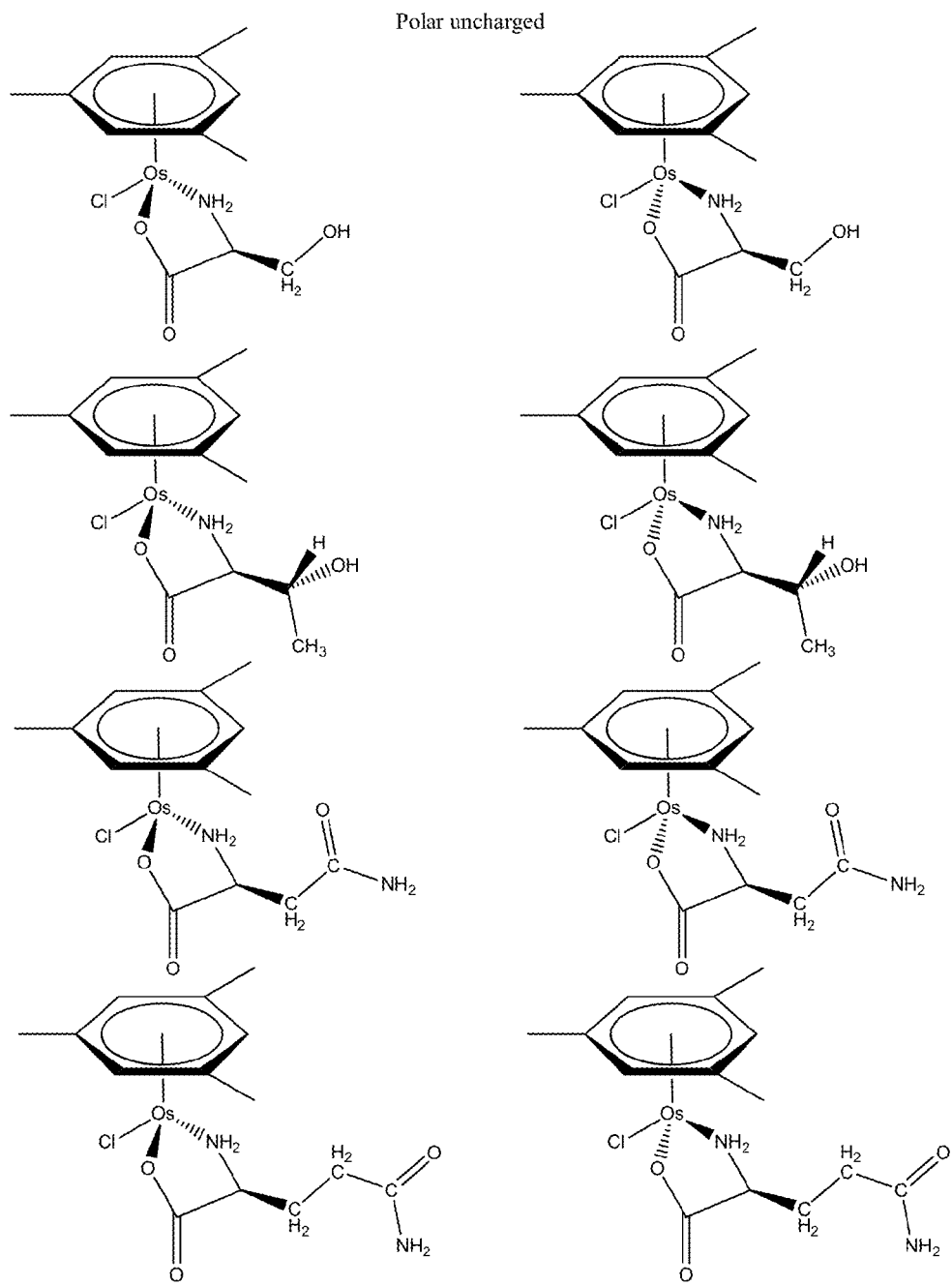
Figure 3F:
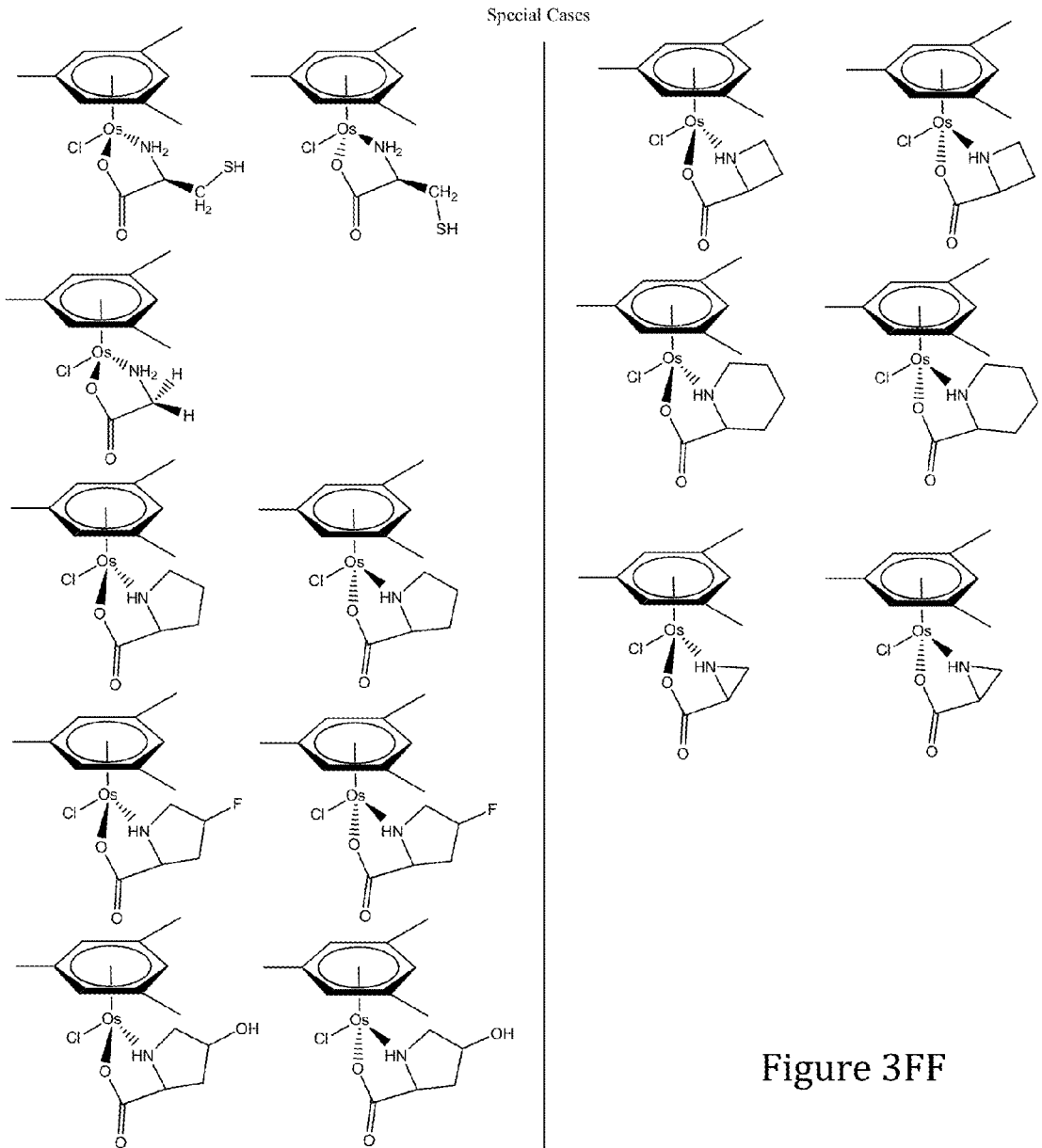
Figure 3G:
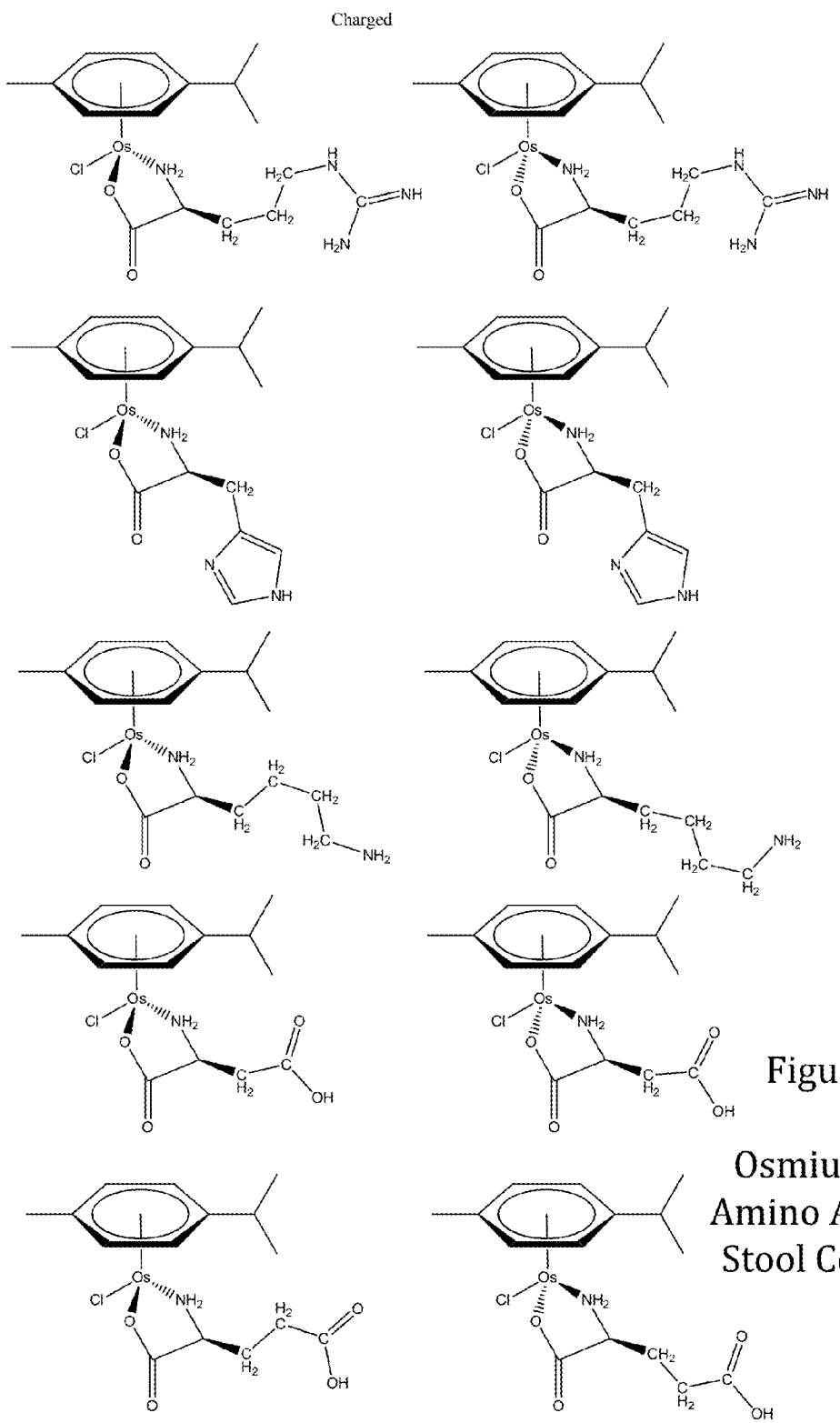
Figure 3H:
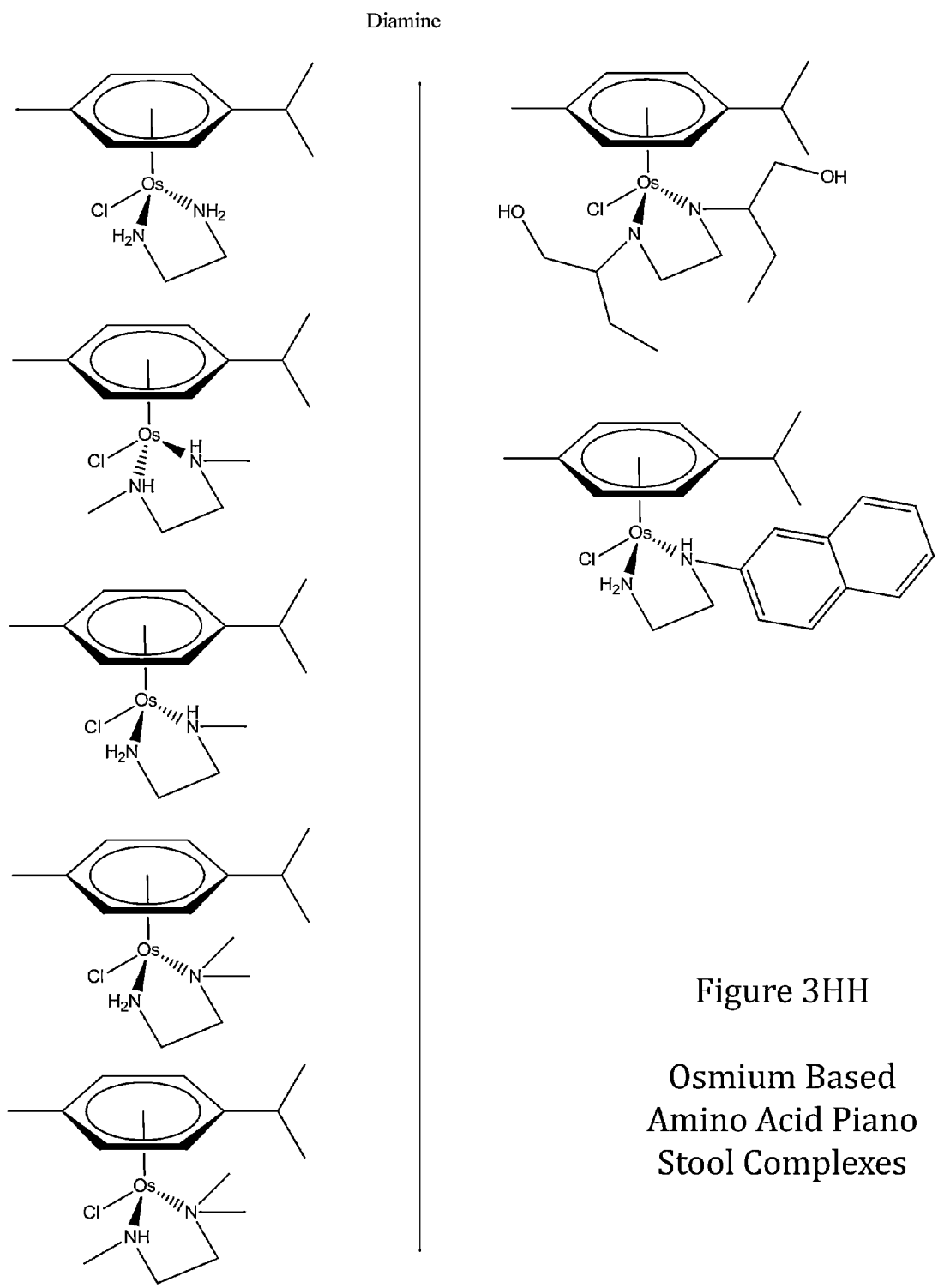
Figure 3I:
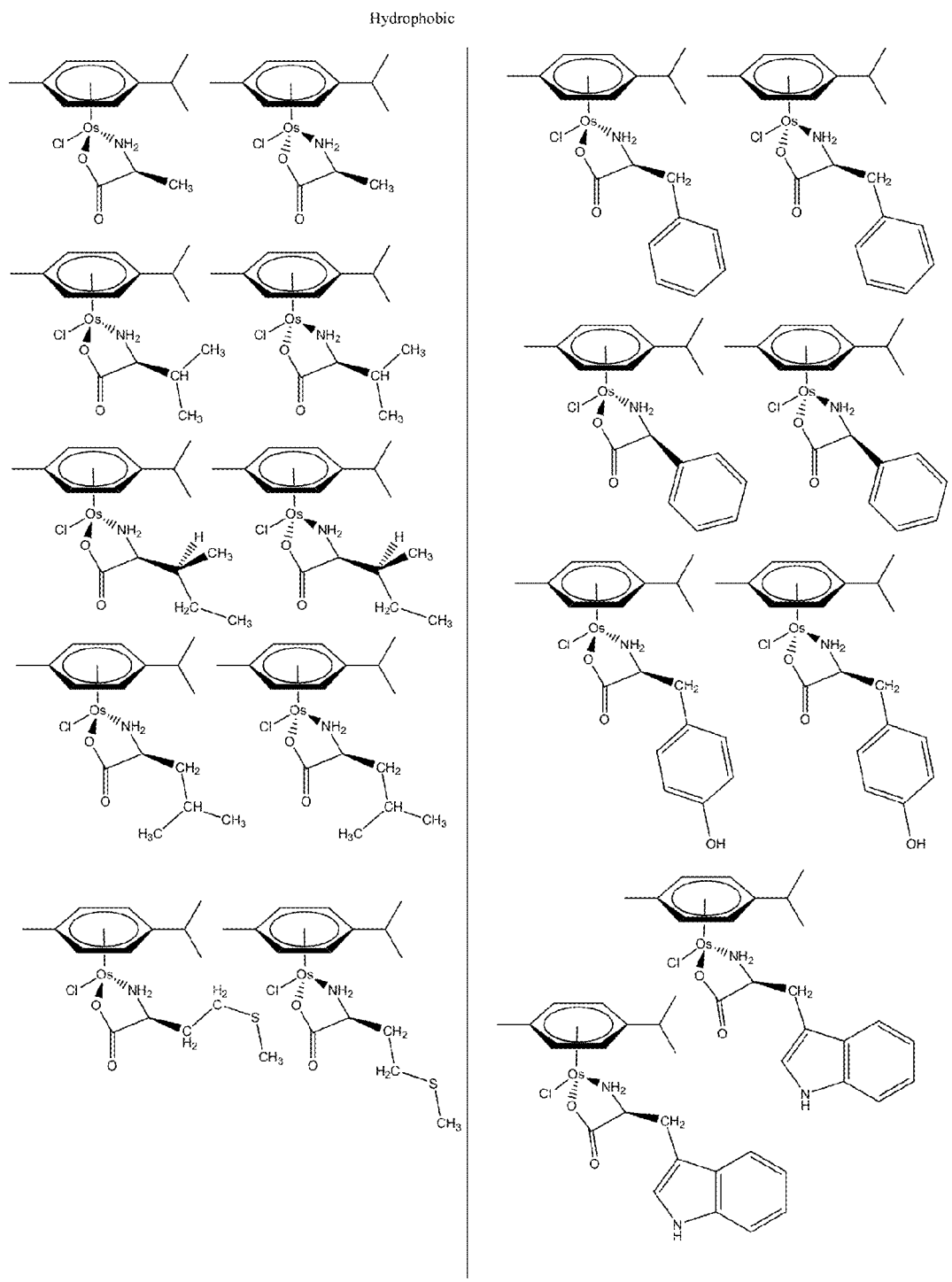
Figure 3J:
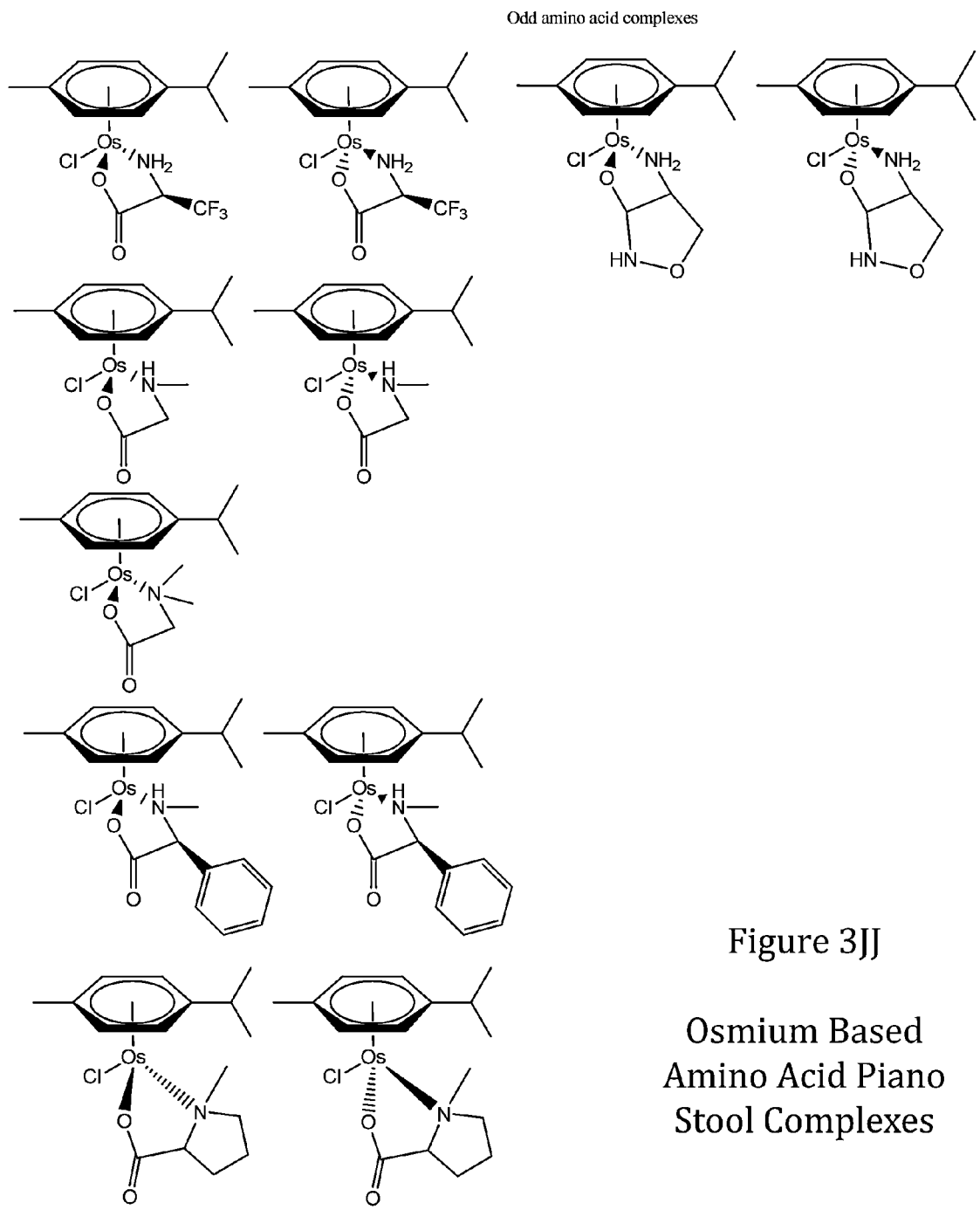
Figure 3K:
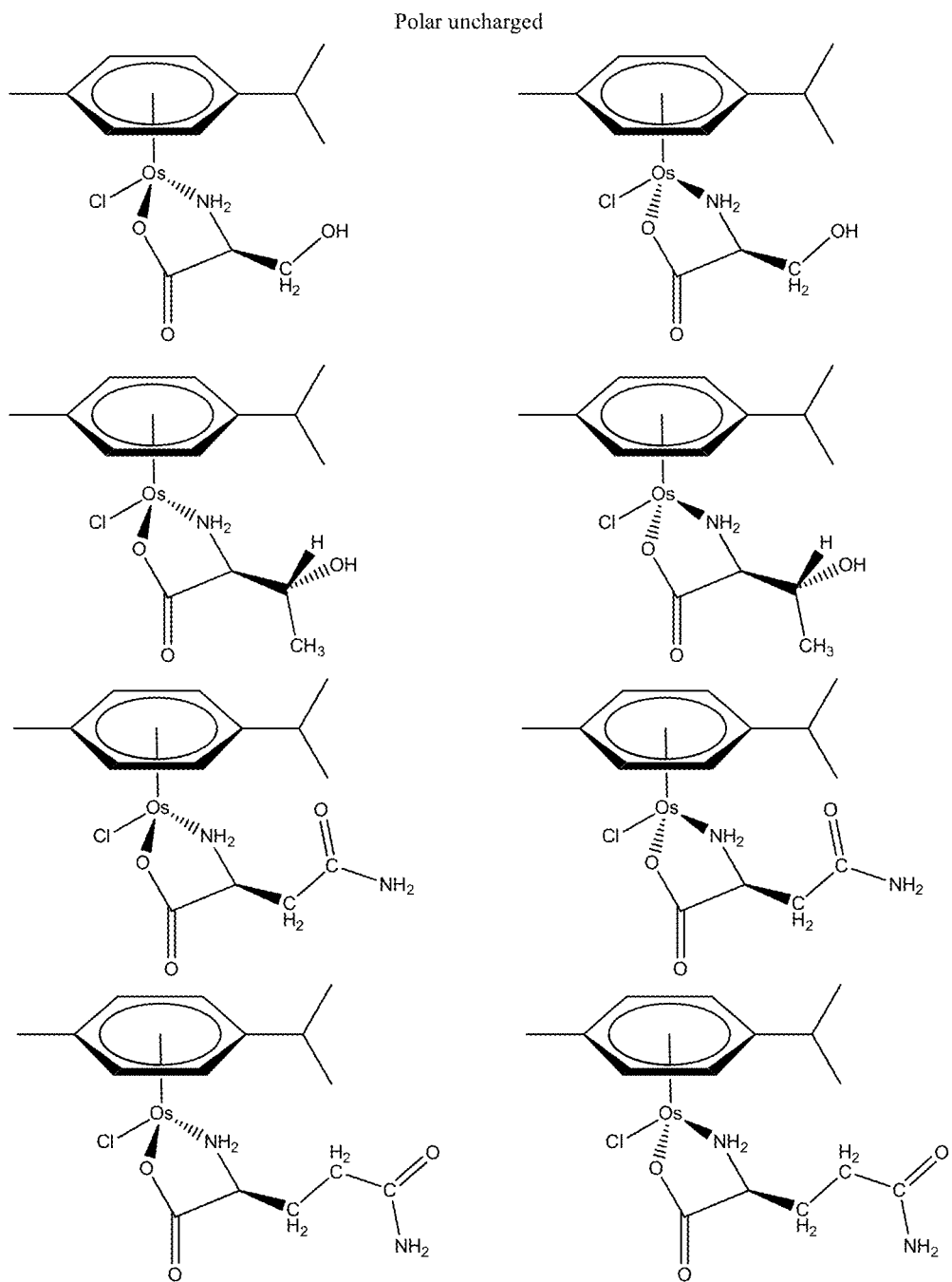
Figure 3L:
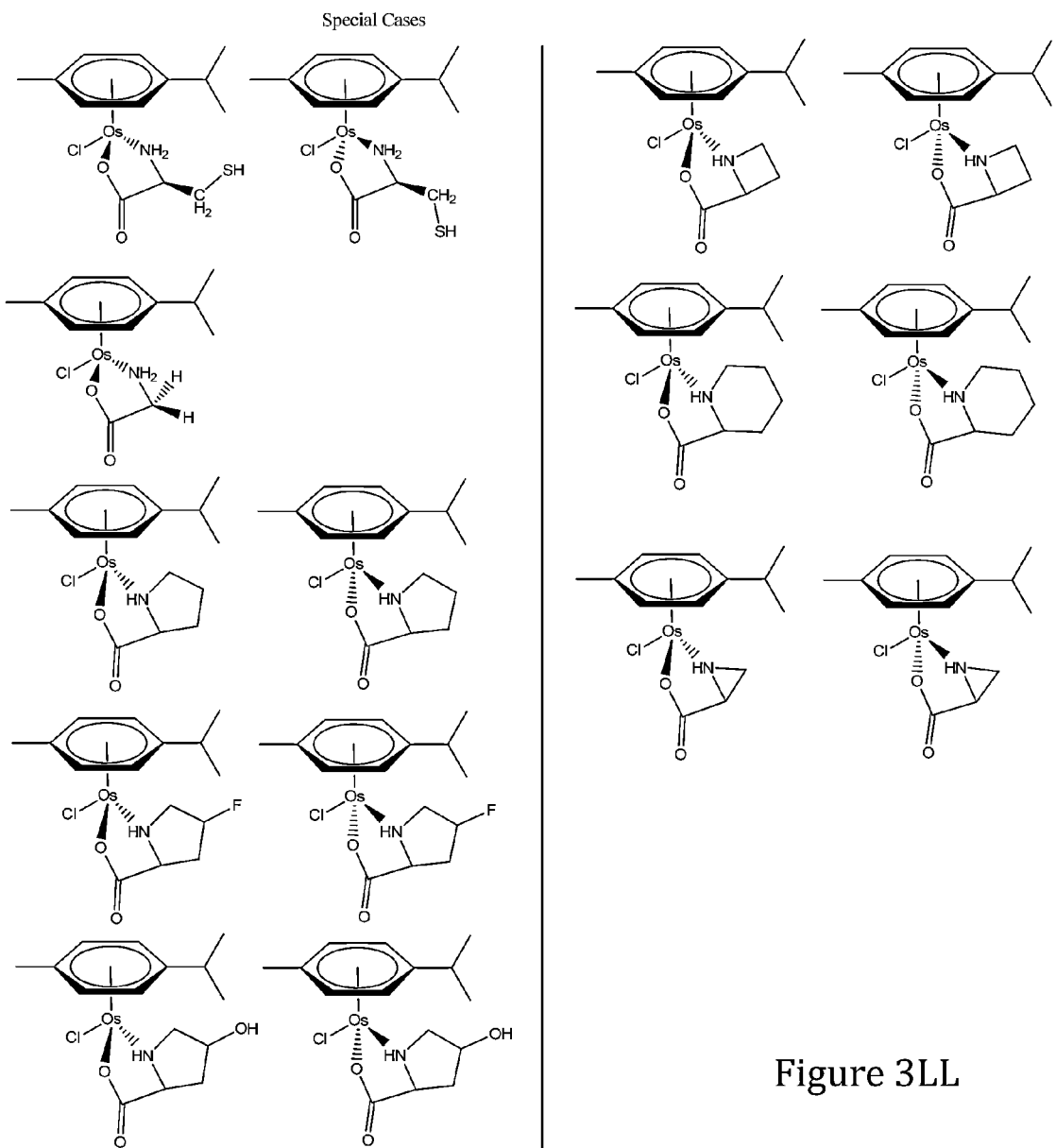
Figure 3M:
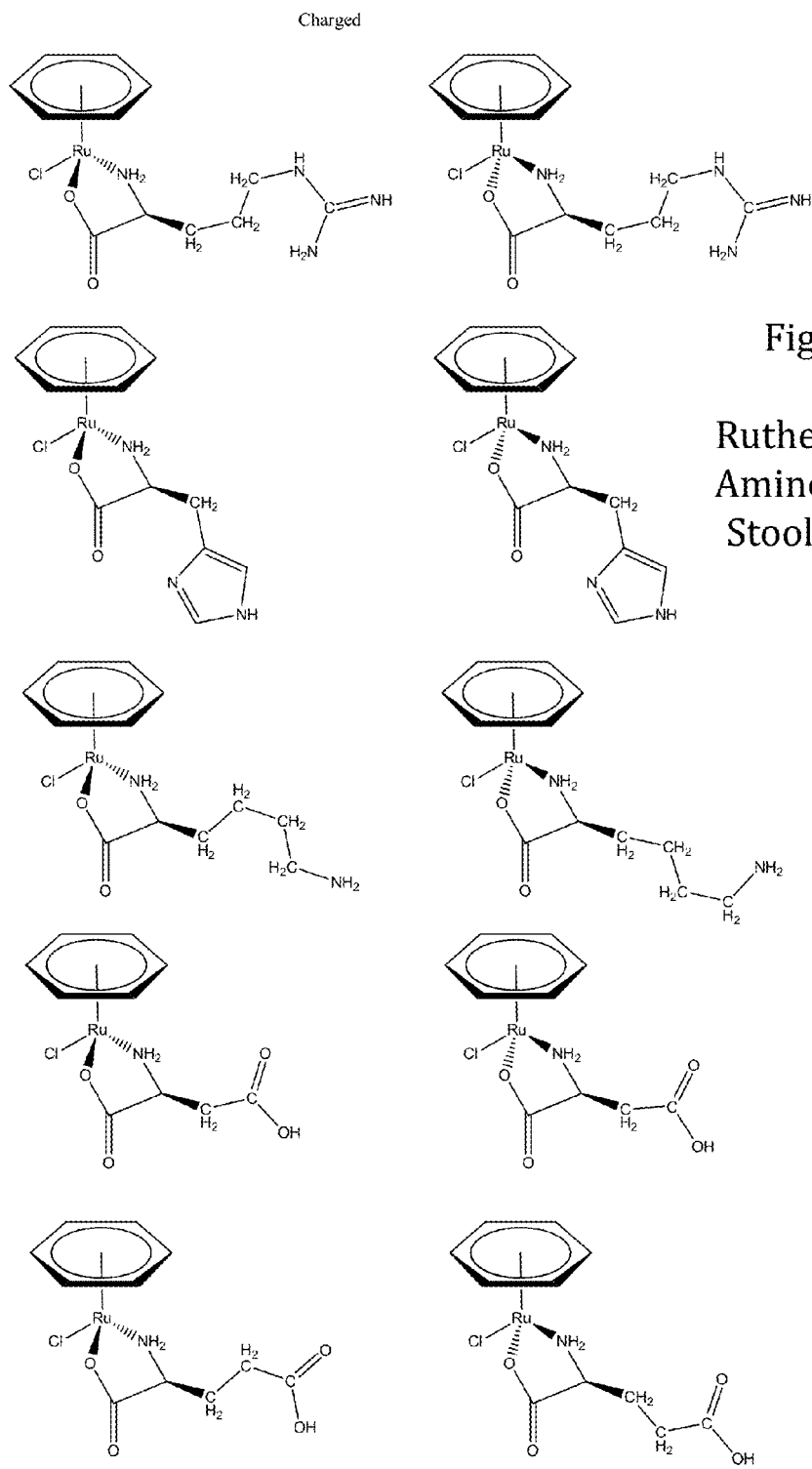

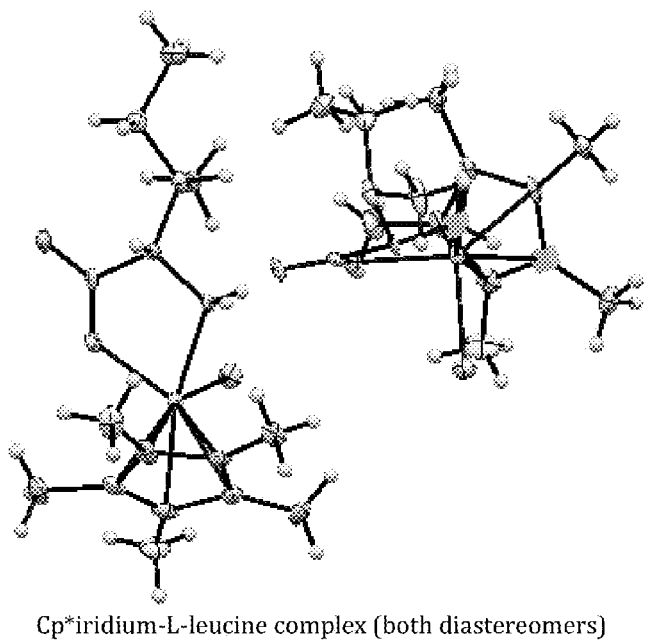
Cp*iridium-L-leucine complex (both diastereomers)
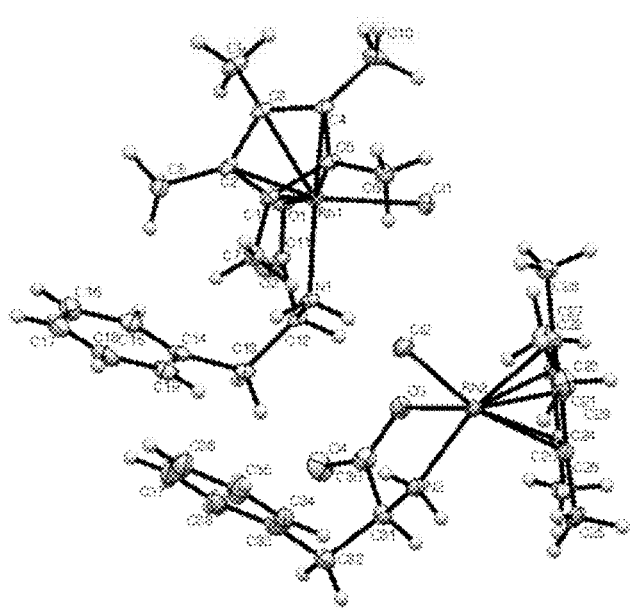
Cp*rhodium-L-phenylalanine complex (both diastereomers)
Figure 3B. Structures of Crystallographically Characterized Amino Acid Piano Stool Complexes of Ir and Rh Iridium Based Amino Acid Piano Stool Complexes Iridium Based Amino Acid Piano Stool Complexes Diamine Iridium Based
Amino Acid Piano
Stool Complexes Iridium Based Amino Acid Piano Stool Complexes Polar Uncharged Side Chains Iridium Based Amino Acid Piano Stool Complexes Iridium Based Amino Acid Piano Stool Complexes Iridium Based
Amino Acid Piano
Stool Complexes Iridium Based Amino Acid Piano Stool Complexes Iridium Based Amino Acid Piano Stool Complexes Iridium Based Amino Acid Piano Stool Complexes Iridium Based Amino Acid Piano Stool
Complexes Iridium Based
Amino Acid Piano
Stool Complexes Osmium Based Amino Acid Piano Stool Complexes Diamine
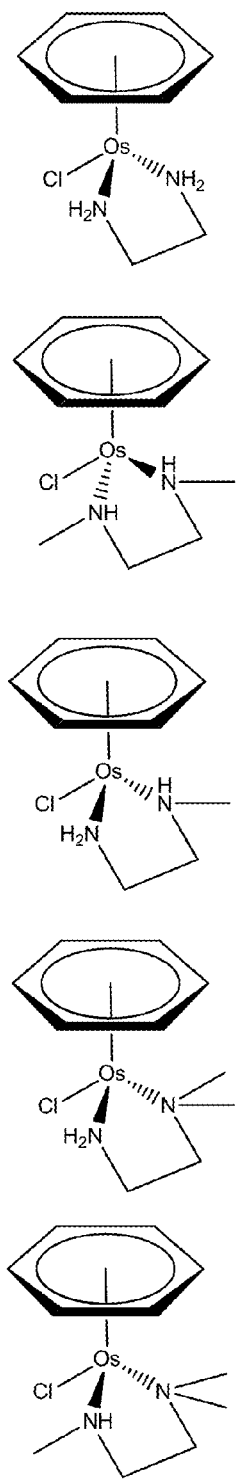
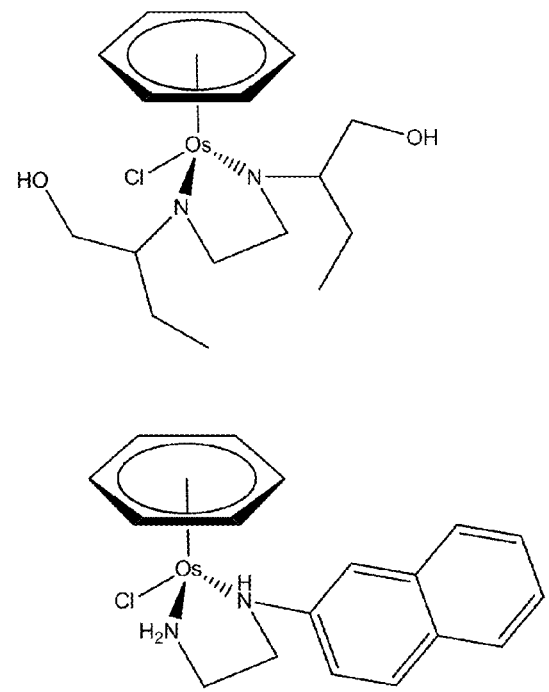
Figure 3P
Osmium Based
Amino Acid Piano
Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based
Amino Acid Piano
Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Osmium Based Amino Acid Piano Stool Complexes Ruthenium Based Amino Acid Piano Stool Complexes Diamine
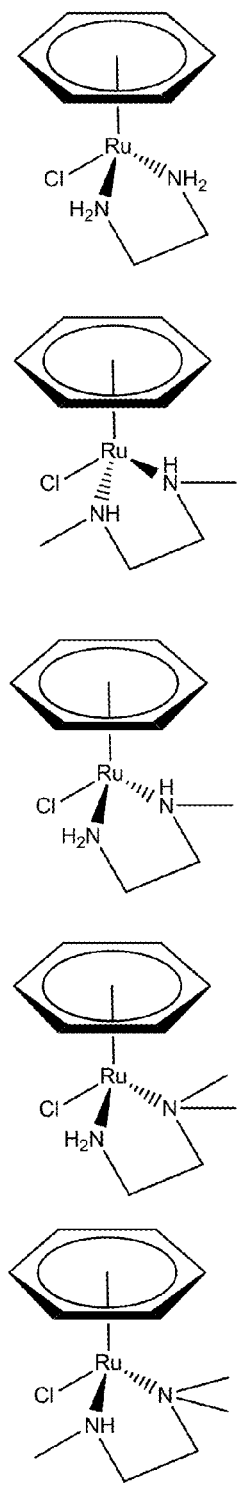
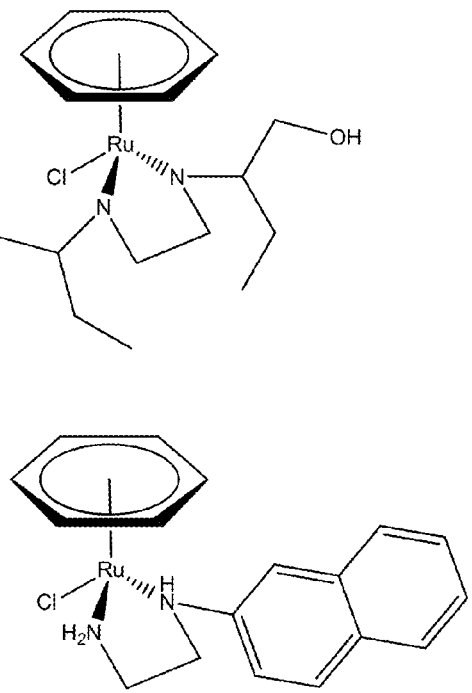
Figure 3NN
Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes Special Cases Ruthenium Based
Amino Acid Piano
Stool Complexes Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes Ruthenium Based Amino Acid Piano Stool Complexes

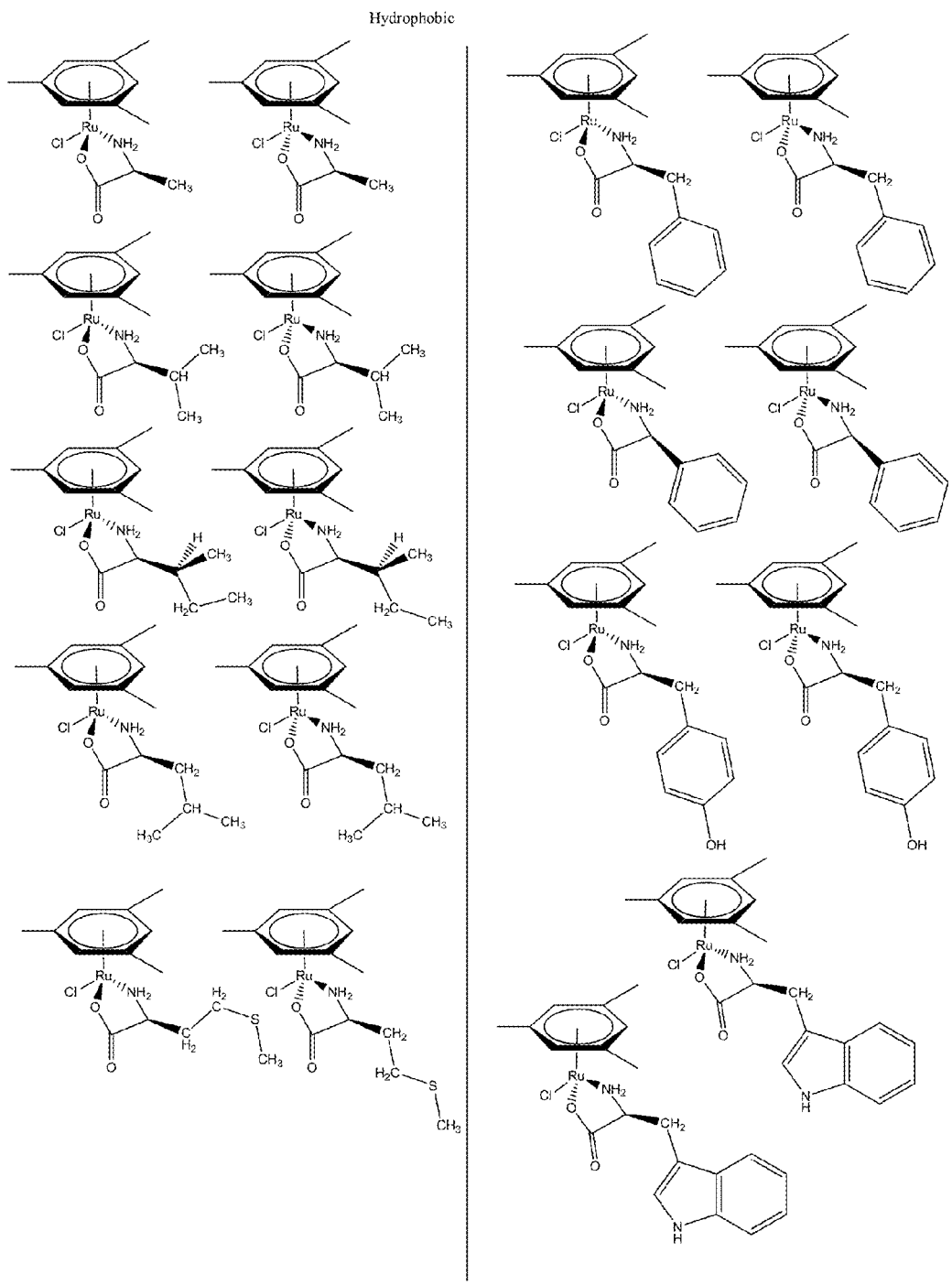
Figure 3AAA
Ruthenium Based Amino Acid Piano Stool Complexes

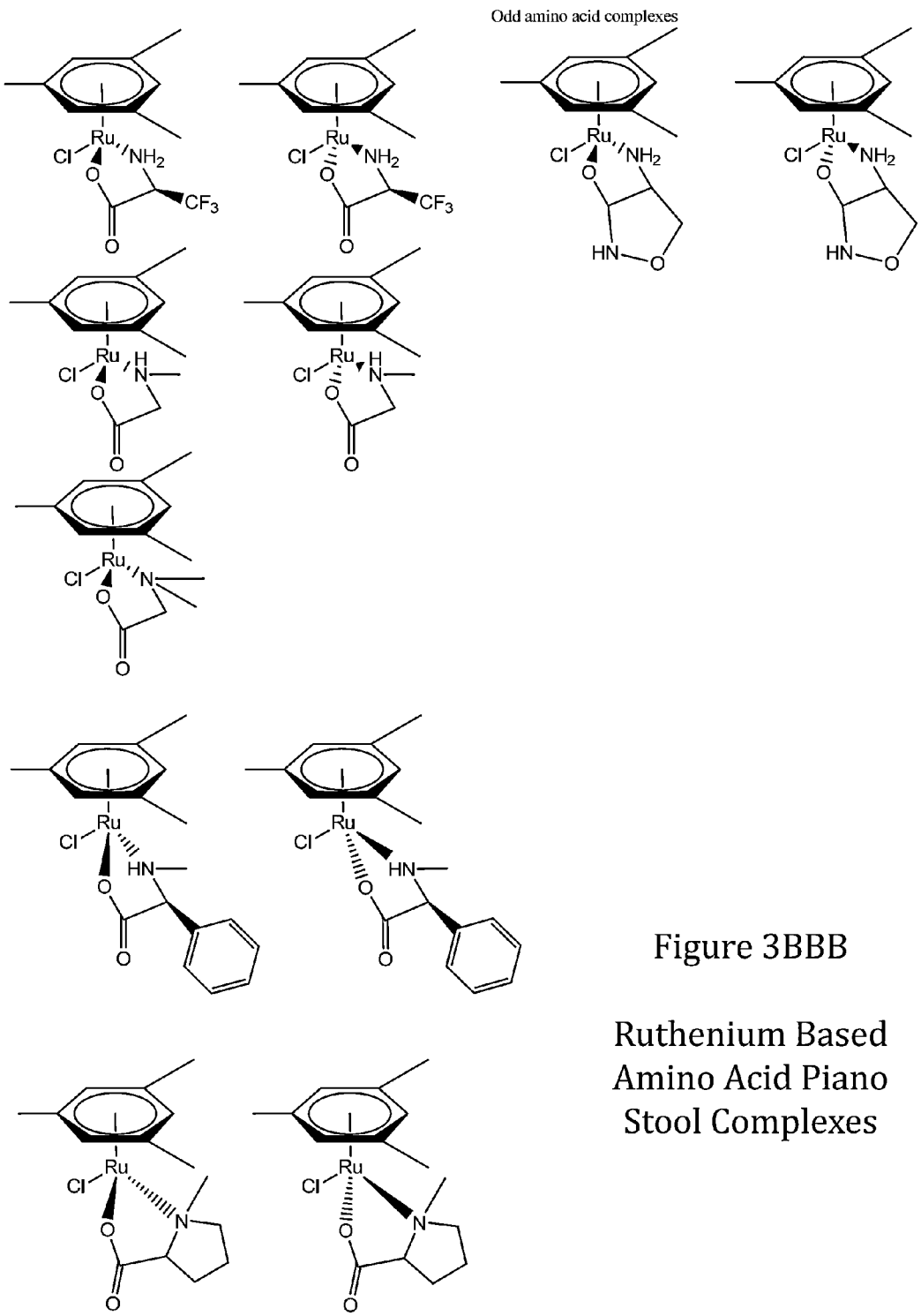
Figure 3BBB
Ruthenium Based Amino Acid Piano Stool Complexes

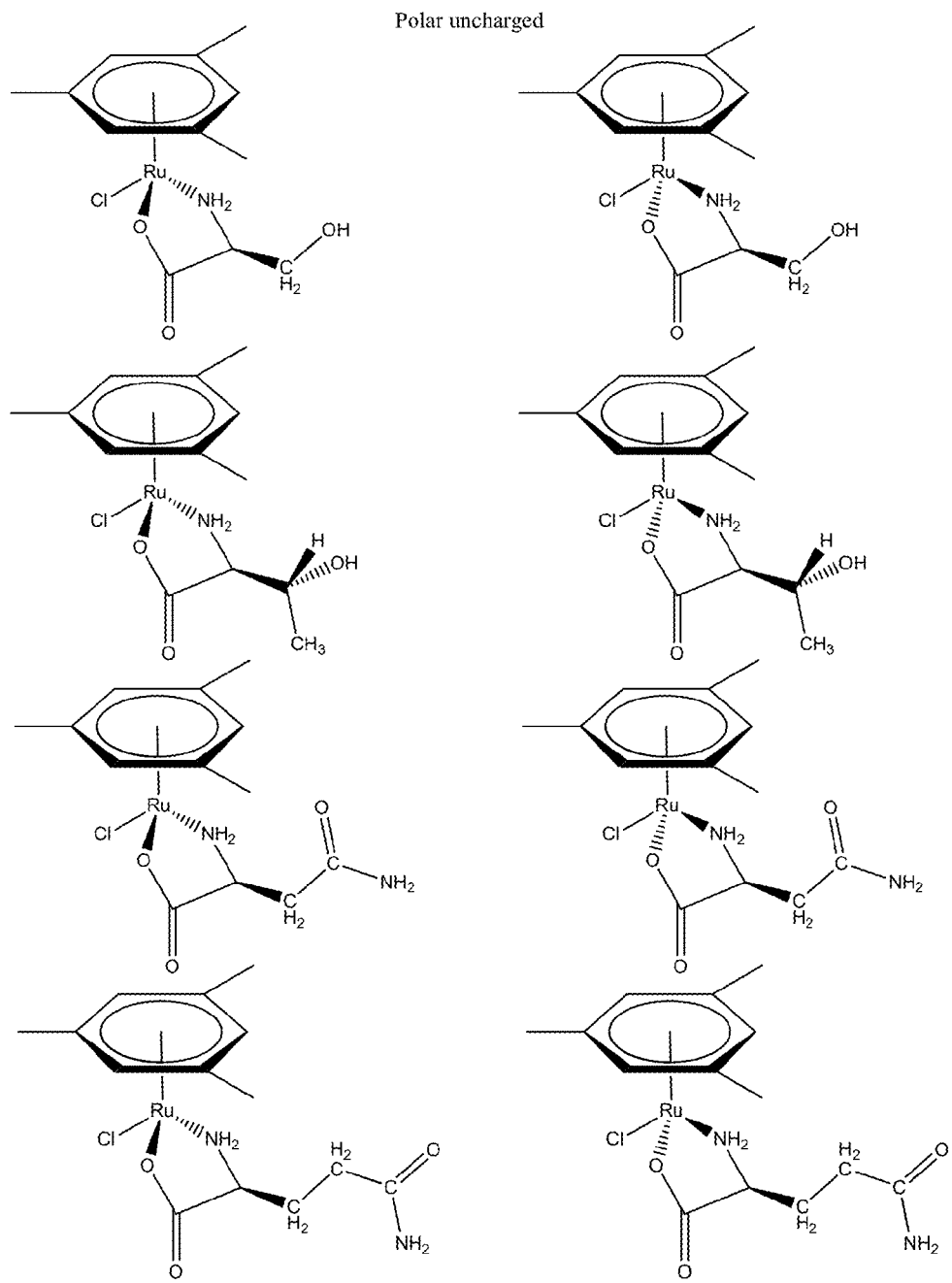
Figure 3CCC
Ruthenium Based Amino Acid Piano Stool Complexes

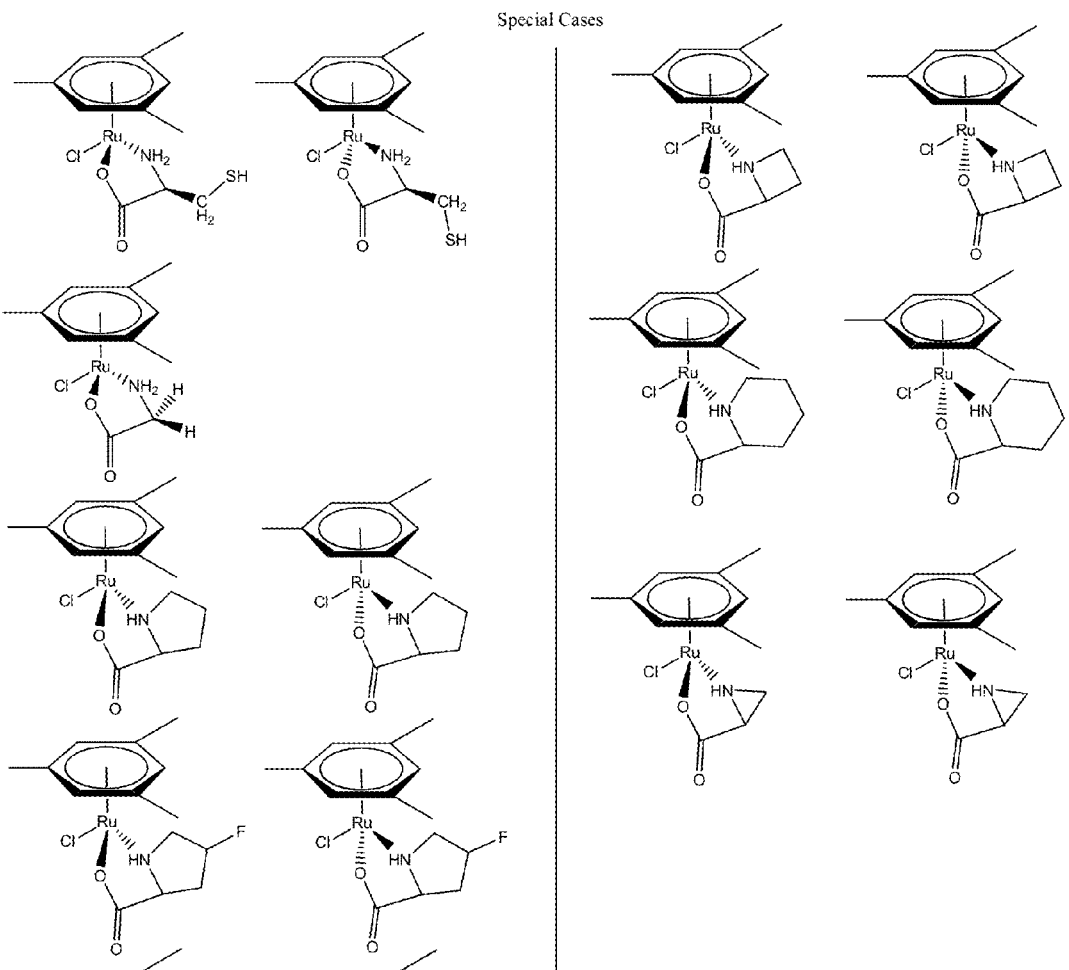
Figure 3DDD
Ruthenium Based Amino Acid Piano Stool Complexes

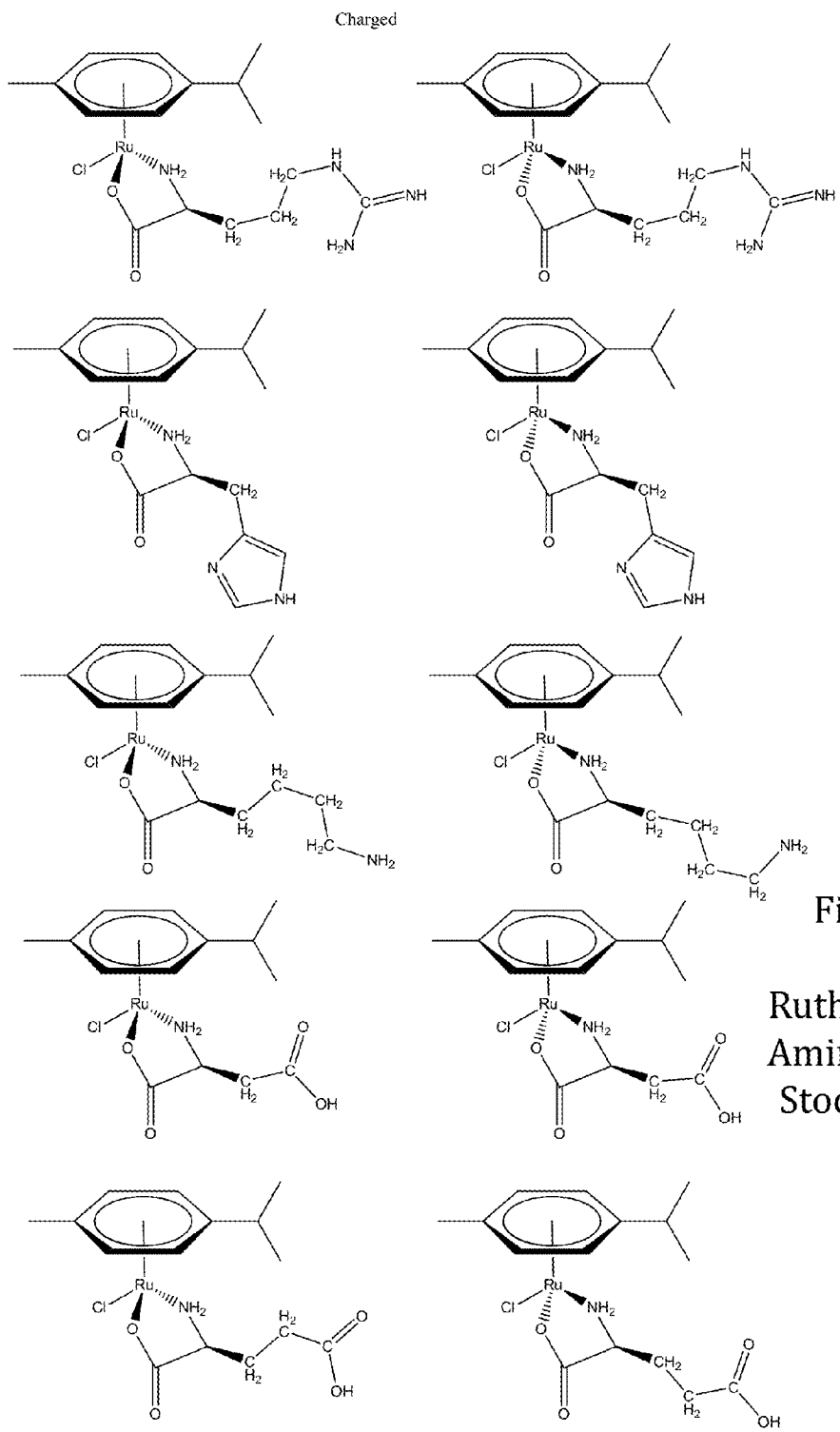
Figure 3EEE
Ruthenium Based Amino Acid Piano Stool Complexes

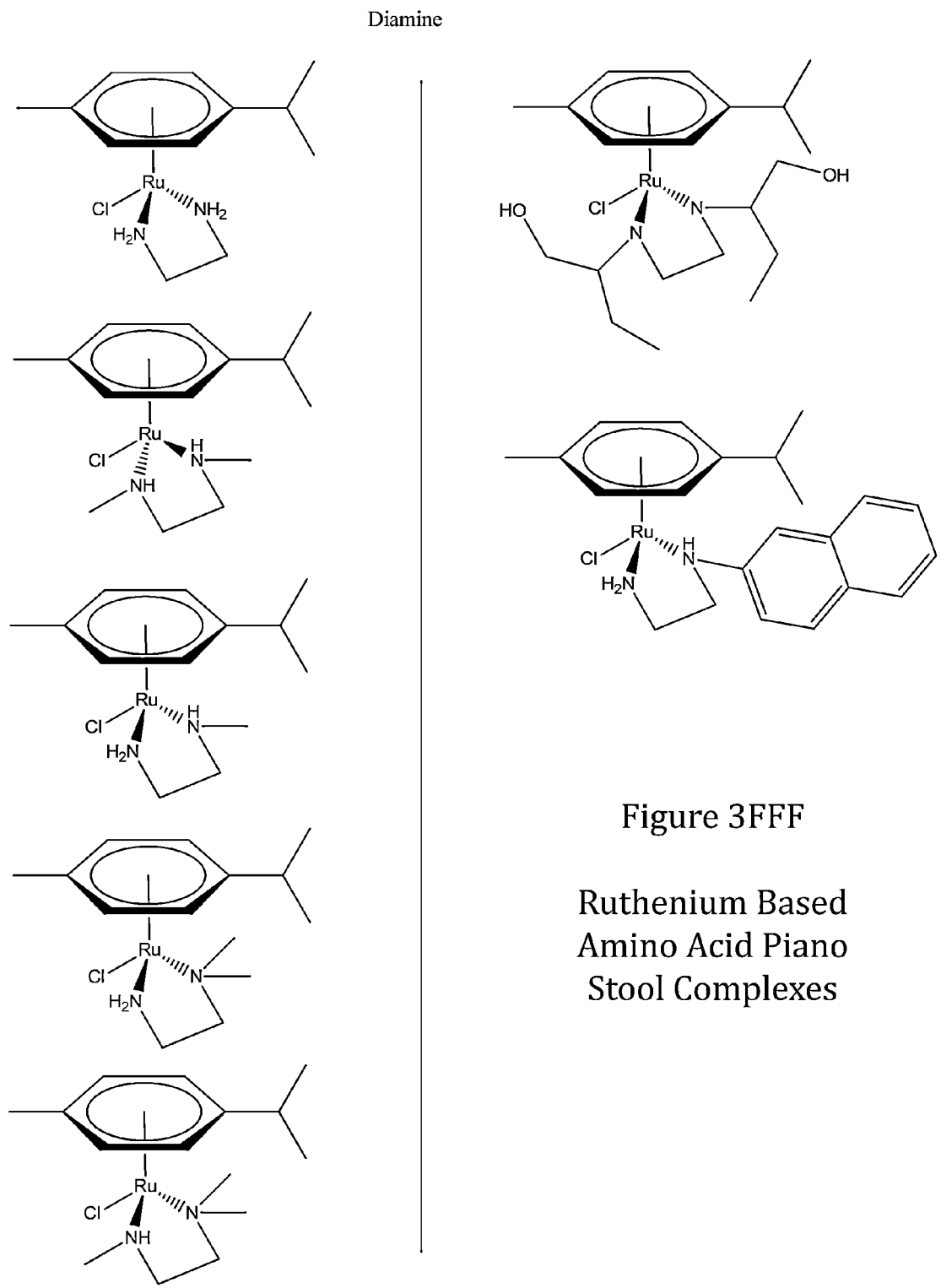
Figure 3FFF
Ruthenium Based Amino Acid Piano Stool Complexes

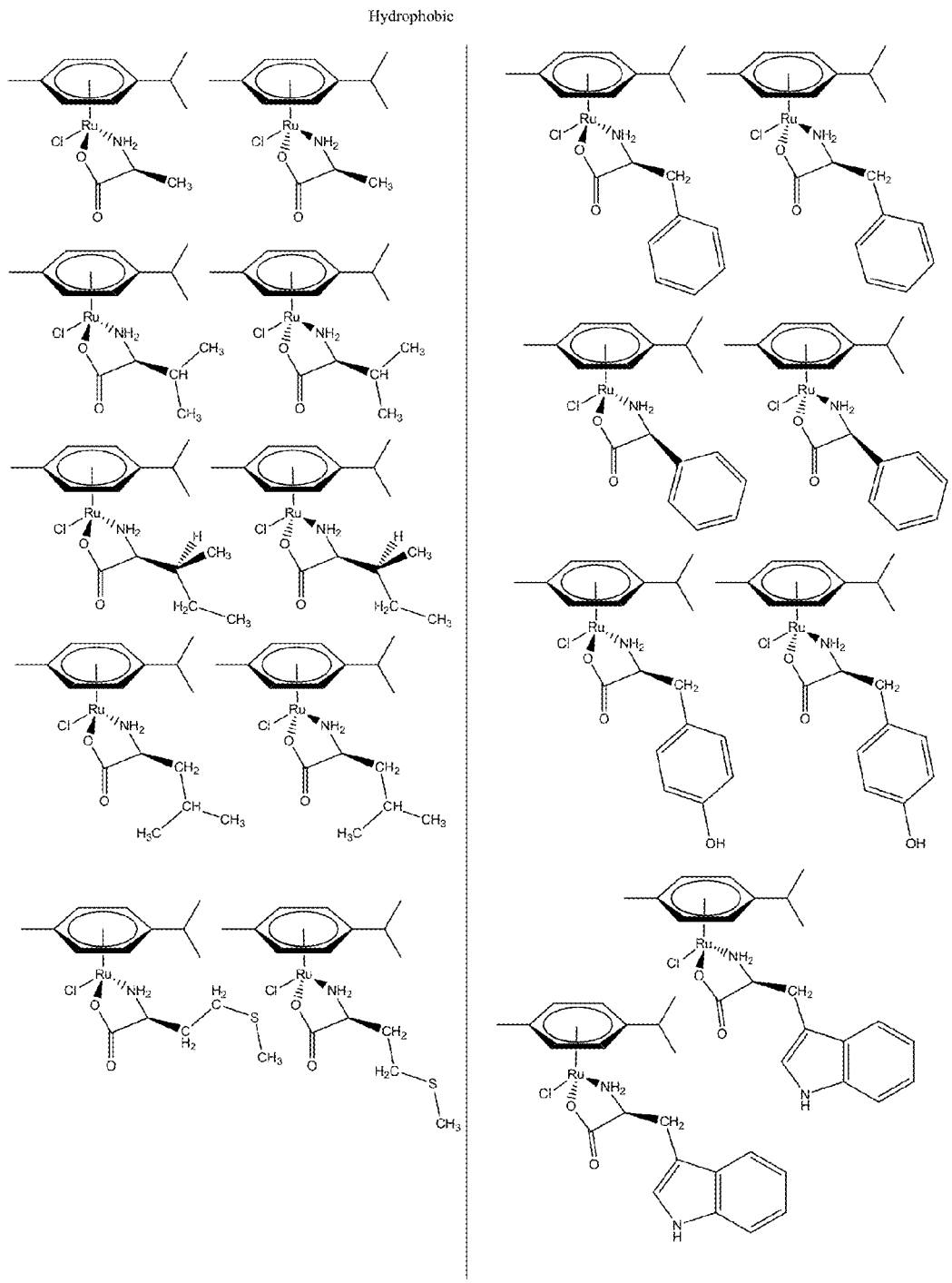
Figure 3GGG
Ruthenium Based Amino Acid Piano Stool Complexes

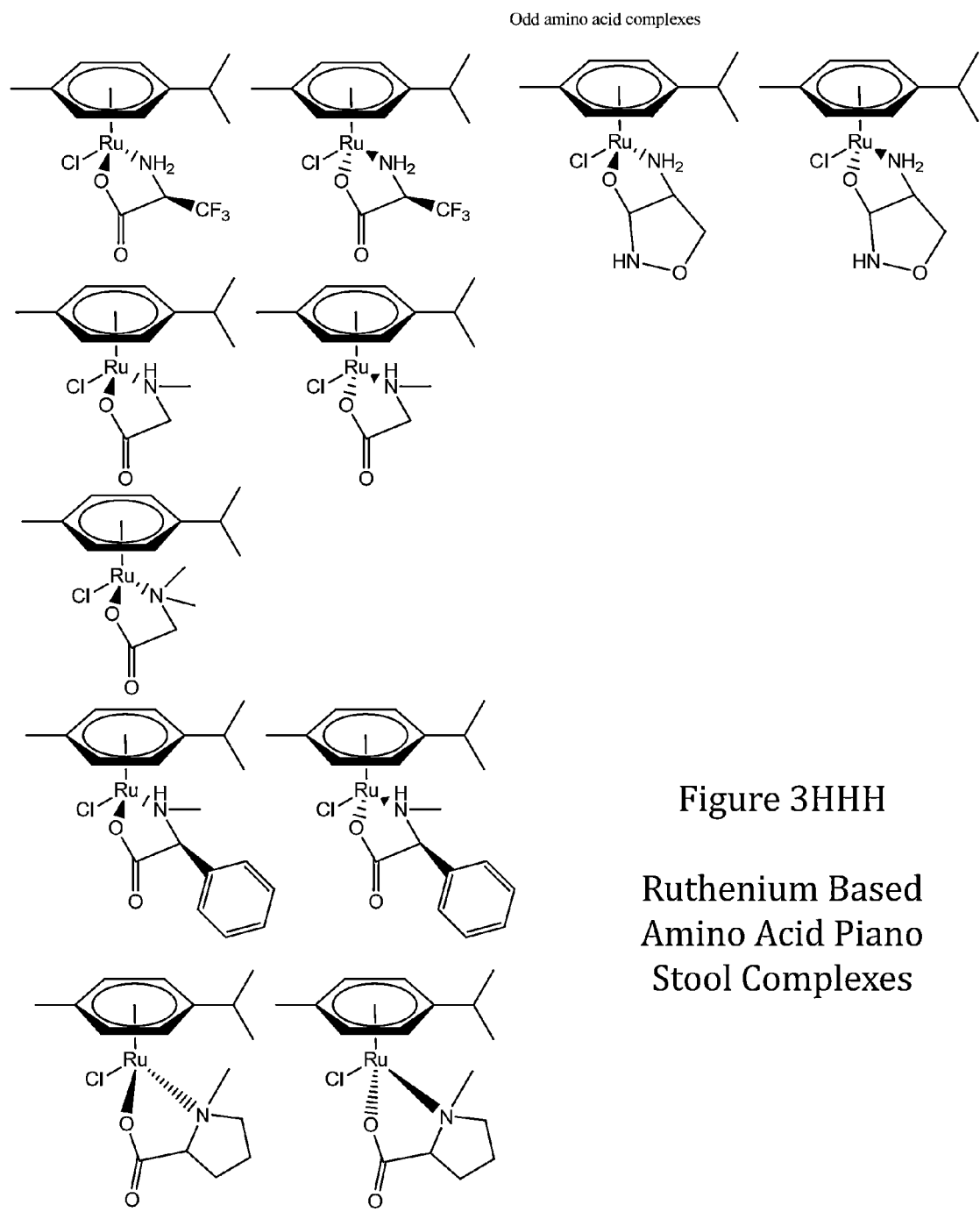
Figure 3HHH
Ruthenium Based Amino Acid Piano Stool Complexes

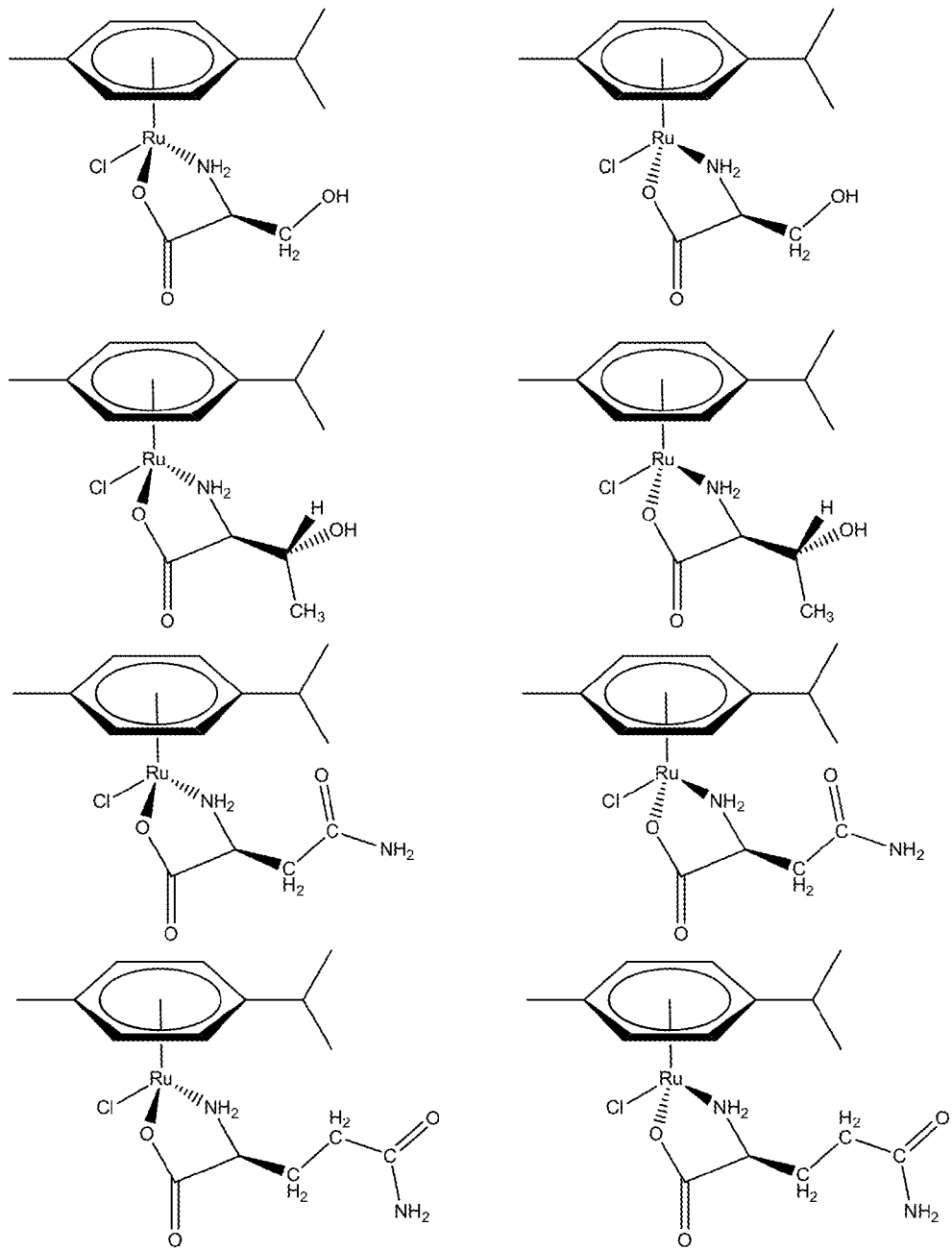
Figure 3III
Ruthenium Based Amino Acid Piano Stool Complexes

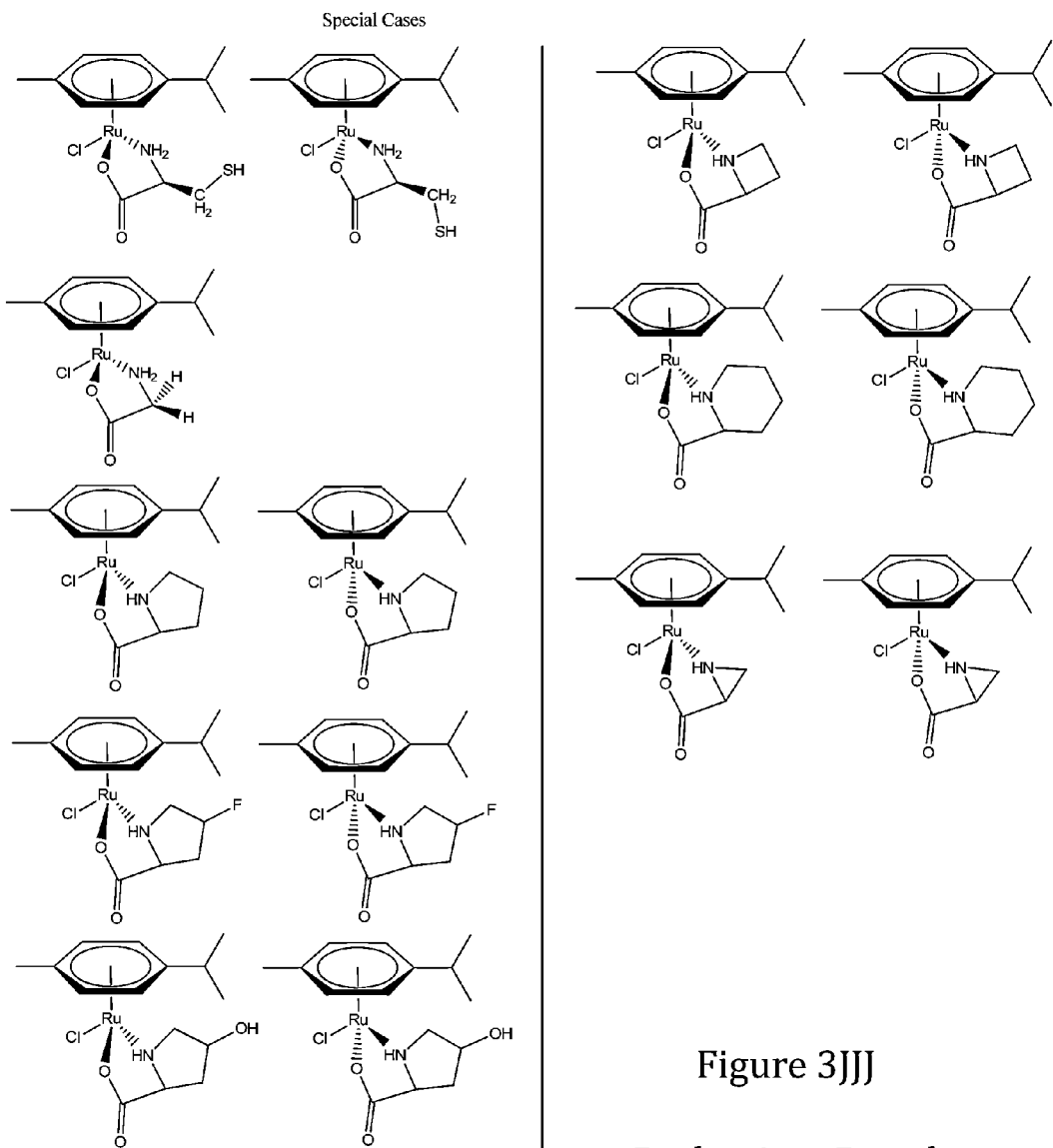
Figure 3JJJ
Ruthenium Based Amino Acid Piano Stool Complexes

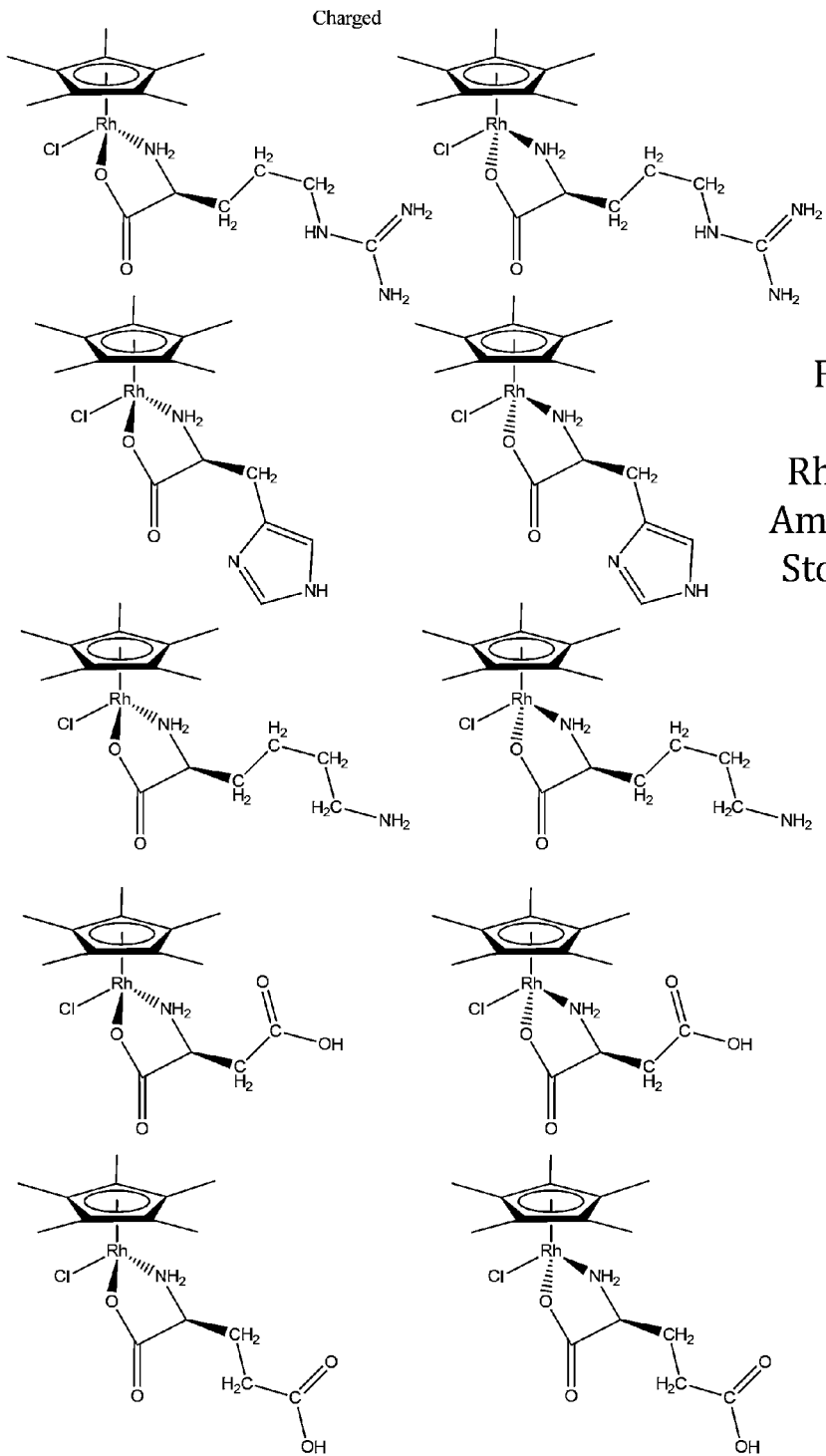
Figure 3KKK
Rhodium Based Amino Acid Piano Stool Complexes

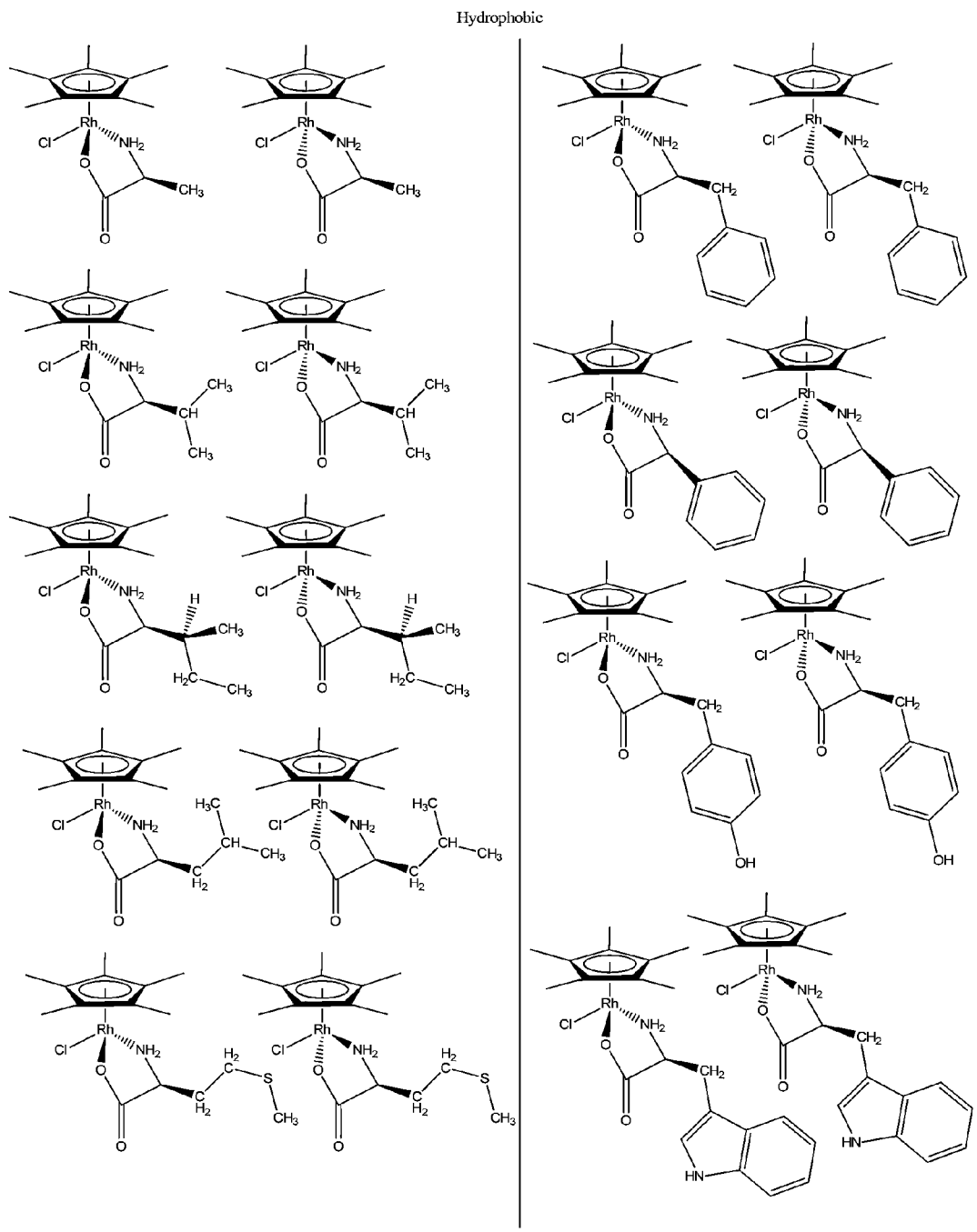
Figure 3LLL
Rhodium Based Amino Acid Piano Stool Complexes

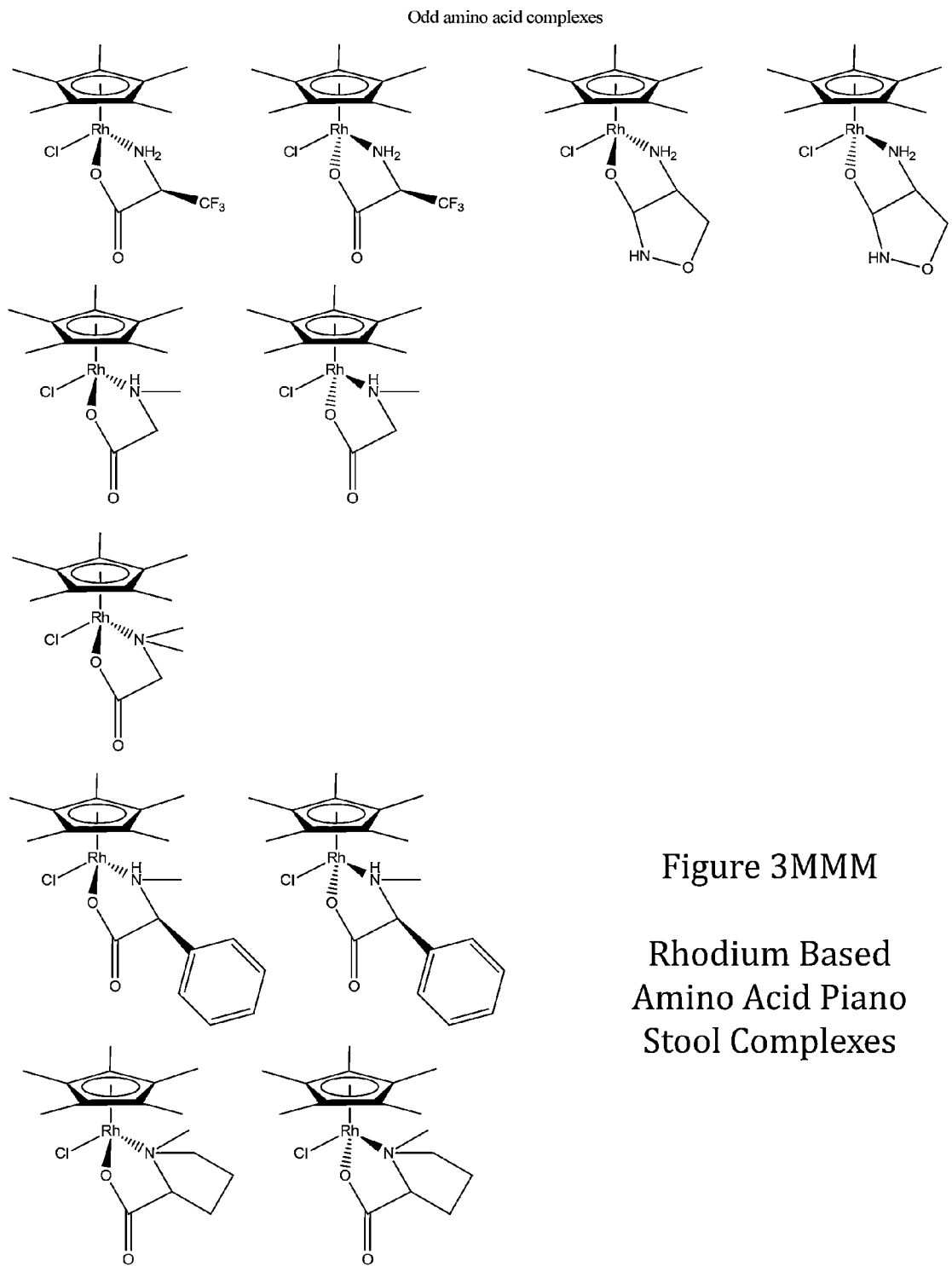
Figure 3MMM
Rhodium Based Amino Acid Piano Stool Complexes

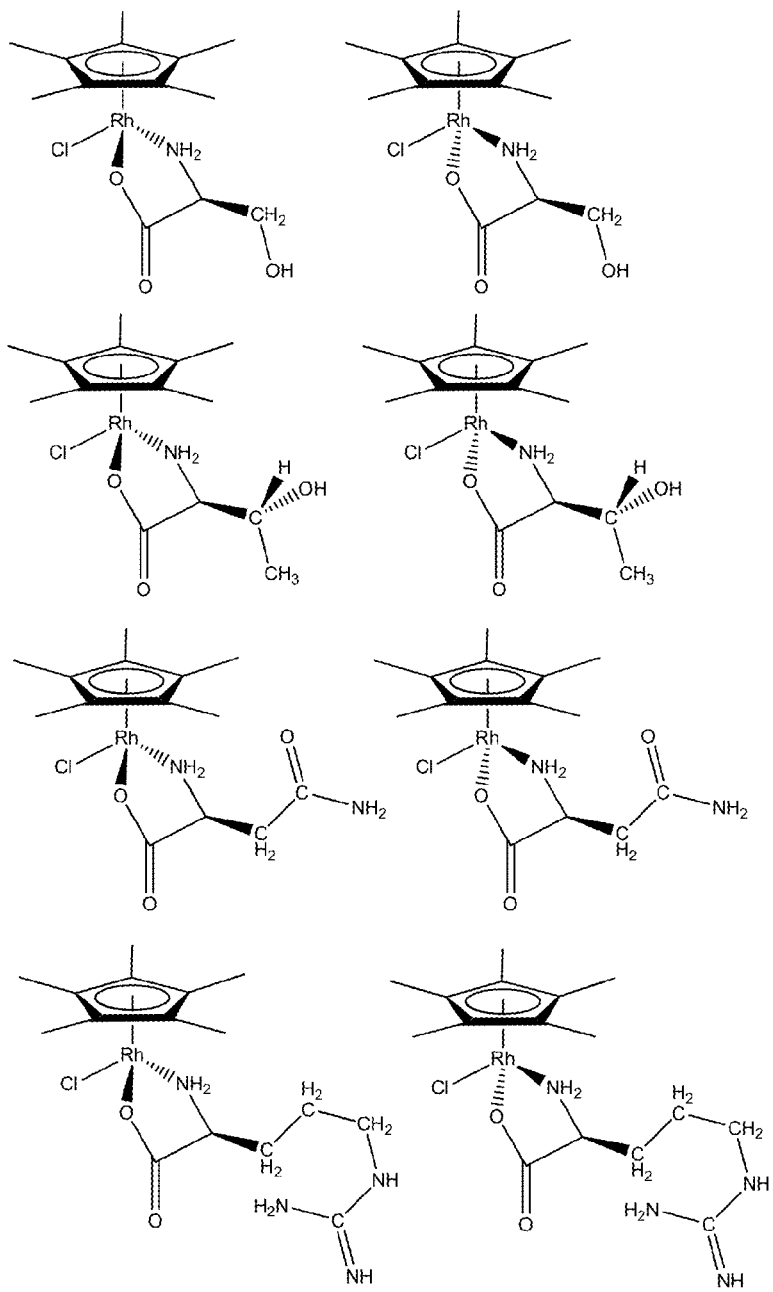
Figure 3NNN
Rhodium Based Amino Acid Piano Stool Complexes

Diamine
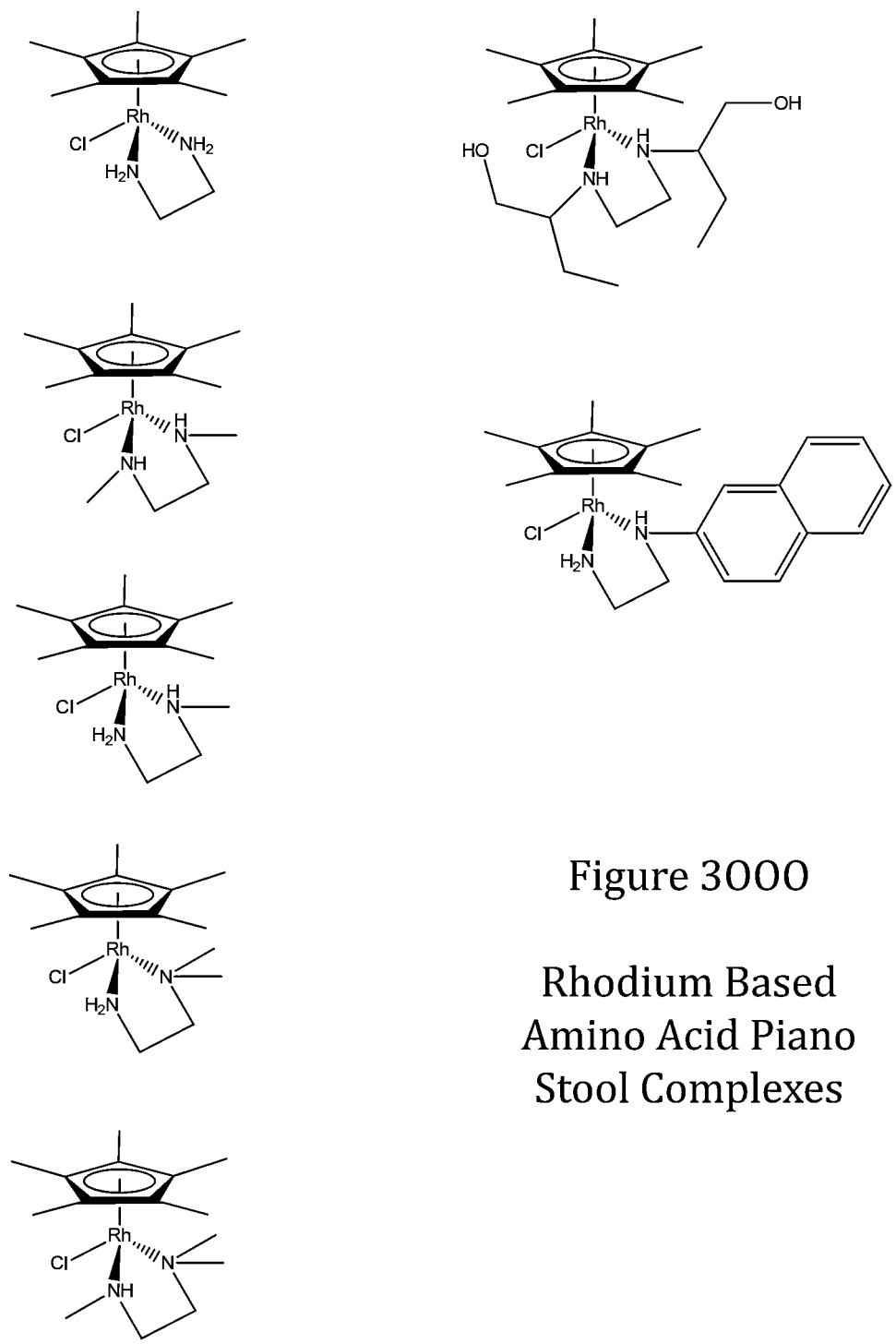
Figure 3000
Rhodium Based
Amino Acid Piano
Stool Complexes

Figure 3O:
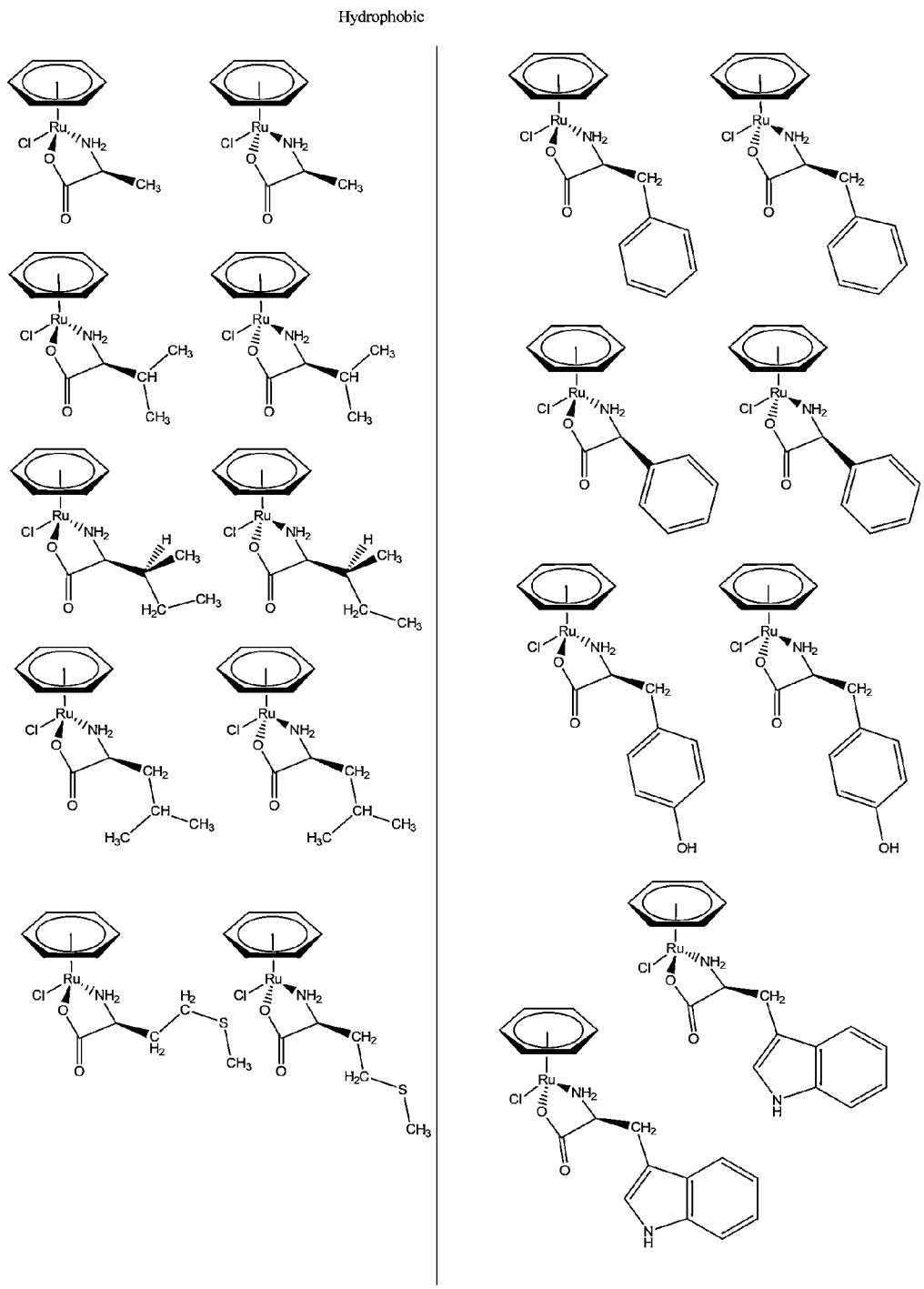
Figure 3P:
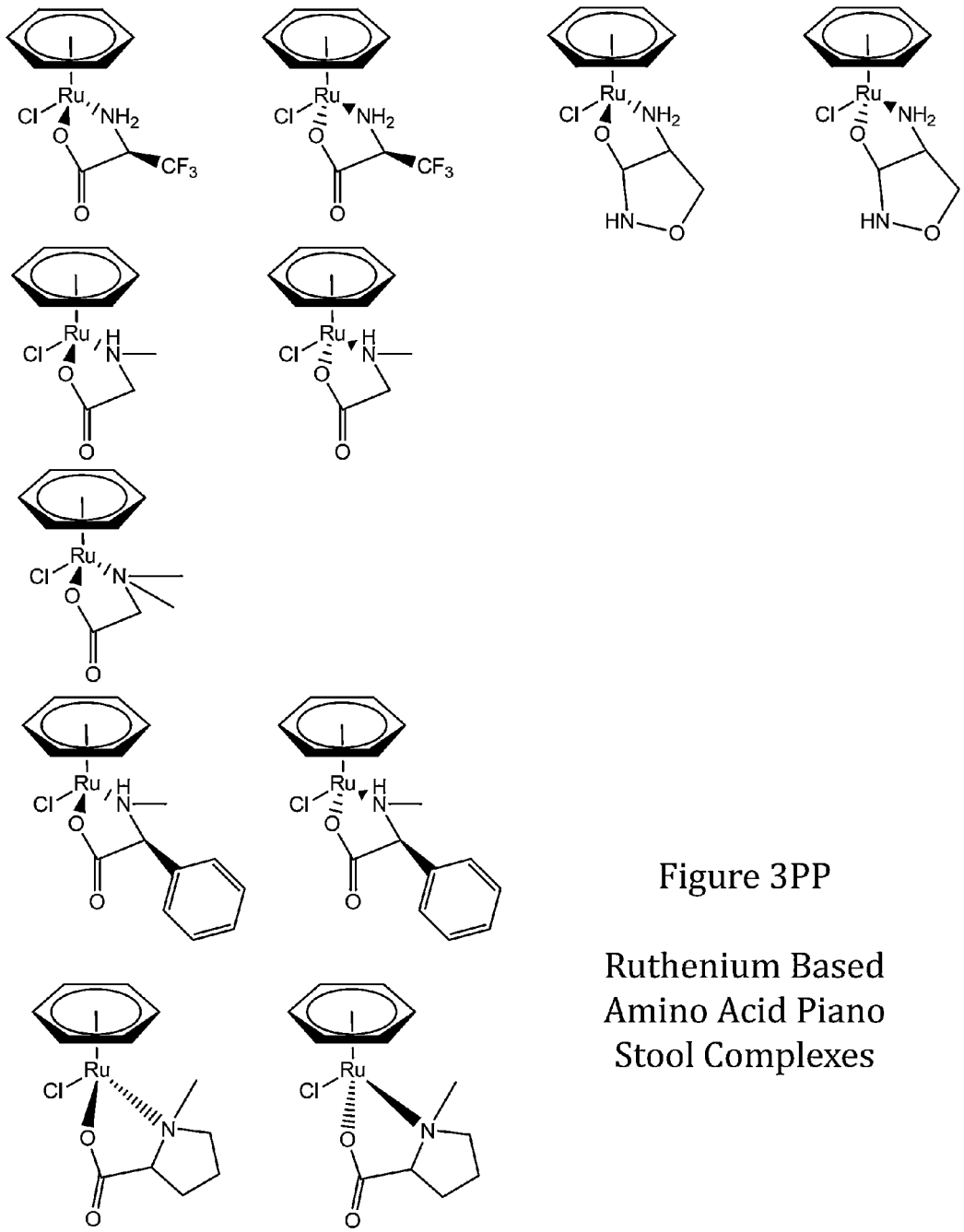
Figure 3Q:
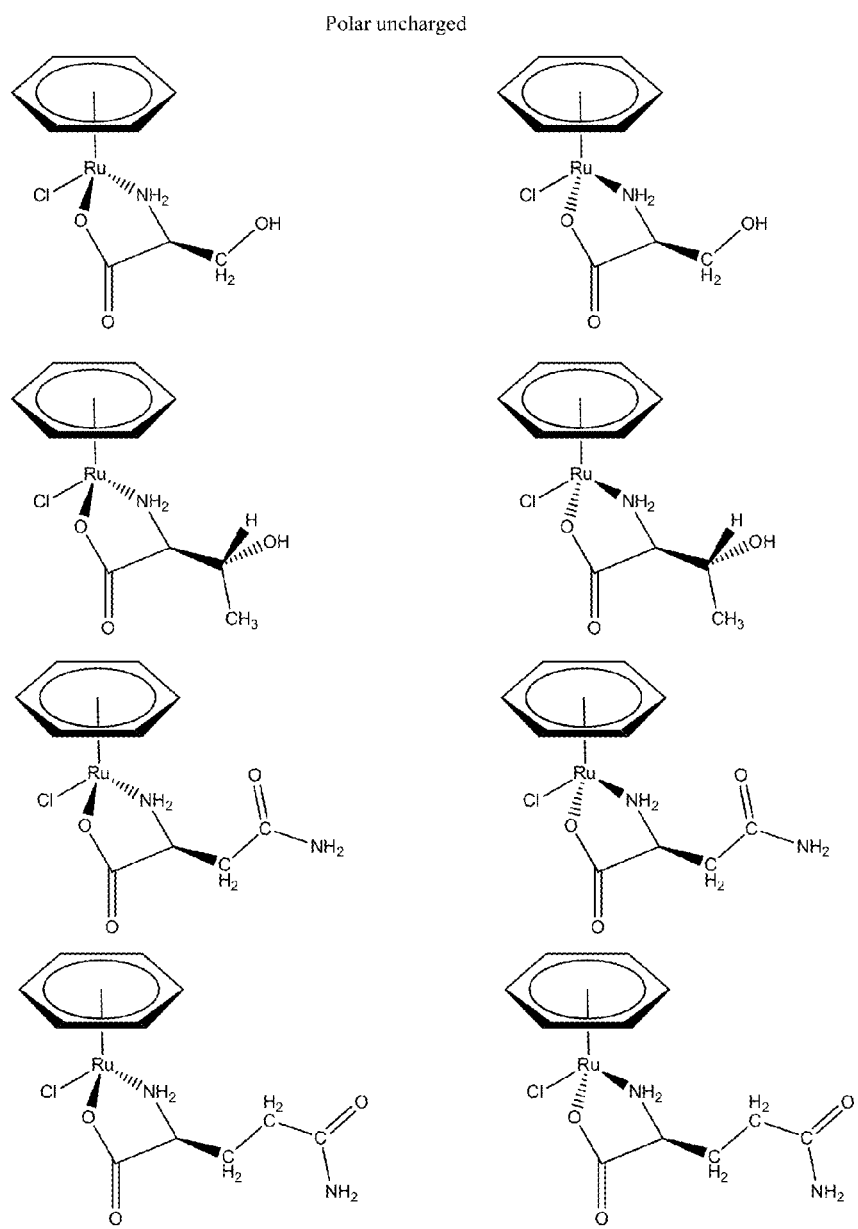
Figure 3R:
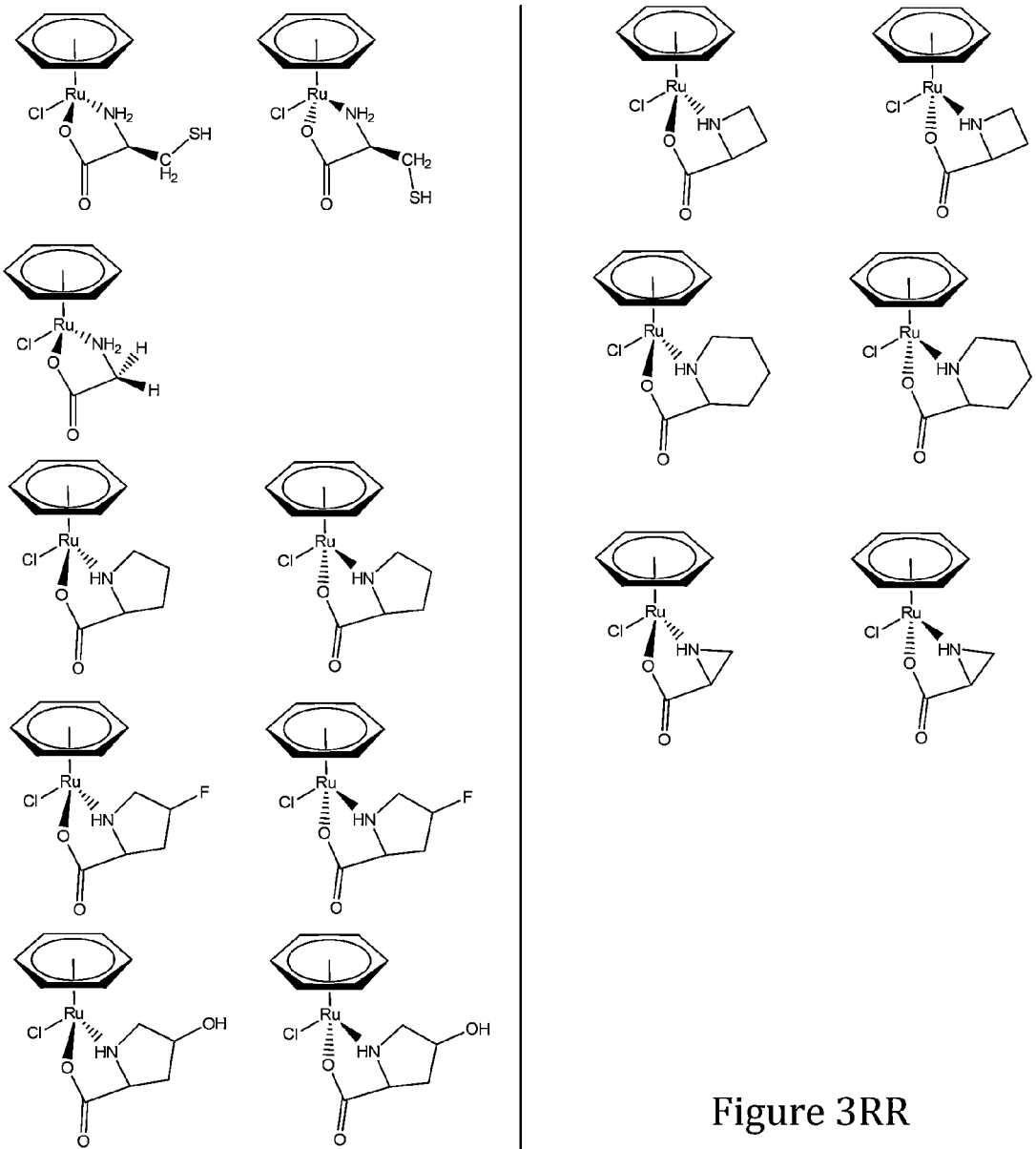
Figure 3S:
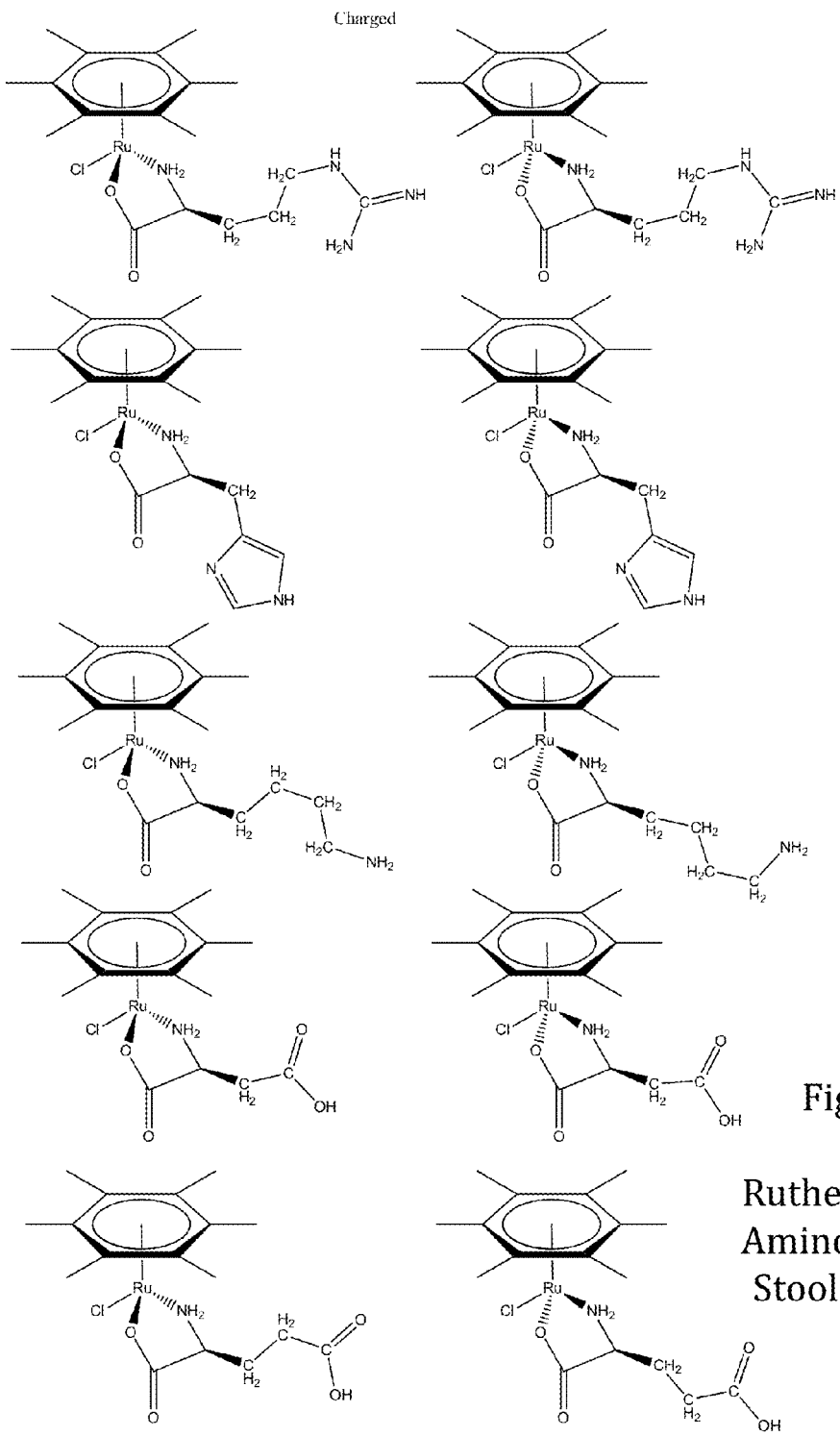
Figure 3T:
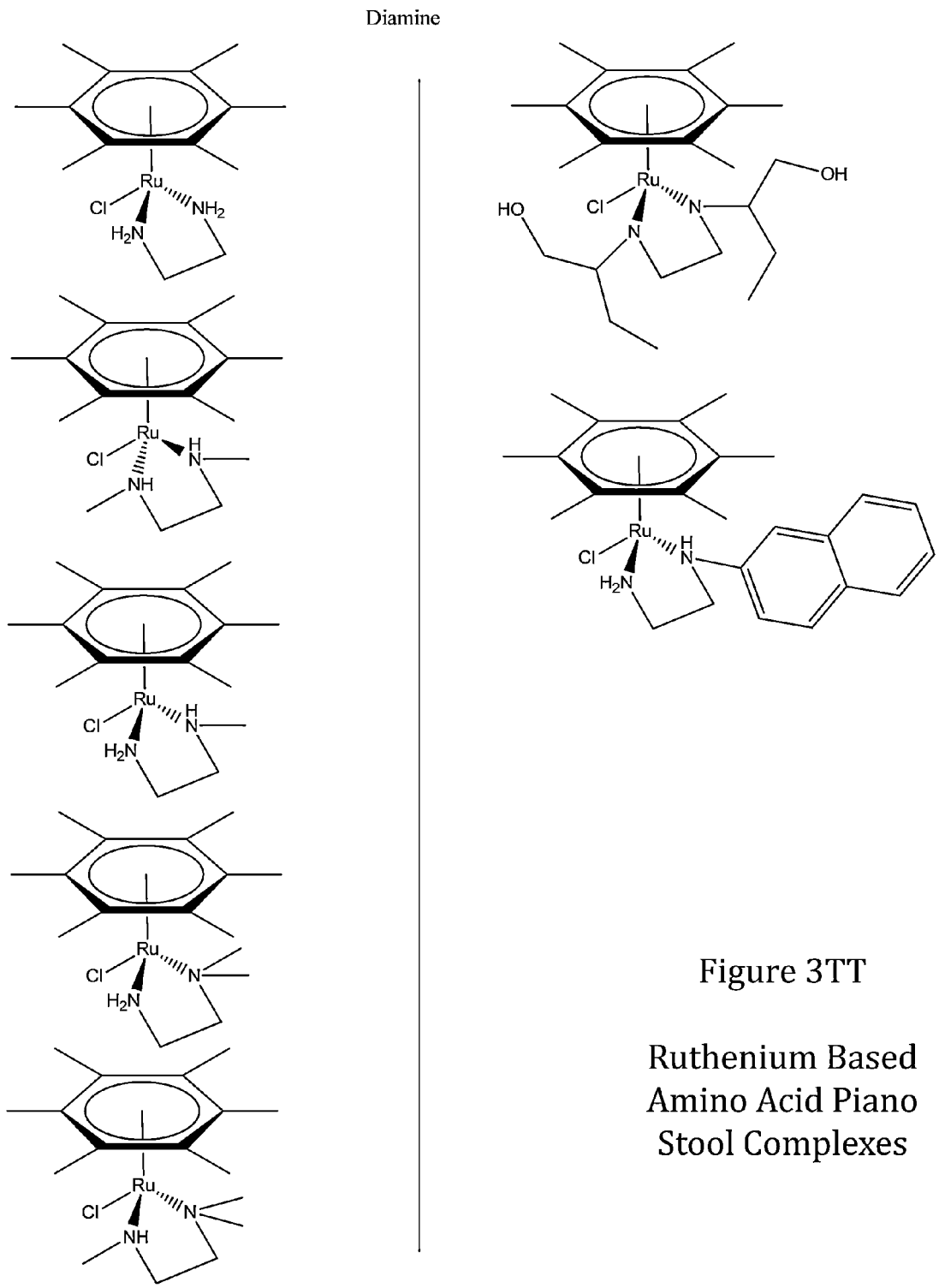
Figure 3U:
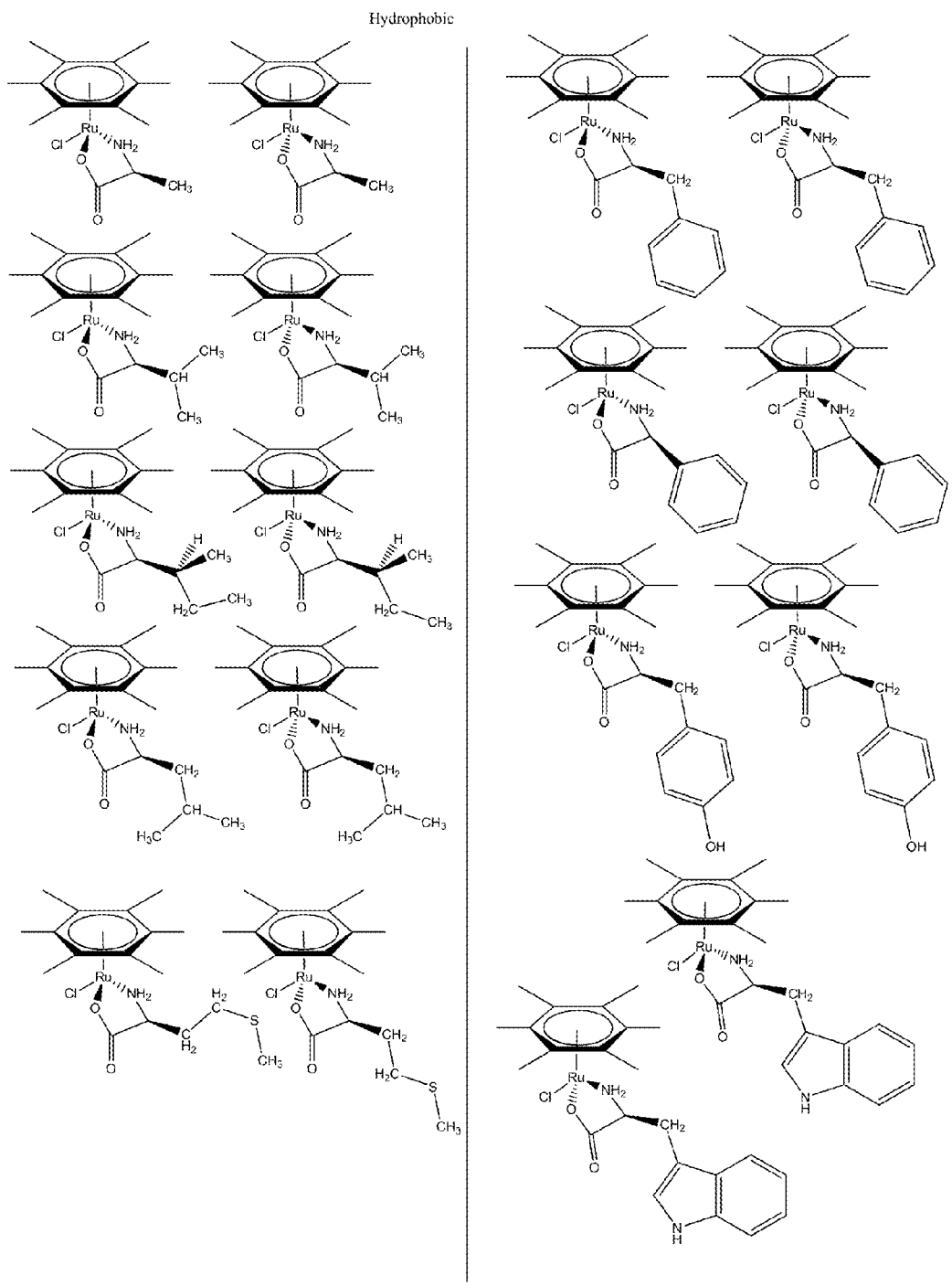
Figure 3V:
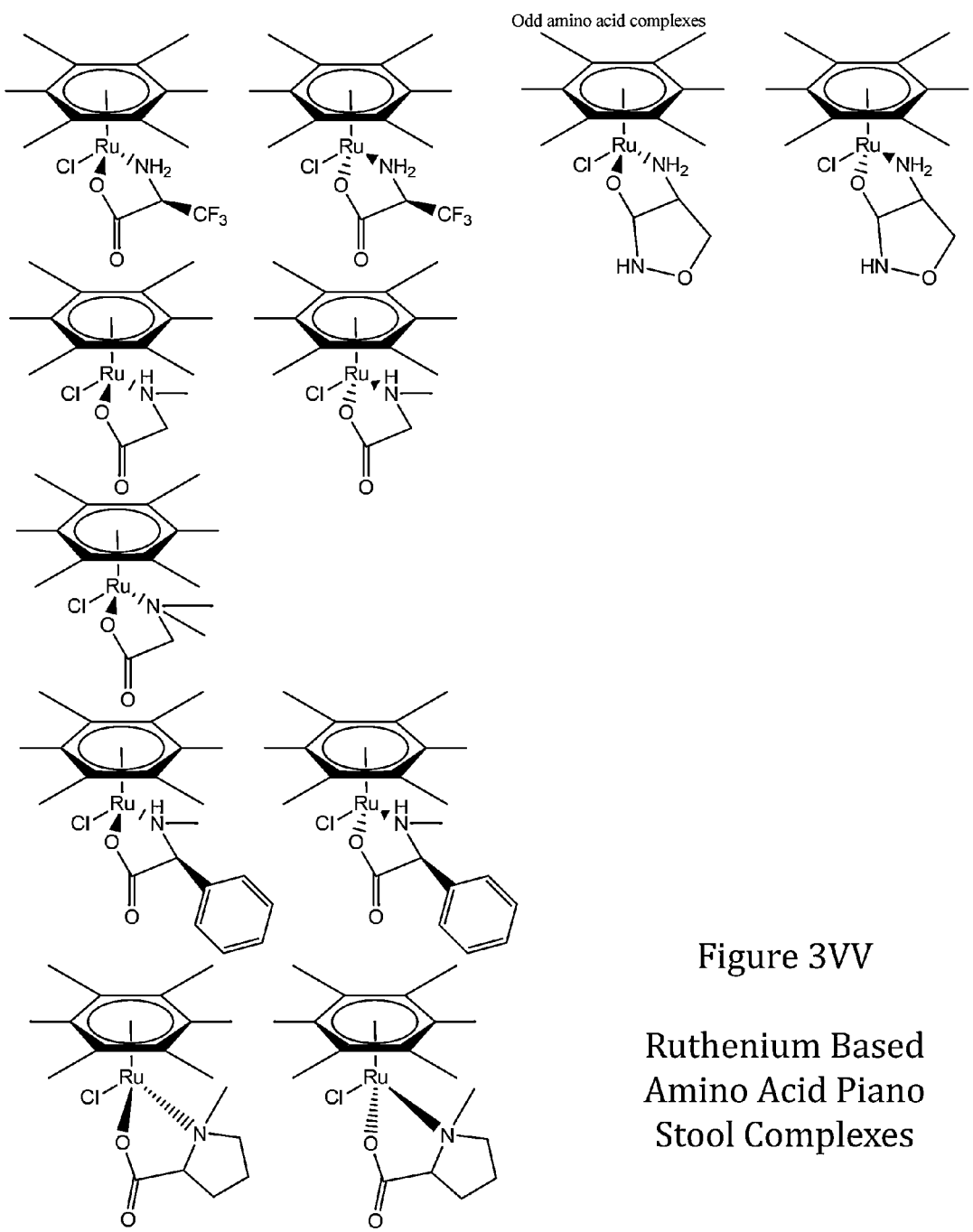
Figure 3W:
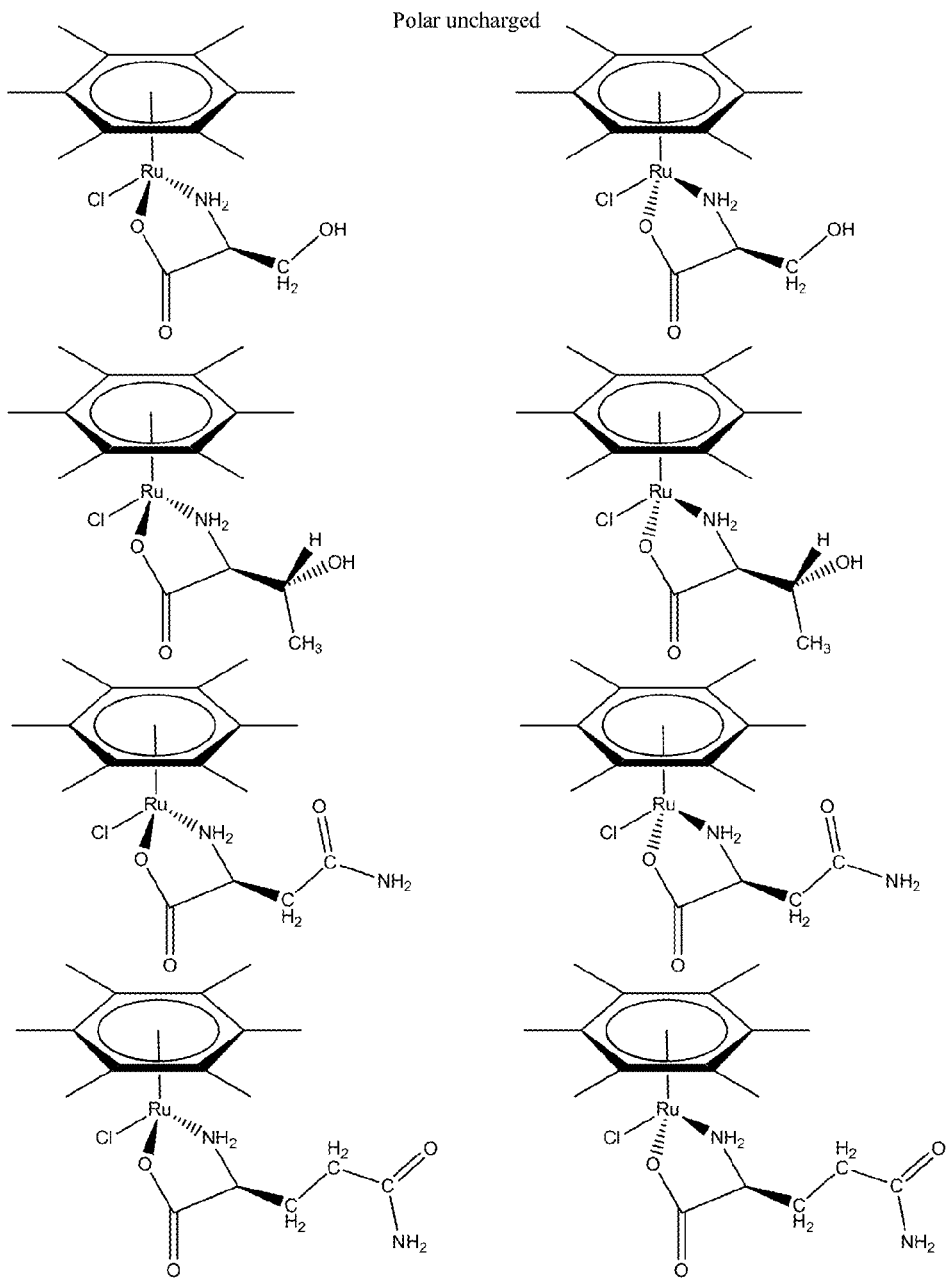
Figure 3X:
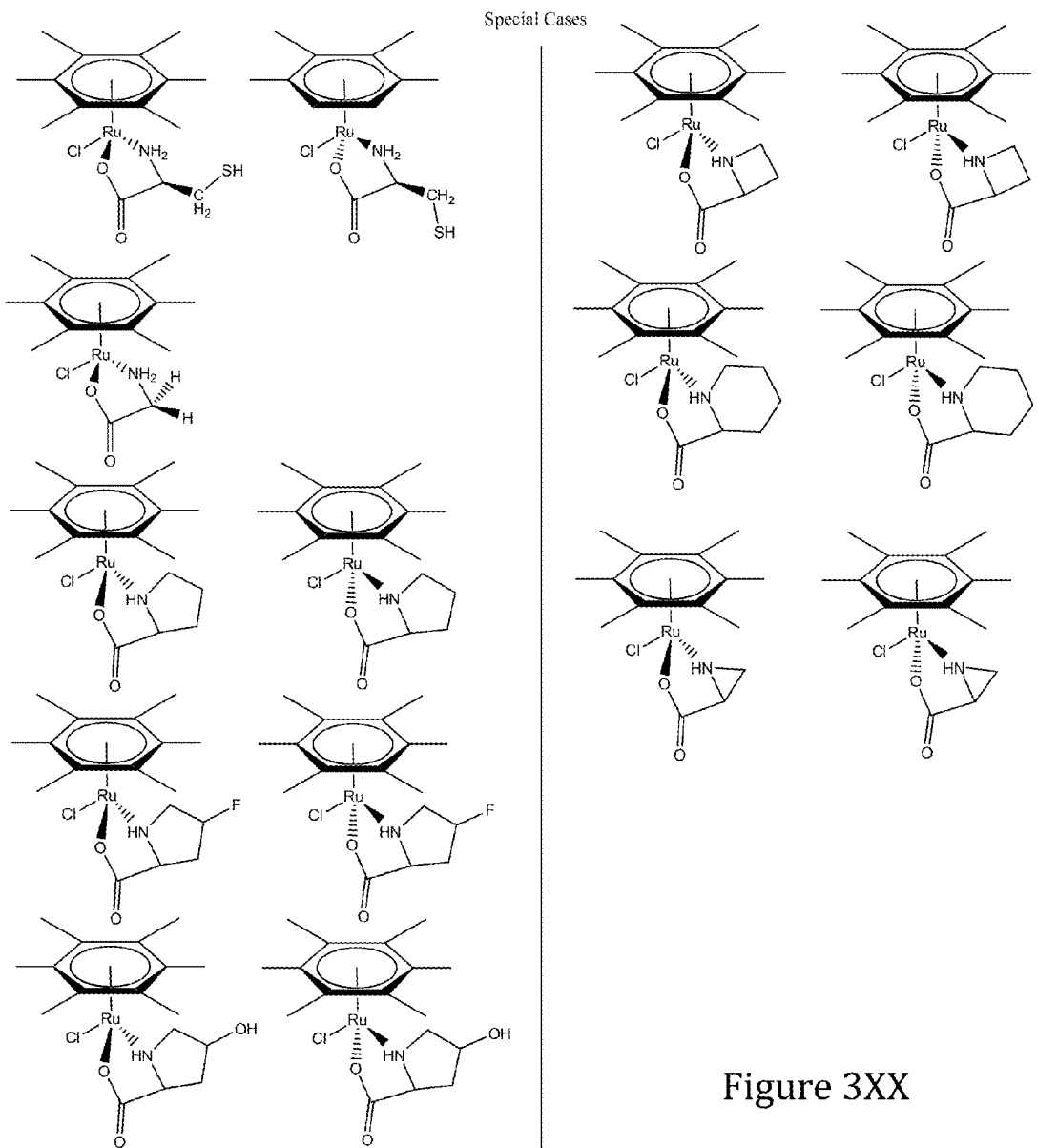
Figure 3Y:
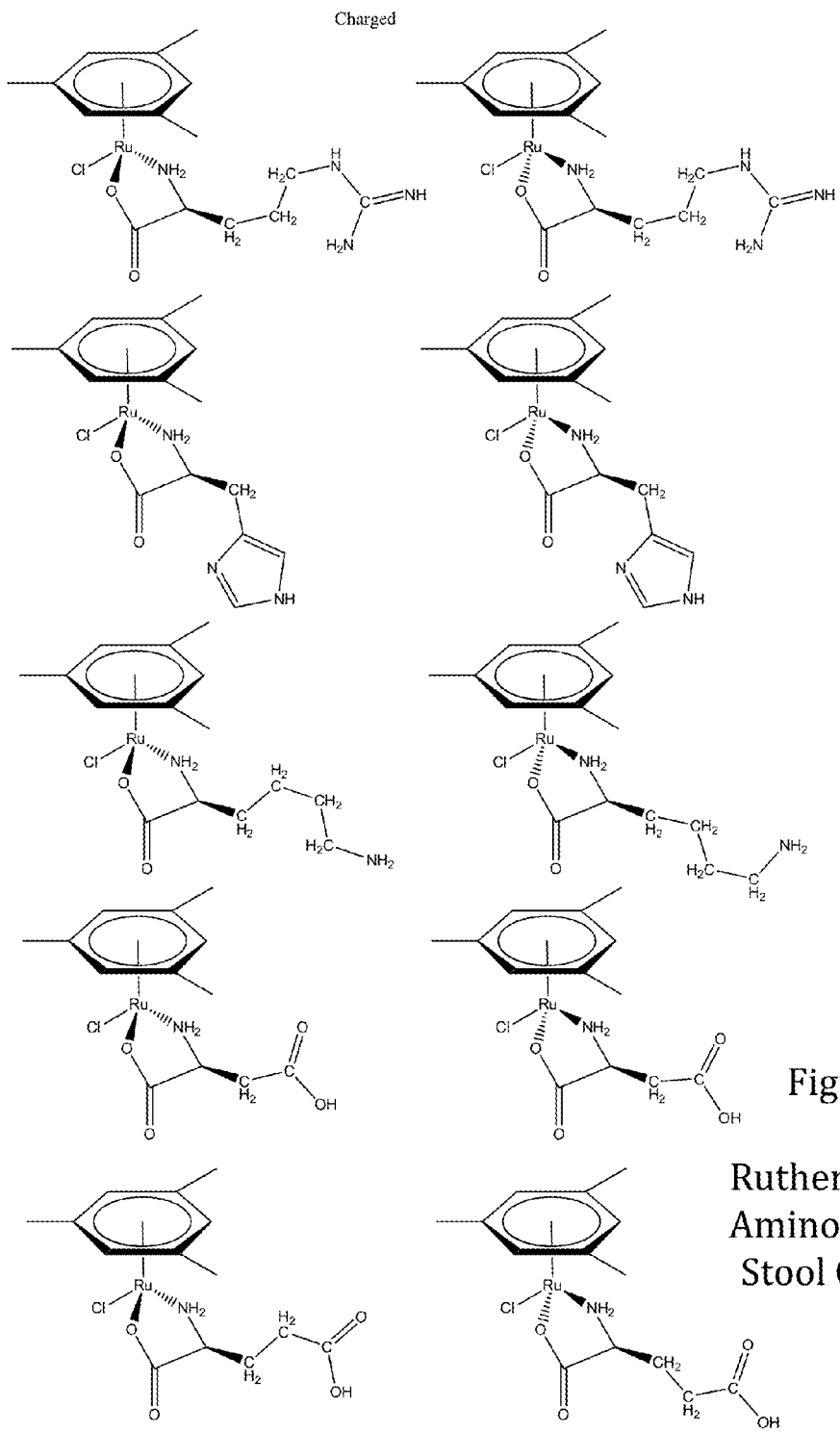
Figure 3Z:
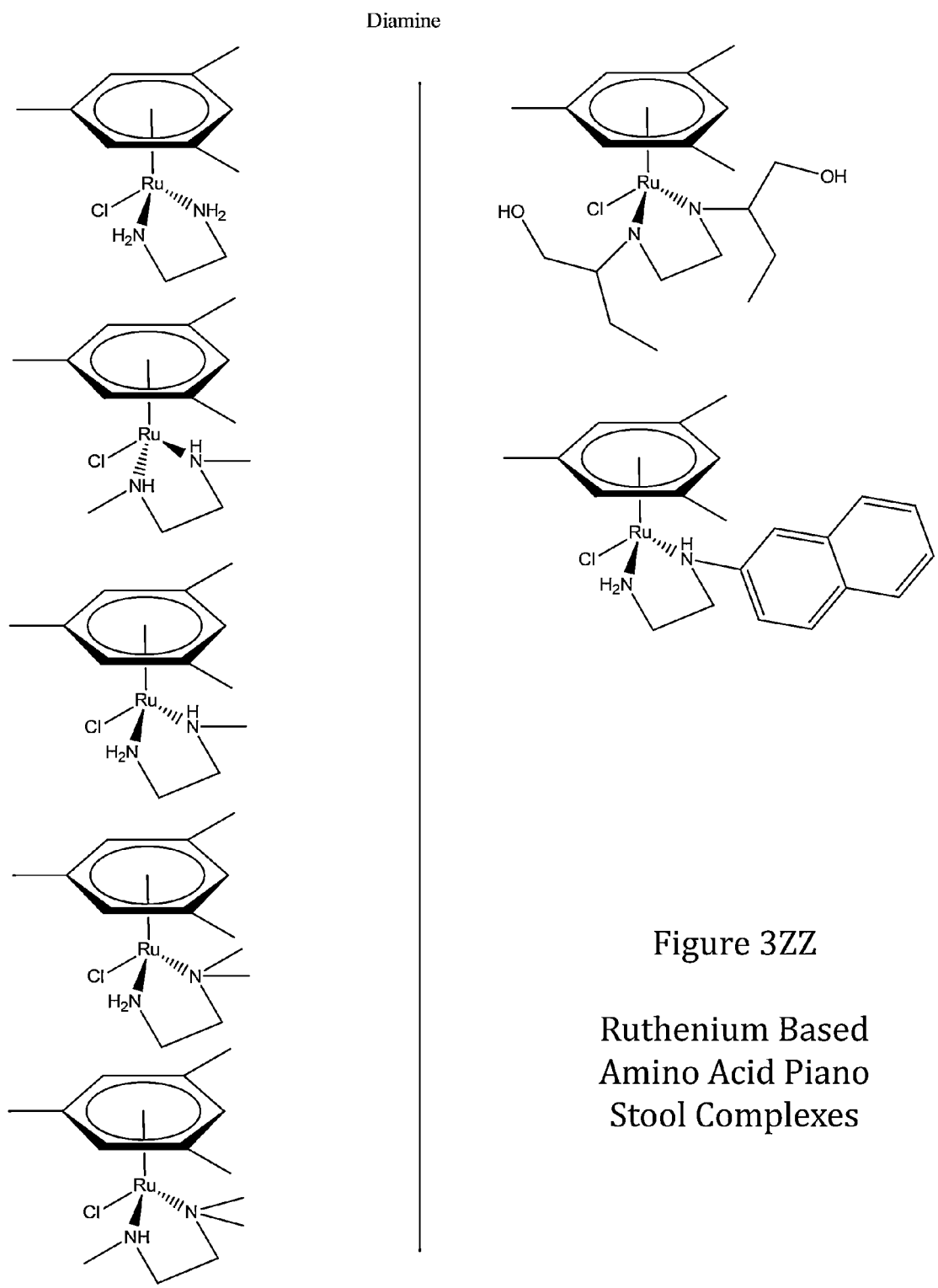

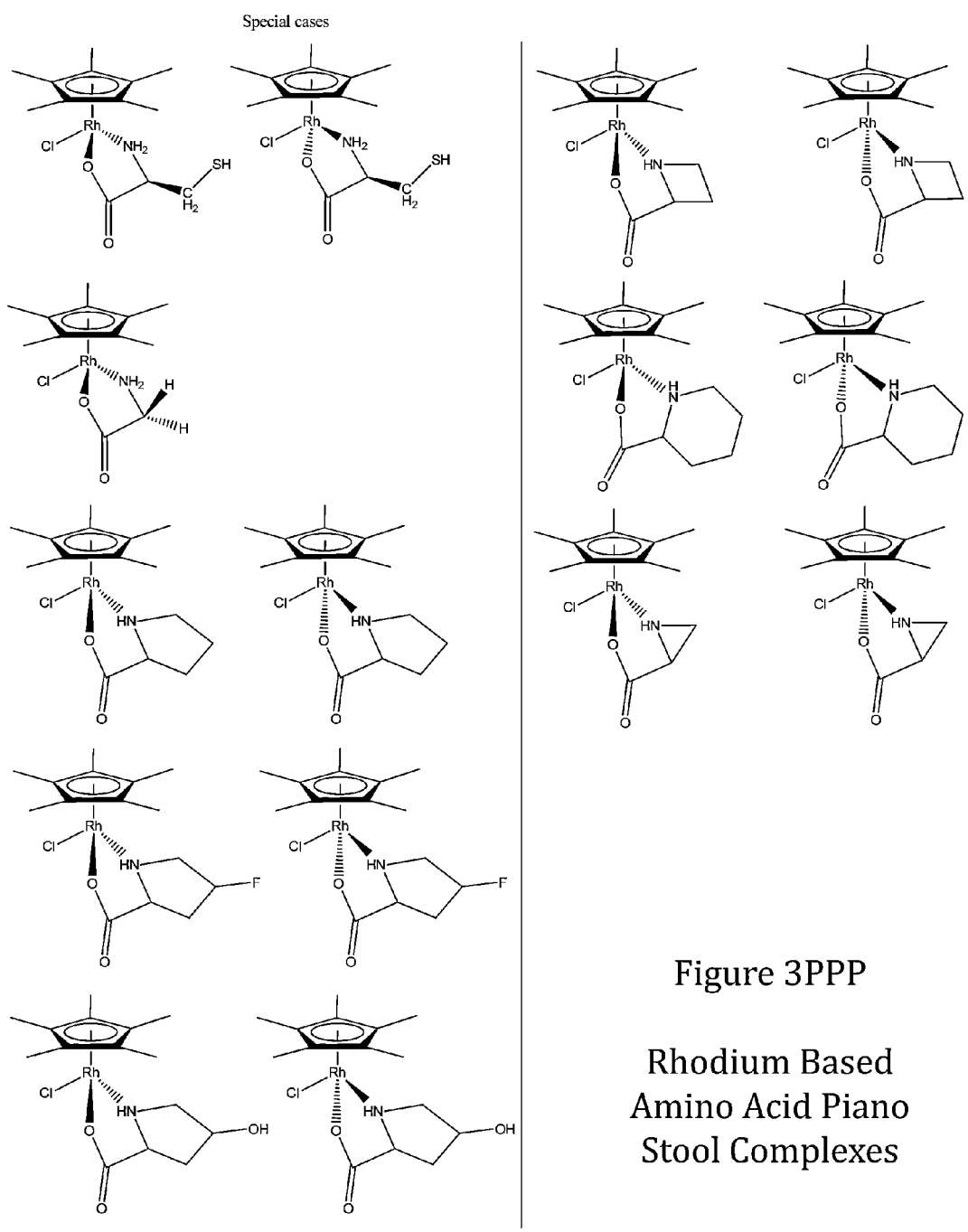
Figure 3PPP
Rhodium Based Amino Acid Piano Stool Complexes

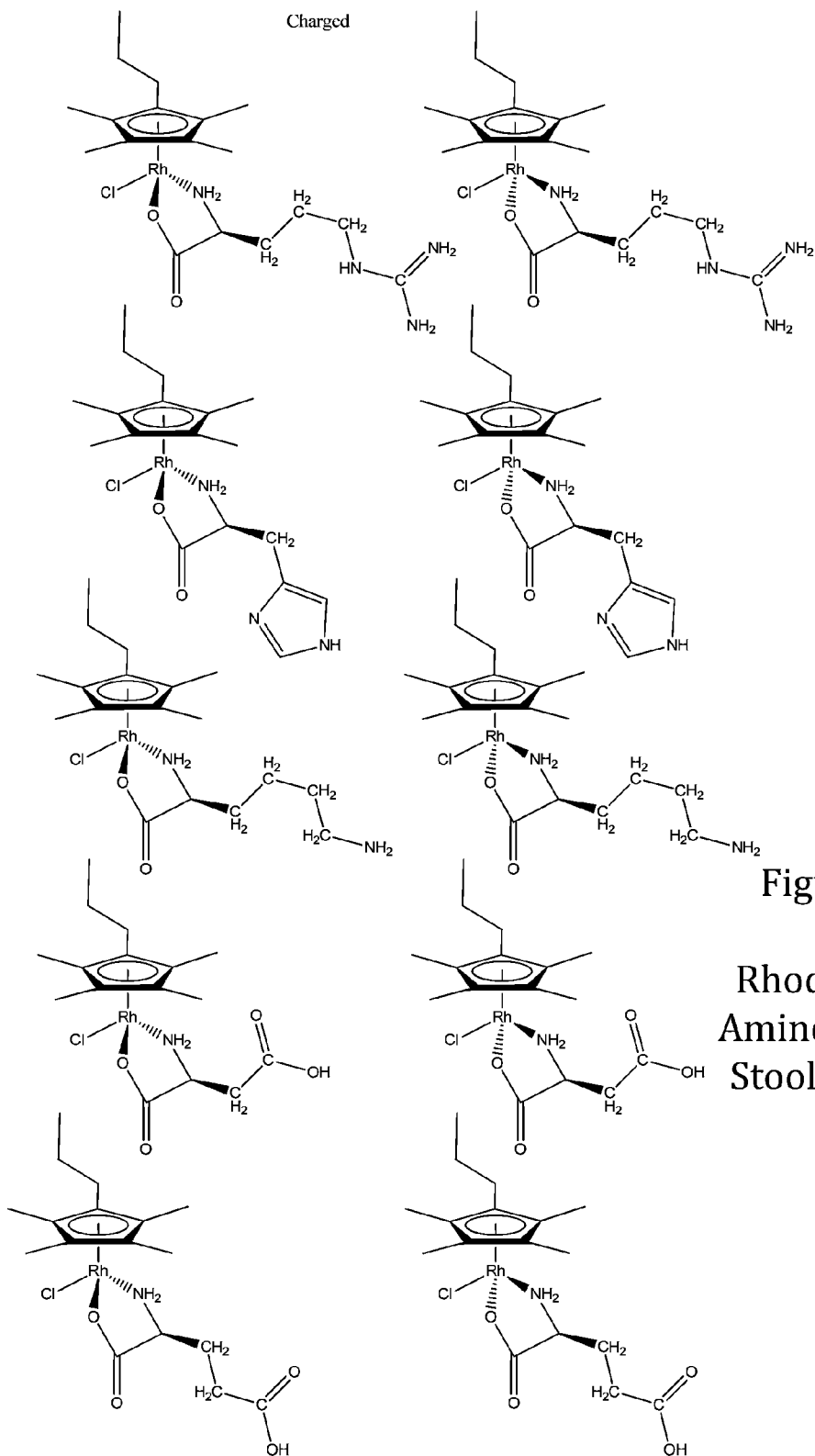
Figure 3QQQ
Rhodium Based Amino Acid Piano Stool Complexes

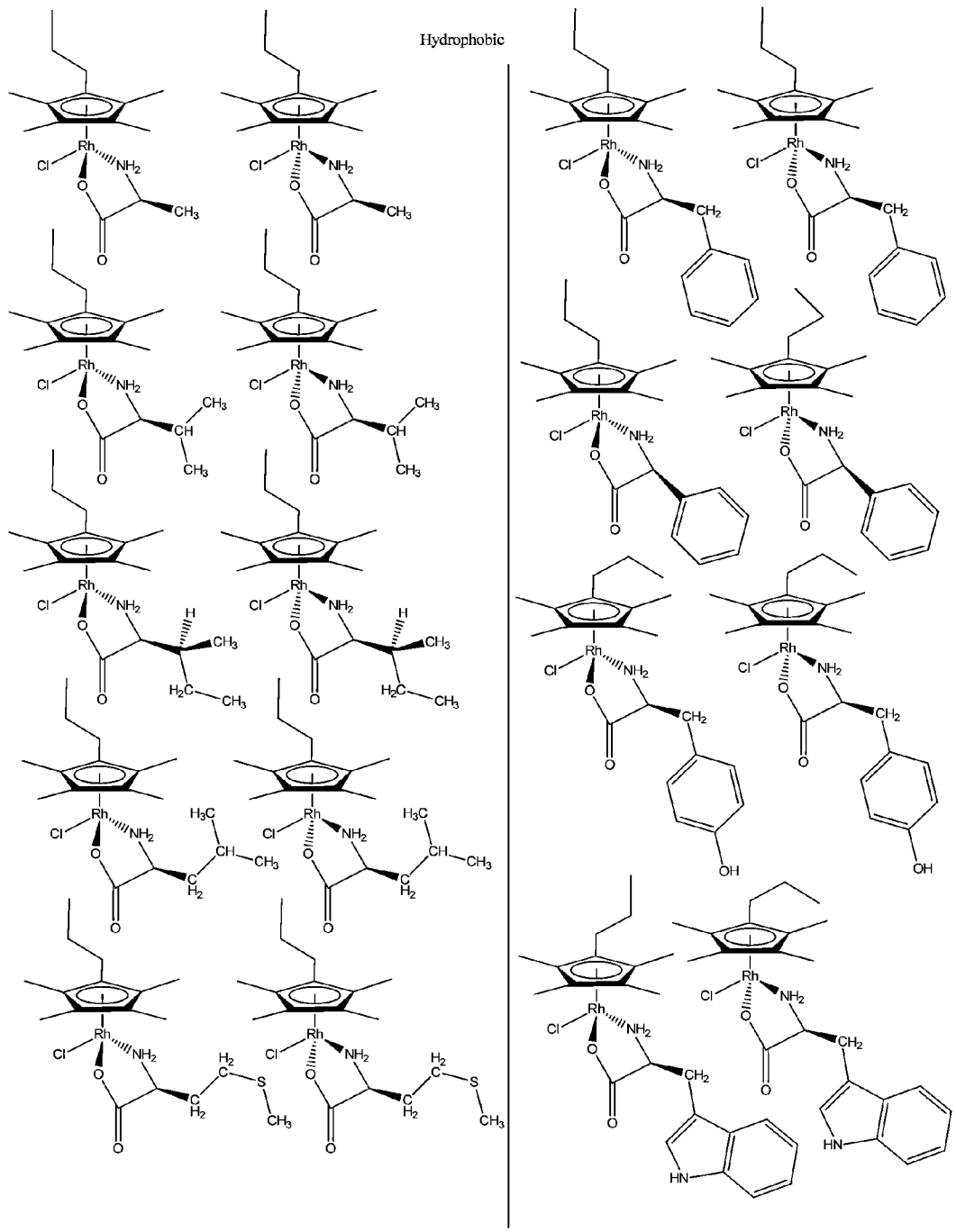
Figure 3RRR
Rhodium Based Amino Acid Piano Stool Complexes

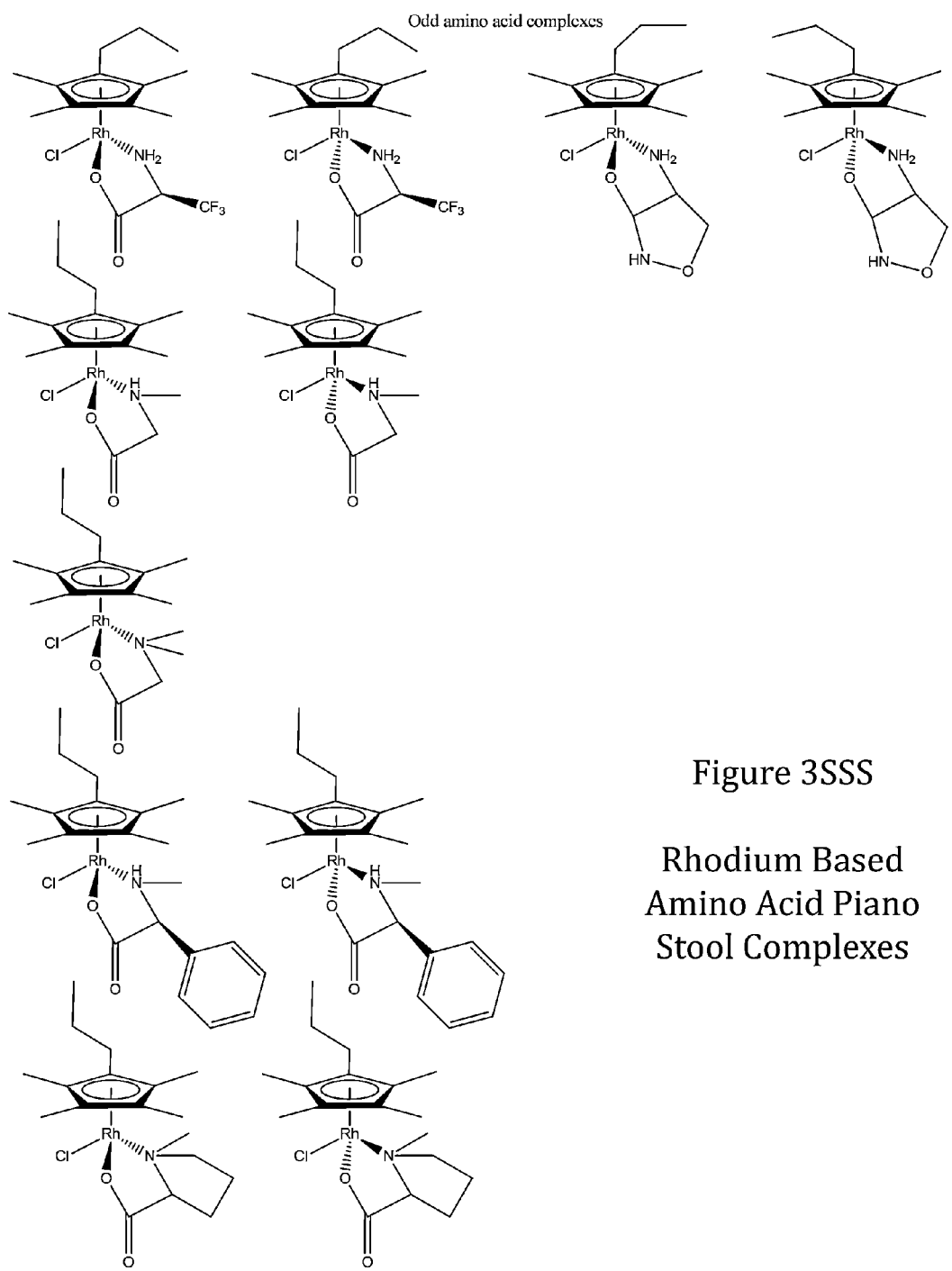
Figure 3SSS
Rhodium Based Amino Acid Piano Stool Complexes

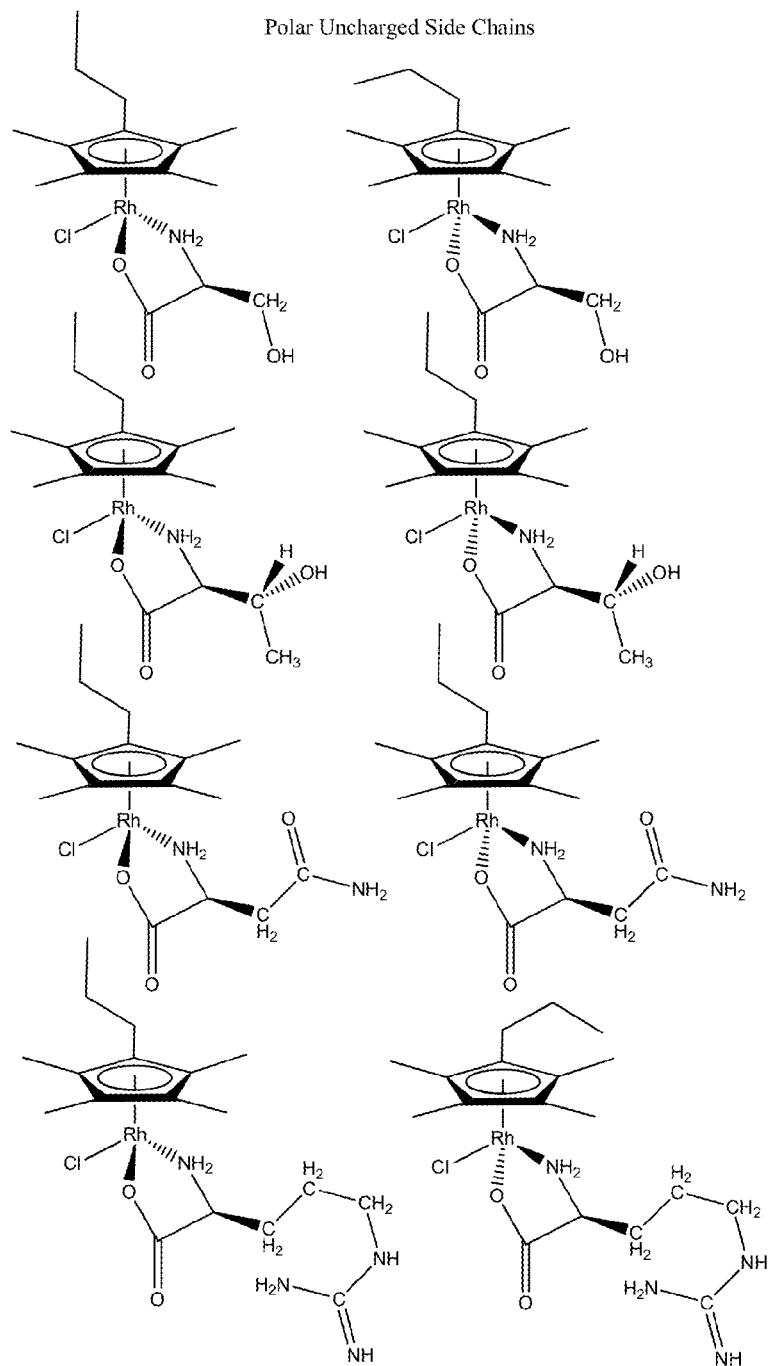
Figure 3TTT
Rhodium Based Amino Acid Piano Stool Complexes

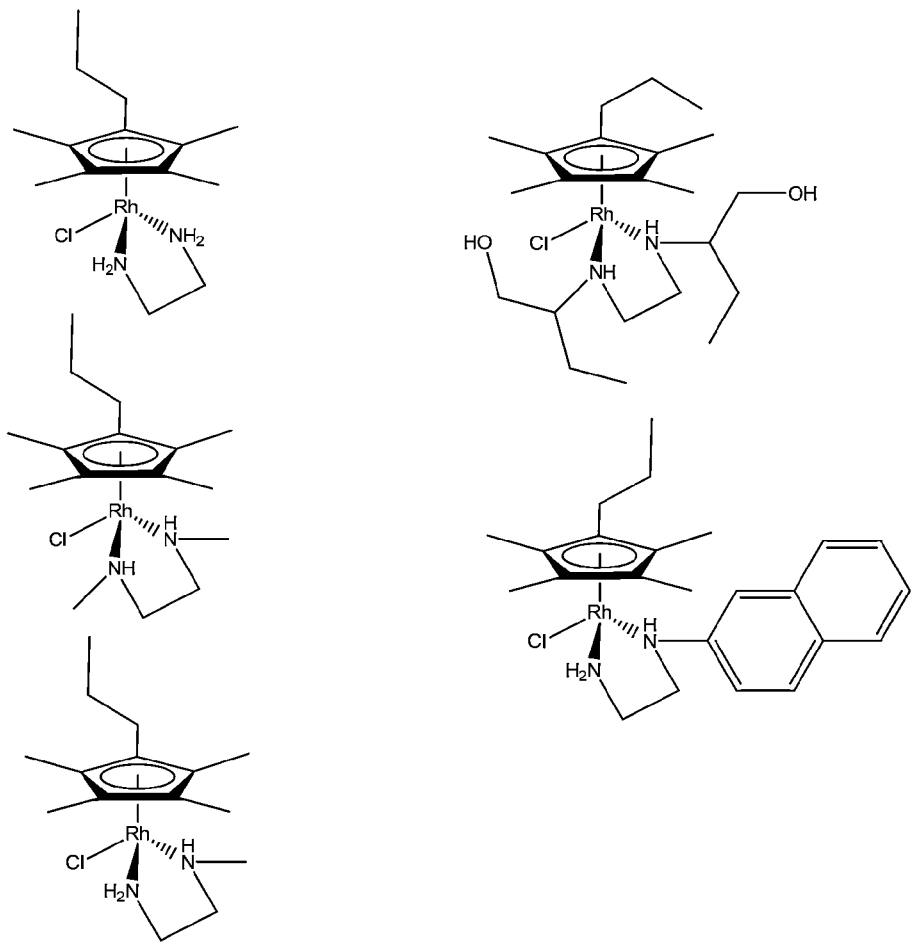
Figure 3UUU
Rhodium Based Amino Acid Piano Stool Complexes

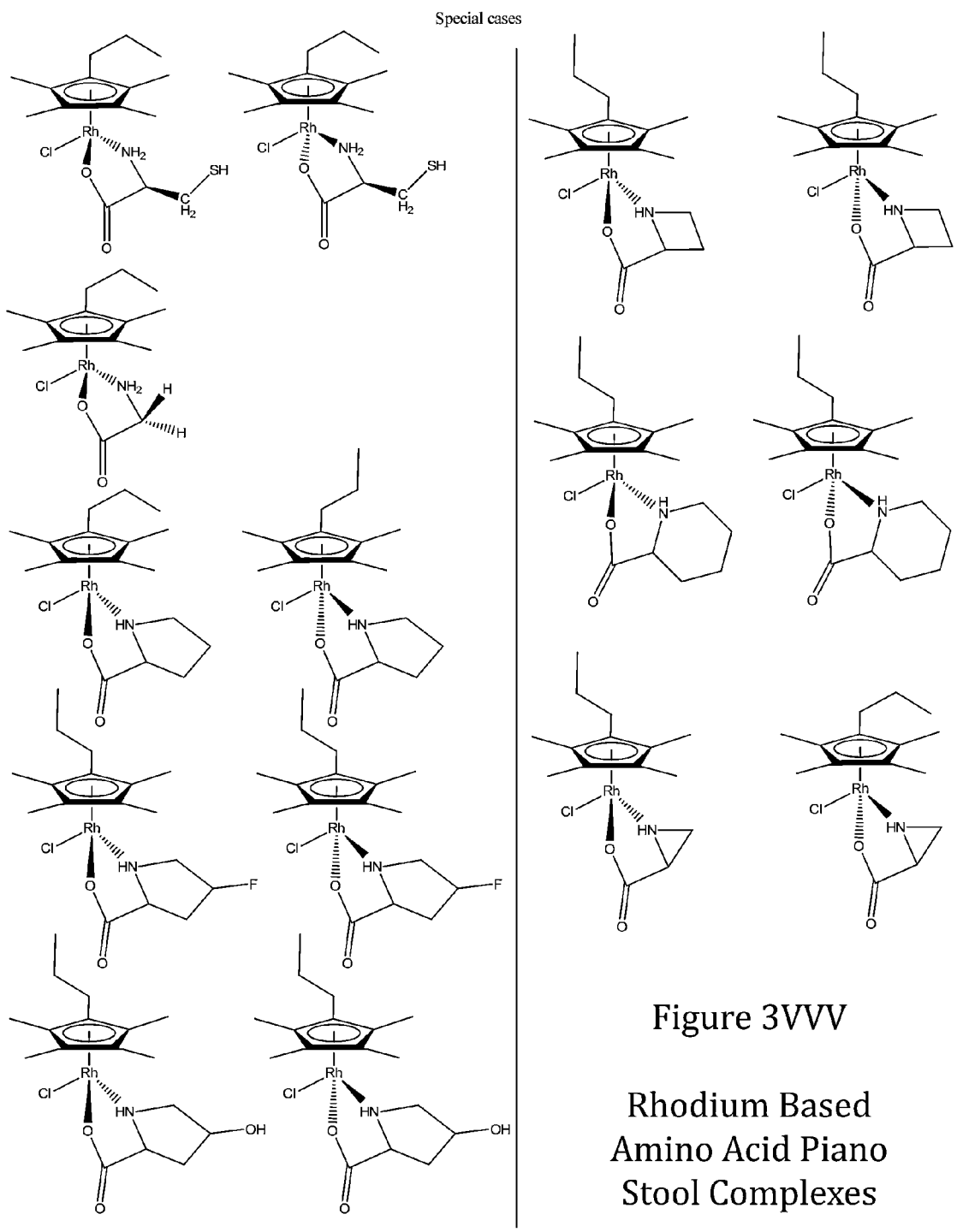
Figure 3VVV
Rhodium Based Amino Acid Piano Stool Complexes

TRANSITION METAL COMPLEXES OF AMINO ACIDS AND RELATED LIGANDS AND THEIR USE AS CATALYSTS, ANTI-MICROBIALS, AND ANTI-CANCER AGENTS

CROSS-REFERENCE TO RELATED APPLICATIONS

This application relies on the disclosure of and claims priority to and the benefit of the filing date of U.S. Provisional Application No. 61/547,844, filed Oct. 17, 2011, the disclosure of which is hereby incorporated by reference herein in its entirety.

BACKGROUND OF THE INVENTION

1. Field of the Invention

The present invention relates to the fields of chemistry and pharmaceuticals. Embodiments of the present invention provide transition metal complexes of amino acids. Transition metal complexes of embodiments of the invention may be used as antimicrobial, anti-malarial, and anti-cancer agents, as well as catalysts in chemical reactions. Such compounds of the invention are particularly useful for combating multi-drug resistance against a broad range of microbials, including gram positive and gram negative bacteria.

2. Description of Related Art

Recent studies show there are currently too few drugs in the pipeline that offer improved treatment over existing drugs and which are capable of treating infections caused by ESKAPE pathogens. The ESKAPE pathogens, i.e., the species *Enterococcus faecium, Staphylococcus aureus, Klebsiella pneumoniae, Acinetobacter baumannii, Pseudomonas aeruginosa*, and *Enterobacter*, are known for causing a majority of hospital infections and for being able to escape the effectiveness of currently approved drugs. Multi-drug resistant strains such as MRSA are growing and the WHO estimates two billion people are infected with a latent form of *M. tuberculosis*. See Schwartz M., Aug. 9, 2006, Drug-resistant strains of tuberculosis are more virulent than experts assumed, Stanford Report. To address this issue, the Infectious Diseases Society of America has launched a collaborative effort called the 10×'20 initiative with the goal of introducing ten new, safe, and effective antibiotics by the year 2020. See Clin Infect Dis. (2010) 50 (8):1081-1083, e-published Mar. 9, 2010, doi: 10.1086/652237.

Metals are known to play important roles in biological systems. Generally this is limited to first row transition metals. Second and third row metals are generally thought of as toxic in nature. The use of transition metal compounds in medicine has a rich history with one of the most well-known compounds being cis-Platin, a platinum containing compound that is a very effective anti-cancer compound for hard tumors.

A review of the literature examining studies on the biological activities of transition metal complexes shows that the bulk of the studies have been directed toward finding compounds active against various types of cancers. See Dabrowiak, J. C., Metals in Medicine. First ed.; John Wiley & Sons, Ltd: West Sussex, UK, 2009; (b) Hansen, H. R.; Farver, O. In Metals in medicine: inorganic medicinal chemistry, CRC Press: 2010; pp 151-171; (c) Bruijnincx, P. C. A.; Sadler, P. J., New trends for metal complexes with anticancer activity. Curr. Opin. Chem. Biol. 2008, 12, 197-206. Other transition metal complexes traditionally used to treat cancer are listed below, as Formulas A-C:

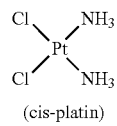
(cis-platin)

Formula A

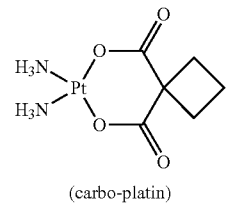
(carbo-platin)

Formula B

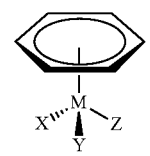
(metal arene complexes)

Formula C

Known mechanisms of action for transition metal drugs include having the structure for interstrand crosslink inhibiting (e.g., Formula D below) and preventing normal enzymatic functions of the DNA replication cycle. DNA has been isolated and examined using NMR and X-ray crystallographic studies performed. See Dabrowiak, Metals in Medicine; J. Wiley and Sons LTD, 2009 (Vol. 1).

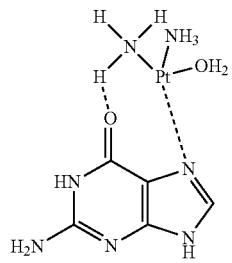

Formula D

Amino acids, the naturally occurring building blocks of proteins, make excellent ligands for transition metals, being able to bind in a bidentate fashion through the oxygen and nitrogen to the metal as illustrated below in Formulas E and F:

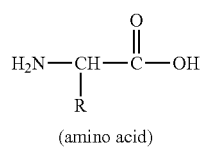
(amino acid)

Formula E

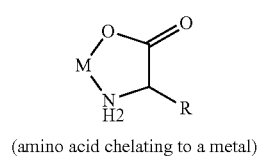
(amino acid chelating to a metal)

Formula F

Traditionally, amino acid complexes and transition metals have been used in non-biological roles. Catalysis using amino acid derivatives is popular due to the modular nature of amino acids, (changing the R group for example), and that amino acids offer an inexpensive source of chiral building blocks. Amino acids and their derivatives are commonly used in the asymmetric reduction of ketones to their corresponding alcohols. See Manville, C. V.; Docherty, G.; Padda, R.; Wills, M., Application of Proline-Functionalised 1,2-Diphenylethane-1,2-diamine (DPEN) in Asymmetric Transfer Hydrogenation of Ketones, European Journal of Organic Chemistry 2011, (34), 6893-6901; See Carmona, D.; Viguri, F.; Pilar Lamata, M.; Ferrer, J.; Bardaji, E.; Lahoz, F. J.; Garcia-Orduna, P.; Oro, L. A., Ruthenium amino carboxylate complexes as asymmetric hydrogen transfer catalysts, Dalton Transactions 2012, 41 (34), 10298-10308; see Ahlford, K.; Adolfsson, H., Amino acid derived amides and hydroxamic acids as ligands for asymmetric transfer hydrogenation in aqueous media, Catalysis Communications 2011, 12 (12), 1118-1121; and see Breuil, P.-A. R.; Reek, J. N. H., Amino Acid Based Phosphoramidite Ligands for the Rhodium-Catalyzed Asymmetric Hydrogenation, European Journal of Organic Chemistry 2009, (35), 6225-6230 ("Breuil 2009"). They have also been used in asymmetric reduction of alkenes. See Breuil 2009.

The discovery of cis-platin and other related platinum complexes jump-started the investigation of the platinum group's potential biological role. See Rosenberg, B., Platinum compounds: a new class of potent antitumour agents, Nature (London) 1969, 222 (5191), 385-6. Due to this, a large variety of platinum based amino acid complexes have been created. See Chandrasekharan, M., Cysteine complexes of palladium (II) and platinum(II), Inorganica chimica acta 1973, 7 (1), 88-90; and see Vicol, O., Some complex combinations of Pd(II) with methionine, Journal of inorganic & nuclear chemistry 1979, 41 (3), 309-315; and see Ziegler, C. J.; Sandman, K. E.; Liang, C. H.; Lippard, S. J., Toxicity of platinum(II) amino acid (N,O) complexes parallels their binding to DNA as measured in a new solid phase assay involving a fluorescent HMG1 protein construct readout, JBIC, J. Biol. Inorg. Chem. 1999, 4; 402-411; and see Slyudkin, O. P.; Tulupov, A. A., Chiral complexes of Pt with amino acids: Synthesis, structure, properties, Russ. J. Coord. Chem. 2005, 31, 77-85.

The most extensive work on platinum group metals and amino acids was done by Wolfgang Beck and co-workers. in a series of articles titled "Metal Complexes with Biologically Important Ligands." Their group has published on a variety of compounds with what are termed biologically important ligands and is at least up to 175 in a series of papers with this title, many of them being ligands derived from amino acids. See Schreiner, B.; Wagner-Schuh, B.; Beck, W., Metal complexes of biologically important ligands, CLXXV, Pentamethylcyclopentadienyl half-sandwich complexes of rhodium (III) and iridium(III) with Schiff bases from 2-(diphenylphosphino)benzaldehyde and alpha-amino acid esters, Zeitschrift fuer Naturforschung, B: A Journal of Chemical Sciences 2010, 65 (6), 679-686. The papers focused on synthesis, characterization, and interesting structural findings, but did not lend themselves to direct application.

Ruthenium based amino acid complexes have also been studied for their potential anti-cancer role. See Habtemariam, A.; Melchart, M.; Fernandez, R.; Parsons, S.; Oswald, I. D. H.; Parkin, A.; Fabbiani, F. P. A.; Davidson, J. E.; Dawson, A.; Aird, R. E.; Jodrell, D. I.; Sadler, P. J., Structure-Activity Relationships for Cytotoxic Ruthenium(II) Arene Complexes Containing N,N-, N,O-, and O,O-Chelating Ligands, J. Med. Chem. 2006, 49, 6858-6868. Other noble metals such as iridium and rhodium are often overlooked. Extension of amino acid based platinum metal systems to areas other than anti-cancer treatments is an area of interest as well.

It has been known to use organometallic compounds for their antimicrobial properties. Traditionally, synthesis processes focused on creating compounds similar to cis-platin. One such synthesis scheme is illustrated below in Scheme A. See, e.g., Vasić, G. P.; Glodjović, V. V.; Radojeviće, I. D.; Stefanović, O. D.; Comić, L. R.; Djinović, V. M.; Trifunović, S. R., *Stereospecific ligand and their complexes: V. Synthesis, characterization and antimicrobial activity of palladium(II) complexes with some alkyl esters of (S,S)-ethylenediamine-N,N-di-2-propanoic acid, Inorg. Chim. Acta,* 63 (2010) 3606-3610; ISSN: 0020-1693; DOI: 10.1016/j.ica.2010.05.046. Such compounds, however, routinely were found to have high cytotoxicity effects. Additionally, using these models, minimum inhibitory concentrations (MIC) achieved have only been around 30 ug/mL. Accordingly, due to the high toxicity and low effectiveness, work on these types of compounds has slowed.

Scheme A

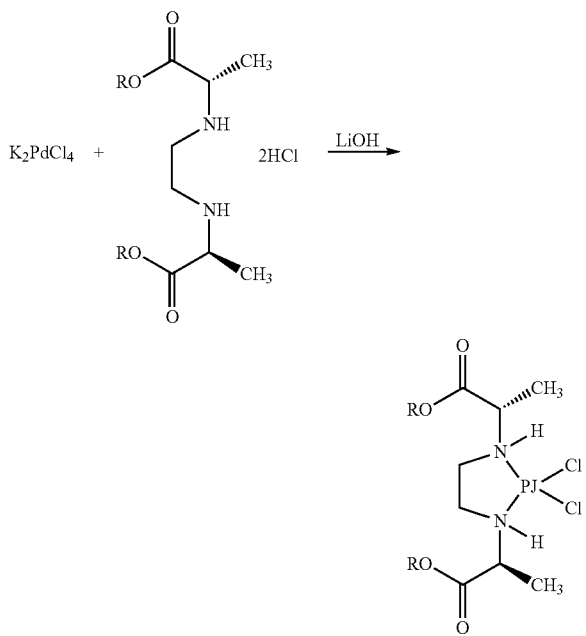

The work was performed to provide a set of ligands that could have ester variation as well as stereo isomer variation using ethylene diamine derivatives, with palladium as the main metal of focus. Examples of such compounds are illustrated in Formulas G-I below.

Formula G

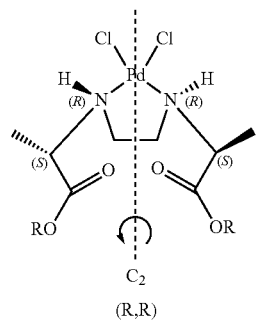

-continued

Formula H

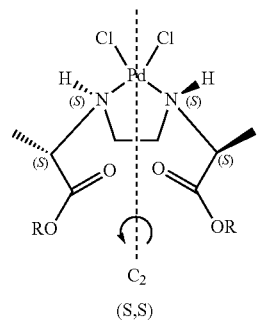

(S,S)

Formula I

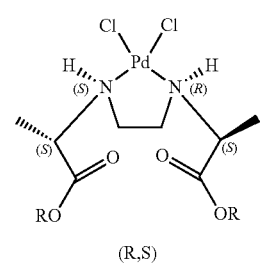

(R,S)

Other attempts at synthesizing organometallic compounds for use as antimicrobials included using existing antimicrobials as ligands. In some cases, such compounds were shown to combat developed resistance in some organisms. In particular, the coordination of zinc, cadmium, nickel, palladium or platinum with such ligands has been studied. See Zengin, H.; Dolaz, M.; Golcu, A. Curr. Anal. Chem. 2009, 5, 358. Coordination showed to have a greater effect on inhibition than the antimicrobial by itself. An example of using an existing antimicrobial (Lorcarbef, or LOR) as a ligand is illustrated in Formula J.

Formula J

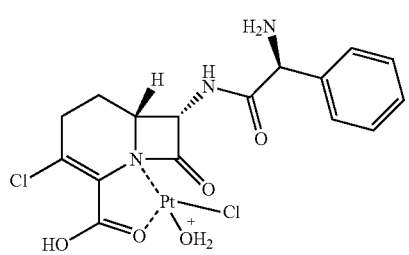

Another approach involved the use of macrocyclic ligands. See Soni Rani, Sumit Kumar, Sulekh Chandra, Spectrochimica Acta Part A: Molecular and Biomolecular Spectroscopy Volume 78, Issue 5 2011, 1507-1514. The idea was to create a cyclic tetradentate ligand for Pd, Pt, Ru, and Ir and modify the —R groups on outer ring carbons to increase either hydrophobic or hydrophilic properties, as shown in Formula K.

Formula K

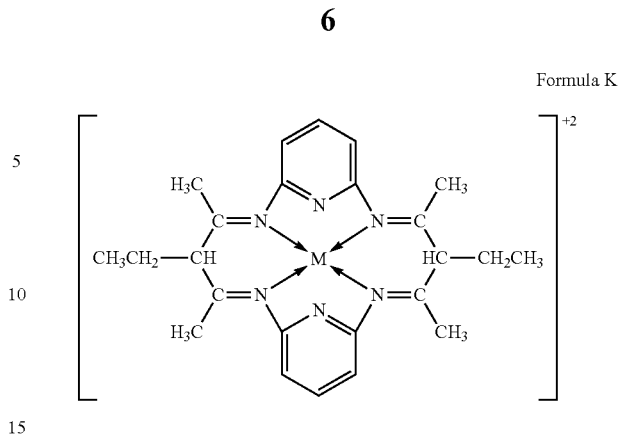

Other techniques involving modifying current antimicrobials with an organometallic group to create new effects to overcome resistance have been used. For example, it has been known to modify pentamidine with $Ir[COD]Cl_2$, which has been used to combat *P. jirovecii*, a severe type of pneumonia seen in HIV patients.

Formula L

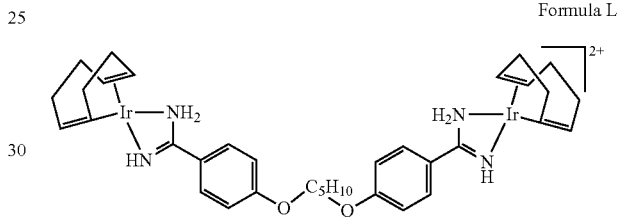

Most work for clinical applications have been with malaria (Plasmodium). For example, as illustrated in Formula M below, the incorporation and modification of chloroquine to metal arene structure is known to provide synergistic effects (Ferroquine—currently stage II). See Beckford, F.; Dourth, D.; Shaloski, M.; Didion, J.; Thessing, J.; Woods, J.; Crowell, V.; Gerasimchuk, N.; Gonzalez-Sarrias, A.; Seeram, N. P., Half-sandwich ruthenium-arene complexes with thiosemicarbazones: synthesis and biological evaluation of [($\eta^6$-p-cymene)Ru(piperonal thiosemicarbazones)Cl]Cl complexes, 2011 August; 105(8):1019-29, J. Inorg. Biochem. 2011. Still few compounds are available to combat other bacterial infections.

Formula M

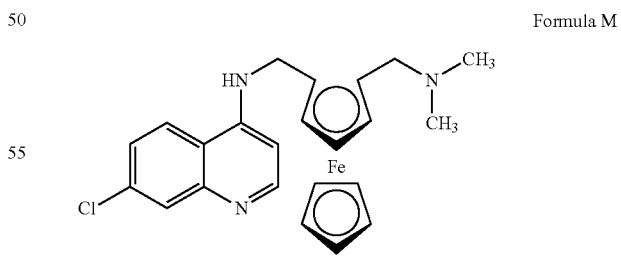

Very few studies, however, have examined the biological activity in general and anti-microbial activity in specific of amino acid complexes of transition metals. Al-Fregi et al researched the antibacterial activity of four complexes of the type [Pt(AA)(BAMC)] where AA is a dicarboxylate amino acid of glutamate or aspartate and the (BAMC) is a 1,4-bis (amino methylene)cyclohexane. See Al-Fregi, A. A.; Abood, H. A. A.; Al-Saimary, I. E., The antibacterial activity of 1.4 (amino methylene)cyclohexane platinum (II) and palladium (II) dicarboxylate amino acid complexes. Internet J. Microbiol. 2007, 4, DOI: 10.5580/1a1f. These complexes were studied in vitro against eight bacteria including *Staph aureus, Staph epidermis*, β-*hemolytic streptococci, viridance streptococci, E. coli, Enterobacter, Klebsiella*, and *Pseudomonas aeruginosa*. The lowest minimum inhibitory concentration (MIC) value found was 100 ug/mL, with most showing antibacterial activity only at 250 ug/mL or higher.

Spera et al evaluated palladium (II) complexes of S-allyl-L-cysteine through antibacterial assays. See Spera, M. B. M.; Quintao, F. A.; Ferraresi, D. K. D.; Lustri, W. R.; Magalhaes, A.; Formiga, A. L. B.; Corbi, P. P., Palladium(II) complex with S-allyl-L-cysteine: new solid-state NMR spectroscopic measurements, molecular modeling and antibacterial assays. Spectrochim Acta A Mol Biomol Spectrosc 2011, 78 (Copyright (C) 2011 U.S. National Library of Medicine.), 313-8. While their methodology does not allow for an accurate calculation of MIC values, ballpark calculations would indicate that the lowest possible MIC values are in the 200+ ug/mL range and probably significantly higher. The complex was most effective against *Staph aureus* (Gram positive), *E. coli*, and *Pseudomonas aeruginosa* (Gram negative). However, testing of simple palladium chloride complexes shows the activity most likely stems from the $Pd^{+2}$ ion and not from any properties of the complexes themselves.

Currently there is limited research in the field of organometallic anti-microbials, a class of anti-microbials with promising potential. As can been seen from previous attempts at developing effective anti-microbials, what is especially needed are biologically active organometallic compounds to combat multi-drug resistant strains of bacteria.

SUMMARY OF THE INVENTION

Organometallic complexes according to embodiments of the invention provide potent anti-bacterial agents against resistant strains of bacteria and mycobacteria. The tailoring of organometallic based anti-microbials is highly beneficial due to the fact that these compounds are highly customizable, there are several different metal arene combinations, there are numerous naturally occurring amino acids, and they are relatively cheap and have uncomplicated syntheses.

A broad range of amino acid based transition metal complexes are provided by embodiments of the invention. Generally provided are three broad categories of such complexes. Category I comprises bis-amino acid complexes of square planar metal complexes comprising, for example, palladium and platinum. Category II comprises octahedral amino acid complexes of, for example, iridium(III) with other ancillary ligands such as trialkylphosphines. Category III comprises "piano stool" complexes of for example ruthenium, osmium, rhodium and iridium. Category IV comprises square planar complexes of metals.

Objects of the invention include Category I complexes, for example, which comprise bis-amino acid complexes of any of the following types of Formula 1:

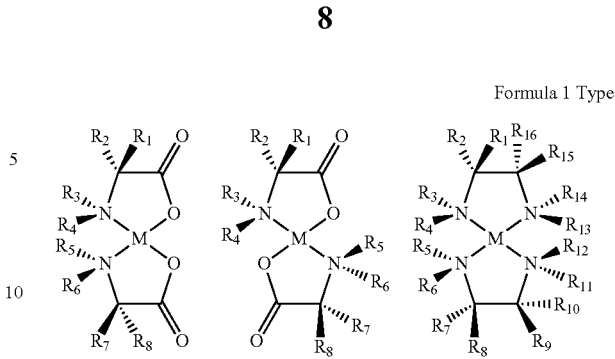

Formula 1 Type wherein $R_{1-16}$ are each independently chosen from hydrogen and a $C_{1-20}$ alkyl group, or one or more of $R_{1-16}$, together or independently, are capable of forming a 3-, 4-, 5-, 6-, 7-, or 8-membered ring together with the nitrogen or carbon atom to which they are attached and an adjacent carbon or nitrogen atom; and wherein M is a lanthanide, actinide, or transition metal;

or an enantiomer thereof, or a diastereoisomer thereof, or a racemic mixture of stereoisomers thereof, or a salt thereof, or any combination thereof.

Category II octahedral amino acid complexes of the invention, for example, can comprise any compound of any of the following types of Formula 2 complexes:

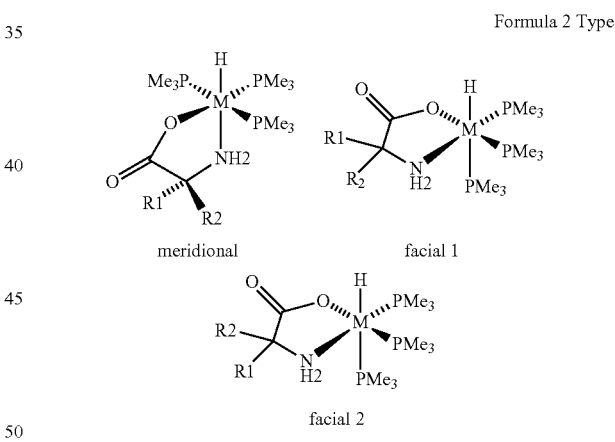

Formula 2 Type wherein M is chosen from cobalt, rhodium, iridium, iron, ruthenium, osmium, manganese, technetium, and rhenium, or any other transition or lanthanide or actinide metal; and wherein $R_{1-2}$ are the same or different and are chosen from H, $CH_3$, $CH_2CH_3$, $C_6H_5$, and $C_{1-20}$ alkyl groups, and optionally $R_1$ and/or $R_2$ either together or separately form a 3-, 4-, 5-, 6-, 7-, or 8-membered ring with the carbon to which they are attached and with nitrogen to which the carbon is attached;

or an enantiomer thereof, or a diastereoisomer thereof, or a racemic mixture of stereoisomers thereof, or a salt thereof, or any combination thereof.

Further objects of the invention include Category III complexes, which can comprise any piano stool complex of Formula 3:

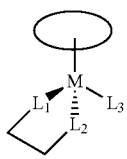

Formula 3 Type wherein M is chosen from any transition, lanthanide, or actinide metal; and wherein $L_1$, $L_2$ is a chelating amino acid and where $L_3$ is a halogen; and wherein

is an aromatic ligand capable of pi-complexing to the metal;

or an enantiomer thereof, or a diastereoisomer thereof, or a racemic mixture of stereoisomers thereof, or a salt thereof, or any combination thereof.

Also included within the scope of embodiments of the invention are Category IV complexes, which can comprise any square planar complex of Formula 4:

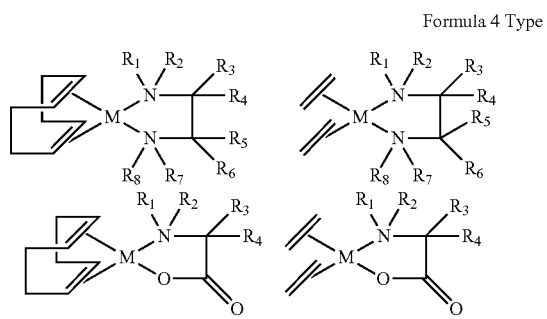

Formula 4 Type wherein $R_1$-$R_8$ are the same or different and are chosen from H, $CH_3$, $CH_2CH_3$, $C_6H_5$ and any $C_{1-20}$ alkyl substituent; wherein

is an unsubstituted $C_{1-20}$ alkene group, or an alkene group substituted with a chelating dialkene or substituted with a substituted or unsubstituted olefin or cyclic olefin; and wherein M is any transition or lanthanide or actinide metal; or an enantiomer thereof, or a diastereoisomer thereof, or a racemic mixture of stereoisomers thereof, or a salt thereof, or any combination thereof.

Such square planar metal complexes of Formula 4 can include complexes wherein the alkene group substituted with a chelating dialkene is an alkene group substituted with norbornadiene. Additional square planar metal complexes of Formula 4 can include such compounds wherein the alkene group is substituted with an olefin or cyclic olefin chosen from propene, butene or cyclooctene. Complexes of Formula 4 can comprise a metal M chosen from cobalt, rhodium, iridium, iron, ruthenium, osmium, manganese, technetium, and rhenium.

Methods of using bis-amino acid complexes of Formula 1, and/or octahedral amino acid complexes of Formula 2, and/or piano stool complexes of Formula 3, and/or square planar complexes of Formula 4, or enantiomers thereof, or diastereoisomers thereof, or racemic mixtures of stereoisomers thereof, or salts thereof, or any combination thereof, as a catalyst, or as an anti-microbial, anti-bacterial, or anti-cancer agent are also encompassed by the invention.

Additionally, methods of treating subjects afflicted with disease relating to microbials, bacteria and cancer are also included within embodiments of the invention. For example, methods comprising administering any one or more of bis-amino acid complexes of Formula 1, and/or octahedral amino acid complexes of Formula 2, and/or piano stool complexes of Formula 3, and/or square planar complexes of Formula 4, or enantiomers thereof, or diastereoisomers thereof, or racemic mixtures of stereoisomers thereof, or salts thereof, or any combination thereof, to a subject in an amount sufficient to kill target microbial, bacteria, or cancer cells and reduce or prevent symptoms of disease associated with the target are included within embodiments of the present invention.

As will be discussed in further detail below, the structure-activity relations that seem to be factors in the success of such compounds include that an amino acid ligand with a hydrophobic side chain is preferred, that a hydrogen-bond donor on the amino acid ligand is preferred, and/or that an L-amino acid would seem to be preferred over D-amino acids.

Various configurations of complexes of embodiments of the invention can be used to treat gram positive bacteria, gram negative bacteria, mycobacteria, plasmodia, amoebae, yeasts, and fungi, for example. Specific target micro-organisms that complexes of the invention can be used to treat include gram-positive bacteria, such as *Staphylococcus aureus*, methicilin-resistant *S. aureus* (MRSA), *M. luteus* and *Staphylococcus epidermidis*, which typically have incubation periods on the order of about 48 hours, and mycobacteria, including for example *M. avium, M. chelonae, M. intracelluare, M. marinum, M. smegmatis, M. abscessus*, which typically have an incubation period of about 7-10 days. Additionally, proteobacteria and *E. coli* are also targets within the scope of the invention. In the context of this specification it its noted that the target bacteria may be a known lab strain or a strain isolated from a patient for in vitro treatment or in vivo treatment can also be performed.

Other target micro-organisms include, but are not limited to, *P. jirovecii, Staph epidermis, β-hemolytic streptococci, viridance streptococci, Enterobacter, Klebsiella, Pseudomonas, Pseudomonas aeruginosa, Plasmodium, Actinobacteria, Actinomyces, Actinomyces israelii, Bacillales, Bacillus Clostridium, Clostridium acetobutylicum, Clostridium aerotolerans, Clostridium argentinense, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paraputrificum, Clostridium perfringens, Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium,*

*Clostridium tetani, Clostridium thermosaccharolyticum, Clostridium tyrobutyricum, Corynebacterium, Corynebacterium bovis, Corynebacterium diphtherias, Corynebacterium granulosum, Corynebacterium jeikeium, Corynebacterium minutissimum, Corynebacterium renale, Enterococcus, Lactobacillales, Listeria, Nocardia, Nocardia asteroides, Nocardia brasiliensis, Nocardia farcinica, Propionibacterium acnes, Rhodococcus equi, Sarcina, Solobacterium moorei, Staphylococcus, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus muscae, Staphylococcus nepalensis, Staphylococcus pettenkoferi, Staphylococcus saprophyticus, Staphylococcus succinus, Staphylococcus warneri, Staphylococcus xylosus, Strangles, Streptococcus, Streptococcus agalactiae, Streptococcus anginosus, Streptococcus bovis, Streptococcus canis, Streptococcus iniae, Streptococcus lactarius, Streptococcus mitis, Streptococcus mutans, Streptococcus oxalis, Streptococcus parasanguinis, Streptococcus peroris, Streptococcus pneumoniae, Streptococcus pyogenes, Streptococcus ratti, Streptococcus salivarius, Streptococcus sanguinis, Streptococcus sobrinus, Streptococcus suis, Streptococcus salivarius* subsp. *thermophilus, Streptococcus uberis, Streptococcus vestibularis,* and *Streptococcus viridans*. Even more specifically, target micro-ogranisms can include, but are not limited to, the following mycobacteria for example: *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis," M. colombiense, M. indicus pranii, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. africanum, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense*, and *M. tokaiense*.

Minimum Inhibitory Concentrations (MIC) of complexes according to embodiments of the invention can range from values approaching 0 to about 500 μg/mL. Preferred complexes of the invention according to Categories I, II, III, or IV have a MIC ranging from almost 0 to about 10 μg/mL, or from about 1-15 μg/mL, or from about 2-20 μg/mL, or from about 3-25 μg/mL, or from about 4-8 μg/mL, or from about 30-50 μg/mL, or from about 40-75 μg/mL, or for example from about 50-100 μg/mL, or from about 60-125 μg/mL, or from about 80-150 μg/mL, or from about 90-180 μg/mL, or from about 110-200 μg/mL, or from about 130-250 μg/mL, or from about 220-300 μg/mL, or from about 240-350 μg/mL, or from about 260-500 μg/mL, and including from about 280-400 μg/mL.

BRIEF DESCRIPTION OF THE DRAWINGS

The accompanying drawings illustrate certain aspects of some of the embodiments of the present invention, and should not be used to limit or define the invention. Together with the written description, the drawings serve to explain certain principles of embodiments of the invention.

FIGS. 1A-C are schematic diagrams illustrating inventive Category I type structures of crystallographically characterized amino acid complexes of palladium.

FIGS. 1D-E are schematic diagrams illustrating representative palladium based Category I type complexes according to embodiments of the invention.

FIGS. 2A-B are schematic diagrams illustrating inventive Category II type structures of crystallographically characterized amino acid complexes of Iridium(III).

FIGS. 3A-B are schematic diagrams illustrating inventive Category III type structures of crystallographically characterized amino acid piano stool complexes of Iridium (Ir) and Rhodium (Rh) according to embodiments of the invention.

FIGS. 3C-N are schematic diagrams illustrating representative iridium based complexes of Category III according to embodiments of the invention.

FIGS. 3O-LL are schematic diagrams illustrating representative osmium based complexes of Category III according to embodiments of the invention.

FIGS. 3MM-JJJ are schematic diagrams illustrating representative ruthenium based complexes of Category III according to embodiments of the invention.

FIGS. 3KKK-VVV are schematic diagrams illustrating representative rhodium based complexes of Category III according to embodiments of the invention.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Embodiments of the invention provide new and effective anti-microbial and anti-cancer drugs, which are also useful as catalysts in various chemical reactions. Inventive Category I, II, III, and IV compounds, as well as other effective complexes, are disclosed in more detail below. Specific embodiments of the present invention provide various coordination complexes of metals and amino acid ligands useful in the treatment against disease. Methods of synthesizing these drugs are provided, as well as methods of using them including details regarding their effectiveness against various target microbials and cancers.

Specific embodiments of the invention provide methods of treating disease comprising administering to a patient in an effective amount one or more coordination complexes of Categories I, II, III, and/or IV of the invention, wherein the coordination complex or portion thereof contacts and/or interacts with tissues, cells, or a microorganism associated with the disease in a manner sufficient to kill the target microorganism and/or reduce the disease state. Diseases treatable according to embodiments of the invention include malaria, microbial infections, bacterial infections, and cancer. Any compound specifically disclosed or generally disclosed within a genus of compounds described in this specification can be used in the methods of treating according to the invention.

Category I. Bis-Amino Acid Complexes.

Complexes of Formula 1 generally comprise one of the following structures:

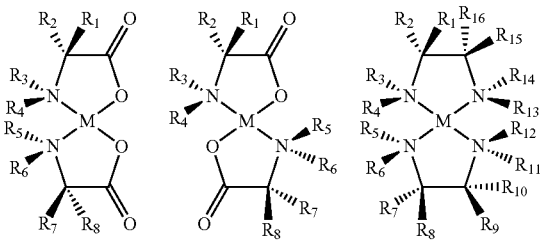

Bis-Amino Acid Complexes of Formula 1 wherein $R_{1-16}$ are each independently chosen from hydrogen and a $C_{1-20}$ alkyl group, or one or more of $R_{1-16}$, together or independently, are capable of forming a 3-, 4-, 5-, 6-, 7-, or 8-membered ring together with the nitrogen or carbon atom to which they are attached and an adjacent carbon or nitrogen atom (such as the Formula 1 type structures in FIG. 1E); and wherein M is a lanthanide, actinide, or transition metal.

In embodiments, preferably $R_{1-16}$ are each independently chosen from hydrogen and $C_{1-20}$ alkyl groups, and wherein preferably $R_{1-16}$ are chosen from hydrogen and, whether substituted or unsubstituted or saturated or unsaturated methyl, ethyl, propyl, butyl, and $C_{5-6}$ alkyl, $C_{1-6}$ cycloalkyl, including phenyl, benzyl, and a $C_6H_6$ group; and M is a lanthanide, actinide, or transition metal capable of forming a chelate complex.

In embodiments of Formula 1 type complexes of the invention, preferably, M is chosen from Co, Rh, Ir, Ni, Pd, Pt, Cu, Ag, or Au.

Optionally $R_{1-2}$, $R_{7-10}$, and $R_{15-16}$ are chosen from H, $CH_3$, $CH(CH_3)CH_2CH_3$, $CH_2CH(CH_3)_2$, $CH(CH_3)_2$, $CH_2(C_6H_5)$, $CH_2(C_8H_6N)$, $CH_2(C_6H_4OH)$, $CH_2(CO)NH_2$, $CH_2SH$, $CH_2CH_2(CO)NH_2$, $CH_2CH_2SCH_3$, $CH_2OH$, $CH(OH)CH_3$, $CH_2COOH$, $CH_2CH_2COOH$, $CH_2CH_2CH_2NH(C=NH)NH_2$, $CH_2(CH_3H_3N_2)$, and $CH_2CH_2CH_2CH_2NH_2$.

Optionally $R_{1-2}$ and $R_{3-4}$, together or independently, or $R_{5-6}$ and $R_{7-8}$, together or independently, or $R_{6-10}$ and $R_{11-12}$, together or independently, or $R_{13-14}$ and $R_{15-16}$, together or independently, are capable of forming a 3-, 4-, 5-, 6-, 7- or 8-membered ring including the nitrogen or carbon atom to which they are attached and an adjacent carbon or nitrogen atom, and wherein the ring can be substituted or unsubstituted with additional $R_{1-16}$ groups.

Optionally $R_{1-2}$ and $R_{15-16}$, together or independently, or $R_{7-8}$ and $R_{6-10}$, together or independently, are capable of forming a 3-, 4-, 5-, 6-, 7- or 8-membered ring including the carbon atom to which they are attached and an adjacent carbon atom, and wherein the ring can be substituted or unsubstituted with additional $R_{1-16}$ groups as defined above. In the context of this specification, it is understood that such fused ring structures in essence replace the $R_{1-16}$ groups which would otherwise be substituents at the indicated locations (usually forming a ring structure between the nitrogen and an adjacent carbon atom or forming a ring structure between two adjacent carbon atoms). This is true for any of the complexes of any of the Category I, II, III, or IV complexes described or illustrated in this specification.

A general procedure for the preparation of bis-amino acid complexes according to embodiments of the invention is shown in Scheme 1 below:

Scheme 1. Synthesis of bis-amino acid complexes (Formula 1 type)

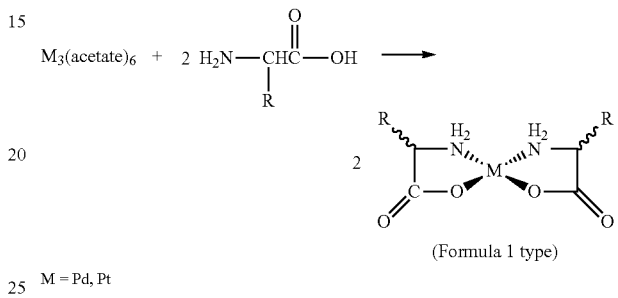

M = Pd, Pt

According to specific embodiments an appropriate precursor compound, such as a Pd(II) or Pt(II) precursor compound or other metal containing compound, is dissolved in water or an alcohol/water mixture and allowed to react with slightly more than two equivalents of an amino acid. Particularly useful precursors can include, for example, palladium(II) and platinum(II) acetate, palladium(II) halides such as palladium (II) chloride, and salts of the tetrahalopalladate(II) ions such as potassium tetrachloropalladate. According to embodiments of the invention, bis-amino acid complexes of Formula 1 can be formed from any amino acid or derivatives thereof. The scope of the invention also includes such compounds of Formula 1 where one or more of the hydrogen atoms on the nitrogen groups, depending on the amino acid(s) precursor used, is replaced with a $C_{1-20}$ alkyl group to result in one or more alkyl substituents on the nitrogen atoms.

Amino acids appropriate for forming any of the complexes according to the invention, for example of Categories I, II, III, or IV and so son can include, but are not limited to Histidine (his), Alanine (ala), Arginine (arg), Leucine (leu), Isoleucine (ile) Asparagine (asn), Lysine (lys), Aspartic acid (asp), Methionine (met), Cysteine (cys), Phenylalanine (phe), Glutamic acid (glu), Threonine (thr), Glutamine (gln), Tryptophan (trp), Glycine (gly), Valine (val), Ornithine (orn), Proline (pro), Selenocysteine (sec), Serine (ser), Taurine (tau), and Tyrosine (tyr), and derivatives thereof. According to embodiments of the invention, amino acids that can be used can also include any molecule comprising amine and carboxylic acid functional groups, as well as one or more side chains.

Compounds of Formula 1 can be prepared, for example, according to the following synthesis procedure. A reaction flask can be charged with 0.15 mmol palladium acetate, 0.30 mmol of amino acid (2 equivalents), 2.5 mL of 50/50 (v/v) acetone/water, and a micro stir bar. The reaction solution is stirred magnetically for approximately 16 hours. The reaction solution turns from a homogeneous clear red-orange to a clear straw/yellow supernatant with a yellow to white precipitate. An odor of acetic acid is noted upon opening the vial. The supernatant is pipetted off to a separate flask and allowed to naturally evaporate yielding crystalline material suitable for catalytic studies. The precipitate is washed with 2×2 mL of distilled water and dried under vacuum. Compounds are analyzed by $^1$H and $^{13}$C NMR, high resolution MS, and X-ray diffraction where suited.

Example I

Synthesis of bis-N,N-dimethylglycinato palladium(II) [DH1-27A]

This exemplary Formula 1 complex, bis-N,N-dimethylglycinato palladium(II), was prepared by charging a four dram vial with 0.0337 grams palladium(II) acetate (1.50×10$^{-4}$ mol) and 2.5 mL of 1:1 (v/v) acetone:water. The mixture was stirred until completely dissolved. To this was added 0.0312 grams N,N-dimethylglycine (3.03×10$^{-4}$ mol, 2.02 equivalents) and left to stir overnight. The reaction solution turned from a dark red-orange to a clear yellow with an off-white precipitate on overnight stirring. An odor of acetic acid was noted when the vial was opened. Supernatant was removed to a new flask and was naturally evaporated until ~0.25 mL remained, with clear yellow needles observed to form. The precipitate was triturated with 2×2 mL H$_2$O and dried under vacuum to yield 43.3 mg product (92.9% yield). Pd(C$_4$H$_8$NO$_2$)$_2$ was identified on the basis of the following data: $^1$H NMR (400 MHz, D$_2$O, δ): 3.42 (s, 2H), 2.69 (s, 6H). MS m/z (relative intensity): 309.0217 (10.8%), 310.0231 (22.4%), 311.0216 (28.8%), 313.0219 (26.2%), 315.0230 (11.8%). X-Ray Crystallography: Mo Kα radiation.

The structure of the resulting Formula 1 complex is shown below:

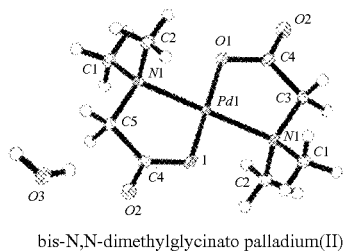

bis-N,N-dimethylglycinato palladium(II)

Example II

Synthesis of bis-prolinato palladium(II) [DH1-29A]

Additionally, Formula 1 compound, bis-prolinato palladium(II) [DH1-29A] was prepared as follows: A four dram vial was charged with 0.0225 grams palladium(II) acetate (1.50×10$^{-4}$ mol) and 2.5 mL of 1:1 (v/v) acetone:water. The mixture was stirred until completely dissolved. To this was added 0.0243 grams proline (3.01×10$^{-4}$ mol, 2.02 equivalents) and left to stir overnight. The reaction solution turned from a dark red-orange to a clear yellow on overnight stirring, with a pale yellow precipitate. An odor of acetic acid was noted when the vial was opened. The supernatant was pipetted into a new vial and allowed to evaporate. Upon crystallization, clear yellow needles were observed. The precipitate was triturated with 2×2 mL H$_2$O and dried under vacuum to yield 31.7 mg product (94.5% yield). Pd(C$_5$H$_8$NO$_2$)$_2$ was identified on the basis of the following data: $^1$H NMR (400 MHz, Deuterium Oxide) δ 3.91-3.66 (m, 1H), 3.15-2.74 (m, 2H), 2.26-1.53 (m, 4H). MS m/z (relative intensity): 333.0223 (10.8%), 334.0236 (22.4%), 335.0224 (28.8%), 337.0224 (26.2%), 339.0236 (11.8%). X-Ray Crystallography: Mo Kα radiation.

The structure of the resulting Formula 1 complex is shown below:

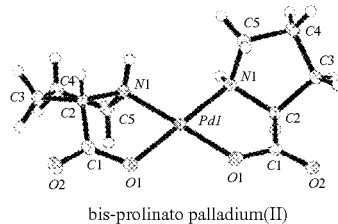

bis-prolinato palladium(II)

Indeed, any number of palladium based Formula 1 complexes can be prepared by similar methods. Representative Formula 1 complexes within the scope of embodiments of the present invention can include but not limited to Pd(alanine)2, Pd(arginine)2, Pd(asparagine)2, Pd(aspartic acid)2, Pd(cystine)2, Pd(glutamine)2, Pd(glutamic acid)2, Pd(glycine)2, Pd(n-methyl glycine)2, Pd(m,n-dimethylglycine)2, Pd(2,2-diphenylglycine)2, Pd(L-phenylglycine)2, Pd(D-phenylglycine)2, Pd(histadine)2, Pd(isoleucine)2, Pd(leucine)2, Pd(lysine)2, Pd(methionine)2, Pd(phenylalanine)2, Pd(proline)2, Pd(N-methyl proline)2, Pd(serine)2, Pd(threonine)2, Pd(tryptophan)2, Pd(tyrosine)2, Pd(valine)2, Pd(D-valine)2, Pd(tert-leucine)2, Pd(hydroxyproline)2, Pd(4-fluoroproline)2, Pd(benzylproline)2, Pd(cysteine)2, Pd(L-pipecolinic acid)2, Pd(L-azetidine-2-COOH)2, and Pd(N-methyl-L-phenylglycine)2. Although these specific examples of Category I type compounds are provided with palladium as the metal, included within the scope of the invention are such compounds where palladium is replaced with any of a lanthanide, actinide, or transition metal capable of forming a chelate complex, and especially where the metal is chosen from cobalt (Co), rhodium (Rh), iridium (Ir), nickel (Ni), platinum (Pt), copper (Cu), silver (Ag), and gold (Au).

The syntheses have been carried out with a variety of naturally occurring and unnatural amino acids with both the D and L enantiomers. All compounds were characterized by NMR spectroscopy and mass spectrometry. In a number of cases, single crystal x-ray crystallography was also used to determine the absolute structure of the complexes. An analysis by XRD (x-ray diffraction) can be performed by any method. For example, in embodiments of the invention, and in particular the structures illustrated in FIGS. 1A-C, 2A-B, and 3A-B, X-ray diffraction data were collected on an Oxford Diffraction Gemini Ultra diffractometer equipped with an EOS area detector and dual x-ray source. The x-ray source was operated in the Molybdenum Kα mode at 50 kV and 40 mA power with a 0.5 mm collimator. The detector distance was 55 mm. Crystals suitable for diffraction were mounted on a cryoloop and analyzed at 100K. Data collection, cell refinement, and data reduction were performed using CrysAlis PRO (Agilent, 2011). Software program(s) used to solve structure and refine structure included SHELXS97 (Sheldrick, 2008). Molecular graphics and the software used to prepare material for publication included OLEX2 (Dolomanov et al., 2009). Absolute configuration of the metal complexes was determined using anomalous dispersion.

Representative examples of crystallographically characterized palladium type bis-amino acid complexes of the invention are provided in FIGS. 1A-C. Although palladium based compounds are illustrated, it is understood that such compounds can also be made wherein the palladium is replaced with any of a lanthanide, actinide, or transition metal capable of forming a chelate complex, and especially where the metal is chosen from cobalt (Co), rhodium (Rh), iridium (Ir), nickel (Ni), platinum (Pt), copper (Cu), silver (Ag), and gold (Au).

Figure 1D:
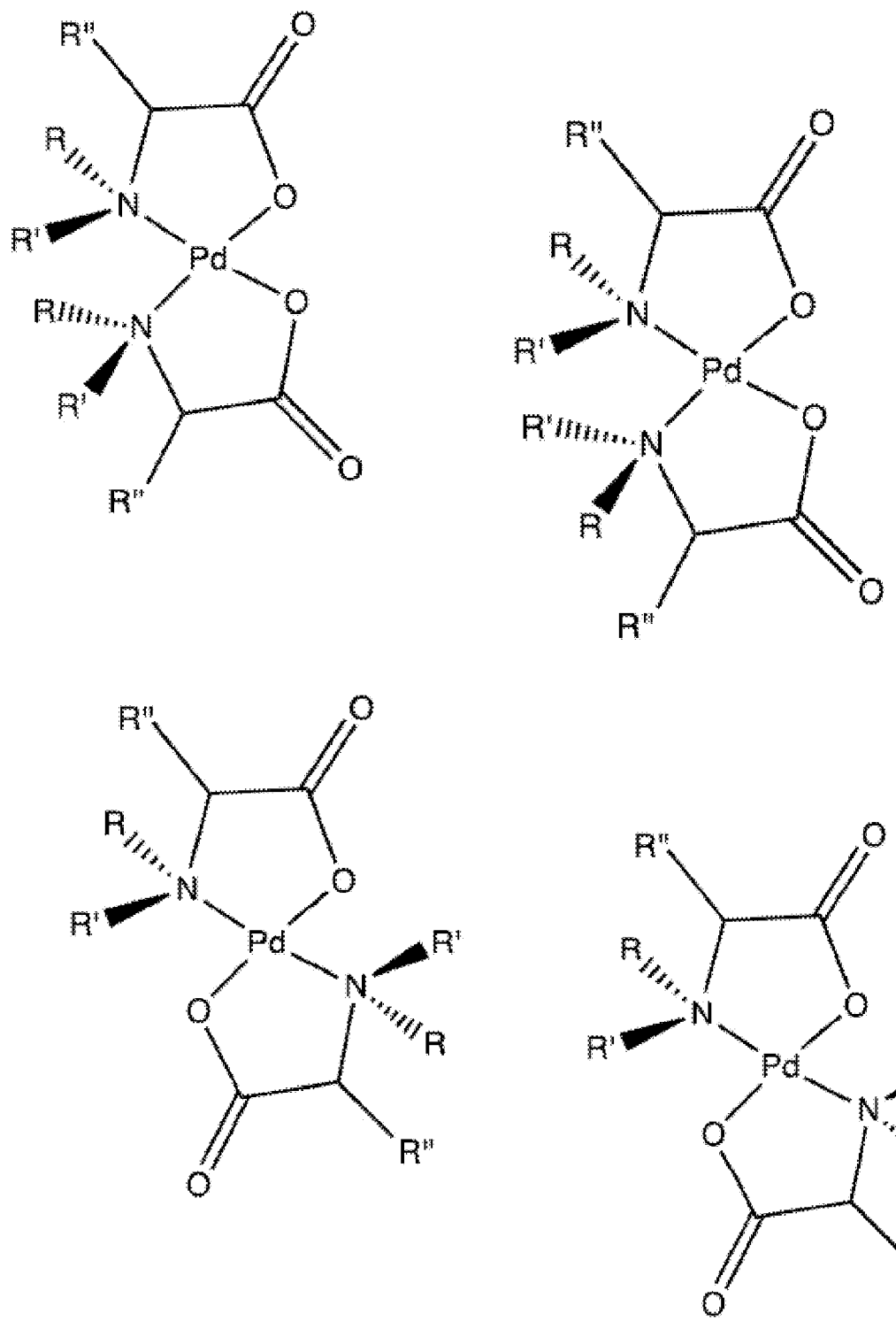
Figure 1E:
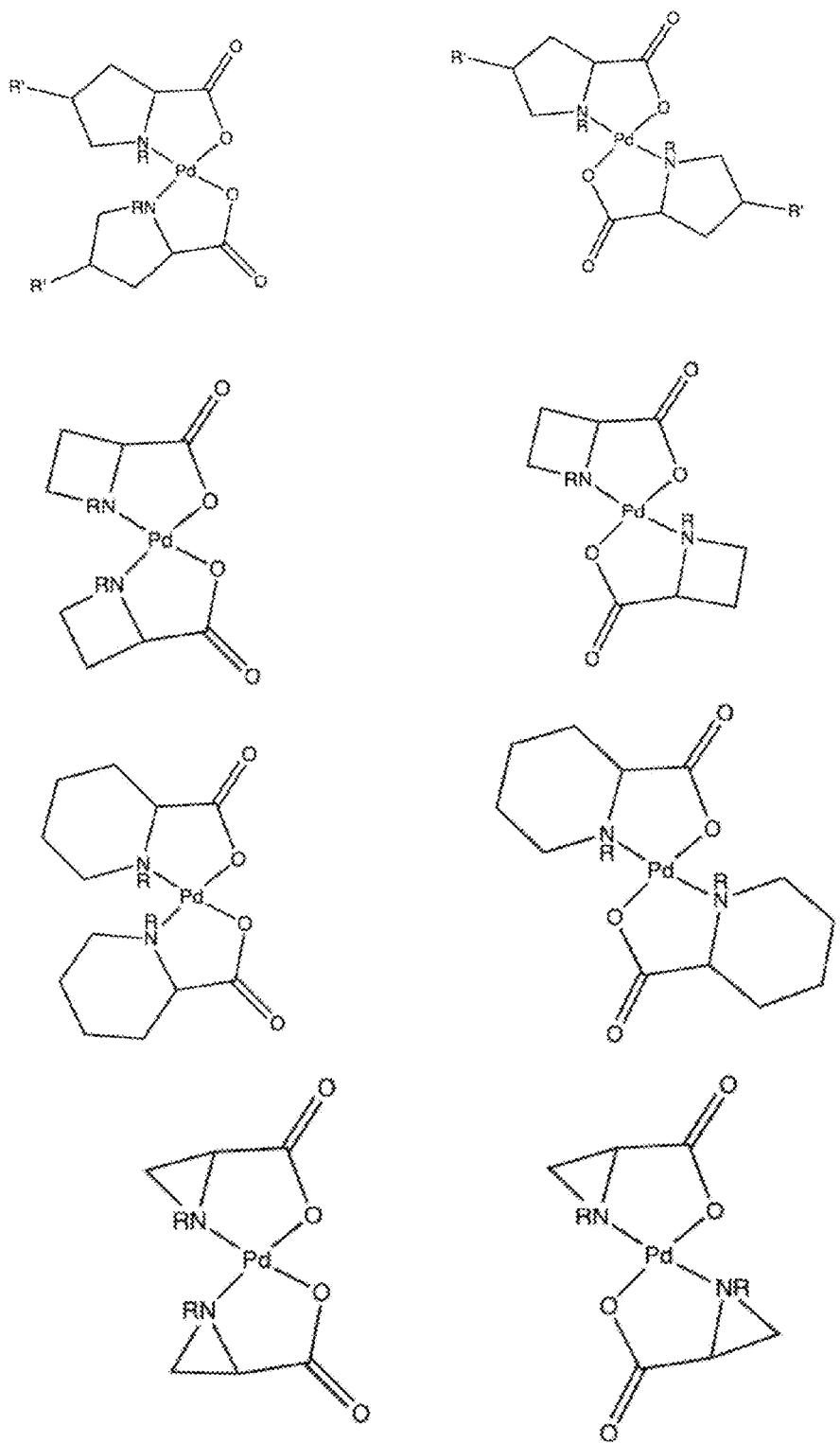

Additional exemplary compounds of Category I are illustrated in FIGS. 1D-E.

In the structures of FIG. 1D, R and R' are chosen from hydrogen and alkyl groups such as methyl, ethyl, propyl, iso-propyl, butyl, t-butyl, $C_{5-6}$ alkyl, $C_{1-6}$ cycloalkyl, phenyl, and benzyl, and substituted or unsubstituted, or saturated or unsaturated alkyl or cycloalkyl groups; while R" is chosen from H, $CH_3$, $CH(CH_3)CH_2CH_3$, $CH_2CH(CH_3)_2$, $CH(CH_3)_2$, $CH_2(C_6H_5)$, $CH_2(C_8H_6N)$, $CH_2(C_6H_4OH)$, $CH_2(CO)NH_2$, $CH_2SH$, $CH_2CH_2(CO)NH_2$, $CH_2CH_2SCH_3$, $CH_2OH$, $CH(OH)CH_3$, $CH_2COOH$, $CH_2CH_2COOH$, $CH_2CH_2CH_2NH(C=NH)NH_2$, $CH_2(CH_3H_3N_2)$, and $CH_2CH_2CH_2CH_2NH_2$; and wherein R or R' independently or together with R" are capable of forming a 3-, 4-, 5-, 6-, 7- or 8-membered ring including the nitrogen or carbon to which they are attached and an adjacent carbon or nitrogen, and wherein the ring can be substituted or unsubstituted with additional R or R' groups as defined above. Although such fused ring structures are described herein as being "formed from" the specified R groups, in actuality the ring replaces the R groups (e.g., R, R', or R") that would otherwise be bonded to the nitrogen and adjacent carbon. This is the case for all similar fused ring structures described within the context of this specification for any of the inventive complexes.

With respect to FIGS. 1D-E as well, it is understood that palladium can be replaced by of a lanthanide, actinide, or transition metal capable of forming a chelate complex, and especially where the metal is chosen from cobalt (Co), rhodium (Rh), iridium (Ir), nickel (Ni), platinum (Pt), copper (Cu), silver (Ag), and gold (Au). Further, regarding the structures shown in FIG. 1E, R is chosen from H or $CH_3$ and R' is chosen from H, OH, F, or benzyl.

Example III

Bacteriological Activity of Complexes of Formula 1

Biological activities of complexes of Formula 1 were tested against various strains of bacteria using the following general procedure. It is noted that complexes of Formula 2 and Formula 3 were tested using the same procedure. Generally, 96 well plate dilution tests were performed using a 96-well plate consisting of 8 rows and 12 columns. Each well is charged with the test organism in the appropriate growth medium. The test complex is also dissolved in the test medium and the first well is charged with sufficient complex solution to provide a concentration of 250 ug/mL. Each subsequent well undergoes a 2-fold dilution of the complex (organism concentration remains the same) so that the concentration of test compound decreases from 250 to 125 to 62 to 31 to 15 to 7.5 to 3.7 to 1.85 and so on. Well 12 is used as a control with no test complex. The plates are incubated for 48 hrs in the case of bacteria and 4-5 days in the case of mycobacteria. The wells are read using a spectrophotometer measuring turbidity at 540 nm. A high optical density indicates significant cell growth while a low optical density indicates significant inhibition. All results reported are normalized in terms of inhibition of cell growth and reported as MICs.

Table I shows results in terms of MICs for various palladium bis-amino acid complexes. Biological activity is expressed in terms of the Minimum Inhibitory Concentration (MIC) in units of micrograms per mL. The MIC is the lowest concentration of the complex at which full inhibition of organism growth is observed. Thus, the lower the MIC, the more active the compound. While the palladium complexes were not screened against the full spectrum of organisms investigated for the other categories, two of the complexes showed excellent biological activity and low MICs for methicillin-resistant *Staphylococcus aureus* (MRSA).

TABLE I

| Activity of Pd(AA)₂ Complexes against MRSA | |
|---|---|
| Complex | MIC |
| Pd(Pro)₂ | 7.5 ug/mL |
| Pd(Val)₂ | 9.0 ug/mL |
| Pd(Ser)₂ | inactive |
| Pd(Ala)₂ | inactive |

In this category, as illustrated, the palladium(II) bis-proline and the palladium(II) bis-valine complexes show significant activity against MRSA. It is clear that the biological activity does not come from the compounds decomposing into $Pd^{+2}$ ions since all would show the same level of activity if that were the case. While the target of these complexes and their exact mechanism of action is unknown at this time, it would appear that a significant hydrophobic group on the amino acid is a factor for increased biological activity. Thus, groups such as methyl are adequate, but longer hydrocarbyl/alkyl chains such as ethyl, propyl, butyl and higher carbon-containing chains are more preferred as well as isomers of any alky chain greater than three carbons. In addition, large non-polar aromatic groups such as phenyl, napthyl and groups containing a higher number of carbon atoms are also preferred.

Category II. Octahedral Complexes with Amino Acids.

A general procedure for the preparation of octahedral amino acid complexes is shown in Scheme 2 below:

Scheme 2. Synthesis of octahedral amino acid complexes (Formula 2)

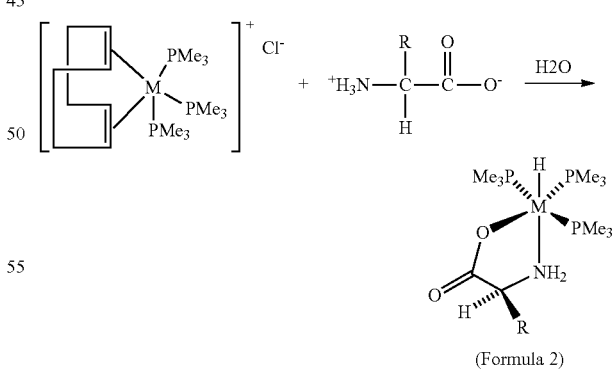

(Formula 2)

Amino acid complexes of Formula 2 can be formed from any amino acid or amino acid derivative, including any of the amino acids listed above with respect to the disclosure of the complexes of Category I. Although as illustrated, the nitrogen comprises hydrogen as substituents, depending on the amino acid used, one or more of the hydrogen atoms can be replaced with an R group.

Complexes of Category II can comprise any compound of Formula 2:

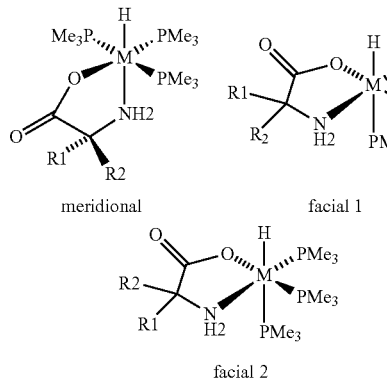

meridional   facial 1 facial 2 wherein M may be Co, Rh, Ir, Fe, Ru, Os, Mn, Tc, Re and any other transition or lanthanide or actinide metal. Charges on the complexes may vary from 0 to +4 depending on the metal and ligand combination; and $R_{1-2}$ may be the same or different and are chosen from H, $CH_3$, $CH_2CH_3$, $C_6H_5$ and any other number of $C_{1-20}$ alkyl groups, optionally $R_1$ and/or $R_2$ either together or separately form a 3-, 4-, 5-, 6-, 7-, or 8-membered ring with the carbon atom to which they are attached and the nitrogen adjacent the carbon atom.

Compounds synthesized were characterized by NMR spectroscopy and mass spectrometry. In several cases, single crystal x-ray diffractometry was used to confirm the structure as well as determine the absolute configuration of the complexes. Representative compounds of Formula 2 characterized by x-ray crystallography are pictured in FIGS. 2A-B.

Octahedral iridium(III) complexes of Formula 2 were tested against various strains of bacteria using the procedure described above for Formula 1. Biological activity is expressed in terms of the MIC in units of micrograms per mL.

Against MRSA and *S. aureous*, the valine, leucine and proline complexes of Formula 2 all showed high activity, but the tyrosine complex did not. Tyrosine has a polar, hydrophilic phenolic group, and, as was the case for the palladium compounds, it would appear that a hydrophobic group on the amino acid is a factor for anti-bacterial activity.

TABLE II

Biological Activity (MICs) of HIr(PMe$_3$)$_3$ amino acid complexes

|  | MRSA | S. aureous |
|---|---|---|
| HIr(val)(PMe$_3$)$_3$ | 7.5 ug/mL | 7.5 ug/mL |
| HIr(leu)(PMe$_3$)$_3$ | 7.5 ug/mL | 7.5 ug/mL |
| HIr(pro)(PMe$_3$)$_3$ | 3.9 ug/mL | 3.9 ug/mL |
| HIr(tyr)(PMe$_3$)$_3$ | INACTIVE | INACTIVE | val = valine;
leu = leucine;
pro = proline;
tyr = tyrosine

Within this category of compounds, the HIr(pro)(PMe$_3$)$_3^+$ complex also showed very high activity (1 μg/mL) against *M. luteus*, another gram positive bacterium as well as a mycobacterium, *M. Smegmatis*.

TABLE IIA

Biological Activity (MICs) of Complexes Against *E. Coli*

E. coli

| Compounds | MIC ug/mL |
|---|---|
| Ir(COD)(PMe$_3$)$_3$ | 60 |
| Ir(Val)(PMe$_3$)$_3$ | 60 |
| Ir(Ala)(PMe$_3$)$_3$ | 125 |
| Ir(Pro)(PMe$_3$)$_3$ | 15 |
| Ir(Phe)(PMe$_3$)$_3$ | 30 |

COD = 1,5, cyclooctadiene;
Val = valine;
Ala = alanine;
Pro = proline;
Phe = phenylalanine Biological activity of complexes of the invention against *E. coli* demonstrates the effectiveness of such complexes against bacteria of the gram negative variety.

Category III. Amino Acid Piano Stool Complexes.

A "piano stool" complex is one in which a metal is complexed by a large pi-bonded cyclic ligand such as cyclopentadienyl or benzene (or substituted derivatives thereof.) They are so-called because the arrangement of ligands approximates the look of a piano stool with the pi-complexed cyclic ligand being the "seat" and the other ligands forming the "legs." Representative Category III complexes are illustrated below using a schematic drawing of a generic piano stool complex of Formula 3:

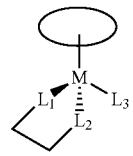

Formula 3

According to embodiments of the invention, metal atom M may be chosen from any transition, lanthanide, or actinide metal. Representative atoms M can for example be chosen from cobalt, rhodium, iridium, iron, ruthenium, osmium, manganese, technetium, rhenium, respectively, Co, Rh, Ir, Fe, Ru, Os, Mn, Tc, and Re. Representative Category III complexes according to embodiments of the invention include where $L_1$, $L_2$ is a chelating amino acid and where $L_3$ is any halogen, such as fluorine, chlorine, bromine, or iodine, as well as any other anionic ligand capable of dissociating from the metal such as carboxylates (acetate, benzoate, trifluoroacetate among others), triflate, sulfonate, thiocyanate, tetrafluoroborate, hexafluorophosphate. Amino acid complexes of Formula 3 can be formed from any amino acid or amino acid derivative, including any of the amino acids listed above with respect to the disclosure of the complexes of Category I or II. Further, for example, the $L_1$, $L_2$ chelates can comprise an N,O chelate comprising:

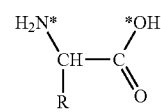

wherein the nitrogen (N) and oxygen (O) atoms bond with M;

wherein the atoms indicated with * possess the property known as chirality and can be formed in one of two isomers, either D or L depending on its ability to rotate plane polarized light; and wherein R is chosen from any of:

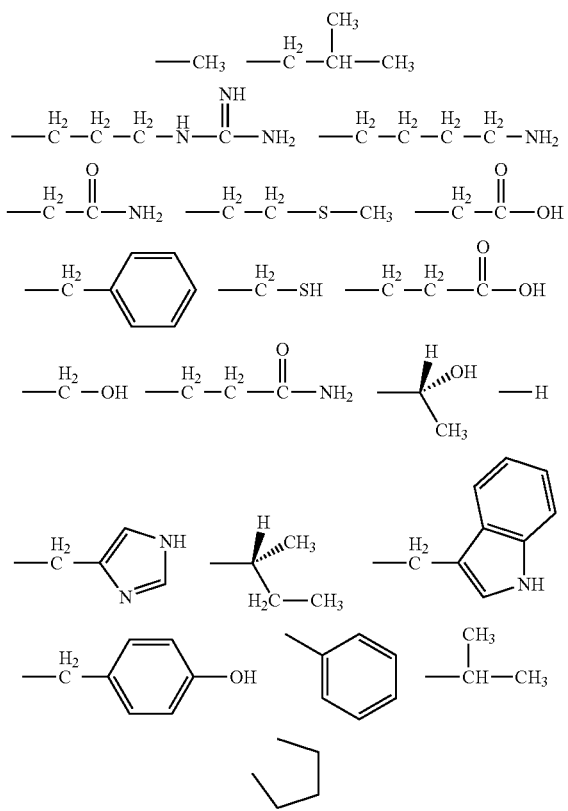

or R is chosen from any $C_{1-20}$ alkyl group, such as any $C_{1-6}$, or $C_{3-10}$, or $C_{5-8}$ alkyl group, whether substituted or unsubstituted, and R can additionally bind to the N atom or to the carbon atom (where R replaces the oxygen of the carbonyl group) to form a ring structure, such as a 3-, 4-, 5-, 6-, 7-, 8-, or 9-membered ring structure comprising a substituted or unsubstituted alkyl group with or without heteroatoms (e.g., N, O, or S) and optionally substituted with a halogen or hydroxyl group, including for example where R together with both carbon atoms of the $L_1$, $L_2$ chelate forms a 5-membered ring structure where R is —$CH_2$—O—NH— (replacing the carbonyl oxygen), or including for example a 5-membered ring structure where R is chosen from —$CH_2CH_2CH_2CH_2$— or —$CH_2CH_2CH_2$— or —$CH_2CH_2$— or —$CH_2$— and binds with the carbon and nitrogen atoms of the $L_1$, $L_2$ chelate and is optionally substituted with a fluorine, iodine, bromine, or chlorine atom or a hydroxyl group, or R is $CF_3$, in addition, one or more of the hydrogen atoms on the nitrogen of the $L_1$, $L_2$ chelate can be replaced with one or more $C_{1-10}$ alkyl group, such as one or more methyl, ethyl, propyl, or butyl groups, including for example two methyl groups, or the $L_1$, $L_2$ chelates can comprise an N,N chelate comprising:

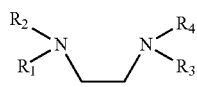

wherein the nitrogen (N) atoms bond with M and wherein $R_1$-$R_4$ are chosen from any of the following in any combination:

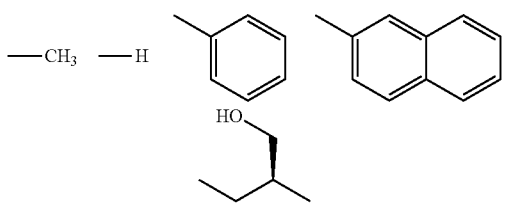

Representative Formula 3 complexes can comprise as the "seat" (represented by the oval in Formula 3),

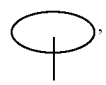

any aromatic ligand capable of pi-complexing to a metal. Preferred aromatic ligands include but are not limited to 5-, 6-, 7-, or 8-membered rings, substituted or unsubstituted, such as cyclopentadienyl, substituted cyclopentadienyl, benzyl or substituted benzyl. The ligands can contain heteroatoms, such as O, N, or S, as a member of the ring. Such representative piano "seat" type ligands for example can include:

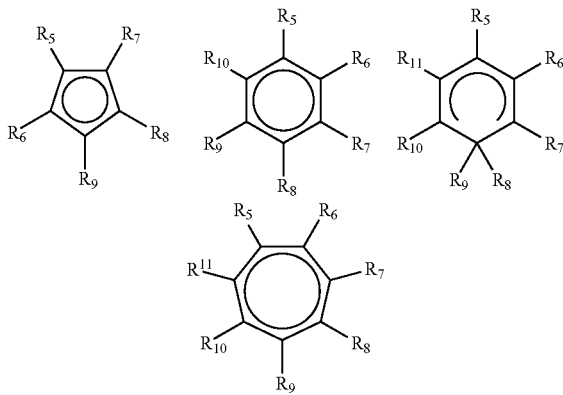

wherein $R_{5-11}$ can be the same or different and chosen from hydrogen or any hydrocarbyl group comprising from 1-20 carbon atoms. Representative R-groups for $R_{5-11}$ can for example be chosen from a hydrogen atom, a methyl (—$CH_3$) group, an ethyl (—$CH_2CH_3$) group, a propyl group (—$C_3H_7$), a butyl (—$C_4H_9$) group, a phenyl (—$C_6H_5$) group, a benzyl group, a $C_{1-10}$ alkyl group, whether substituted or unsubstituted, or a $C_{11-20}$ alkyl group, whether substituted or unsubstituted.

Examples provided in this specification are representative of the types of complexes included within the scope of the invention and do not limit the invention to the specific species disclosed. For example, where a 6-membered ring is illustrated or described, species of the invention can alternatively include a 5-, 7-, or 8-membered ring instead. Further, where substituents are shown or described with respect to a species comprising a 6-membered ring, it is understood that such substituents are equally applicable to 5-, 7-, or 8-membered rings.

Likewise, in the context of this specification, where specific structures of complexes of the invention (including Complexes I, II, III, or IV and so on) are illustrated or described, it is understood that alternative structures are also included within the scope of the invention even though illustrations of specific alternatives may not be provided. For example, where complexes are shown or described as having a chlorine atom as the $L_3$ ligand, it should be understood that the scope of the invention includes complexes alternatively comprising any other halogen atom instead, such as fluorine, bromine or iodine. Where a particular R-group is shown or described on an amino acid or as a substituent on any of the complexes described in this specification, it is understood that the R-group could be substituted for any R-group substituent of any of the complexes of Categories I, II, III, and IV and so on. For example, where R is —$CH_2OH$ and is shown or described on an iridium based complex of the N,O chelate variety of Complex III, it should be understood that the R-group —$CH_2OH$ can also be a substituent on a Category III osmium based complex of the N,N chelate variety.

Preferred complexes of Formula 3 include those wherein M is chosen from Ir, Ru, or Os. Alternatively preferred complexes comprise M as Co or Fe. The series of compounds of Category I represented by some of these permutations are synthesized by the general reaction shown in Scheme 3 as follows:

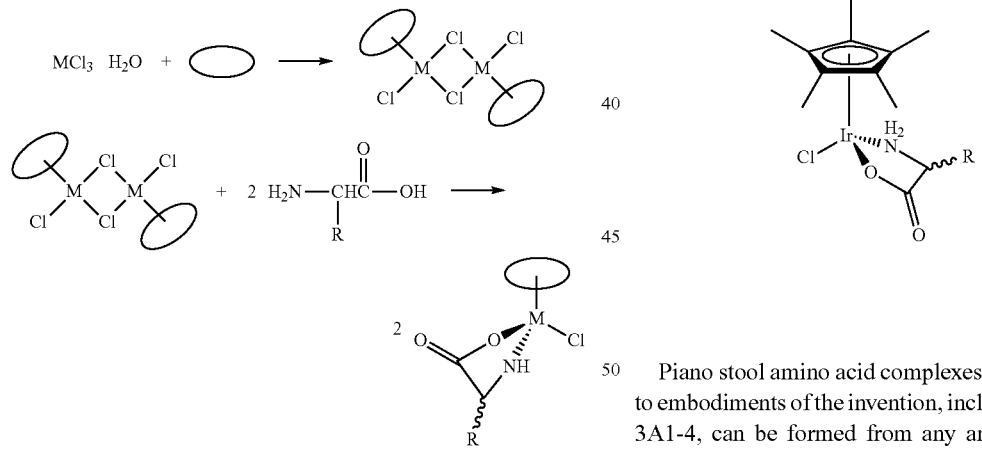

Representative compounds of Formula 3 were characterized by both NMR spectroscopy and mass spectrometry. In several cases, the structure was confirmed and absolute configuration determined by single crystal x-ray diffractometry. Exemplary crystallographically characterized complexes in this category are shown in FIGS. 3A-B.

Formulas 3A and 3B below show specific species of representative compounds of the Formula 3 type included within the scope of the invention. In particular, Formulas 3A1-4 show more specific structures for representative cyclopentadienyl-based compounds of Rh and Ir according to embodiments of the invention, and in particular cyclopentadienyl (Cp) and pentamethylcyclopentadienyl (Cp*) Amino Acid Complexes of Rhodium or Iridium. Other metals can also be used, including for example cobalt, iron, ruthenium, osmium, manganese, technetium, and rhenium or any transition, lanthanide, or actinide metal.

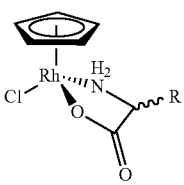

Formula 3A1

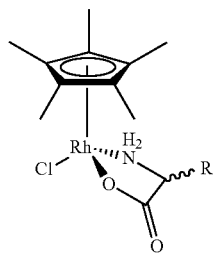

Formula 3A2

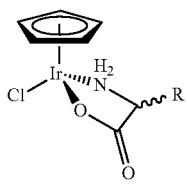

Formula 3A3

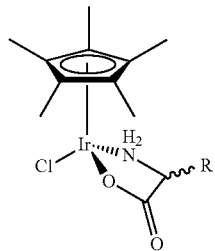

Formula 3A4

Piano stool amino acid complexes of Formula 3 according to embodiments of the invention, including those of Formulas 3A1-4, can be formed from any amino acid. Although as illustrated, the nitrogen comprises hydrogen as substituents, depending on the amino acid used, one or more of the hydrogen atoms can be replaced with an R group, as defined above with respect to the general Formula 3 type complex illustrated above.

Formulas 3B1-6 show more specific diagrams for representative benzene-based piano stool complexes according to embodiments of the invention, including benzene, p-cymene, and hexamethylbenzene amino acid complexes of ruthenium and osmium. Substitutions other than methyl are possible on the 5- or 6-membered rings of any of the Formula 3 compounds of the invention and can include for example any alkyl group comprising from 1-20 carbon atoms.

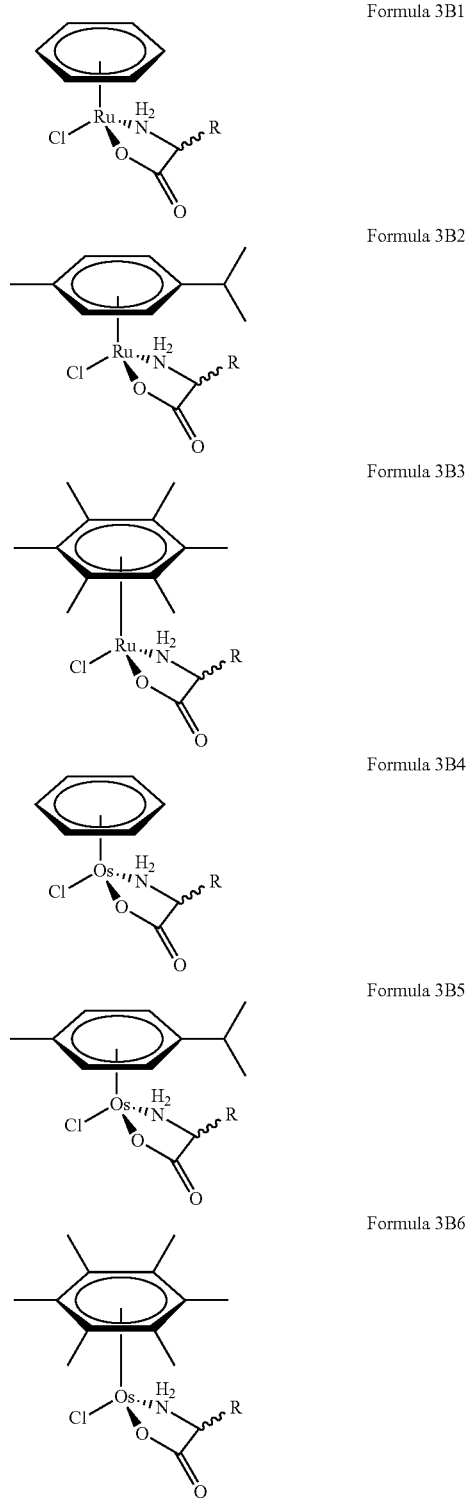

Formula 3B1
Formula 3B2
Formula 3B3
Formula 3B4
Formula 3B5
Formula 3B6

Other exemplary structures of complexes of the Formula 3 type are illustrated in the figures. More specifically, iridium based Formula 3 complexes are shown in FIGS. 3C-N, while osmium based Formula 3 complexes are shown in FIGS. 3O-LL, while ruthenium based Formula 3 complexes are shown in FIGS. 3MM-JJJ, and rhodium based Formula 3 complexes are shown in FIGS. 3KKK-VVV. It is noted that although particular species may be illustrated within these figures and within the description provided by this specification, it is understood that these are merely representations of the numerous species encompassed by embodiments of the invention and as such the metal and ligands shown for a particular species are interchangeable with the metal or ligands of another species.

The biological activities of the piano-stool complexes were tested against various strains of bacteria using the general procedure described above with respect to the complexes of Formula 1 and Formula 2. Biological activity is expressed in terms of the Minimum Inhibitory Concentration (MIC) in units of micrograms per mL. By far, the most widely tested group in this work is the piano-stool category. Table III shows the MICs against *M. smegmatis*, *M. chelonae* and *M. abscessus* for a series of Ir piano stool complexes.

TABLE III

Biological Activity (MIC) for Iridium Piano Stool Complexes

| Complex | *M. smegmatis* MIC | *M. chelonae* MIC | *M. abscessus* MIC |
| --- | --- | --- | --- |
| Ir(Cp*)L-Ala | 7.5 ug/mL | 7.5 ug/mL | 7.5 ug/mL |
| Ir(Cp*)L-Val | 3.9 ug/mL | 7.5 ug/mL | 7.5 ug/mL |
| Ir(Cp*)D-Val | 250 ug/mL | 250 ug/mL | Inactive |
| Ir(Cp*)L-Pro | 3.9 ug/mL | 7.5 ug/mL | 3.9 ug/mL |
| Ir(Cp*)L-Tyr | n/a | Inactive | n/a |
| Ir(Cp*)L-Phe | 3.9 ug/mL | 3.9 ug/mL | 7.5 ug/mL |
| Ir(Cp*)L-Ser | n/a | Inactive | n/a |
| Ir(Cp*)L-Leu | 3.9 ug/mL | 3.9 ug/mL | n/a |
| Ir(Cp*)L-Iso | 7.5 ug/mL | 7.5 ug/mL | 7.5 ug/mL |
| Ir(Cp*)L-Gln | 3.9 ug/mL | 3.9 ug/mL | 3.9 ug/mL |

Again, very low MICs represent high biological activity against the organism. Also, note once again that a hydrophilic side chain such as found in serine and tyrosine causes a loss of biological activity. The change from L-valine to D-valine results in either complete inactivity or a large increase in the MIC.

Example IV

Synthesis/Characterization of Piano Stool Complex Examples

Half-sandwich iridium(III) α-amino acid (Aa) complexes of the formula $[(\eta^5\text{-Me}_5C_5)Ir(Aa)\text{—Cl}]$ were prepared and characterized and are provided here numbered as complexes 1-27. The complexes are highly soluble in water due to chloride disassociation and formation of mon-aqua cation. Reaction with sodium formate forms the subsequent iridium hydride complex. The molecular structures of $[(\eta^5\text{-Me}_5C_5)Ir(Aa)\text{-Cl}]$ (Aa=L-Pro, L-F-Pro, D-MePro, L/D-Phe, L-Ser, L-Aze) are reported.

Reaction of $[IrCp*Cl_2]_2$ with α-amino acid presence of base leads to the formation of complexes 1-27. The complexes uptake a piano-stool configuration, with the amino acid forming a bidentate chelate between the amino and carboxylate groups, similar to amino-alcohol and diamine ligands, as illustrated below in Scheme 4.

Scheme 4. Synthesis and general configuration of piano stool iridium amino acid complexes

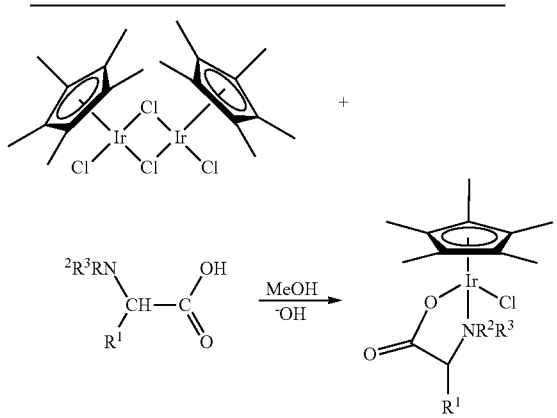

Upon chelation, the iridium center becomes a chiral site, owing to the formation of two diastereomers (otherwise referred to as diastereoisomers). In the cases of alkylated nitrogens, (complexes 6, 17, 18, 19, 20, 21, 25, 26), the amine nitrogen also becomes a stereogenic site, with the possibility of formation of up to 4 diastereomers. However, in the cases of complexes 17, 18, 19, 20, 21, and 25, only two diastereoemers were observed, in each case referring to the configuration at the metal site (R or S). In the case of the N-methyl-glycinate complex, only one configuration was observed. According to embodiments of the invention, complexes of Categories I, II, III, or IV to the extent such compounds include racemic mixtures of diastereomers, the diastereomers can be present in ratios of from 0:100 or from 100:0, such as from approaching 0:100, or from 5:95, or from 10:90, or from 15:85, or from 20:80, or from 25:75, or from 30:70, or from 35:65, or from 40:60, or from 45:55, or from 50:50, or from 55:45, or from 60:40, or from 65:35, or from 70:30, or from 75:25, or from 80:20, or from 85:15, or from 90:10, or from 95:5, or from or approaching 100:0.

TABLE IV

Summary of molar ratios of amino acid complexes

| Complex | Amino Acid | Molar Ratio |
|---|---|---|
| 1a/1b | L-Alanine | 56/44 |
| 2a/2b | L-Asparginine | 84/16 |
| 3a/3b | L-Aspartic Acid | 51/49 |
| 4a/4b | L-Cysteine | n/a |
| 5 | Glycine | n/a |
| 6 | N-methyl-Glycine | n/a |
| 7 | N,N-Dimethyl-Glycine | n/a |
| 8 | L-Glutamic Acid | n/a |
| 9 | D-Histidine | n/a |
| 10a/10b | L-Isoleucine | 50/50 |
| 11a/11b | L-Leucine | n/a |
| 12 | Lysine | n/a |
| 13a/13b | L-Methionine | 61/39 |
| 14a/14b | L-Phenylalanine | 69/31 |
| 15a/15b | D-Phenylalanine | 70/30 |
| 16a/16b | L-Phenylglycine | 42/58 |
| 17a/17b | L-Proline | 93/7 |
| 18a/18b | d-Proline | 93/7 |
| 19a/19b | hydroxy-L-Pro | 73/27 |
| 20a/20b | Fluoro-L-Pro | 70/30 |
| 21a/21b | N-Methyl-D-Pro | n/a |
| 22a/22b | L-serine | 62/38 |
| 23a/23b | L-Threonine | 68/32 |
| 24a/24b | L-Valine | 53/47 |
| 25a/25b | L-Azetidine | 93/7 |
| 26a/26a | L-pipcolinic | 74/26 |

Unlike the mono-tosylated DPEN ligand commonly used in ATH reactions, the diasteoreomeric ratio will have a range dependent on steric constraints, with simpler R groups (Alanine) forming a 56/44 mixture and bulkier R groups giving a ratio of 70/30 in the case of phenylalanine. Proline based variants have been shown to be more selective in their reactions, giving ratios as high as 93/7 (ref to Beck). The addition of an electron withdrawing group such as fluorine changes the ratio, as seen in complex 20. The molar ratios of the diastereomers are summarized above in Table IV. The ORTEP plot from single crystal diffraction of the L-phenylalanine complex clearly shows two diastereomers with differing configuration at the metal site, as shown below:

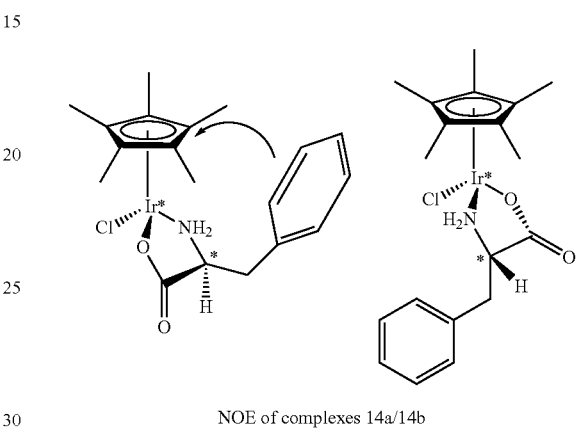

NOE of complexes 14a/14b

D-phenylgylcine forms the opposite configuration at the metal site. The configuration in the solid state can be corroborated through NMR experiments, specifically NOE (Nuclear Overhauser Effect). Selective pulsing of the Cp* region of the major component of complex 14 results in the enhancement of the protons in the aromatic region, where as irradiation of the Cp* region of the minor component results in no enhancement. Therefore the major component of complex 14 is of the configuration $S_{Ir}S_C$ (14a), with the minor component having a configuration of $R_{Ir}S_C$ (14b):

In the case of complex 10, the minor component adopts the configuration of $S_{Ir}S_C$. The R-group of the isoleucine displays an NOE interaction with the Cp* ring. The major component lacks this interaction, due to the configuration of $R_{Ir}S_C$, as shown below:

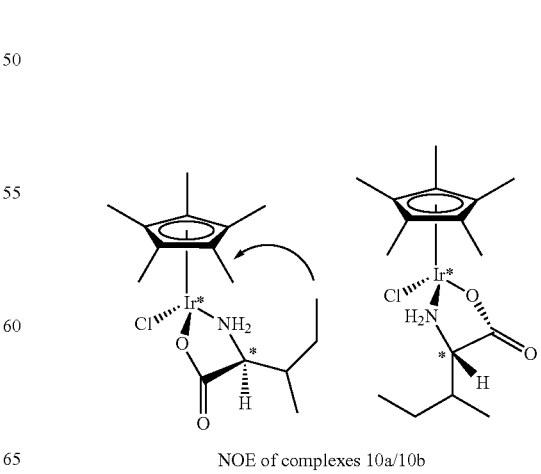

NOE of complexes 10a/10b

As stated previously, in the case of methylated amine systems the nitrogen acts as a third chiral site. In the case of L-pipocolinic acid, the nitrogen adopts an S configuration in both configurations, ($R_{Ir}S_CS_N$, $S_{Ir}S_CS_N$). Again NOE experiments allowed for this assignment, as is illustrated below:

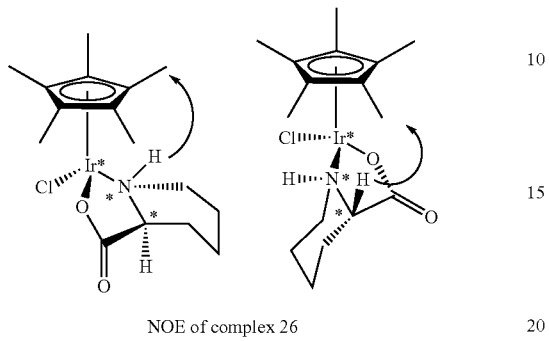

NOE of complex 26

In the case of 26a, the configuration is $S_{Ir}S_CS_N$, as seen from pulsing the amine proton and subsequent enhancement of the Cp* methyls. 26b, the minor component is $R_{Ir}S_CS_N$ with a clear interaction between the alpha carbon proton and the Cp* methyls.

The smaller ring systems of proline and azetidine induce the opposite chirality ($R_N$) at the nitrogen upon chelation. The NOE spectrum obtained for the major diastereomers of 17, 19, 20, and 25 show an interaction between the N—CH$_2$ protons and the Cp* methyls. The minor configurations again lack this relationship. However, the amine proton is significantly closer in the minor component, (2.847 A vs 3.177 A). This is displayed in the NOE spectrum of minor diastereomer. In each case of these smaller ring systems, the chirality of the nitrogen is the same of that of the chiral carbon, $R_{Ir}S_CS_N$ and $S_{Ir}S_CS_N$, or in the case of D-proline $R_{Ir}R_CR_N$ and $S_{Ir}R_CR_N$.

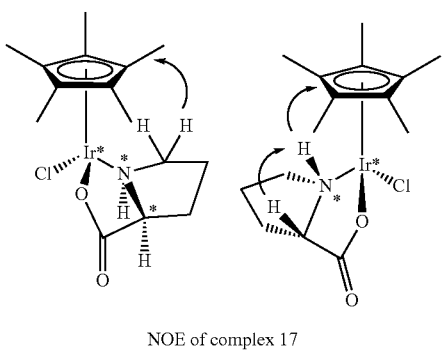

NOE of complex 17

Amino acids with coordinating side chains, (cysteine, aspartic acid, lysine, methionine), allow for the formation of addition diastereomers. In the case of cysteine up to 5 configurations are possible. The $^{13}$C NMR displays 5 different signals in the Cp* region.

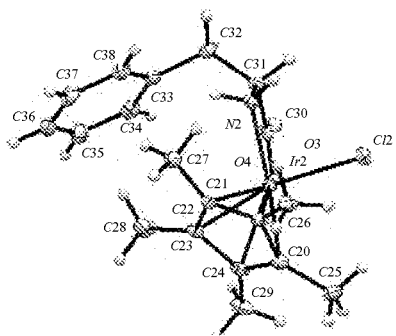

ORTEP drawing showing the two diasteroemers of the L-Phenylalanine complex. All hydrogens except amino omitted for clarity. Ellipsoids shown at 50% probability.

These complexes are highly soluble in water due to chloride exchange and subsequent formation of a mono-aqua cation. In addition they are stable for more than a year in solution unlike diamine counter parts which can break down in months. See Wu, X. F.; Liu, J. K.; Di Tommaso, D.; Iggo, J. A.; Catlow, C. R. A.; Bacsa, J.; Xiao, J. L., A multilateral mechanistic study into asymmetric transfer hydrogenation in water. Chem.-Eur. J. 2008, 14 (25), 7699-7715. The water solubility is important for two reasons, the first being the potential biological role the complexes are designed to play, and for "green" aqueous catalysis.

The open coordination site allows formation of a metal-hydride complex through beta-hydride elimination (Scheme 5). Upon addition of 5 equivalents of sodium formate, the pale yellow solution of 17 turns a dark red color with evolution of $CO_2$ gas. The hydride peaks appear over the course of 20 minutes in $D_2O$. In the case of the 17 complex, the signals appears at −7.84 and −8.53. Their respective Cp* signals appearing at 1.66 and 1.68. The ratios of the hydride complexes, (53/47) is closer to a racemic mixture than the parent chloride complexes. This trend occurs with complexes 20 and 25 as well, with hydride ratios of 63/47 and 54/46 respectively.

Scheme 5. Chloride exchange and formation of Hydride by way of beta hydride elimination

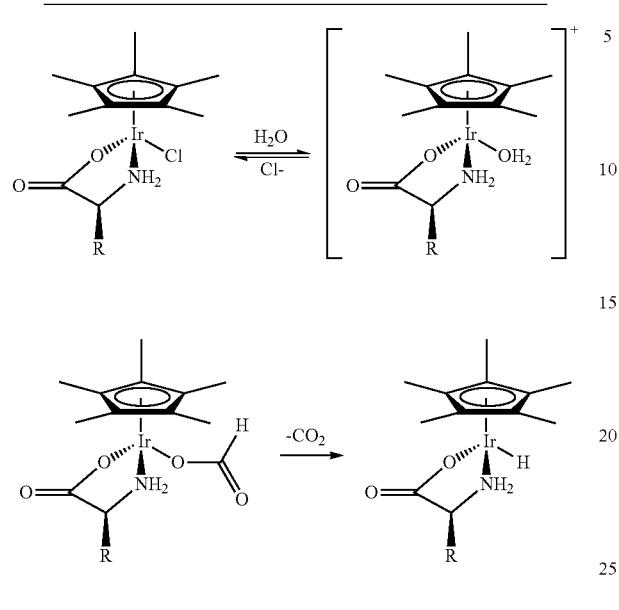

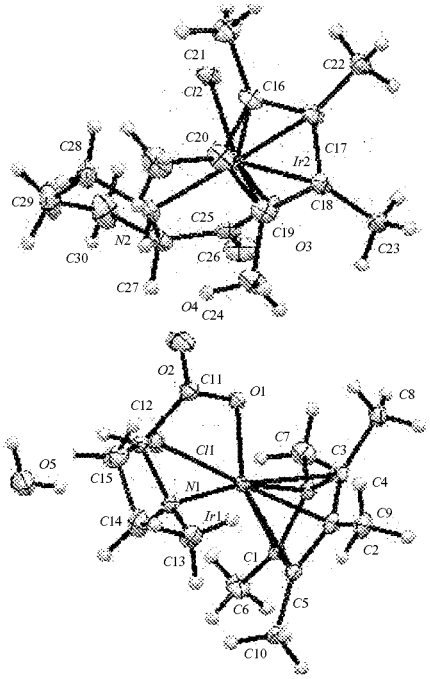

ORTEP showing complex 14. All hydrogens except amino hydrogens omitted for clarity. Ellipoids shown at 50% probability.

The water solubility combined with formation of a hydride from sodium formate makes these complexes interesting candidates for asymmetric transfer hydrogenation, (ATH), due to low cost and modular nature of amino acids.

The formation of two diastereomers is problematic for ATH since each diastereomer will favor the opposite enantiomer. N-methyl variants of amino acids would side step such an issue by have only one "active" diastereomer. A comparison of the torsional angle between the H—N—Ir—Cl bond as well as the distance between the amine proton and the chloride displays this, (table V).

TABLE V

Torsional angles & Hydrogen - Chloride distances of complexes

| Complex | Configuration at metal | Torsional Angle | H—Cl Distance |
|---------|------------------------|-----------------|---------------|
| 14a/14b | R | −4.363 | 2.576 |
|         | S | 40.03  | 2.859 |
| 17a/17b | S | 55.126 | 3.029 |
|         | R | 170.462 | 4.027 |
| 25a     | S | 58.591 | 2.989 |
| 20a     | S | 49.387 | 2.936 |

The high torsional angle and large distance between the active amine proton and chloride show that the R configuration of 17b would not be active in ATH, leaving only one diastereomer to reduce the ketone to the corresponding alcohol.

An addition advantage of amino acids for ATH is that D/L variants should in theory give the opposite chiral alcohol. This leads to a cost effective method to effectively switch the configuration of the product.

Unless otherwise stated, synthetic work was carried out in air with untreated solvents. Commercially available reagents were obtained from the following sources: $IrCl_3 \cdot xH_2O$, $RhCl_3 \cdot xH_2O$ (Pressure Chemical), L-Alanine, L-Valine, D-Valine, L-Leucine, L-Isoleucine, D-Isoleucine, D-Phenylalanine, L-Proline, D-Proline, D-N-Methyl-Proline (Alfa Aesar), D-Alanine, L-Phenylglycine, D-Phenylglycine, L-Tyrosine, L-Phenylalanine, L-Histidine, L-Cysteine, D-Cysteine (Sigma Aldrich), Glycine (Fisher).

$[IrCp^*Cl_2]_2$ and $[RhCp^*Cl_2]_2$ were synthesized as previously reported. See White, C., Inorganic Syntheses (η5-Pentamethylcyclopentadienyl)Rhodium and -Iridium Compounds. Inorganic syntheses 1992, 29, 228-234.

The general procedure for synthesis of Ir(III)Cp*Cl Amino acid (AA) complexes was carried out as follows. A 100 mL Shlenk Flask was charged with appropriate amounts of $[IrCp^*Cl_2]_2$, amino acid, potassium hydroxide, and methanol with magnetic stirring. Upon addition of solvent the solution changed from orange to yellow over the course of 2 hr to 24 hr. After approximately 24 hrs the solvent was removed via reduced pressure. The complex was extracted with 3×5 mL of dichloromethane and filtered to remove excess amino acid and potassium hydroxide.

In the synthesis for Cp*IrCl(L-Alanine) (1a/1b), following the general procedure: $[IrCp^*Cl_2]_2$ (0.1500 g, 1.886 mmol), L-Alanine (0.0689 g (7.73 mmol), and KOH (0.0430 g 7.664 mmol) were reacted in methanol (50 mL) to give 1 (0.1498 g 88.1%), (56/45 molar ratio). 1a/1b was identified based on the following information:

1a: $^1$H NMR (400 MHz, $CDCl_3$) δ 6.91 (m, 1H NHH), 3.49 (m, 1H CHOO), 3.32 (m, 1H NHH), 1.69 (s, 15H Cp*Me), 1.43 (d, J=7.1 Hz, 3H, $CH_3$). $^{13}$C NMR (101 MHz, $CDCl_3$) δ 183.42 (COO), 84.19 (Cp*), 53.04 (Cα), 21.33 ($CH_3$), 9.23 (Cp*Me).

1b: $^1$H NMR (400 MHz, CDCl$_3$) δ 5.32 (m, 1H NHH), 4.37 (m, 1H NHH), 3.65 (m, 1H CHOO), 1.69 (s, 15H Cp*Me), 1.39 (d, J=7.1 Hz, 3H CH$_3$). $^{13}$C NMR (101 MHz, CDCl$_3$) δ 185.36 (COO), 84.14 (Cp*), 52.04 (Cα), 19.33 (CH$_3$), 9.23 (Cp*Me).

HRMS/ESI+ (m/z): [M+Na]+ calcd for C$_{13}$H$_{20}$ [193Ir] N Na O$_2$ 438.1015. Found 438.0992. Anal. Calcd for C$_{13}$H$_{21}$ClIrNO$_2$: C, 34.62; H, 4.69. Found: C, 34.57; H, 4.65.

In the synthesis for Cp*IrCl (L-Asparginine) (2a/2b) following the general procedure: [IrCp*Cl$_2$]$_2$ (0.100 g, 1.26 mmol), L-Asparginine (0.0348 g (2.635 mmol), and KOH (0.0148 g 2.635 mmol) were reacted in Methanol (50 mL) to give 2 (0.1049 g 83.8%), (mol ratio 84/16). 2a/2b was identified based on the following information:

2a: $^1$H NMR (400 MHz, CD$_3$OD) δ 6.10 (s br, 1H NHH), 5.55 (s br, 1H NHH), 4.20 (m, 1H CHOO), 2.72 (dd, J=18.2, 5.0 Hz, 1H CHH), 2.53 (dd, J=18.2, 2.5 Hz, 1H CHH), 1.71 (s, 15H Cp*Me). $^{13}$C NMR (101 MHz, CDCl$_3$) δ 185.27 (COO), 171.55 (CNO), 83.46 Cp*, 55.39 CH, 29.64 CH$_2$, 8.69 Cp*Me.

2b: $^1$H NMR (400 MHz, CD$_3$OD) δ 3.65 (m, 1H CHOO), 2.85-2.77 (m, CHH), 1.69 (s, 15H Cp*Me). $^{13}$C NMR (101 MHz, CD$_3$OD) δ 7.37 (Cp*Me).

HRMS/ESI+ (m/z): [M+H]+ calcd for C$_{14}$H$_{23}$Cl [193Ir] N$_2$O$_3$ 495.1021. Found 495.1017. Anal. Calcd for C$_{14}$H$_{23}$Cl [193Ir] N$_2$O$_3$; C, 34.04; H, 4.49. Found C, 34.31; H, 4.69.

In the synthesis for Cp*IrCl (L-Aspartic Acid) (3a/3b) following the general procedure: [IrCp*Cl$_2$]$_2$ (0.1000 g, 1.26 mmol), L-Aspartic acid (0.071 g (5.33 mmol), and KOH (0.03 g 5.33 mmol) were reacted in Methanol (30 mL) to give 3 (0.1070 g 86.12%) (mol ratio 51/49). 3a/3b was identified based on the following information:

3a: $^1$H NMR (400 MHz, CD$_3$OD) δ 5.57 (s br, 1H NHH), 5.33 (s br, 1H NHH), 3.67 (m, 1H CHOO), 2.73 (m, 2H CH$_2$), 1.69 (s, 15H Cp*Me). $^{13}$C NMR (101 MHz, CDCl$_3$) δ 84.12 (Cp*), 53.36 (Cα), 29.51 (COH$_2$), 9.08 (Cp*Me).

3b: $^1$H NMR (400 MHz, CD$_3$OD) δ 6.16 (s br, 1H NHH), 5.66 (s br, 1H NHH), 4.16 (m, 1H CHOO), 2.87 (m, 2H CH$_2$), 1.69 (s, 15H Cp*Me). $^{13}$C NMR (101 MHz, CDCl$_3$) δ 84.37 (Cp*), 53.36 (Cα), 29.51 (CH$_2$O), 9.24 (Cp*Me). HRMS/ESI+ (m/z): [M+H]+ calcd for C$_{14}$H$_{22}$Cl [193Ir] N O$_4$ 496.0861. Found 496.0814.

In the synthesis for Cp*IrCl (L-Cysteine) (4) following the general procedure: [IrCp*Cl$_2$]$_2$ (0.1500 g, 1.886 mmol), L-Cysteine (0.0689 g (7.73 mmol), and KOH (0.0430 g 7.664 mmol) were reacted in Methanol (50 mL) to give 4 (0.1498 g 88.1%). 4 was identified based on the following information: $^1$H NMR (400 MHz, D$_2$O, 300 k. HRMS/ESI+ (m/z): [M+H]+ calcd for C13H21 [193Ir] N O$_2$S 448.0917. Found 448.0917.

In the synthesis for Cp*IrCl (Glycine) (5) following the general procedure: [IrCp*Cl$_2$]$_2$ (0.1500 g, 1.886 mmol), L-Glycine (0.0580 g (7.73 mmol), and KOH (0.0430 g 7.664 mmol) were reacted in Methanol (25 mL) to give 5 (0.1310 g 79.5%). 5 was identified based on the following information $^1$H NMR (400 MHz, CDCl$_3$) δ 6.49 (br s, 2H, NH$_2$), 3.45 (d, J=6.0 Hz, 2H)CH$_2$, 1.71 (s, 15H) Cp*Me. $^{13}$C NMR (101 MHz, CDCl$_3$) δ 183.44 (COO), 84.10 (CP*), 45.30 (CH$_2$), 9.16 (Cp*Me). HRMS/ESI+ (m/z): [M+H]+ calcd for C$_{12}$H$_{19}$N O$_2$ [193Ir] 402.104. found, 402.1059.

In the synthesis for Cp*IrCl (N-methyl-Glycine) (6) following the general procedure: [IrCp*Cl$_2$]$_2$ (0.1000 g, 1.26 mmol), N-methyl-Glycine (0.0454 g (5.1 mmol), and KOH (0.0284 g 5.1 mmol) were reacted in Methanol (50 mL) to give 6 (0.0824 g 79.7%). 6 was identified based on the following information: $^1$H NMR (400 MHz, CDCl$_3$) δ 7.08-6.97 (m, 1H, NH), 3.38-3.33 (m, 2H, CH$_2$), 2.77 (d, J=5.6 Hz, 3H, NCH$_3$), 1.65 (s, 15H, Cp*Me). $^{13}$C NMR (101 MHz, CDCl$_3$) δ 183.39 (COO), 83.89 (Cp*), 55.73 (CH), 39.91 (NCH$_3$), 8.83 (Cp*Me). HRMS/ESI+ (m/z): [M+Na]+ calcd for C$_{13}$H$_{21}$Cl [193Ir] N Na O$_2$ 474.0782. found 474.079. Anal. Calcd for C$_{13}$H$_{21}$ClIrNO$_2$; C, 34.62; H, 4.69. Found: C, 35.00; H, 4.83.

In the synthesis for Cp*IrCl (N,N-dimethyl-Glycine) (7) following the general procedure: [IrCp*Cl$_2$]$_2$ (0.1000 g, 1.26 mmol), L-N-methyl-Glycine (0.0531 g (5.1 mmol), and KOH (0.0284 g 5.1 mmol) were reacted in Methanol (30 mL) to give 7 (0.0824 g 42.6%). 7 was identified based on the following information: $^1$H NMR (400 MHz, CDCl$_3$) δ 4.09 (d, J=14.6 Hz, 1H, CH), 3.10 (s, 3H, NCH$_3$), 3.00 (d, J=14.6 Hz, 1H, CH), 2.94 (s, 3H, NCH$_3$), 1.62 (s, 15H, Cp*Me). $^{13}$C NMR (101 MHz, CDCl$_3$) δ 180.47 (COO), 84.25 (Cp*), 66.26 (CH$_2$), 56.25 (NCH$_3$), 50.58 (NCH$_3$), 9.01 (Cp*Me). HRMS/ESI+ (m/z): [M+Na]+ calcd for C$_{14}$H$_{24}$Cl [193Ir] N O$_2$ 466.1119. found 466.1117. Anal. Calcd for C$_{14}$H$_{23}$ClIrNO$_2$; C, 36.16; H, 4.99. Found: C, 35.57; H, 4.95.

In the synthesis for Cp*IrCl (L-Glutamic Acid) (8) following the general procedure: [IrCp*Cl$_2$]$_2$ (0.1000 g, 1.255 mmol), L-Glutamic Acid (0.0800 g (5.44 mmol), and KOH (0.030 g 5.35 mmol) were reacted in Methanol (30 mL) to give 8 (0.1032 g 80.8%). 8 was identified based on the following information: $^1$H NMR (400 MHz, CDCl$_3$) δ 5.74 (br s, 1H, NH), 4.11 (br s, 1H, NH), 3.63-3.52 (m, 1H, CH), 2.64-2.50 (m, 2H, CH$_2$), 2.08-1.97 (m, 2H, CH$_2$), 1.70 (s, 15H, Cp*Me). $^{13}$C NMR (101 MHz, CDCl$_3$) δ 184.19 (COO), 176.81 (COO), 84.01 (Cp*), 55.72 (CH), 32.37 (CH$_2$), 27.68 (CH$_2$), 9.01 (Cp*Me). HRMS/ESI+(m/z): [M+H]+ calcd for C$_{15}$H$_{24}$ [193Ir] N O$_4$ 475.1329. found 475.1343.

In the synthesis for Cp*IrCl (D-Histidine) (9) following the general procedure: [IrCp*Cl$_2$]$_2$ (0.1500 g, 1.886 mmol), L-Histidine (0.120 g (7.73 mmol), and KOH (0.0434 g 7.73 mmol) were reacted in Methanol (50 mL) to give 9 (0.0800 g 41.0%). 9 was identified based on the following information: $^1$H NMR (400 MHz, CD$_3$OD) δ 8.16 (d, J=1.3 Hz, 1H), 7.12 (s, 1H), 4.21 (dt, J=5.5, 3.7 Hz, 1H), 3.36-3.31 (m, 1H), 3.27 (dd, J=4.0, 1.2 Hz, 1H), 1.77 (s, 15H). $^{13}$C NMR (101 MHz, CD$_3$OD) δ 185.05 (COO), 137.58 (ArC), 132.36 (ArC), 115.54 (ArC), 85.23 (Cp*), 53.21 (CH), 26.57 (CH$_2$), 7.60 (Cp*Me). HRMS/ESI+ (m/z): [M+H]+ calcd for C16H24Cl [193Ir] N$_3$O$_2$ 518.1181. found 518.1171.

In the synthesis for Cp*IrCl (L-Isoleucine) (10) following the general procedure: [IrCp*Cl$_2$]$_2$ (0.1500 g, 1.886 mmol), L-Isoleucine (0.1014 g (7.73 mmol), and KOH (0.0434 g 7.73 mmol) were reacted in Methanol (30 mL) to give 10 (0.1072 g 57.6%) (mol ratio 50/50). 10 was identified based on the following information $^1$H NMR (400 MHz, cdcl3) δ 4.09 (d, J=14.6 Hz, 1H), 3.10 (s, 3H), 3.00 (d, J=14.6 Hz, 1H), 2.94 (s, 3H), 1.62 (s, 15H). $^{13}$C NMR (101 MHz, cdcl3) δ 182.40 (COO), 179.50 (COO), 84.17 (Cp*), 83.92 (Cp*), 63.11 (NCH), 59.28 (NCH), 37.72 (CHR$_3$), 37.04 (CHR$_3$), 24.15 (CH$_2$), 23.96 (CH$_2$), 16.28 (CH$_3$), 16.32 (CH$_3$), 12.04 (CH$_3$), 11.96 (CH$_3$), 9.17 (Cp*Me), 9.01 (Cp*Me). HRMS/ESI+ (m/z): [M+H]+ calcd for C16H26 [193Ir] N O$_2$ 458.162. found 458.1638.

In the synthesis for Cp*IrCl (L-Leucine) (11) following the general procedure: [IrCp*Cl$_2$]$_2$ (0.1500 g, 1.886 mmol), L-Leucine (0.1014 g (7.73 mmol), and KOH (0.0434 g 7.73 mmol) were reacted in Methanol (30 mL) to give 11 (0.1072 g 57.6%). 11 was identified based on the following information: $^1$H NMR (400 MHz, cdcl3) δ 4.09 (d, J=14.6 Hz, 1H), 3.10 (s, 3H), 3.00 (d, J=14.6 Hz, 1H), 2.94 (s, 3H), 1.62 (s, 15H). HRMS/ESI+ (m/z): [M+H]+ calcd for C16H26 [193Ir] N O$_2$ 458.162. found 458.1638.

In the synthesis for Cp*IrCl (L-Lysine) (12) following the general procedure: [IrCp*Cl$_2$]$_2$ (0.1500 g, 1.886 mmol), L-Lysine (0.1014 g (7.73 mmol), and KOH (0.0434 g 7.73 mmol) were reacted in Methanol (30 mL) to give 12 (0.1072 g 57.6%). 12 was identified based on the following information: HRMS/ESI+ (m/z): [M+H]+ calcd for C$_{16}$H$_{29}$ [193Ir] N$_2$O$_2$ 509.1541. found 509.1534.

In the synthesis for Cp*IrCl (L-Methionine) (13) following the general procedure: [IrCp*Cl$_2$]$_2$ (0.1500 g, 1.886 mmol), L-Methionine (0.101 g (7.73 mmol), and KOH (0.0434 g 7.73 mmol) were reacted in Methanol (50 mL) to give 18 (0.1794 g 93.1%). 13a/b was identified based on the following information: 13a: $^1$H NMR (400 MHz, cd3od) δ 4.09 (d, J=4.3 Hz, 1H NHH), 3.45 (dd, J=7.4, 5.2 Hz, 1H, CHOO), 3.27-3.21 (m, 1H NHH), 2.80 (s, 3H SCH$_3$), 2.59 (ddd, J=8.6, 6.6, 2.3 Hz, 2H CH$_2$), 2.09-2.02 (m, 1H CHH), 1.95-1.85 (m, 1H CHH), 1.75 (s, 15H Cp*Me). $^{13}$C NMR (101 MHz, cd3od) δ 89.74 (Cp*), 54.77 (CH), 33.25 (CH$_2$), 28.61 (CH$_2$), 13.65 (SCH$_3$), 7.16 (Cp*Me). 13b: $^1$H NMR (400 MHz, cd3od) δ 4.04 (d, J=4.7 Hz, 1H NHH), 3.29-3.26 (m, 1H NHH), 2.94 (dt, J=13.7, 6.7 Hz, 1H CHOO), 2.48 (s, 3H SCH$_3$), 2.39 (d, J=6.4 Hz, 2H CH$_2$), 2.09-2.01 (m, 2H CH$_2$), 1.77 (S, 15H Cp*Me). $^{13}$C NMR (101 MHz, CD$_3$OD) δ 89.66 (Cp*). HRMS/ESI+ (m/z): [M+NH$_4$]+ calcd for C$_{15}$H$_{28}$ [193Ir] N$_2$O$_2$S 493.1495. found 493.1475.

In the synthesis for Cp*IrCl (L-Phenylalanine) (14a/14b) following the general procedure: [IrCp*Cl$_2$]$_2$ (0.1500 g, 1.886 mmol), L-Phenylalanine (0.128 g (7.73 mmol), and KOH (0.0434 g 7.73 mmol) were reacted in Methanol (50 mL) to give 14a/b (0.1754 88.2%) (mol ratio 69/31). 14 was identified based on the following information:

14a: $^1$H NMR (400 MHz, cdcl$_3$) δ 7.35-7.21 (m, 6H ArH), 3.93 (s, 1H NHH), 3.82 (dt, J=13.0, 6.4 Hz, 1H CHOO), 3.76 (d, J=9.2 Hz, 1H NHH), 3.30 (dd, J=14.3, 6.0 Hz, 1H CHH), 3.03 (dd, J=14.3, 4.9 Hz, 1H CHH), 1.47 (s, 15H Cp*Me). $^{13}$C NMR (101 MHz, CDCl$_3$) δ 129.74 (ArC), 129.35 (ArC), 129.26 (ArC), 83.93 (Cp*), 55.06 (COO), 38.36 (CH$_2$), 8.80 (Cp*Me).

14b: $^1$H NMR (400 MHz, CDCl$_3$) δ 7.35-7.21 (m, ArH), 4.06 (br s, 1H NHH), 3.57 (br s, 1H NHH), 3.50-3.44 (m, 1H CHOO), 3.41 (d, J=7.0 Hz, 1H CHH), 2.91 (dd, J=15.2, 10.8 Hz, 1H CHH), 1.60 (s, 15H Cp*Me). $^{13}$C NMR (101 MHz, CDCl$_3$) δ 84.18 (Cp*), 9.09 (Cp*Me).

HRMS/ESI+ (m/z): [M+H]+ calcd for C19H24 [193Ir] N O2 492.1464. found 492.1476. Anal. Calcd for C$_{19}$H$_{25}$ClIrNO$_2$: C, 43.3%; H, 4.78%. Found: C, 42.71%; H, 4.78%. X-Ray Crystallography: Mo Kα radiation.

In the synthesis for Cp*IrCl (D-Phenylalanine) (15a/b) following the general procedure: [IrCp*Cl$_2$]$_2$ (0.1000 g, 1.26 mmol), D-Phenylalanine (0.087 g (5.14 mmol), and KOH (0.029 g 5.14 mmol) were reacted in Methanol (50 mL) to give 15a/b (0.1169 88.4%) (mol ratio 70/30). 15a/b was identified based on the following information:

15a $^1$H NMR (400 MHz, CDCl$_3$) δ 7.38-7.29 (m, 6H ArH), 4.59 (br s, 1H NHH), 4.16 (br s, 1H NHH), 3.64-3.54 (m, 1H CHOO), 3.38 (dd, J=14.3, 5.7 Hz, 1H CHH), 3.11 (dd, J=14.3, 4.7 Hz, 1H CHH), 1.53 (s, 15H Cp*Me). $^{13}$C NMR (101 MHz, CDCl$_3$) δ 182.60 (COO), 136.40 (ArC), 129.91 (ArC), 129.47 (ArC), 127.72 (ArC), 84.08 (Cp*), 55.19 (αC), 38.54 (CH$_2$), 8.94 (Cp*Me).

15b: $^1$H NMR (400 MHz, CDCl$_3$) δ 7.40-7.27 (m, 6H ArH), 3.50-3.44 (m, 1H CHH), 3.03 (dd, J=14.7, 9.2 Hz, 1H CHH), 1.66 (s, 15H Cp*Me). $^{13}$C NMR (101 MHz, CDCl$_3$) δ 129.55 (ArC), 84.31 (Cp*), 9.26 (Cp*Me).

HRMS/ESI+ (m/z): [M+H]+ calcd for C$_{19}$H$_{24}$ [193Ir] N O$_2$ 492.1464. found 492.1476. X-Ray Crystallography: Mo Kα radiation In the synthesis for Cp*IrCl (L-Phenylglycine) (16a/16b) following the general procedure: [IrCp*Cl$_2$]$_2$ (0.1000 g, 1.26 mmol), L-Proline (0.0434 g (3.77 mmol), and KOH (0.0211 g 3.77 mmol) were reacted in Methanol (30 mL) to give 16a/16b (0.1067 89.1%) (mol ratio 52/48). 16a/16b was identified based on the following information:

16a: $^1$H NMR (400 MHz, CDCl$_3$) δ 7.180-7.119 (m, 5H ArH), 6.50 (br s, 1H NHH), 4.22-4.14 (m, 1H CHOO), 3.52 (t, J=10.4 Hz, 1H NHH), 1.63 (s, 15H Cp*Me). $^{13}$C NMR (101 MHz, cdcl$_3$) δ 180.94 (COO), 140.65 (ArC), 129.26 (ArC), 128.86 (ArC), 127.95 (ArC), 84.26 (Cp*), 58.89 (αCH), 9.23 (Cp*Me).

16b: $^1$H NMR (400 MHz, CDCl$_3$) δ 7.35-7.26 (m, 5H ArH), 4.71 (Br s, 1H NHH), 4.52-4.45 (m, 1H CHOO), 4.11 (br s, 1H NHH), 1.50 (s, 15H Cp*Me). $^{13}$C NMR (101 MHz, CDCl$_3$) δ 181.47 (COO), 138.65 (ArC), 129.77 (ArC), 128.44 (ArC), 128.10 (ArC), 84.21 (Cp*), 61.02 (αCH), 9.05 (Cp*Me).

In the synthesis for Cp*IrCl (L-Proline) (17a/17b) following the general procedure: [IrCp*Cl$_2$]$_2$ (0.1000 g, 1.26 mmol), L-Proline (0.0434 g (3.77 mmol), and KOH (0.0211 g 3.77 mmol) were reacted in Methanol (30 mL) to give 17a/17b (0.1067 89.1%) (mol ratio 93/7). 17a/17b was identified based on the following information:

17a $^1$H NMR (400 MHz, CDCl$_3$) δ 4.64 (br s, 1H NH), 4.04 (dd, J=16.3, 8.2 Hz, 1H CHOO), 3.59 (dt, J=11.1, 5.5 Hz, 1H NCHH), 2.95 (qd, J=11.0, 5.8 Hz, 1H NCHH), 2.31-2.19 (m, 1H CHH), 2.11-2.00 (m, 1H CHH), 1.96 (ddd, J=15.8, 10.5, 6.5 Hz, 1H CHH), 1.75 (ddd, J=6.7, 6.1, 4.5 Hz, 1H CHH), 1.67 (s, 15H Cp*Me). $^{13}$C NMR (101 MHz, CDCl$_3$) δ 184.19 (COO), 84.21 (Cp*), 62.42 (αCH), 54.65 (CH$_2$), 28.66 (CH$_2$), 27.13 (CH$_2$), 9.21 (Cp*Me).

17b: $^1$H NMR (400 MHz, CDCl$_3$) δ 6.73 (br s, 1H NH), 4.25-4.18 (m, 1H CHOO), 3.70 (d, J=14.5 Hz, 1H NCHH), 3.42-3.29 (m, 1H NCHH), 3.27-3.21 (m, 1H CHH), 2.17 (s, 2H CH$_2$), 1.70 (s, 15H Cp*Me). $^{13}$C NMR (101 MHz, CDCl$_3$) δ 9.00 (Cp*Me).

HRMS/ESI+ (m/z): [M+H]+ calcd for C$_{15}$H$_{24}$Cl [193Ir] N O$_2$ 478.1119. found 492.113. Anal. Calcd for C$_{15}$H$_{23}$ClIrNO$_2$: C, 37.77; H, 4.86. Found: C, 37.79%; H, 5.06%. X-Ray Crystallography: Mo Kα radiation.

In the synthesis for Cp*IrCl (D-Proline) (18a/18b) following the general procedure: [IrCp*Cl$_2$]$_2$ (0.1000 g, 1.26 mmol), D-Proline (0.0434 g (3.77 mmol), and KOH (0.0211 g 3.77 mmol) were reacted in Methanol (30 mL) to give 18a/18b (0.1036 86.5%), (mol ratio 93/7). 18a/18b was identified based on the following information:

18a: $^1$H NMR (400 MHz, CDCl$_3$) δ 4.71 (br s, 1H NH), 4.03 (dd, J=16.3, 8.3 Hz, 1H CHOO), 3.66-3.53 (m, 1H NCHH), 2.94 (qd, J=11.0, 5.9 Hz, 1H NCHH), 2.30-2.20 (m, 1H CHH), 2.09-2.00 (m, 1H CHH), 2.00-1.90 (m, 1H CHH), 1.81-1.71 (m, 1H CHH), 1.68-1.66 (m, 15H Cp*Me). $^{13}$C NMR (101 MHz, CDCl$_3$) δ 184.24 (COO), 84.19 (Cp*), 62.31 (CH), 54.67 (CH$_2$), 28.71 (CH$_2$), 27.14 (CH$_2$), 9.21 (Cp*Me).

18b: $^1$H NMR (400 MHz, CDCl$_3$) δ 6.79 (br s, 1H NH), 3.77-3.67 (m, 1H CHOO), 3.28-3.17 (m, 1H NCHH), 2.19-2.11 (m, 2H CH$_2$), 1.69 (s, 15H Cp*Me). $^{13}$C NMR (101 MHz, CDCl$_3$) δ 83.83 (Cp*), 8.98 (Cp*Me).

In the synthesis for Cp*IrCl (L-Trans-4-Hydroxyproline) (19a/19b) following the general procedure: [IrCp*Cl$_2$]$_2$ (0.1000 g, 1.26 mmol), L-Trans-4-Hydroxyproline (0.0702 g (5.36 mmol), and KOH (0.0300 g 5.35 mmol) were reacted in Methanol (30 mL) to give 19a/19b (0.1103 89.13%), (mol ratio 73/27). 19a/19b was identified based on the following information:

19a $^1$H NMR (400 MHz, acetone) δ 5.40 (br s, 1H NH), 4.42-4.36 (m, 1H CH—OH), 4.02 (dd, J=16.6, 8.1 Hz, 1H CHOO), 3.64 (dd, J=11.9, 5.1 Hz, 1H NCHH), 3.02 (td, J=11.8, 3.3 Hz, 1H NCHH), 2.10-2.07 (m, 2H CH$_2$), 1.68 (s, 15H Cp*Me). $^{13}$C NMR (101 MHz, CDCl$_3$) δ 185.58 (COO), 84.32 (Cp*), 71.86 (C—O), 61.94 (αCH), 61.54 (CH), 38.18 (CH), 9.25 (Cp*Me).

19b: $^1$H NMR (400 MHz, acetone) δ 7.00 (br s, 1H NH), 4.33-4.28 (m, 1H CH—OH), 4.18-4.09 (m, 2H NCH$_2$), 3.96-3.88 (m, 1H CHOO), 3.17-3.10 (m, 1H CHH), 2.20 (td, J=12.2, 3.7 Hz, 2H CH$_2$), 1.71 (s, 15H Cp*Me). $^{13}$C NMR (101 MHz, CDCl$_3$) δ 84.18 (Cp*), 9.08 (Cp*Me).

HRMS/ESI+ (m/z): [M+H]+ calcd for C15H24Cl [193Ir] N O3 494.1068. found 494.1057. Anal. Calcd for C$_{15}$H$_{23}$ClIrNO$_3$: C, 36.54; H, 4.70. Found: C, 37.06; H, 4.86.

In the synthesis for Cp*IrCl (L-Trans-4-Fluoroproline) (20a/20b) following the general procedure: [IrCp*Cl$_2$]$_2$ (0.1000 g, 1.26 mmol), L-Trans-4-Fluoroproline (0.042 g (3.14 mmol), and KOH (0.0176 g 3.14 mmol) were reacted in Methanol (30 mL) to give 20a/20b (0.0903 g 72.68%). 20a/20b was identified based on the following information:

20a: $^1$H NMR (400 MHz, CDCl$_3$) δ 5.24 (dm J=52.1 Hz, 1H CFH) 4.98-4.88 (m, 1H NH), 4.36-4.28 (dd, J=17.2, 7.3 1H, CHOO), 3.78-3.64 (m, 1H NCHH), 3.00 (dtd, J 37.2, 12.7, 2.4 Hz, 1H NCHH), 2.49-2.39 (m, 2H CH$_2$), 1.66 (s, 15H Cp*Me). $^{13}$C NMR (101 MHz, CDCl$_3$) δ 183.11 (COO), 95.07-93.14 (d, J=176.38, C—F), 84.43 (Cp*), 61.08 (C), 59.55 (d, J=21.5 Hz, C—F), 36.20 (d, J=21.5 Hz, C—F), 9.21 (Cp*Me).

20b: $^1$H NMR (400 MHz, CDCl$_3$) δ 7.31 (dd, J=15.6, 7.6 Hz, 1H NH), 5.14 (dm, J=52.1 Hz), 4.28-4.21 (m, 1H CHOO), 3.99 (dddd, J=42.0, 13.1, 6.9, 3.3 Hz, 1H NCHH), 3.55-3.41 (m, 1H NCHH), 2.39-2.28 (m, 2H CH$_2$), 1.68 (s, 15H Cp*Me). $^{13}$C NMR (101 MHz, CDCl$_3$) δ 184.16 (COO), 84.14 (Cp*), 95.60 (d, J=176.38 Hz C—F, 61.81 (αCH), 57.80 (d, J=21.5 Hz CH$_2$), 37.79 (d, J=21.5 Hz CH$_2$), 9.00 (Cp*Me).

HRMS/ESI+ (m/z): [M+H]+ calcd for C$_{15}$H$_{23}$Cl F [193Ir] N O$_2$ 496.1025. Found 496.1. Anal. Calcd for C$_{15}$H$_{22}$ClFIrNO$_2$: C, 36.40%; H, 4.48%. Found: C, 36.18%; H, 4.35%. X-Ray Crystallography: Mo Kα radiation In the synthesis for Cp*IrCl (D-N-Methyl-Proline) (21) following the general procedure: [IrCp*Cl$_2$]$_2$ (0.1000 g, 1.26 mmol), N-Methyl-D-Proline (0.0434 g (3.77 mmol), and KOH (0.0211 g 3.77 mmol) were reacted in Methanol (30 mL) to give 21 (0.0895 72.6%). 21 was identified based on the following information:

21: $^1$H NMR (400 MHz, C$_6$D$_6$) δ 4.07 (d, J=10.5 Hz, 1H CHOO), 2.72 (dd, J=18.6, 7.8 Hz, 1H NCHH), 2.52 (d, J=19.2 Hz, 1H NCHH), 2.40 (d, J=7.5 Hz, 1H CHH), 2.34 (s, 3H NCH$_3$), 1.51 (t, J=13.4 Hz, 1H CHH), 1.21 (d, J=11.2 Hz, 2H CH$_2$), 1.09 (s, 14H). $^{13}$C NMR (101 MHz, CDCl$_3$) δ 182.89 (COO), 84.06 (Cp*), 71.76 (αCH), 63.60 (CH$_2$), 47.00 (NCH$_3$), 24.17 (CH$_2$), 22.36 (CH$_2$), 9.15 (Cp*Me).

HRMS/ESI+ (m/z): [M+H]+ calcd for C$_{15}$H$_{24}$Cl [193Ir] N O$_2$ 478.1119. found 492.113 Anal. Calcd for C$_{15}$H$_{23}$ClIrNO$_2$: C, 37.77; H, 4.86. Found: C, 37.79%; H, 5.06% X-Ray Crystallography: Mo Kα radiation In the synthesis for Cp*IrCl (L-Serine) (22a/22b) following the general procedure: [IrCp*Cl$_2$]$_2$ (0.1500 g, 1.88 mmol), L-Serine (0.0813 g (7.79 mmol), and KOH (0.0813 g 7.73 mmol) were reacted in Methanol (50 mL) to give 22a/22b (0.1508 85.6%) (mol ratio 62/38). 22a/22b was identified based on the following information:

22a: $^1$H NMR (400 MHz, dmso) δ 5.33 (t, J=9.7 Hz, 1H NHH), 5.05 (t, J=9.7 Hz, 1H NHH), 3.55 (t, J=5.4 Hz, 2H, CH$_2$—OH), 3.18 (dt, J=17.1, 8.4 Hz, 1H αCH) 1.59 (s, 15H Cp*Me). $^{13}$C NMR (101 MHz, CDCl$_3$) δ 181.57 (COO), 84.51 (Cp*), 63.06 (C—OH), 58.84 (αCH), 9.19 (Cp*Me).

22b: $^1$H NMR (400 MHz, dmso) δ 6.26 (t, J=9.7 Hz, 1H NHH), 4.87 (t, J=5.3 Hz, 1H CH—OH), 4.06 (t, J=9.7 Hz, 1H NHH), 3.63 (dt, J=11.6, 5.9 Hz, 1H αCH), 1.60 (s, 1H Cp*Me). $^{13}$C NMR (101 MHz, CDCl$_3$) δ 183.48 (COO), 84.17 (Cp*), 62.05 (CH$_2$—OH), 57.42 (αCH), 9.03 (Cp*Me).

HRMS/ESI+ (m/z): [M+H]+ calcd for C13H21 [193Ir] N O3 433.1178. found 433.1178. Anal. Calcd for C$_{13}$H$_{21}$ClIrNO$_3$: C, 33.44; H, 4.53. Found: C, 33.37; H, 4.30. X-Ray Crystallography: Mo Kα radiation In the synthesis for Cp*IrCl (L-Threonine) (23a/23b) following the general procedure: [IrCp*Cl$_2$]$_2$ (0.1500 g, 1.88 mmol), L-Threonine (0.0813 g (7.79 mmol), and KOH (0.0813 g 7.73 mmol) were reacted in Methanol (50 mL) to give (23a/23b) (0.1508 85.6%) mol ratio 68/32. (23a/23b) was identified based on the following information:

23a: $^1$H NMR (400 MHz, dmso) δ 5.46-5.37 (m, 1H NHH), 5.00 (d, J=5.5 Hz, 1H CH—OH), 4.69-4.61 (m, Hz, 1H), 4.05-3.97 (br s, 1H OH), 2.86 (d, J=14.3 Hz, 1H αCH), 1.59 (s, 15H, Cp*Me), 1.12 (d, J=6.6 Hz, 3H CH$_3$).

HRMS/ESI+ (m/z): [M+H]+ calcd for C$_{14}$H$_{24}$[193Ir] N O$_3$ 484.1044. found 484.1044. Anal. Calcd for C$_{14}$H$_{23}$ClIrNO$_3$: C, 34.96; H, 4.82. Found: C, 34.61; H, 4.74. X-Ray Crystallography: Mo Kα radiation In the synthesis for Cp*IrCl (L-Valine) (24a/24b) following the general procedure: [IrCp*Cl$_2$]$_2$ (0.1500 g, 1.88 mmol), L-Valine (0.091 g, 7.73 mmol), and KOH (0.043 g, 7.73 mmol) were reacted in methanol (50 mL) to give 24a/24b (0.1450 g 77.3%) mol ratio 53/47. (24a/24b) was identified based on the following information:

24a: $^1$H NMR (400 MHz, dmso) δ 5.46-4.36 (m, 1H NHH), 4.53-4.44 (m, 1H, NHH), 3.03-2.93 (m, 1H, αCH), 2.08 (dd, J=10.9, 6.4 Hz, 1H CH—(CH$_3$)$_2$), 1.60 (s, 15H, Cp*Me), 0.97-0.91 (m, 3H CH$_3$), 0.82 (d, J=7.0 Hz, 3H, CH$_3$). $^{13}$C NMR (101 MHz, dmso) δ 182.44 (COO), 83.30 (Cp*), 61.72 (αCH), 31.31 (CH$_2$), 19.30 (CH$_3$), 17.38 (CH$_3$), 8.89 (Cp*Me).

24b: $^1$H NMR (400 MHz, dmso) δ 6.05-5.95 (m, 1H, NHH), 3.61-3.53 (m, 1H, NHH), 3.02-2.93 (m, 1H, αCH), 2.12-2.04 (m, 1H CH—(CH$_3$)$_2$), 1.61 (s, 15H, Cp*Me), 0.97-0.90 (m, 3H, CH$_3$), 0.73 (d, J=7.0 Hz, 3H, CH$_3$). $^{13}$C NMR (101 MHz, dmso) δ 180.22 (COO), 83.76 (Cp*), 60.10 (αCH), 31.05 (CH$_2$), 19.35 (CH$_3$), 17.15 (CH$_3$), 9.04 (Cp*Me).

HRMS/ESI+ (m/z): calcd for C$_{15}$H$_{25}$NO$_2$ [193Ir] 445.1542. found 445.1564.

Anal. Calcd for C$_{15}$H$_{25}$ClIrNO$_2$; C, 37.61; H, 5.26. Found: C, 37.34; H, 5.34.

In the synthesis for Cp*IrCl (L-azetidine-2-carboxylic acid) (25a/25b) following the general procedure: And was identified based on the following: [IrCp*Cl$_2$]$_2$ (0.1000 g, 1.26 mmol), L-azetidine-2-carboxylic acid (0.0434 g (3.77 mmol), and KOH (0.0211 g 3.77 mmol) were reacted in Methanol (30 mL). information:

25a: $^1$H NMR (400 MHz, CDCl$_3$) δ 5.46 (br s, 1H, NH), 4.53-4.40 (m, 1H, CHOO), 4.36-4.20 (m, 1H, N—CHH), 3.91-3.81 (m, 1H, N—CHH), 2.94 (dtd, J=17.6, 9.8, 7.8 Hz, 1H, CHH), 2.40 (ddt, J=12.0, 8.9, 6.2 Hz, 1H, CHH), 1.68 (s, 15H, Cp*Me). $^{13}$C NMR (101 MHz, CDCl$_3$) δ 185.84 (COO), 84.04 (Cp*), 60.61 (αCH), 50.99 (CH$_2$), 26.18 (CH$_2$), 9.03 (Cp*Me).

25b: $^1$H NMR (400 MHz, CDCl$_3$) δ 6.99 (brs, 1H, NH), 4.88-4.77 (m, 1H, CHOO), 4.10-4.00 (m, 1H, N—CHH), 4.00-3.92 (m, 1H, N—CHH), 2.73-2.64 (m, 1H, CHH), 2.64-

2.52 (m, 1H, CHH), 1.66 (d, J=2.9 Hz, 15H). $^{13}$C NMR (101 MHz, CDCl$_3$) δ 8.90 (Cp*Me).

HRMS/ESI+ (m/z): [M+H]+ calcd for C14H22Cl [193Ir] N O2 464.0963. found 464.0952.

In the synthesis for Cp*IrCl (L-Piperidine-2-carboxylic acid) (26a/26b) following the general procedure: And was identified based on the following: [IrCp*Cl$_2$]$_2$ (0.1000 g, 1.26 mmol), L-azetidine-2-carboxylic acid (0.0480 g (3.77 mmol), and KOH (0.0211 g 3.77 mmol) were reacted in Methanol (30 mL) to give 26a/26b (0.1152 g 93.5%) mol ratio (74/26). 26a/26b were identified based on the following information:

26a: $^1$H NMR (400 MHz, Chloroform-d) δ 3.86 (t, J=12.3 Hz, 1H, NH), 3.55-3.47 (m, 1H, N—CHH), 3.10 (td, J=12.1, 3.0 Hz, 1H, CHOO), 3.00 (qd, J=12.3, 3.2 Hz, 1H, N—CHH), 2.28-2.20 (m, 1H, CHH), 1.97 (d, J=8.0 Hz, 1H, CHH), 1.86-1.79 (m, 2H, CH$_2$), 1.66 (s, 15H, Cp*Me), 1.58-1.46 (m, 4H, CH$_2$—CH$_2$). $^{13}$C NMR (101 MHz, Chloroform-d) δ 177.76 (COO), 84.41 (Cp*), 66.24 (αCH), 53.67 (N—CH$_2$), 30.79 (CH$_2$), 27.79 (CH$_2$), 23.61 (CH$_2$), 9.31 (Cp*Me).

26b: $^1$H NMR (400 MHz, Chloroform-d) δ 4.97 (br s, 1H, NH), 3.76 (td, J=11.6, 2.8 Hz, 1H, CHOO), 3.28-3.15 (m, 2H, N—CH$_2$), 2.11 (d, J=10.8 Hz, 1H, CHH), 1.72-1.67 (m, 1H, CHH), 1.64 (s, 15H, Cp*Me), 1.46-1.37 (m, 4H, CH$_2$—CH$_2$). $^{13}$C NMR (101 MHz, Chloroform-d) δ 84.02 (Cp*), 62.50 (αCH), 53.42 (N—CH$_2$), 28.53 (CH$_2$), 26.78 (CH$_2$), 23.86 (CH$_2$), 8.86 (Cp*Me).

HRMS/ESI+ (m/z): calcd for C$_1$H$_2$NO$_2$ [193Ir] 492.1276; 492.1253.

Example V

Biological Activity of Rhodium-Based Piano Stool Complexes

Table VI lists biological activity data for representative rhodium piano stool compounds.

TABLE VI

Biological Activity (MICs) for Rhodium Piano Stool Complexes

|  | M. smegmatis | M. chelonae | M. abscessus |
|---|---|---|---|
| Rh(Cp*)Phen | 3.9 ug/mL | 3.9 ug/mL | 3.9 ug/mL |
| Rh(Cp*)Leu | 3.9 ug/mL | 3.9 ug/mL | 3.9 ug/mL |
| Rh(Cp*)Val | 7.5 ug/mL | 14 ug/mL | 15 ug/mL |
| Rh(Cp*)ala | 7.5 ug/mL | 15 ug/mL | 14 ug/mL |
| Rh(Cp*)pro | 3.9 ug/mL | 7.5 ug/mL | 7.5 ug/mL |

As demonstrated in Table VI, it is clear from the low MIC values that the Rhodium based piano stool complexes are also quite active.

Example VI

Biological Activity of Ruthenium-Based Piano Stool Complexes

Table VII shows the biological activity of representative ruthenium-based piano stool complexes. A piano-stool complex of ruthenium shows activity comparable to those found for rhodium. The last entry in the table, that of the Ru chloro-bridged dimer that does not have an amino acid ligand is totally inactive. Thus, it would appear that the foundation metal framework is insufficient by itself for biological activity—rather the amino acid ligand appears to play a role in this function.

TABLE VII

Biological Activity (MICs) for Ruthenium Piano Stool Complexes

|  | M. smegmatis | M. chelonae | M. abscessus |
|---|---|---|---|
| Ru(p-cymene)Val | 7.5 ug/mL | 7.5 ug/mL | 7.5 ug/mL |
| Ru(p-cymene)phen | 3.9 ug/mL | 7.5 ug/mL | 7.5 ug/mL |
| Ru(p-cymene)leu | 3.9 ug/mL | 7.5 ug/mL | 7.5 ug/mL |
| Ru(p-cymene)ala | 7.5 ug/mL | 7.5 ug/mL | 7.5 ug/mL |
| [Ru(p-cymene)Cl]2 | NA | NA | NA |

Category IV. Square planar complexes of metals. Square planar complexes of metals with alkenes and amino acids or diamines work against MRSA. Category IV compounds generally conform to the structure of Formula 4 below:

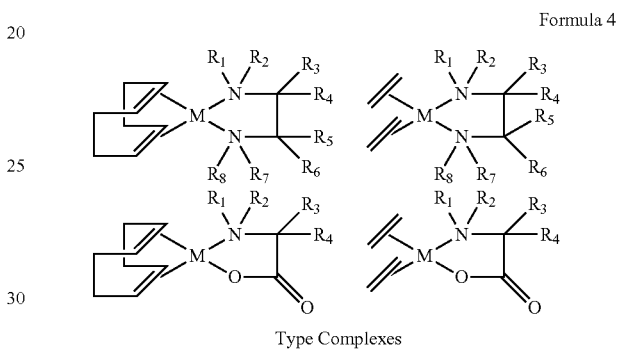

Formula 4

Type Complexes wherein R$_1$-R$_8$ may be the same or different and includes H, CH$_3$, CH$_2$CH$_3$, C$_6$H$_5$ and any other number of C$_{1-20}$ alkyl substituents.

Substitution on the alkene groups is also possible with other chelating dialkenes such as norbornadiene. Substitution of the alkenes with other substituted olefins such as propene, butene or cyclic olefins such as cyclooctene is possible.

M may be Co, Rh, Ir, Fe, Ru, Os, Mn, Tc, Re and any other transition or lanthanide or actinide metal. Charges on the complexes may vary from 0 to +4 depending on the metal and ligand combination.

Specific Formula 4 structures within the scope of the invention for example include:

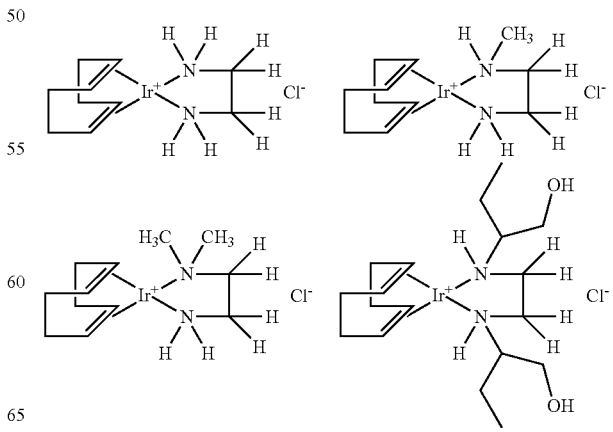

TABLE VIIIA

Test results of Complexes against gram positive MRSA

| Compound | MIC ug/mL |
|---|---|
| [Ir(COD)(ethylenediamine)]Cl | 8.1 |
| [Ir(COD)(N-methylethylenediamine)]Cl | 16.2 |
| [Ir(COD)(N,N-dimethylethylenediamine)]Cl | >250 |
| [Ir(COD)(ethambutol)]Cl | 8.1 |

TABLE VIIIB

Activity of Alkenes and Diamines used Alone against MRSA

| MRSA | S. Aur | PI-1 | PI-34380 | PI-34864 | PI-36361 | PI-53016 | PI-52300 | PI-43300 |
|---|---|---|---|---|---|---|---|---|
| 4 (N—Me-phen) | >250 ug/mL | >250 ug/mL | >250 ug/mL | >250 ug/mL | >250 ug/mL | >250 ug/mL | >250 ug/mL | >250 ug/mL |
| 4 (Napthalenediamine) | 7.5 ug/mL | 15 ug/mL | 7.5 ug/mL | 7.5 ug/mL | 7.5 ug/mL | 7.5 ug/mL | 7.5 ug/mL | 7.5 ug/mL |
| 4 (N,N-dimethyl ethylenediamine) | >250 ug/mL | >250 ug/mL | >250 ug/mL | >250 ug/mL | >250 ug/mL | >250 ug/mL | >250 ug/mL | >250 ug/mL |

When used alone some of the compounds used as ligands in the inventive complexes are not active against MRSA, including ethylenediamine, N-methylethylenediamine, N,N-dimethylethylenediamine, ethambutol (a prescribed medication for mycobacteria including tuberculosis), and N-methylphenyl, while other compounds are, such as Napthalenediamine. By complexing these compounds with Ir(COD), where COD=1,5-cycloctadiene, for example, a potent antibiotic against MRSA is obtained. This synergistic effect may be seen with other known antibiotic agents complexed to Ir[COD] or Rh[COD].

Efficacy Testing.

Example VII

Time Course of Killing Mycobacteria, Staphylococcus aureus and Methicillin-resistant S. aureus (MRSA) by Transition Metal-Amino Acid Complexes A number of iridium (Ir), ruthenium (Ru), and rhodium (Rh) transition metal-L-α-amino acid complexes have strong, broad spectrum anti-mycobacterial activity and broad spectrum antibiotic activity against Staphylococcus aureus and methicillin-resistant S. aureus (MRSA). Complexes where the transition metal was linked to the amino acid through a cyclopentadienyl group (CP*) had the highest activity. In particular, Ir-CP*-L-phenylalanine, Ir-CP*-L-phenylglycine, Ir-CP*-L-proline, Rh-CP*-L-phenylalanine, Rh-CP*-L-phenylglycine, and Rh-CP*-L-proline had the highest activity. Further, minimal bactericidal concentrations (MBC) were equal to the minimal inhibitory concentrations (MIC) indicating that the complexes were bactericidal and/or indicating that the complexes were staphylocidal.

An objective of the efficacy testing was to measure killing of mycobacteria by exposure to transition metal-amino acid complexes. The mycobacterial strains used were Mycobacterium smegmatis strain VT307, Mycobacterium bovis strain BCG, and Mycobacterium abscessus strain AAy-P-1, along with transition metal-amino acid complexes, stock concentrations 1 mg/mL in M7H9 broth, Ir-CP*-L-phenylalanine (compound 9A), Rh-CP*-L-phenylglycine (compound 8B), and GR-1 (Ru-mesitilene-phenylglycine).

Another objective was to measure killing of S. aureus and MRSA by exposure to transition metal-amino acid complexes. The strains used were S. aureus strain ATCC 6358 and MRSA strain 34380, along with stock concentrations 1 mg/mL in 1/10-strength Brain Heart Infusion Broth (BHIB), Ir-CP*-napthalene diamine (compound 6K-48) and Ir-COD-ethambutol (compound 6K-50).

TABLE IX

Drug-Mycobacterium Combinations

| Mycobacterium Strain | Transition Metal Amino Acid | Concentration |
|---|---|---|
| M. smegmatis VT307 | 9A (Ir-CP*-phenylalanine) | 10 μg/mL |
| M. bovis BCG | 9A (Ir-CP*-phenylalanine) | 15 μg/mL |
| M. abscessus AAy-P-1 | 8B (Rh-CP*-phenylglycine) | 15 μg/mL |
| M. bovis BCG | 8B (Rh-CP*-phenylglycine) | 7 μg/mL |
| M. smegmatis VT307 | GR-1 (Ru-mesitilene-phenylglycine) | 7.5 μg/mL |

TABLE X

Drug-Staphylococcus Combinations

| S. aureus or MRSA Strain | Transition Metal Amino Acid | Concentration |
|---|---|---|
| S. aureus ATCC 6358 | 6K-48 (Ir-CP*-napthalene diamine) | 10 μg/mL |
| MRSA 34380 | 6K-48 (Ir-CP*-napthalene diamine) | 10 μg/mL |
| S. aureus ATCC 6358 | 6K-50 (Ir-COD-ethambutol) | 10 μg/mL |
| MRSA 34380 | 6K-50 (Ir-COD-ethambutol) | 10 g/mL |

The process used to grow the mycobacteria was to inoculate a single colony into 2 mL of Middlebrook 7H9 broth containing 0.5% (vol/vol) glycerol and 10% (vol/vol) oleic acid-albumin (M7H9) in a 16×125 mm screw cap tube and incubate 7 days at 37° C. without aeration. Then, inoculate 1 mL of that culture into 24 mL of M7H9 in a Nephalometry flask; incubate 7 days at 37° C. with aeration (60 rpm), and measure turbidity (abs 580 nm) daily and plot on semi-log paper. And finally, measure the colony-forming units (CFU)/mL of the 7 day (mid-log phase) culture by dilution and spreading 0.1 mL on M7H10 agar.

The process used to grow the Staphylococcus was to inoculate a single colony into 2 mL of 1/10-strength BHIB in a 16×125 mm screw cap tube and incubate overnight at 37° C. without aeration. Then, inoculate 1 mL of that culture into 24 mL of BHIB in a Nephalometry flask; incubate at 37° C. with aeration (60 rpm) and measure turbidity (abs 580 nm) hourly and plot on semi-log paper. Then, measure the colony-forming units (CFU)/mL of a mid-log phase culture by dilution and spreading 0.1 mL on BHIB agar.

Measurement of Transition Metal-Amino Acid Susceptibility.

For the mycobacterial, susceptibility of the transition metal amino was measured by the following process, for each combination listed in Table IX above, inoculate 10 mL of M7H9 broth in a 125 mL flask with a volume of culture sufficient to read a final density of $10^5$ CFU/mL. Then, to the mycobacterial suspension add a sufficient volume of the transition metal-amino acid complex from the stock to equal the final concentration indicated in the Table. Next, immediately and at 1, 2, and 3 hr, remove a 1 mL sample and measure surviving CFU/mL by spreading 0.1 mL (in triplicate) of undiluted, $10^{-1}$, $10^{-2}$, and $10^{-3}$ fold diluted suspensions on M7H10 agar. Then, incubate plates at 37° C. for 7-10 days and count colonies. Repeat each combination at least once (2 sets of data).

For the *Staphylococcus*, susceptibility was measured as follows. For each combination listed in Table X above, inoculate 10 mL of ⅒-strength BHIB in a 125 mL flask with a volume of culture sufficient to reach a final density of $10^5$ CFU/mL (usually a 1,000-fold dilution of the mid-log phase culture). To the *S. aureus* or MRSA suspension add a sufficient volume of the transition metal-amino acid complex from the stock to equal the final concentration indicated in Table X. Immediately and at 1, 3, and 6 hr, remove a 1 mL sample and measure surviving CFU/mL by spreading 0.1 mL (in triplicate) of undiluted, $10^{-1}$, $10^{-2}$, and $10^{-3}$ fold diluted suspensions on BHIB agar. Incubate plates at 37° C. for 2 days and count colonies. Repeat each combination at least once (2 sets of data).

Calculations.

Calculations were measured by calculating the average CFU/mL at each time point and using the initial CFU/mL as 100% survival, calculate percent survival at each time point and plotting surviving fraction versus time on semi-log paper.

Example VIII

Examples Demonstrating Effectiveness of Various Complexes

Metal Coordinated α-Amino Acids were tested for their effectiveness in use as anti-mycobacterial agents. Several of the piano stool complexes of the Formula 3 type were tested for their effectiveness against various mycobacteria, including:

(1)
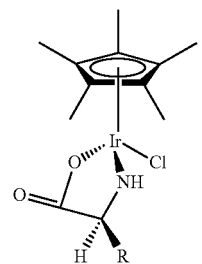
Formula 3A4

(2)
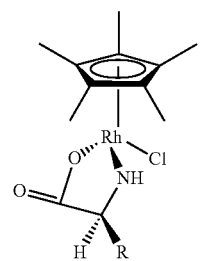
Formula 3A2

(2)
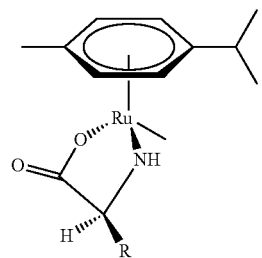
Formula 3B2

(4)
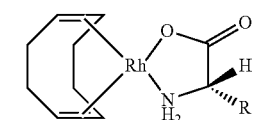
Formula 3C

The effectiveness of these complexes against various mycobacteria is reported below in Table XI.

TABLE XI

Biological Activity (MICs) for Formula 3 Type Complexes
Minimal Inhibitory Concentration (MIC) g/L

| Compound | M. smegmatis | M. avium | M. intra-cellulare | M. abscessus | M. marinum | M. bovis | M. chelonae |
| --- | --- | --- | --- | --- | --- | --- | --- |
| 1 (L-gly) | 0.061 | >0.250 | >0.250 | 0.125 | >0.250 | N/A | 0.125 |
| 1 (L-pro) | 0.010 | 0.125 | 0.061 | 0.015 | >0.250 | 0.015 | 0.015 |
| 1 (L-ala) | 0.015 | >0.250 | 0.061 | 0.031 | >0.250 | 0.031 | 0.061 |
| 1 (L-phe) | 0.010 | >0.250 | 0.061 | 0.061 | >0.250 | 0.015 | 0.015 |
| 1 (L-phengly) | 0.005 | >0.250 | 0.015 | 0.031 | >0.250 | 0.010 | 0.010 |
| 1 (L-val) | 0.017 | >0.250 | >0.250 | 0.061 | >0.250 | 0.031 | 0.031 |
| 1 (L-ser) | >0.250 | >0.250 | N/A | N/A | N/A | N/A | N/A |
| 1 (L-gln) | 0.061 | >0.250 | N/A | N/A | N/A | N/A | N/A |
| 1 (D-val) | >0.250 | >0.250 | N/A | N/A | N/A | N/A | N/A |
| 1 (D-pro) | >0.250 | >0.250 | >0.250 | >0.250 | >0.250 | >0.250 | >0.250 |
| 1 (L-leu) | 0.032 | >0.250 | 0.032 | 0.032 | >0.250 | N/A | 0.032 |
| 1 (L-iso) | 0.015 | >0.250 | 0.032 | 0.032 | >0.250 | 0.015 | 0.032 |
| 1 (L-hyp) | >0.250 | >0.250 | N/A | N/A | N/A | N/A | N/A |
| 1 (L-N-methylgly) | >0.250 | >0.250 | N/A | N/A | N/A | N/A | N/A |

TABLE XI-continued

Biological Activity (MICs) for Formula 3 Type Complexes
Minimal Inhibitory Concentration (MIC) g/L

| Compound | M. smegmatis | M. avium | M. intra-cellulare | M. abscessus | M. marinum | M. bovis | M. chelonae |
|---|---|---|---|---|---|---|---|
| 1 (L-N-methylpro) | >0.250 | >0.250 | N/A | N/A | N/A | N/A | N/A |
| 2 (L-gly) | 0.061 | >0.250 | >0.250 | 0.061 | >0.250 | N/A | 0.125 |
| 2 (L-pro) | 0.009 | >0.250 | 0.061 | 0.012 | >0.250 | 0.012 | 0.012 |
| 2 (L-ala) | 0.015 | >0.250 | 0.061 | 0.031 | >0.250 | 0.025 | 0.061 |
| 2 (L-phe) | 0.009 | >0.250 | 0.061 | 0.031 | >0.250 | 0.012 | 0.031 |
| 2 (L-phengly) | 0.007 | >0.250 | 0.015 | 0.015 | >0.250 | 0.007 | 0.015 |
| 2 (L-val) | 0.015 | >0.250 | >0.250 | 0.061 | >0.250 | 0.031 | 0.061 |
| 2 (L-ser) | >0.250 | >0.250 | >0.250 | >0.250 | >0.250 | N/A | >0.250 |
| 2 (L-gln) | 0.032 | >0.250 | 0.032 | 0.032 | >0.250 | N/A | 0.032 |
| 2 (D-val) | >0.250 | >0.250 | >0.250 | >0.250 | >0.250 | N/A | >0.250 |
| 2 (D-pro) | >0.250 | >0.250 | >0.250 | >0.250 | >0.250 | N/A | >0.250 |
| 2 (L-leu) | 0.021 | >0.250 | 0.061 | 0.061 | >0.250 | N/A | 0.031 |
| 2 (L-iso) | 0.010 | >0.250 | 0.061 | 0.031 | >0.250 | N/A | 0.031 |
| 2 (L-hyp) | >0.250 | >0.250 | >0.250 | >0.250 | >0.250 | N/A | >0.250 |
| 2 (L-N-methylgly) | >0.250 | >0.250 | >0.250 | >0.250 | >0.250 | N/A | >0.250 |
| 2 (L-N-methylpro) | >0.250 | >0.250 | >0.250 | >0.250 | >0.250 | N/A | >0.250 |
| 3 (L-gly) | >0.250 | >0.250 | >0.250 | >0.250 | >0.250 | >0.250 | >0.250 |
| 3 (L-phe) | >0.250 | >0.250 | >0.250 | >0.250 | >0.250 | >0.250 | >0.250 |
| 3 (L-ala) | >0.250 | >0.250 | >0.250 | >0.250 | >0.250 | >0.250 | >0.250 |
| 3 (L-ser) | >0.250 | >0.250 | >0.250 | >0.250 | >0.250 | >0.250 | >0.250 |
| 3 (en) | 0.125 | >0.250 | 0.061 | 0.061 | >0.251 | N/A | 0.061 |
| 3 (N-methyl en) | >0.250 | >0.250 | >0.250 | >0.250 | >0.250 | >0.250 | >0.250 |
| 3 (N,N-methyl en) | >0.250 | >0.250 | >0.250 | >0.250 | >0.250 | >0.250 | >0.250 |
| 3 (EMB) | 0.061 | >0.250 | >0.250 | 0.061 | >0.250 | N/A | 0.061 |
| 4 (L-gly) | 0.125 | 0.061 | >0.250 | 0.061 | N/A | N/A | 0.125 |
| 4 (L-phenylgly) | 0.061 | 0.032 | >0.250 | 0.031 | N/A | N/A | 0.031 |
| 4 (L-val) | 0.125 | 0.125 | >0.250 | >0.250 | N/A | N/A | 0.061 |
| 4 (L-ala) | >0.250 | 0.125 | >0.250 | >0.250 | N/A | N/A | 0.061 |

Multiple species of mycobacteria were isolated, *Mycobacterium avium* strain A5, *Mycobacterium chelonae* strain EO-P-1, *Mycobacterium intracellulare*, *Mycobacterium marinum* ATCC 927, *Mycobacterium abscessus* strain AAy-P-1, *Mycobacterium bovis* strain BCG and *Mycobacterium smegmatis* strain mc$^2$155, were used to test the possible antimycobacterial properties of a catalog of different metal coordinated α-amino acids. Strains of mycobacteria were grown in 100 ml of Middlebrook 7H9 broth medium (BBL Microbiology Systems, Cockeysville, Md.) containing 0.5% (vol/vol) glycerol and 10% (vol/vol) oleic acid-albumin (M7H9) in 500-ml nephelometer flasks to mid-log phase (7 days) at 37° C. with aeration (60 rpm). To test the susceptibility of the mycobacteria towards these compounds minimal inhibition concentration (MIC) studies were performed. MICs were reported as lowest concentration that showed complete inhibition of growth. The studies were performed as described (see Williams A A, Sugandhi E W, Macri R V, Falkinham J O, Gandour R D. Antimicrobial activity of long-chain, water-soluble, dendritic tricarboxylato amphiphiles. J Antimicrob Chemoth 2007; 59:451e8; and see Sugandhi E W, Macri R V, Williams A A, Kite B L, Slebodnick C, Falkinham J O, et al., Synthesis, critical micelle concentrations, and antimycobacterial properties of homologous, dendritic amphiphiles. Probing intrinsic activity and the "cutoff" effect. J Med Chem 2007; 50:1645e50) with varying cell densities using 96 well microtiter plates.

Incubation temperature for *M. smegmatis*, *M. abscessus*, *M. chelonae*, *M. avium*, *M. bovis*, *M. intracellulare*, and *M. chelonae* was 37° C. and 30° C. for *M. marinum*. The MICs were then measured after a 7 day growth period mixed with varying concentrations of the compounds of interest.

A total of 39 α-amino acids metal coordinated compounds were tested against each strain of the mycobacteria using the media and processes described above. Each of these measurements was recorded by measuring the absorbance at 540 nm for each of the microtiter well plates used. MICs for each compound according to microorganism are listed in Table X. Each result was then recorded by measuring the absorbance at 540 nm to determine the amount of red blood cell lysis.

Effects of Molecular Weight.

Given the size of each of the compounds in relation to the varying metal centers, it was determined that the smaller molecules would have lower MIC but would have similar molar concentration values. Iridium in place of Rhodium shows for the same set of ligands that either metal would give approximately the same molar MIC. From this it can be theorized that the metal centers are playing similar roles since the ligand set for each was the same in each study.

Organometallic Ligand Variation.

It is interesting to note that none of the Cyclooctadiene (COD) derivatives shows activity. Due to the lack of the halogen on the metal center as compared to the Cp* variants, these compounds derived from Cyclooctadiene are unable to coordinate in a similar way to with proteins in the intracellular matrix. This suggests even further that the mode of action may be directly linked to a protein binding between either the metal center with RNA, DNA, or some enzymatic protein in the cell. The ability for these compounds using COD to enter the cell is still unknown.

Hydrophobic vs. Hydrophilic Amino Acids.

Mycobacteria show a specificity for certain types of amino acid ligands. Determining the susceptibility of each the mycobacteria tested in relation to each amino acid is listed in table 1. It can be determined that the smaller hydrophobic amino acids have the greatest effect on the MIC of each the mycobacteria. L-phenylglycine used with any of the Cp* metal centers showed to have the lowest MIC for any of the mycobacteria listed. Switching the amino acid ligand to a hydrophilic, polar amino acid as in L-serine or L-aspartic acid show no inhibition of growth at any of the concentrations tested. Neither of the metal centers with these amino acids had little to no variation in their MIC.

With the large membranes composed of mostly hydrophobic side chains in mycobacteria, the relationship of either of the side chains would increase the susceptibility of each of the compounds tested. *M. smegmatis* is the fastest growing mycobacteria tested with the smallest outer membrane used above. Its shown to be the most susceptible to the hydrophobic amino acid ligand complexes tested. Given this result, the side chains of the amino acids is the most significant factor in determining whether the metal center will be active. Aiding in either mixing with the membrane barrier protecting the cells or disrupting the membrane seems to be the function of the amino acids as the ligand.

Mechanism of Action.

Theorized per the results of hydrophobic and hydrophilic and the cell lysis studies, the compounds are having and intracellular effect instead of interfering with the outer membrane barrier. Since these compounds are not being used in lysis of the cells and that the hydrophobic aspect is needed to show activity, the compounds are entering the cell per their hydrophobicity. Once the exposed in the intracellular matrix, a disruption of normal functions is taken place. Suggesting that the protein synthesis whether through RNA transcription or the inability for cells to undergo DNA transcription is being interrupted in one of the cellular processes.

Example IX

Toxicology Studies

As a first step to determine the toxicity of compounds of the invention for normal cells, representative compounds were examined for hemolysis of blood cells. In this procedure, concentrations of 250 ug/mL down to 1 ug/mL were tested for blood hemolysis and compared with a compound, TX-100 (a surfactant), known to cause blood cell lysis. In all cases TX-100 caused lysis while the tested complexes did not.

Further toxicology tests were also performed using various complexes of the invention and in accordance with the following procedures. Toxicology tests were performed using CCL-81 cells, which are from normal human bronchial epithelium and obtained from autopsy of non-cancerous individuals. The cells were subcultured and passaged. Such cells are especially useful in their ability to undergo squamous differentiation in response to serum, and can be used to screen chemical and biological agents for ability to induce or affect differentiation and/or carcinogenesis. The cell line used in toxicology tests was *Cercopithecus aethiops* (African Green Monkey Vero). The Vero cell line was initiated from the kidney of a normal adult African green monkey and obtained from ATCC, classified as a BSL-2 organism.

A growth medium (RPMI, 10% FBS, 1% pen/strep) is prepared by warming RPMI, FBS, and pen/strep in 37° C. water bath. Optionally, the RPMI and FBS can be filter sterilized using, for example, 0.2 um PES filter system. An appropriate volume of pen/strep (preferably not filter sterilized) is then added and the combination mixed. An example of a complete growth media that can be used is one using RPMI: 1640+10% FBS+1% Strep/Pen). To prepare 50 mL of growth media combine 445 mL RPMI:1640, 50 mL FBS (fetal bovine serum), and 5 mL pen/strep (10,000 units/mL). To prepare 250 mL, combine 222.5 mL RPMI:1640, 25 mL FBS (fetal bovine serum), and 2.55 mL pen/strep (10,000 units/ mL). To prepare 50 mL, 44.5 mL RPMI:1640, 5 mL FBS (fetal bovine serum), and 0.5 mL pen/strep (10,000 units/mL) are combined. It is recommended that antibiotics can be eliminated if cells and/or supernatant will be used in experiments involving bacterial infection of the cells.

Cells can be cultured from frozen cryo-stock as follows. A vial of cells is removed from the vapor phase of liquid nitrogen and thawed by continuously swirling the vial in a 37° C. water bath until only a small ice pellet remains (about 60-90 seconds). The vial can be sprayed down with a 70% alcohol solution and the solution is allowed to evaporate. An exemplary crypto-freezing medium (90% FBS, 10% DMSO) can be prepared by combining 2.5 mL DMSO with 22.5 mL FBS to obtain 25 mL. It is preferred to store the DMSO at room temperature and not warm prior to use. The FBS can be filter sterilized in 50 mL sterile filter, then the DMSO added and mixed. It is recommended that the crypto-freezing medium can be re-frozen up to three times.

Passaging of Cells. The culture medium is removed and discarded and the cells washed with 10 mL of cold DPBS (Ca++/Mg++ free). 2.5-5 mL of warm 0.25% Trypsin/0.1% EDTA solution is added to the flask and cells are observed under an inverted microscope until the cells release (usually with 2 to 5 minutes). To avoid clumping, it is preferred not to agitate the cells by hitting or shaking the flask while waiting for the cells to detach. Cells that are difficult to detach may be placed at 37° C. to facilitate dispersal. 5 mL ml of complete growth medium is added and the cells aspirated by gentle pipetting. The cell suspension is then transferred to a centrifuge tube which is spun at approximately 500×g at 4° C. for 5 min. the supernatant is discarded and the cell pellet is resuspended in 1-5 mL fresh growth medium (RPMI, 10% FBS, 1% p/s). Using a sterile glass pipette, new flasks (such as 75 cm$^2$ tissue culture flasks) can be inoculated with 2-6 drops of resuspended cell culture. The culture flasks are placed in incubators at 37 C, 5% $CO_2$. Approximately every 2-3 days, the medium can be aspirated and replaced with 20-25 mL fresh growth medium (RPMI, 10% FBS, 1% p/s).

The preparation, treatment, and collection of cells can be performed as follows. Confluence is checked under an inverted microscope. Preferably, cells are used in the toxicology assays when they reach about 80% confluence. Passaging of the cells is then performed as described above. Cells are counted on a hemocytometer and cell concentration determined using for example 90 ul PBS/trypan blue solution+10 ul cells. Cells are seeded in an appropriately sized tissue culture plate or flask at the desired concentration. Cells are allowed to adhere by incubating at 37 C under 5% $CO_2$ for at least 4 hrs (or preferably overnight). Cells are washed with cold DPBS (Ca++/Mg++ free) to remove FBS. Add appropriate medium and volume for assay and allow cells to acclimate for 2-4 hrs. It is noted that cells are typically serum-starved by the addition of RPMI and that pen/strep should not be added for assays involving treatment with bacterial cultures. The medium is removed and the cells washed again wash cells with DPBS. Then the desired medium in the appropriate volume is added for the assay. Cells are treated with a selected complex and cultured under conditions appropriate for the treatment. Cells are then treated with MTT cell proliferation assay (source ATCC).

Cryo-preservation of cells can be performed as follows. In a 37° C. water bath, 1× Trypsin/EDTA is warmed. A crypto-freezing medium (e.g., as provided below). Cells lines are preferably harvested in mid-logarithmic growth (<80% confluence) using standard procedures. The culture medium is aspirated from the culture flask and cells washed gently with about 10 mL 1×PBS$^{(Ca++, Mg++Free)}$. An amount of warm 1× Trypsin/EDTA (2.5 mL) is added to the culture flask (75 cm$^2$) and allowed to sit for about 1-2 mins. Disassociation is then verified using a microscope. About 5 mL media is added to the culture flask and cells collected in a 15 mL centrifuge tube. Cells are pelletted by centrifugation (5 min/4° C./1200 rpm) and the supernatant removed. Cell pellet is re-suspended in 1 mL complete media or DPBS. Cell concentration is calculated using a hemocytometer (10 ul cells+85 ul DPBS+5 ul trypan blue). Cells are centrifuged to obtain a pellet (5 min/4° C./1200 rpm) and re-suspended in crypto-freezing medium at approximately 2-5×10$^6$ cells/mL. Cells are transferred to cryovials by approximately 1 mL aliquots. Cells are then frozen (e.g., at about −80° C.) and preferably overnight. For particularly sensitive strains, freezing can be performed at about −20° C. overnight, then at about −80° C. overnight. After at least 24 hrs at −80° C., store the frozen cells in the vapor phase of liquid nitrogen.

Example X

Complexes as Catalysts in the Asymmetric Reduction of Ketones to their Corresponding Alcohols These transition metal compounds also show catalytic activity for a number of chemical transformations including hydrogenation, transfer hydrogenation and hydroformylation. Where pro-chiral substrates are used, the chiral amino acid complexes induce chirality in the product. Thus the transfer hydrogenation of acetophenone using formic acid as the hydrogen source gives predominantly only one of the two possible enantiomer alcohols.

Asymmetric Transfer Hydrogenation of Pinacolone.

The interest in the herein reported iridium complexes was their role in homogenous catalysis in aqueous media. Specifically in the asymmetric reduction of aliphatic ketones to their chiral alcohols, which has proven to be a challenge for prior systems.

Several complexes of the type [(η$^5$-Cp*)Ir(aa)Cl] were tested for catalytic reduction of pinacolone to 3,3-dimethylbutan-2-ol in water with sodium formate acting as the hydrogen donor.

Scheme 6

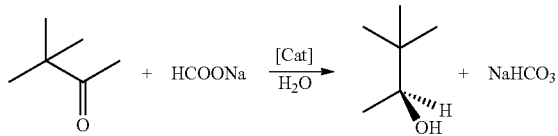

Generally, the catalysis reactions described in this specification can be carried out at room temperature and open to air with no inert gas protection. Substrate/Catalyst/formate ratios were 1/0.1/5 or 1/0.05/5. The reactions take place over the course of 24 hours depending on the amino acid used. The use of sodium formate prevents the reverse reaction from occurring, which leads to a decrease in selectivity, as observed when iso-propyl alcohol is used as solvent and donor. More particular experimental protocols for various types of catalysis reactions are described in more detail below.

Amino acids consisting of a ring system as R groups produced the best selectivities, Prolinate, Azetidine-2-carboxylate, and piperidine-2-carboxylate complexes. Of these the azetidine-2-carboxylate complex had the highest selectivity of 92 percent. The larger ring systems of prolinate and piperidine-2-carboxylate showed decreased selectivity.

Of the prolinate variants, the Trans-4-fluoro-L-proline had the highest selectivity, (85%), though at a decreased activity. The 4-trans-hydroxy-L-proline variant maintained 14's selectivity, but had a decreased rate of conversion.

Full methylation of the amino portion of the amino acid completely shuts down activity, as seen in the case of N,N-dimethyl-glycinate and N-methyl-prolinate. Over the course of several days no conversion was observed at all. This is not totally surprising since these are bifunctional catalysts, with the hydride acting as a base and the amine proton acting as an acid. The mechanistic work of Xiao would lead to the conclusion that an amine proton is required for catalytic activity.

Of the other systems tested, only phenylglycinate has any selectivity, though much lower than the other variants, (26 percent). The results of catalytic testing are summarized in table XII.

TABLE XII

Catalytic Testing of Complexes

| Entry | Complex | Configuration | t (h) | Conversion (%) | ee (%) |
|---|---|---|---|---|---|
| 1 | Cp*Ir(L-Proline) | R | 66 | 99 | 82 |
| 2 | Cp*Ir(F-L-Proline) | R | 24 | 50 | 85 |
| 3 | Cp*Ir(OH-L-Proline) | R | 24 | 25 | 82 |
| 4 | Cp*Ir(L-Pip) | S | 67 | 99 | 48 |
| 5 | Cp*Ir(D-Proline) | S | 24 | 85 | 77 |
| 6 | Cp*Ir(L-Aze) | R | 68 | 99 | 93 |
| 7 | P-CymeneRu(L-Proline) | R | 75 | 13 | 55 |
| 8 | Cp*Rh(L-Proline) | R | 75 | 80 | 66 |
| 9 | Cp*Rh(F-L-Proline) | R | 48 | 30 | 80 |

As stated previously, the prolinate variant having selectivity over other non-methylated amino acids was not totally surprising upon inspection of the torsional angle between the amine hydrogen and chloride. However, no selectivity was observed with signally methylated glycine. This is interesting since this variant should also only have one "active" diastereomer.

The induction of chirality can be justified sterically. In systems showing selectivity in aromatic systems, the CH$_3$ Pi interaction stabilizes the six-membered transition state. Aliphatic ketones lack such a mechanism for stabilization.

Analysis of the crystal structure of the active complexes reveals how chirality in the product is induced. The L-prolinate and other ring containing amino acids force the acidic hydrogen and basic hydride into an alignment that favors one enantiomer. As illustrated below, an example showing a six membered transition state showing favored (left) and disfavored (right) substrate interaction is provided:

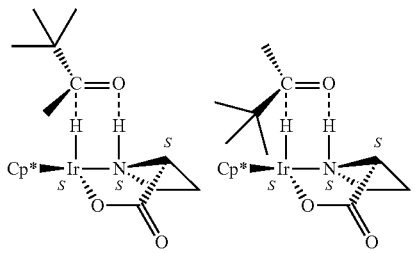

This interaction assumes that the mechanism for transfer hydrogenation in water as described by Xiao applies to our systems. As shown through NMR, an iridium hydride is formed through beta-hydride elimination of sodium formate.

This active catalyst then forms a six-membered transition state with the C=O of 3,3-dimethylbutan-2-one. Both proton and hydride are then transferred, resulting in an unsaturated iridium complex. The active catalyst is then be regenerated by water and additional formate.

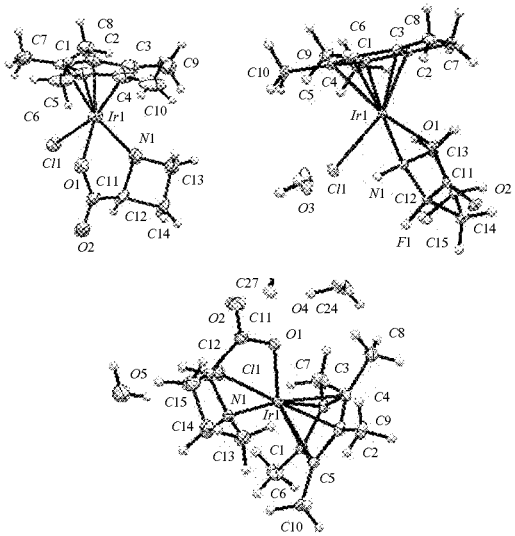

TABLE XIII

|  | F-proline | Aze | L-proline |
|---|---|---|---|
| Ir-G | 1.767 | 1.769 | 1.766 |
| Ir—Cl | 2.4260(6) | 2.415(2) | 2.4260(1) |
| Ir—N | 2.140(2) | 2.106(7) | 2.140(2) |
| Ir—O1 | 2.086(2) | 2.130(6) | 2.086(2) |
| O1—C11 | 1.283(3) | 1.23(3) | 1.283(3) |
| C11—C12 | 1.524(4) | 1.54(1) | 1.524(1) |
| C12—N | 1.505(4) | 1.52(1) | 1.505(4) |
| N—C13 | 1.494(3) | 1.50(1) | 1.494(4) |
| G-Ir—Cl | 127.29 | 126.81 | 125.69 |
| G-Ir—N | 134.17 | 133.46 | 136.16 |
| G-Ir—O1 | 129.40 | 132.52 | 128.44 |
| Cl—Ir—O1 | 86.27 | 83.9(2) | 86.38(5) |
| N—Ir—O | 77.74 | 78.0(3) | 77.23(8) |
| N—Ir—Cl | 84.17 | 83.4(2) | 85.34(6) |

Acetophenone Reductions.

Scheme 7

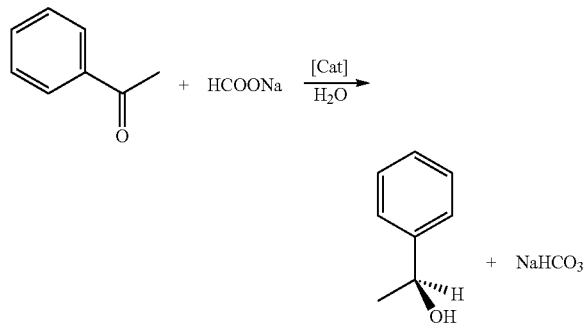

TABLE XIV

Catalytic Testing of Complexes

| Entry | Complex | Configuration | t (h) | Conversion (%) | ee (%) |
|---|---|---|---|---|---|
| 1 | Cp*Ir(L-Pip) | R | 36 | 99 | 26 |
| 2 | Cp*Ir(L-Proline) | R | 36 | 88 | 20 |
| 3 | Cp*Ir(F-L-Proline) | R | 36 | 88 | 20 |
| 4 | Cp*Ir(L-Phenylalanine) | S | 36 | 91 | 5 |
| 5 | Cp*Ir(D-Proline) | S | 36 | 52 | 20 |
| 6 | Cp*Ir(N-Methyl-Glycine) |  | 36 | 84 | 0 |
| 7 | Cp*Ir(L-Aze) | R | 36 | 91 | 37 |
| 9 | Cp*Ir(L-Phenylglycine) | R | 36 | 24 | 7 |

Representative Catalytic Procedures. Asymmetric transfer hydrogenation in water: In cases of both substrates: No inert air protection was used. In a 2 dram vial, Catalyst, substrate, and sodium formate, were charged and then dissolved in 2 mL of DI water. Substrate to Catalyst ratio was 100/1, with formate to ketone ratio of 5 to 1. The reactions were monitored via GC on a DB-5 column. ee's were determined via GC on a CP-ChiraSil-Dex CB 25 m×0.25 μm. Asymmetric transfer hydrogenation in IPA: In cases of both substrates: No inert air protection was used. In a 2 dram vial, Catalyst, substrate, and base, were charged and then dissolved in 2 mL of isopropyl alcohol. Substrate to Catalyst ratio was 100/1, with base to catalyst ratio of 2 to 1, 5 to 1, or 10 to 1. The reactions were monitored via GC on a DB-5 column. ee's were determined via GC on a CP-ChiraSil-Dex CB 25 m×0.25 μm. Asymmetric hydrogenation: In cases of both substrates: No inert air protection was used. In a Parr Bomb, Catalyst, substrate, and base, were charged and then dissolved in solvent, (water, or neat alcohol). Hydrogen pressure was 30 PSI. Substrate to Catalyst ratio was 100/1, with base to catalyst ratio of 12 to 1, 5 to 1, or 10 to 1. ee's were determined via GC on a CP-ChiraSil-Dex CB 25 m×0.25 μm.

Example XI

Complexes as Catalysts in the Oxidative Coupling Reaction of Boronic Acid with an Alkene A general procedure for using complexes of the invention as catalysts in the oxidative coupling reaction of boronic acid with an alkene can be as follows: a 15 mL flask is charged with 50 mg of the boronic acid, 3 mL of DMF, 5 mol % catalyst (based on the boronic acid) and 3 equivalents of alkene (also based on the boronic acid). An oxygen balloon is fitted and the reaction stirred for 48 hours at room temperature. 10 mL ethyl acetate is then added and then the reaction mass is washed with 2×10 mL $H_2O$. The water washings are discarded and the organic layer is dried over $MgSO_4$. Analysis of the reaction products is carried out by GC-MS.

More particularly, for example, complexes of the invention can be used as catalyst for the reaction of phenylboronic acid with methyl tiglate. A general procedure for this task can include the following: a 15 mL round bottom flask was charged with 47.7 mg phenylboronic acid, 5.2 mg of DH1-29A [cis-bis-(prolinato palladium(II)] catalyst, and 3 mL N,N-dimethylformamide with a stir bar. 147 μL methyl tiglate was added via syringe and an oxygen balloon was fitted to the flask and filled. The reaction was left to stir in the hood for 3 days. Upon reacting, the reaction mass turned a light amber color. 10 mL ethyl acetate was added and the reaction mass washed with 2×10 mL $H_2O$. The organic layer was collected and dried over $MgSO_4$. The dried organic layer was analyzed by GC-MS and these species were detected:

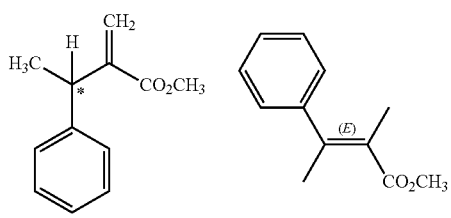

Chemical Formula: C₁₂H₁₄O₂    Chemical Formula: C₁₂H₁₄O₂
Molecular Weight: 190.24    Molecular Weight: 190.24

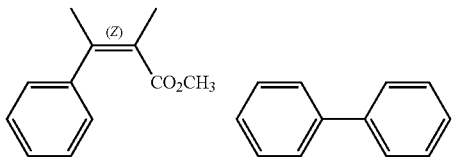

Chemical Formula: C₁₂H₁₄O₂    Chemical Formula: C₁₂H₁₀
Molecular Weight: 190.24    Molecular Weight: 154.21

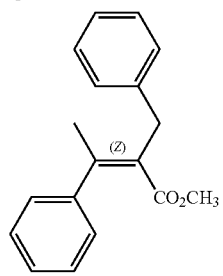

Chemical Formula: C₁₈H₁₈O₂
Molecular Weight: 266.33

Table XV shows representative complexes according to the invention used as catalyst in the reaction of various combinations of boronic acid with an alkene.

TABLE XV

Catalyst, Boronic Acid, and Alkene Combinations

| Catalyst | PBA | p-TFM-PBA | p-OCH3-PBA | MT | 1Ac-1Cp | t-2M2B |
|---|---|---|---|---|---|---|
| Pd(Pro)2 | ✓ | | | ✓ | | |
| Pd(Pro)2 | ✓ | | | | ✓ | |
| Pd(Pro)2 | ✓ | | | | | ✓ |
| Pd(Pro)2 | | ✓ | | ✓ | | |
| Pd(Pro)2 | | | ✓ | ✓ | | |
| Pd(aspartic acid)2 | ✓ | | | ✓ | | |
| Pd(glycine)2 | ✓ | | | ✓ | | |
| Pd(n-methyl glycine)2 | | | | ✓ | | |
| Pd(n,n-dimethylglycine)2 | ✓ | | | ✓ | | |
| Pd(isoleucine)2 | ✓ | | | ✓ | | |
| Pd(lysine)2 | ✓ | | | ✓ | | |
| Pd(phenylalanine)2 | ✓ | | | ✓ | | |
| Pd(N-methyl proline)2 | ✓ | | | ✓ | | |
| Pd(serine)2 | ✓ | | | ✓ | | |
| Pd(hydroxyproline)2 | ✓ | | | ✓ | | |
| Pd(4-fluoroproline)2 | ✓ | | | ✓ | | |
| Pd(benzylproline)2 | ✓ | | | ✓ | | |

Abbreviations: PBA = phenylboronic acid; p-TFM-PBA = para-(trifluoromethyl)phenylboronic acid; p-OCH3-PBA = para-(methoxy)phenylboronic acid; MT = methyl tiglate; 1Ac-1Cp = 1-acetyl-1-cyclopentene; and t-2M2B = trans-2-methyl-2-butenal.

Example XII

Anti-Cancer Biological Activity

Complexes of the invention can also be used as anti-cancer compounds. Some of the complexes may have a structure/activity relationship that differs from those found in the anti-microbial studies. Embodiments of Categories I, II, III, or IV of the invention can be useful against cancer, tumors, and tumor-related disorders. See, e.g., Raymond Wai-Yin Sun et al., "Some uses of transition metal complexes as anti-cancer and anti-HIV agents," Dalton Trans., 2007, 4884-4892, The Royal Society of Chemistry, e-published Sep. 18, 2007 DOI: 10.1039/b705079h, which reference is hereby incorporated by reference herein in its entirety, and which provides in vitro studies that can be used to show the efficacy of the complexes described herein.

The compounds described in this specification have the potential for treatment of the most common cancers reported by the American Cancer Society. See American Cancer Society: Cancer Facts and Figures 2012, Atlanta, Ga.: American Cancer Society, 2012. These are, bladder cancer, breast cancer, colon cancer, rectal cancer, endometrial cancer, kidney cancer, leukemia, lung cancer, melanoma, non-Hodgkin's lymphoma, pancreatic cancer, prostate cancer, and thyroid cancer, which are all preferred targets of the complexes.

Representative cancers that compounds of the invention may be used to treat include but are not limited to oral cancer, lip and oral cavity cancer, oropharyngeal cancer, head and neck cancer, nasal cavity and paranasal sinus cancer, nasopharyngeal cancer, laryngeal cancer, hypopharyngeal cancer, esophageal cancer, cancer of the upper jaw, tongue cancer, lip cancer, liver cancer, lung cancer, non-small cell lung cancer, pancreatic cancer, prostate cancer, thyroid cancer, colon cancer, rectal cancer, large bowel cancer, colorectal cancer, anal cancer, kidney cancer, vulvar cancer, uterine cancer, breast cancer, urethra cancer, small intestine cancer, bile duct cancer, bladder cancer, ovarian cancer, uretheral tumor, gallbladder cancer, biliary tract cancer, digestive system cancer, stomach cancer, parathyroid cancer, penile cancer, testicular tumor, vaginal cancer, and bone cancer, to name a few. In yet other embodiments the cancer is a carcinoma, a tumor, a neoplasm, a lymphoma, a melanoma, a glioma, a sarcoma, or a blastoma. Hodgkin's lymphoma, leukemia-related disorders, mycosis fungoides, and myelodysplastic syndrome may also be treated with compounds of the invention.

In addition to the anti-cancer agents of the invention being applicable to treating malignant tumors, such agents may also be applicable to benign tumors. Complexes of embodiments of the invention may also be used to suppress cancer metastasis, and in particular, as a cancer metastasis suppressing agent after surgery.

In embodiments, the lymphoma can be any of malignant lymphoma, nervous system lymphoma, AIDS-related lymphoma, non-Hodgkin's lymphoma, cutaneous T-cell lymphoma, and Waldenstrom's macroglobulinemia. In other embodiments the blastoma can be any of retinoblastoma, medulloblastoma, neuroblastoma, pleuropulmonary blastoma, glioblastoma, pulmonary blastoma, and hemangiblastomas.

Tumors that can be targets of complexes of the invention can include astrocytic tumors, ovarian germ cell tumors, supratentorial primitive neuroectodermal tumors, malignant mesothelial tumors, Wilms tumors, extragonadal germ cell tumors, pituitary tumors, gastrinoma, germ cell tumors, brain tumors, pineal and supratentorial primitive neuroectodermal tumors, gestational trophoblastic tumors, pituitary tumors, somatostatin-secreting tumors, carcinoids, central cerebral astrocytoma, endodermal sinus tumors, glucagonoma, plasmacytoma, hepatic adenoma, insulinoma, medulloepithelioma, vipoma, and pheochromocytoma. Examples of benign tumors as targets for the complexes can include hemangiomas, hepatocellular adenoma, cavernous haemiangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Melanoma, such as malignant melanoma, acral lentiginous melanoma, uveal melanoma, lentigo maligna melanomas, superficial spreading melanoma, intraocular melanoma, adenocarcinoma nodular melanoma, and hemangioma, are also potential targets for the anti-cancer agents of the invention.

The carcinomas can include any of cholangiocarcinoma, adenocarcinoma, basal cell carcinoma, squamous carcinoma, invasive squamous cell carcinoma, squamous cell carcinoma, adenosquamous carcinoma, adenoid cystic carcinoma, adrenocortical carcinoma, well differentiated carcinoma, serous carcinoma, small cell carcinoma, large cell carcinoma, islet cell carcinoma, oat cell carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

Carcinoma Cell Culture Assay.

Colon carcinoma cells (HCT-116) are proliferated and prepared under the guidelines and procedures set forth by ATCC cellular protocol. Catalog number CCL-247™. This cell line is a biosafety level 1. The preparation, culturing, and passaging of cells can be performed as follows. For the Complete Growth Medium (RPMI, 10% FBS, 1% pen/strep), warm RPMI, FBS, and pen/strep in 37° C. water bath. Next, filter sterilize appropriate volume of RPMI and FBS using 0.2 um PES filter system. Then, add appropriate volume pen/strep (do NOT filter sterilize) and mix. When culturing the cells from frozen cryo-stock, remove a vial of cells from the vapor phase of liquid nitrogen. Next allow the vial contents to thaw by continuously swirling the vial in a 37° C. water bath until only a small ice pellet remains (60-90 seconds). Then, spray the vial down with a 70% alcohol solution and allow the solution to evaporate. For the passaging of cells, Remove and discard culture medium. Wash cells with 10 mL of cold DPBS (Ca++/Mg++ free). Add 2.5-5 mL of warm 0.25% Trypsin/ 0.1% EDTA solution to flask and observe cells under an inverted microscope until the cells release (usually with 2 to 5 minutes). Note: To avoid clumping do not agitate the cells by hitting or shaking the flask while waiting for the cells to detach. Cells that are difficult to detach may be placed at 37° C. to facilitate dispersal. Add 5 mL ml of complete growth medium and aspirate cells by gently pipetting. Transfer cell suspension to centrifuge tube and spin at approximately 5 min, 500×g, 4° C. Discard supernatant and resuspend cell pellet in 1 mL-5 mL fresh growth medium (RPMI, 10% FBS, 1% p/s). Label new 75 cm2 tissue culture flasks for cell name, date, and passage number. Using sterile glass pipette, inoculate new flasks with 2-6 drops of resuspended cell culture. 20-35 mL. Place culture flasks in incubators at 37 C, 5% CO2. Every 2-3 days, aspirate medium and replace with 20-25 mL fresh growth medium (RPMI, 10% FBS, 1% p/s). The Assay Protocol $IC_{50}$ can be performed as follows. Count cells in 75 cm² flasks using a hemocytometer. Using the protocol for passaging of cells place cell remove cells from the 75 cm2 flasks and create a cell suspension (5×10^5 cell density) for the 96 well plate assay. Note: total cell suspension volume for 96 well plates should be approximately 5 mL of Eagles growth media. Next, plate 50 uL of cell suspension into each of the 96 wells. Add 50 uL of Eagles media to each of the 96 wells. Prepare MTS reagent (Process adapted from Promega). Add 100 uL of PMS to 2.0 mL of MTS solution. Pipette 20 uL of the MTS/PMS solution into each of the 96 well plates. Treat the well plates with 50 uL of known concentration of compound (Leave last column empty for control positive control). Incubate the plate for 1-4 hours at 37° C. in a humidified, 5% CO2 atmosphere. After 4 hours record and measure the absorbance of each plate at 490 nm. Compare positive control absorbance with treated cell wells absorbance to find IC50 (IC50 is the concentration of compound to inhibit approximately 50% of cellular growth). See CellTiter 96® AQueous Non-Radioactive Cell Proliferation Assay. Technical Bulletin. Promega. And see Product Information Sheet for ATCC® CCL-247™. Cell Line Designation: HCT. ATCC Catalog No. CCL-247™. ATCC®.

TABLE XVI

Expected Carcinoma Results. IC50 recorded in mg/mL

| | HCT-116 |
|---|---|
| 1(L-Phen) | 30.25 |
| 1(-Phengly) | 15.5 |
| 1(L-Val) | 150 |
| 1(L-Pro) | 10.5 |
| 1(L-Ala) | 25 |
| 2(L-Phen) | 20.5 |
| 2(-Phengly) | 7.5 |
| 2(L-Val) | 250 |
| 2(L-Pro) | 7.5 |
| 2(L-Ala) | 30 |

Example XIII

Efficacy of Compounds Against Malaria

Malaria testing can be performed using any procedure for verifying the effectiveness of the inventive compounds. For example, the procedure outlined in "IN VITRO MICROTEST (MARK III) FOR THE ASSESSMENT OF THE RESPONSE OF *Plasmodium falciparum* TO CHLOROQUINE, MEFLOQUINE, QUININE, AMODIAQUINE, SULFADOXINE/PYRIMETHAMINE AND ARTEMISININ" provided by the World Health Organization under CDT/MAL/97.20 Rev. 2 2001 is one such exemplary procedure.

It is expected that complexes of the invention would be effective antimalarial and anti-cancer agents considering the favorable results of other metal complexes against such targets. See, e.g., Alberto Martinez, et al., "The mechanism of antimalarial action of the ruthenium (II)-chloroquine complex $[RuCl_2(CQ)]_2$," J. Biol. Inorg. Chem. (2008) 13:703-712, DOI 10.1007/s00775-008-0356-9, published online Feb. 28, 2008; and see, e.g., Chandima S. K. Rajapakse, et al., "Synthesis, Characterization, and in vitro Antimalarial and Antitumor Activity of New Ruthenium(II) Complexes of Chloroquine," Inorganic Chemistry, Vol. 48, No. 3, 2009, pgs. 1122-1131, published online Jan. 2, 2009. The ruthenium-chloroquine complexes described in these previous studies demonstrated effectiveness against malaria parasites *Plasmodium falciparum* and *P. Berghei* (in vivo), as well as against the growth of colon cancer cells. In particular, the studies demonstrate that the potency of the ruthenium-chloroquine complexes against malaria is consistently higher than that of chloroquine diphosphate.

TABLE XVII

Expected Malaria Results. IC50 recorded in nM.
*Plasmodium falciparum*

| Compounds | IC50 in nM |
|---|---|
| Ir(COD)ethambutol | 35 |
| Ir(COD)ethylenediamine | 60 |
| Ir(COD)N-methyl(en) | 400 |
| Ir(COD)N,N-dimethyl(en) | 250 |
| Ir(val)(Pme3)3 | 60 |
| Ir(tyr)(Pme3)3 | 80 |
| Ir(leu)(Pme3)3 | 25 |
| Ir(pro)(Pme3)3 | 15 |
| 1 (L-gly) | 400 |
| 1 (L-pro) | 75 |
| 1 (L-ala) | 150 |
| 1 (L-phe) | 60 |
| 1 (L-phengly) | 25 |
| 1 (L-val) | 125 |
| 1 (L-ser) | 400 |
| 1 (L-gln) | 250 |
| 1 (D-val) | 120 |

As shown and described in this specification, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Indeed, it will be apparent to those skilled in the art that various modifications and variations can be made in the practice of the present invention without departing from the scope or spirit of the invention. Furthermore, no limitations are intended to the details of construction or design herein shown, other than as described in the claims below.

Methods of treating disease are included within the scope of the present invention. Such methods can comprise administering to a patient in an effective amount one or more coordination complexes of Categories I, II, III, and/or IV of the invention, wherein the coordination complex or portion thereof contacts and/or interacts with tissues, cells, or a microorganism associated with the disease in a manner sufficient to kill the target microorganism and/or reduce the disease state. Diseases treatable according to embodiments of the invention include malaria, microbial infections, bacterial infections, and cancer. Any compound specifically disclosed or generally disclosed within a genus of compounds described in this specification can be used in the methods of treating according to the invention.

Administering of compounds of the invention can be performed in any manner, such as by oral, parenteral, intramuscular, intravenous, cutaneous, subcutaneous, nasal, intraocular, transepithelial, intraperitoneal, topical (such as dermal, ocular, rectal, nasal, inhalation and aerosol), rectal, and/or stomach tube routes. Pharmaceutical compositions can be prepared in any acceptable form, such as in the form of capsules, powder, tablets, a suspension, or solution, optionally in admixture with a pharmaceutically acceptable carrier or diluents. Forms and dosages of appropriate pharmaceutical compositions that are appropriate for administration to humans and other warm blooded mammals can be formulated based on the information provided in this specification in combination with techniques well known in the art. For example, administration protocols disclosed in U.S. Pat. No. 6,716,826 entitled "Compounds and Their Uses;" U.S. Pat. No. 4,167,564 entitled "Biological Assimilation of Metals;" or U.S. Pat. No. 5,824,673 entitled "Pharmaceutical Compositions Comprising Metal Complexes;" can in particular be used to administer compounds and compositions of the invention.

The present invention has been described with reference to particular embodiments having various features. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. All numbers and ranges disclosed above may vary by some amount. As used in this specification, the singular forms "a," "an," and "the" include plural referents unless the context clearly dictates otherwise. While compositions and methods are described in terms of "comprising," "containing," or "including" various components or steps, the compositions and methods can also "consist essentially of" or "consist of" the various components and steps. It is intended that the specification and examples be considered as exemplary in nature and that variations that do not depart from the essence of the invention are intended to be within the scope of the invention.

Further, the references cited in this disclosure are hereby incorporated by reference herein in their entireties, especially for information that is well known in the art for example with respect to use, effectiveness, or preparation of the inventive compounds. If there is any conflict in the usages of a word or term in this specification and one or more patent or other documents that may be incorporated herein by reference, the definitions that are consistent with this specification should be adopted.

The invention claimed is:

1. A piano stool complex of Formula 3:

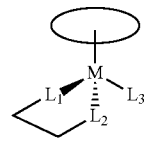

Formula 3 wherein M is chosen from any transition metal that is not ruthenium or osmium, or M is chosen from any lanthanide or actinide-metal; and wherein $L_1$, $L_2$ is an N,O chelate and where $L_3$ is a halogen; and wherein

is an aromatic ligand capable of pi-complexing to the metal; wherein the N,O chelate is:

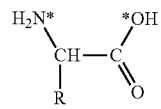

wherein the nitrogen (N) and oxygen (O) atoms bond with M, wherein the atoms indicated with * are chiral; and wherein R is chosen from any of:

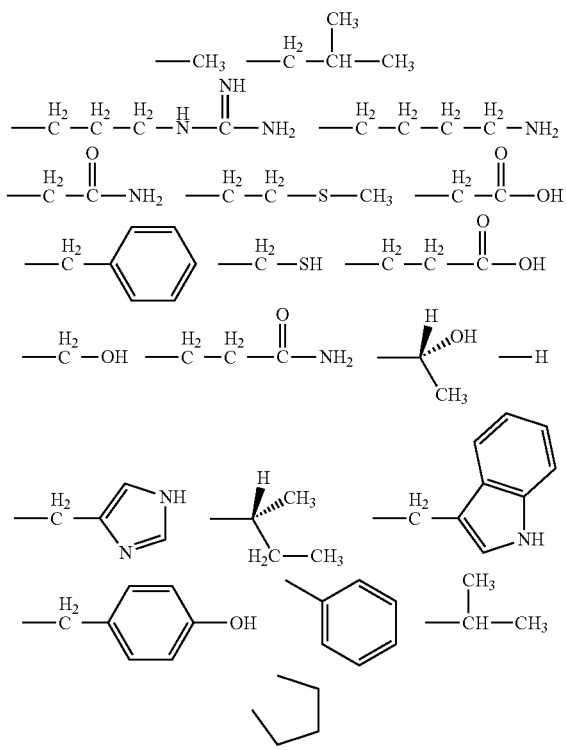

or wherein R is chosen from a substituted or unsubstituted, saturated or unsaturated $C_{1-20}$ alkyl group, and optionally R additionally bonds with the adjacent nitrogen atom or adjacent carbon atom (where R replaces the oxygen of the carbonyl group) to form a 3-, 4-, 5-, 6-, 7-, 8-, or 9-membered ring structure, wherein the ring structure is unsubstituted or comprises an alkyl substituent, and wherein the ring structure comprises one or more heteroatom, and wherein the ring structure is optionally substituted with a halogen or hydroxyl group;

or wherein R is $CF_3$; and optionally one or more hydrogen atom on the nitrogen of the $L_1$, $L_2$ chelate is replaced with one or more $C_{1-10}$ alkyl group;

wherein

is chosen from one of the following ligands:

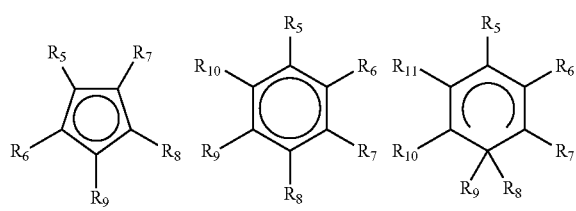

-continued

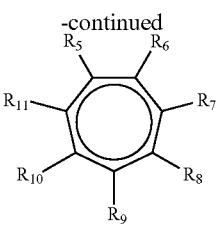

wherein $R_{5-11}$ can be the same or different and chosen from hydrogen or any unsubstituted or unsubstituted alkyl group comprising from 1-20 carbon atoms;

or an enantiomer thereof, or a diastereoisomer thereof, or a racemic mixture of stereoisomers thereof, or a salt thereof, or any combination thereof.

2. The piano stool complex of claim 1, wherein

is chosen from a cyclopentadienyl group, a substituted cyclopentadienyl group, a benzene group, or a substituted benzene group.

3. The piano stool complex of claim 1, wherein $R_{5-11}$ are chosen from a hydrogen atom, a methyl (—$CH_3$) group, an ethyl (—$CH_2CH_3$) group, a propyl group (—$C_3H_7$), a butyl group (—$C_4H_9$), a phenyl (—$C_6H_5$) group, a benzyl group, an unsubstituted or substituted $C_{1-10}$ alkyl group, or an unsubstituted or unsubstituted $C_{11-20}$ alkyl group.

4. The piano stool complex of claim 1, wherein R is chosen from a substituted or unsubstituted, saturated or unsaturated $C_{1-6}$, or $C_{3-10}$, or $C_{5-8}$ alky group.

5. The piano stool complex of claim 1, wherein the halogen is chosen from fluorine, iodine, bromine, or chlorine.

6. The piano stool complex of claim 1, wherein M is chosen from cobalt, rhodium, iridium, iron, manganese, technetium, and rhenium.

7. The piano stool complex of claim 1, wherein M is rhodium or iridium.

8. A piano stool complex of Formula 3:

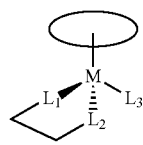

Formula 3 wherein M is ruthenium or osmium; and wherein $L_1$, $L_2$ is an N, O chelate and where $L_3$ is a halogen; and wherein

is an aromatic ligand capable of pi-complexing to the metal;

wherein the N, O chelate is:

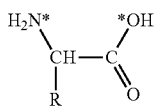

wherein the nitrogen (N) and oxygen (O) atoms bond with M, wherein the atoms indicated with * are chiral; and wherein R is chosen from any of:

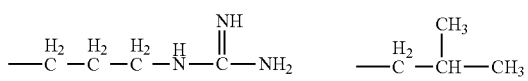

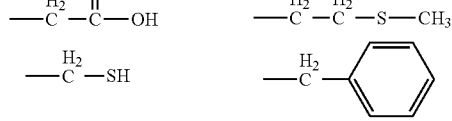

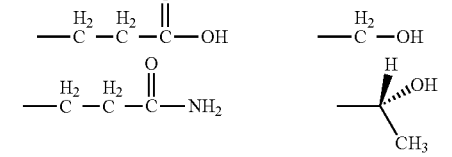

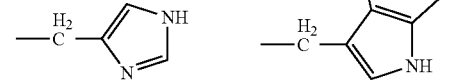

or wherein R is chosen from a substituted or unsubstituted, saturated or unsaturated $C_{1-3}$ or $C_{5-20}$ alkyl group, and optionally R additionally bonds with the adjacent nitrogen atom or adjacent carbon atom (where R replaces the oxygen of the carbonyl group) to form a 3-, 4-, 6-, 7-, 8-, or 9-membered ring structure, wherein the ring structure is unsubstituted or comprises an alkyl substituent, and wherein the ring structure comprises one or more heteroatom, and wherein the ring structure is optionally substituted with a halogen or hydroxyl group;

or wherein R is $CF_3$; and optionally one or more hydrogen atom on the nitrogen of the $L_1$, $L_2$ chelate is replaced with one or more $C_{2-10}$ alkyl group wherein

is chosen from one of the following ligands:

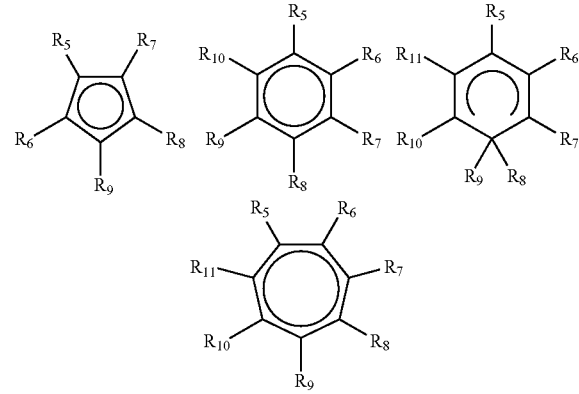

wherein $R_{5-11}$ can be the same or different and chosen from hydrogen or any unsubstituted or unsubstituted alkyl group comprising from 1-20 carbon atoms;

or an enantiomer thereof, or a diastereoisomer thereof, or a racemic mixture of stereoisomers thereof, or a salt thereof, or any combination thereof.

9. The piano stool complex of claim 8, wherein M is ruthenium.

10. The piano stool complex of claim 8, wherein M is osmium.

11. A piano stool complex of Formula 3:

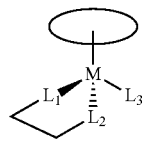

Formula 3 wherein M is chosen from any transition, lanthanide, or actinide metal; and wherein $L_1$, $L_2$ is an N,N chelate and where $L_3$ is a halogen; and wherein

is an aromatic ligand capable of pi-complexing to the metal; wherein the N,N chelate is:

wherein the nitrogen (N) atoms bond with M and wherein $R_1$-$R_4$ may be —H and at least one of $R_1$-$R_4$ is

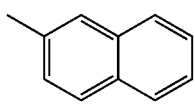 or 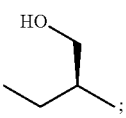 ;

wherein

is chosen from one of the following ligands:

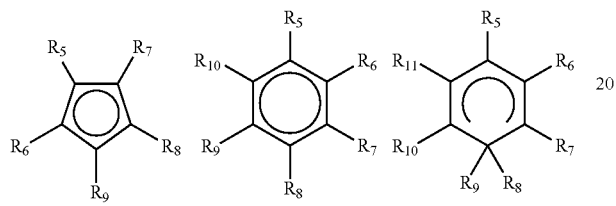

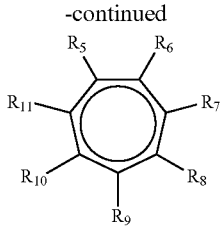

wherein $R_{5-11}$ can be the same or different and chosen from hydrogen or any unsubstituted or unsubstituted alkyl group comprising from 1-20 carbon atoms;

or an enantiomer thereof, or a diastereoisomer thereof, or a racemic mixture of stereoisomers thereof, or a salt thereof, or any combination thereof.

12. The piano stool complex of claim 11, wherein M is chosen from cobalt, rhodium, iridium, iron, ruthenium, osmium, manganese, technetium, and rhenium.

* * * * *